United States Patent
Fikes et al.

(10) Patent No.: US 6,534,482 B1
(45) Date of Patent: Mar. 18, 2003

(54) EXPRESSION VECTORS FOR STIMULATING AN IMMUNE RESPONSE AND METHODS OF USING THE SAME

(75) Inventors: John D. Fikes, San Diego, CA (US); Gary G. Hermanson, Encinitas, CA (US); Alessandro Sette, La Jolla, CA (US); Glenn Y. Ishioka, Solana Beach, CA (US); Brian Livingston, San Diego, CA (US); Robert W. Chesnut, Cardiff-by-the-Sea, CA (US)

(73) Assignee: Epimmune, Inc., San Diego, CA (US)

( * ) Notice: Subject to any disclaimer, the term of this patent is extended or adjusted under 35 U.S.C. 154(b) by 0 days.

(21) Appl. No.: 09/311,784

(22) Filed: May 13, 1999

Related U.S. Application Data

(63) Continuation of application No. 09/078,904, filed on May 13, 1998, now abandoned.
(60) Provisional application No. 60/085,751, filed on May 15, 1998.

(51) Int. Cl.[7] .................. A61K 48/00; C12N 15/00; C12N 15/63

(52) U.S. Cl. .................. 514/44; 435/320.1; 435/325

(58) Field of Search .................. 435/320.1, 325; 514/44

(56) References Cited

U.S. PATENT DOCUMENTS

| | | | |
|---|---|---|---|
| 5,633,234 A | 5/1997 | August et al. | 514/44 |
| 5,736,142 A | * 4/1998 | Sette et al. | 424/185 |

FOREIGN PATENT DOCUMENTS

| | | |
|---|---|---|
| WO | WO 95/07707 | 3/1995 |

OTHER PUBLICATIONS

Del Guercio et. al.; Potent immunogenic short linear peptide constructs composed of B cell epitopes and Pan DR T Helper Epitopes (PADRE) for antibody responses in vivo, 1997, Vaccine vol. 15, No. 4: 441–448.*

Vitiello et al.: "Comparison of cytotoxic T lymphocyte responses induced by peptide or DNA immunization: implications on immunogenicity and immndominance" *Eur. J. Immunol* 27:671–678 (1997).

Thomson et al.: "Targeting a Polyepitope Protein Incorporating Multiple Class II–Restricted Viral Epitopes to the Secretory/Enocytic Pathway Facilitates Immune Recognition by CD4+ Cytotoxic T Lymphocytes: A Novel Approach to Vaccine Design" *Journal of Virology* 2246–2252 (3/98).

Bertoni et al.: Human Class I Supertypes and CTL Repertoires Extend to Chimpanzees[1,2] *Journal of Immunology* 161: 4447–4455 (1998).

Ling–Ling An and J. Lindsay Whitton: "A Multivalent Minigene Vaccine, Containing B Cell, Cytotoxic T–Lymphocyte, and $T_h$ Epitopes from Several Microbes, Induces Appropriate Responses in Vivo and Confers Protection against More that One Pathogen\" *Journal of Virology* 2292–2302 (3/97).

Livingston et. al.: "The Hepatitis B Virus–Specific CTL Response Induced in Humans by Lipopetide Vaccination are Comparable to Those Elicited by Acute Viral Infection[1]" *Journal of Immunology* 159: 1383–1392 (1997).

Alexander et al.: "Derivation of HLA–A11/$K^b$ Transgenic Mice" *Journal of Immunology* 159: 4753–4761 (1997).

Vitiello et al.: "Analysis of the HLA–restricted Influenza–specific Cytotoxic T lymphocyte Response in Transgenic Mice Carrying a Chimeric Human–Mouse Class I Major Histocompatibility Complex" *J. Exp. Med.* 173 1007–1015 (4/91).

Weber et al.: "Immunogenicity of the yeast recombinant p17/p24:Ty virus–like particles (p24–VLP) in healthy volunteers" *Vaccine*, 13(9) 831–734 (1995).

Kuhröber et al.: "DNA vaccination with plasmids encoding the intracellular (HBcAg) or secreted (HBeAg) form of the core protein of hepatitis B virus primes T cell responses to two overlapping $K^b$–and $K^d$–restricted epitopes" *International Immunology* 9(8) 1203–1212 (1997).

Le Borgne et al: "In Vivo Induction of Specific Cytotoxic T Lymphocytes in Mice and Rhesus Macaques Immunized with DNA Vector Encoding an HIV Epitope Fused with Hepatitis B Surface Antigen" *Virology* 240, 304–315 (1998).

Diminsky et al.: "Comparison between hepatitis B surface antigen (HBsAg) particles derived from mammalian cells (CHO) and yeast cells (*Hansenula polymorpha*): composition, structure, and immunogenicity" *Vaccine*, 15(6/7) 637–647 (1997).

Maryse Guéguen and Eric O. Long: "Presentation of a cytosolic antigen by major histocompatibility compex class II molecules requires a long–lived form of the antigen" *Proc. Natl. Acad. Sci. USA* 93 14692–14697 (12/96).

Bonnerot et al.: "Role of B Cell Receptor Igα and Igβ Subunits in MHC Class II–Restricted Antigen Presentation" *Immunity*, 3, 335–347 (9/95).

Liljedahl et al.: "HLA–DO is lysosomal resident which requires association with HLA–DM for efficient intracellular transport" *EMBO Journal* 15(18) 4817–4824 (1996).

Copier et al.: "Targeting Signal and Subcellular Compartments Involved in the Intracellular Trafficking of HLA–DMB[1] " *Journal of Immunology* 157 1017–1027 (1996).

Rammensee et al.: "MHC ligands and peptide motfits: first listing" *Immunogenetics* 41 178–228 (1995).

Alexander et al.: "Development of High Potency Universal DR–Restricted Helper Epitopes by Modification of Affinity DR–Blocking Peptides" *Immunity* 1 751–761 (12/94).

(List continued on next page.)

*Primary Examiner*—Anne M. Wehbe
(74) *Attorney, Agent, or Firm*—Morrison & Foerster LLP

(57) ABSTRACT

The present invention relates to nucleic acid vaccines encoding multiple CTL and HTL epitopes and MHC targeting sequences.

4 Claims, 45 Drawing Sheets

OTHER PUBLICATIONS

Robert A. Uger and Brian H. Barber[2] "Presentation of and Influenza Nucleoprotein Epitope Incorporated into the H–2D$^b$ Signal Sequence Requires the Transporter–Associated with Antigen Presentation[1]" *Journal of Immunology* 158 685–692 (1997).

Anderson et al.: Endogenously Synthesized Peptide with an Endoplasmic Reticulum Signal Sequence Sensitizes Antigen Processing Mutant Cells to Class I–restricted Cell–mediated Lysis *J. Exp. Med.* 174 489–492 (1991).

Jennings et al.: "CD–4 Positive T Lymphocytes are Restricted for the Generation of the Primary by not the Secondary CD8–Positive Cytolytic T Lymphocytes Response to Herpes Simplex Virus in C57BL/6 Mice" *Cellular Immunology* 133 234–252 (1991).

Rahemtulla et al.: "Normal development and function of CD8$^+$ cells but markedly decreased helper cell activity in mice lacking CD4" *Letters to Nature* 353 (Sep. 12, 1991).

Shirai et al.: Use of Intrinsic and Extrinsic Helper Epitopes for In Vivo Induction of Anti–Hepatitis C Virus Cytotoxic T Lymphocytes (CTL) with CTL Epitope Peptide Vaccines *Journal of Infectious Diseases* 173 24–31 (1996).

Thomson et al.: "Minimal epitopes expressed in a recombinant polyepitope protein are processed and presented to CD8$^+$ cytotoxic T cells: Implications for vaccine design" *Proc. Natl. Acad. Sci. USA* 92 5845–5849 (6/95).

Bergmann et al: "Differential Effects of Flanking Residues on Presentation of Epitopes from Chimeric Peptides" *Journal of Virology* 68(8) 5306–5310 (8/94).

Del Val et al.: "Efficient Processing of an Antigenic Sequence for Presentation by MHC Class I Molecules Depends on its Neighboring Residues in the Protein" *Cell* 66 1145–1153 (Sep. 20, 1991).

Toes et al.: "Protective anti–tumor immunity induced by vaccination with recombinant adenoviruses encoding multiple tumor–associated cytotoxic T lymphocyte epitopes in a string–of–beads fashion" *Proc. Natl. Acad. Sci. USA* 94 14660–14665 (12/97).

Hanke et al.: DNA multi–CTL epitope vaccines for HIV and Plasmodium falciparum: immunogenicity in mice *Vaccine* 16(4) 426–435 (1998).

Whitton et al.: "A "String–of–Beads" Vaccine, Comprising Linked Minigenes, Confers Protection form Lethal–Dose Virus Challenge" *Journal of Virology* 67(1) 348–352 (1/93).

Donnelly et al "DNA Vaccines" *Annu. Rev. Immunol.* 15 617–648 (1997).

* cited by examiner

```
         10        20        30        40        50        60        70
    *    *    *    *    *    *    *    *    *    *    *    *    *    *
GCTAGCGCCGCCACCATGGATGACCAACGCGACCTCATCTCTAACCATGAGCAATTGCCCATACTGGGCA
CGATCGCGGCGGTGGTACCTACTGGTTGCGCTGGAGTAGAGATTGGTACTCGTTAACGGGTATGACCCGT
                 M  D  D  Q  R  D  L  I  S  N  H  E  Q  L  P  I  L  G>

80        90       100       110       120       130       140
    *    *    *    *    *    *    *    *    *    *    *    *    *    *
ACCGCCCTAGAGAGCCAGAAAGGTGCAGCCGTGGAGCTCTGTACACCGGTGTTTCTGTCCTGGTGGCTCT
TGGCGGGATCTCTCGGTCTTTCCACGTCGGCACCTCGAGACATGTGGCCACAAAGACAGGACCACCGAGA
 N  R  P  R  E  P  E  R  C  S  R  G  A  L  Y  T  G  V  S  V  L  V  A  L>

150       160       170       180       190       200       220
    *    *    *    *    *    *    *    *    *    *    *    *    *    *
GCTCTTGGCTGGGCAGGCCACCACTGCTTACTTCCTGTACCAGCAACAGGGCCGCCTAGACAAGCTGACC
CGAGAACCGACCCGTCCGGTGGTGACGAATGAAGGACATGGTCGTTGTCCCGGCGGATCTGTTCGACTGG
 L  L  A  G  Q  A  T  T  A  Y  F  L  Y  Q  Q  Q  G  R  L  D  K  L  T>

220       230       240       250       260       270       280
    *    *    *    *    *    *    *    *    *    *    *    *    *    *
ATCACCTCCCAGAACCTGCAACTGGAGAGCCTTCGCATGAAGCTTCCGAAATCTGCCAAACCTGTGGCCA
TAGTGGAGGGTCTTGGACGTTGACCTCTCGGAAGCGTACTTCGAAGGCTTTAGACGGTTTGGACACCGGT
 I  T  S  Q  N  L  Q  L  E  S  L  R  M  K  L  P  K  S  A  K  P  V  A>

290       300       310       320       330       340       350
    *    *    *    *    *    *    *    *    *    *    *    *    *    *
AGTTCGTGGCTGCCTGGACCCTGAAGGCTGCCGCTATGTCCATGGATAACATGCTCCTTGGGCCTGTGAA
TCAAGCACCGACGGACCTGGGACTTCCGACGGCGATACAGGTACCTATTGTACGAGGAACCCGGACACTT
 K  F  V  A  A  W  T  L  K  A  A  A  M  S  M  D  N  M  L  L  G  P  V  K>

360       370       380       390       400       410       420
    *    *    *    *    *    *    *    *    *    *    *    *    *    *
GAACGTTACCAAGTACGGCAACATGACCCAGGACCATGTGATGCATCTGCTCACGAGGTCTGGACCCCTG
CTTGCAATGGTTCATGCCGTTGTACTGGGTCCTGGTACACTACGTAGACGAGTGCTCCAGACCTGGGGAC
 N  V  T  K  Y  G  N  M  T  Q  D  H  V  M  H  L  L  T  R  S  G  P  L>

430       440       450       460       470       480       490
    *    *    *    *    *    *    *    *    *    *    *    *    *    *
GAGTACCCGCAGCTGAAGGGGACCTTCCCAGAGAATCTGAAGCATCTTAAGAACTCCATGGATGGCGTGA
CTCATGGGCGTCGACTTCCCCTGGAAGGGTCTCTTAGACTTCGTAGAATTCTTGAGGTACCTACCGCACT
 E  Y  P  Q  L  K  G  T  F  P  E  N  L  K  H  L  K  N  S  M  D  G  V>

500       510       520       530       540       550       560
    *    *    *    *    *    *    *    *    *    *    *    *    *    *
ACTGGAAGATCTTCGAGAGCTGGATGAAGCAGTGGCTCTTGTTTGAGATGAGCAAGAACTCCCTGGAGGA
TGACCTTCTAGAAGCTCTCGACCTACTTCGTCACCGAGAACAAACTCTACTCGTTCTTGAGGGACCTCCT
 N  W  K  I  F  E  S  W  M  K  Q  W  L  L  F  E  M  S  K  N  S  L  E  E>

570       580       590       600       610       620       630
    *    *    *    *    *    *    *    *    *    *    *    *    *    *
GAAGAAGCCCACCGAGGCTCCACCTAAAGAGCCACTGGACATGGAAGACCTATCTTCTGGCCTGGGAGTG
CTTCTTCGGGTGGCTCCGAGGTGGATTTCTCGGTGACCTGTACCTTCTGGATAGAAGACCGGACCCTCAC
 K  K  P  T  E  A  P  P  K  E  P  L  D  M  E  D  L  S  S  G  L  G  V>

640       650       660
         *    *    *    *    *    *    *
ACCAGGCAGGAACTGGGTCAAGTCACCCTGTGAGGTACC
TGGTCCGTCCTTGACCCAGTTCAGTGGGACACTCCATGG
 T  R  Q  E  L  G  Q  V  T  L  *>
```

FIG.1

```
          10        20        30        40        50        60        70
      *    *    *    *    *    *    *    *    *    *    *    *    *    *
    GCTAGCGCCGCCACCATGGATGACCAACGCGACCTCATCTCTAACCATGAGCAATTGCCCATACTGGGCA
    CGATCGCGGCGGTGGTACCTACTGGTTGCGCTGGAGTAGAGATTGGTACTCGTTAACGGGTATGACCCGT
                     M  D  D  Q  R  D  L  I  S  N  H  E  Q  L  P  I  L  G>

80        90       100       110       120       130       140
      *    *    *    *    *    *    *    *    *    *    *    *    *    *
    ACCGCCCTAGAGAGCCAGAAAGGTGCAGCCGTGGAGCTCTGTACACCGGTGTTTCTGTCCTGGTGGCTCT
    TGGCGGGATCTCTCGGTCTTTCCACGTCGGCACCTCGAGACATGTGGCCACAAAGACAGGACCACCGAGA
     N  R  P  R  E  P  E  R  C  S  R  G  A  L  Y  T  G  V  S  V  L  V  A  L>

150       160       170       180       190       200       210
      *    *    *    *    *    *    *    *    *    *    *    *    *    *
    GCTCTTGGCTGGGCAGGCCACCACTGCTTACTTCCTGTACCAGCAACAGGGCCGCCTAGACAAGCTGACC
    CGAGAACCGACCCGTCCGGTGGTGACGAATGAAGGACATGGTCGTTGTCCCGGCGGATCTGTTCGACTGG
     L  L  A  G  Q  A  T  T  A  Y  F  L  Y  Q  Q  Q  G  R  L  D  K  L  T>

220       230       240       250       260       270       280
      *    *    *    *    *    *    *    *    *    *    *    *    *    *
    ATCACCTCCCAGAACCTGCAACTGGAGAGCCTTCGCATGAAGCTTATCAGCCAGGCTGTGCACGCCGCTC
    TAGTGGAGGGTCTTGGACGTTGACCTCTCGGAAGCGTACTTCGAATAGTCGGTCCGACACGTGCGGCGAG
     I  T  S  Q  N  L  Q  L  E  S  L  R  M  K  L  I  S  Q  A  V  H  A  A>

290       300       310       320       330       340       350
      *    *    *    *    *    *    *    *    *    *    *    *    *    *
    ACGCCGAAATCAACGAAGCTGGAAGAACCCCTCCAGCTTATCGCCCTCCAAACGCTCCTATCCTGTTCTT
    TGCGGCTTTAGTTGCTTCGACCTTCTTGGGGAGGTCGAATAGCGGGAGGTTTGCGAGGATAGGACAAGAA
     H  A  E  I  N  E  A  G  R  T  P  P  A  Y  R  P  P  N  A  P  I  L  F  F>

360       370       380       390       400       410       420
      *    *    *    *    *    *    *    *    *    *    *    *    *    *
    TCTGCTGACCAGAATCCTGACAATCCCCCAGTCCCTGGACGCCAAGTTCGTGGCTGCCTGGACCCTGAAG
    AGACGACTGGTCTTAGGACTGTTAGGGGGTCAGGGACCTGCGGTTCAAGCACCGACGGACCTGGGACTTC
     L  L  T  R  I  L  T  I  P  Q  S  L  D  A  K  F  V  A  A  W  T  L  K>

430
      *    *    *
    GCTGCCGCTTGAGGTACC
    CGACGGCGAACTCCATGG
     A  A  A  *>
```

FIG.2

```
         10        20        30        40        50        60        70
     *    *    *    *    *    *    *    *    *    *    *    *    *    *
GCTAGCGCCGCCACCATGGATGACCAACGCGACCTCATCTCTAACCATGAGCAATTGCCCATACTGGGCA
CGATCGCGGCGGTGGTACCTACTGGTTGCGCTGGAGTAGAGATTGGTACTCGTTAACGGGTATGACCCGT
                  M  D  D  Q  R  D  L  I  S  N  H  E  Q  L  P  I  L  G>

80        90       100       110       120       130       140
     *    *    *    *    *    *    *    *    *    *    *    *    *    *
ACCGCCCTAGAGAGCCAGAAAGGTGCAGCCGTGGAGCTCTGTACACCGGTGTTTCTGTCCTGGTGGCTCT
TGGCGGGATCTCTCGGTCTTTCCACGTCGGCACCTCGAGACATGTGGCCACAAAGACAGGACCACCGAGA
 N  R  P  R  E  P  E  R  C  S  R  G  A  L  Y  T  G  V  S  V  L  V  A  L>

150       160       170       180       190       200       210
     *    *    *    *    *    *    *    *    *    *    *    *    *    *
GCTCTTGGCTGGGCAGGCCACCACTGCTTACTTCCTGTACCAGCAACAGGGCCGCCTAGACAAGCTGACC
CGAGAACCGACCCGTCCGGTGGTGACGAATGAAGGACATGGTCGTTGTCCCGGCGGATCTGTTCGACTGG
 L  L  A  G  Q  A  T  T  A  Y  F  L  Y  Q  Q  Q  G  R  L  D  K  L  T>

220       230       240       250       260       270       280
     *    *    *    *    *    *    *    *    *    *    *    *    *    *
ATCACCTCCCAGAACCTGCAACTGGAGAGCCTTCGCATGAAGCTTATCAGCCAGGCTGTGCACGCCGCTC
TAGTGGAGGGTCTTGGACGTTGACCTCTCGGAAGCGTACTTCGAATAGTCGGTCCGACACGTGCGGCGAG
 I  T  S  Q  N  L  Q  L  E  S  L  R  M  K  L  I  S  Q  A  V  H  A  A>

290       300       310       320       330       340       350
     *    *    *    *    *    *    *    *    *    *    *    *    *    *
ACGCCGAAATCAACGAAGCTGGAAGAACCCCTCCAGCTTATCGCCCTCCAAACGCTCCTATCCTGTTCTT
TGCGGCTTTAGTTGCTTCGACCTTCTTGGGGAGGTCGAATAGCGGGAGGTTTGCGAGGATAGGACAAGAA
 H  A  E  I  N  E  A  G  R  T  P  P  A  Y  R  P  P  N  A  P  I  L  F  F>

360       370       380       390       400       410       420
     *    *    *    *    *    *    *    *    *    *    *    *    *    *
TCTGCTGACCAGAATCCTGACAATCCCCCAGTCCCTGGACGCCAAGTTCGTGGCTGCCTGGACCCTGAAG
AGACGACTGGTCTTAGGACTGTTAGGGGGTCAGGGACCTGCGGTTCAAGCACCGACGGACCTGGGACTTC
 L  L  T  R  I  L  T  I  P  Q  S  L  D  A  K  F  V  A  A  W  T  L  K>

430       440       450       460       470       480       490
     *    *    *    *    *    *    *    *    *    *    *    *    *    *
GCTGCCGCTATGTCCATGGATAACATGCTCCTTGGGCCTGTGAAGAACGTTACCAAGTACGGCAACATGA
CGACGGCGATACAGGTACCTATTGTACGAGGAACCCGGACACTTCTTGCAATGGTTCATGCCGTTGTACT
 A  A  A  M  S  M  D  N  M  L  L  G  P  V  K  N  V  T  K  Y  G  N  M>

500       510       520       530       540       550       560
     *    *    *    *    *    *    *    *    *    *    *    *    *    *
CCCAGGACCATGTGATGCATCTGCTCACGAGGTCTGGACCCCTGGAGTACCCGCAGCTGAAGGGGACCTT
GGGTCCTGGTACACTACGTAGACGAGTGCTCCAGACCTGGGGACCTCATGGGCGTCGACTTCCCCTGGAA
 T  Q  D  H  V  M  H  L  L  T  R  S  G  P  L  E  Y  P  Q  L  K  G  T  F>

570       580       590       600       610       620       630
     *    *    *    *    *    *    *    *    *    *    *    *    *    *
CCCAGAGAATCTGAAGCATCTTAAGAACTCCATGGATGGCGTGAACTGGAAGATCTTCGAGAGCTGGATG
GGGTCTCTTAGACTTCGTAGAATTCTTGAGGTACCTACCGCACTTGACCTTCTAGAAGCTCTCGACCTAC
 P  E  N  L  K  H  L  K  N  S  M  D  G  V  N  W  K  I  F  E  S  W  M>
```

FIG.3A

```
        640         650        660        670        680        690        700
  *     *     *     *     *     *     *     *     *     *     *     *     *     *
AAGCAGTGGCTCTTGTTTGAGATGAGCAAGAACTCCCTGGAGGAGAAGAAGCCCACCGAGGCTCCACCTA
TTCGTCACCGAGAACAAACTCTACTCGTTCTTGAGGGACCTCCTCTTCTTCGGGTGGCTCCGAGGTGGAT
 K  Q  W  L  L  F  E  M  S  K  N  S  L  E  E  K  K  P  T  E  A  P  P>

710         720        730        740        750        760        770
  *     *     *     *     *     *     *     *     *     *     *     *     *     *
AAGAGCCACTGGACATGGAAGACCTATCTTCTGGCCTGGGAGTGACCAGGCAGGAACTGGGTCAAGTCAC
TTCTCGGTGACCTGTACCTTCTGGATAGAAGACCGGACCCTCACTGGTCCGTCCTTGACCCAGTTCAGTG
 K  E  P  L  D  M  E  D  L  S  S  G  L  G  V  T  R  Q  E  L  G  Q  V  T>

780
  *     *
CCTGTGAGGTACC
GGACACTCCATGG
 L  *>
```

FIG.3B

```
          10        20        30        40        50        60        70
     *    *    *    *    *    *    *    *    *    *    *    *    *    *
GCTAGCGCCGCCACCATGGGAATGCAGGTGCAGATCCAGAGCCTGTTTCTGCTCCTCCTGTGGGTGCCCG
CGATCGCGGCGGTGGTACCCTTACGTCCACGTCTAGGTCTCGGACAAAGACGAGGAGGACACCCACGGGC
                M  G  M  Q  V  Q  I  Q  S  L  F  L  L  L  W  V  P>

80        90       100       110       120       130       140
     *    *    *    *    *    *    *    *    *    *    *    *    *    *
GGTCCAGAGGAATCAGCCAGGCTGTGCACGCCGCTCACGCCGAAATCAACGAAGCTGGAAGAACCCCTCC
CCAGGTCTCCTTAGTCGGTCCGACACGTGCGGCGAGTGCGGCTTTAGTTGCTTCGACCTTCTTGGGGAGG
  G  S  R  G  I  S  Q  A  V  H  A  A  H  A  E  I  N  E  A  G  R  T  P  P>

150       160       170       180       190       200       210
     *    *    *    *    *    *    *    *    *    *    *    *    *    *
AGCTTATCGCCCTCCAAACGCTCCTATCCTGTTCTTTCTGCTGACCAGAATCCTGACAATCCCCCAGTCC
TCGAATAGCGGGAGGTTTGCGAGGATAGGACAAGAAAGACGACTGGTCTTAGGACTGTTAGGGGGTCAGG
  A  Y  R  P  P  N  A  P  I  L  F  F  L  L  T  R  I  L  T  I  P  Q  S>

220       230       240       250       260       270       280
     *    *    *    *    *    *    *    *    *    *    *    *    *    *
CTGGACGCCAAGTTCGTGGCTGCCTGGACCCTGAAGGCTGCCGCTAACAACATGTTGATCCCCATTGCTG
GACCTGCGGTTCAAGCACCGACGGACCTGGGACTTCCGACGGCGATTGTTGTACAACTAGGGGTAACGAC
  L  D  A  K  F  V  A  A  W  T  L  K  A  A  A  N  N  M  L  I  P  I  A>

290       300       310       320       330       340       350
     *    *    *    *    *    *    *    *    *    *    *    *    *    *
TGGGCGGTGCCCTGGCAGGGCTGGTCCTCATCGTCCTCATTGCCTACCTCATTGGCAGGAAGAGGAGTCA
ACCCGCCACGGGACCGTCCCGACCAGGAGTAGCAGGAGTAACGGATGGAGTAACCGTCCTTCTCCTCAGT
  V  G  G  A  L  A  G  L  V  L  I  V  L  I  A  Y  L  I  G  R  K  R  S  H>

360       370
     *    *    *    *    *
CGCCGGCTATCAGACCATCTAGGGTACC
GCGGCCGATAGTCTGGTAGATCCCATGG
  A  G  Y  Q  T  I  *>
```

FIG.4

```
          10        20        30        40        50        60        70
     *    *    *    *    *    *    *    *    *    *    *    *    *    *
GCTAGCGCCGCCACCATGGCTGCACTCTGGCTGCTGCTGCTGGTCCTCAGTCTGCACTGTATGGGGATCA
CGATCGCGGCGGTGGTACCGACGTGAGACCGACGACGACGACCAGGAGTCAGACGTGACATACCCCTAGT
              M  A  A  L  W  L  L  L  L  V  L  S  H  C  M  G  I>

80        90        100       110       120       130       140
     *    *    *    *    *    *    *    *    *    *    *    *    *    *
GCCAGGCTGTGCACGCCGCTCACGCCGAAATCAACGAAGCTGGAAGAACCCCTCCAGCTTATCGCCCTCC
CGGTCCGACACGTGCGGCGAGTGCGGCTTTAGTTGCTTCGACCTTCTTGGGGAGGTCGAATAGCGGGAGG
  S  Q  A  V  H  A  A  H  A  E  I  N  E  A  G  R  T  P  P  A  Y  R  P  P>

150       160       170       180       190       200       210
     *    *    *    *    *    *    *    *    *    *    *    *    *    *
AAACGCTCCTATCCTGTTCTTTCTGCTGACCAGAATCCTGACAATCCCCCAGTCCCTGGACGCCAAGTTC
TTTGCGAGGATAGGACAAGAAAGACGACTGGTCTTAGGACTGTTAGGGGGTCAGGGACCTGCGGTTCAAG
  N  A  P  I  L  F  F  L  L  T  R  I  L  T  I  P  Q  S  L  D  A  K  F>

220       230       240       250       260       270       280
     *    *    *    *    *    *    *    *    *    *    *    *    *    *
GTGGCTGCCTGGACCCTGAAGGCTGCCGCTAAGGTCTCTGTGTCTGCAGCCACCCTGGGCCTGGGCTTCA
CACCGACGGACCTGGGACTTCCGACGGCGATTCCAGAGACACAGACGTCGGTGGGACCCGGACCCGAAGT
  V  A  A  W  T  L  K  A  A  A  K  V  S  V  S  A  A  T  L  G  L  G  F>

290       300       310       320       330       340       350
     *    *    *    *    *    *    *    *    *    *    *    *    *    *
TCATCTTCTGTGTTGGCTTCTTCAGATGGCGCAAGTCTCATTCCTCCAGCTACACTCCTCTCCCTGGATC
AGTAGAAGACACAACCGAAGAAGTCTACCGCGTTCAGAGTAAGGAGGTCGATGTGAGGAGAGGGACCTAG
  I  I  F  C  V  G  F  F  R  W  R  K  S  H  S  S  S  Y  T  P  L  P  G  S>

360       370       380
     *    *    *    *    *    *
CACCTACCCAGAAGGACGGCATTAGGGTACC
GTGGATGGGTCTTCCTGCCGTAATCCCATGG
  T  Y  P  E  G  R  H  *>
```

FIG.5

```
           10        20        30        40        50        60        70
       *    *    *    *    *    *    *    *    *    *    *    *    *    *
    GCTAGCGCCGCCACCATGGGCGCTGGGAGGGCCCCCTGGGTGGTGGCTCTGTTGGTGAACCTCATGAGGC
    CGATCGCGGCGGTGGTACCCGCGACCCTCCCGGGGGACCCACCACCGAGACAACCACTTGGAGTACTCCG
                     M  G  A  G  R  A  P  W  V  V  A  L  L  V  N  L  M  R>

80        90       100       110       120       130       140
       *    *    *    *    *    *    *    *    *    *    *    *    *    *
    TGGATTCCATCAGCCAGGCTGTGCACGCCGCTCACGCCGAAATCAACGAAGCTGGAAGAACCCCTCCAGC
    ACCTAAGGTAGTCGGTCCGACACGTGCGGCGAGTGCGGCTTTAGTTGCTTCGACCTTCTTGGGGAGGTCG
     L  D  S  I  S  Q  A  V  H  A  A  H  A  E  I  N  E  A  G  R  T  P  P  A>

150       160       170       180       190       200       210
       *    *    *    *    *    *    *    *    *    *    *    *    *    *
    TTATCGCCCTCCAAACGCTCCTATCCTGTTCTTTCTGCTGACCAGAATCCTGACAATCCCCCAGTCCCTG
    AATAGCGGGAGGTTTGCGAGGATAGGACAAGAAAGACGACTGGTCTTAGGACTGTTAGGGGGTCAGGGAC
     Y  R  P  P  N  A  P  I  L  F  F  L  L  T  R  I  L  T  I  P  Q  S  L>

220       230       240       250       260       270       280
       *    *    *    *    *    *    *    *    *    *    *    *    *    *
    GACGCCAAGTTCGTGGCTGCCTGGACCCTGAAGGCTGCCGCTATACTGAGTGGAGCTGCAGTGTTCCTGC
    CTGCGGTTCAAGCACCGACGGACCTGGGACTTCCGACGGCGATATGACTCACCTCGACGTCACAAGGACG
     D  A  K  F  V  A  A  W  T  L  K  A  A  A  I  L  S  G  A  A  V  F  L>

290       300       310       320       330       340       350
       *    *    *    *    *    *    *    *    *    *    *    *    *    *
    TTGGGCTGATTGTCTTCCTGGTGGGGGTTGTTATCCATCTCAAGGCTCAGAAAGCATCTGTGGAGACTCA
    AACCCGACTAACAGAAGGACCACCCCCAACAATAGGTAGAGTTCCGAGTCTTTCGTAGACACCTCTGAGT
     L  G  L  I  V  F  L  V  G  V  V  I  H  L  K  A  Q  K  A  S  V  E  T  Q>

360       370       380       390       400       410       420
       *    *    *    *    *    *    *    *    *    *    *    *    *    *
    GCCTGGCAATGAGAGTAGGTCCCGGATGATGGAGCGGCTAACCAAGTTCAAGGCTGGACCGGGACATGTC
    CGGACCGTTACTCTCATCCAGGGCCTACTACCTCGCCGATTGGTTCAAGTTCCGACCTGGCCCTGTACAG
      P  G  N  E  S  R  S  R  M  M  E  R  L  T  K  F  K  A  G  P  G  H  V>

430
       *    *
    ACATGAGGTACC ..
    TGTACTCCATGG
     T *>
```

FIG.6

```
         10         20         30         40         50         60         70
    *     *    *     *    *     *    *     *    *     *    *     *    *     *
GCTAGCGCCGCCACCATGGCCAAGTTCGTGGCTGCCTGGACCCTGAAGGCTGCCGCTATGAGTCTTCTAA
CGATCGCGGCGGTGGTACCGGTTCAAGCACCGACGGACCTGGGACTTCCGACGGCGATACTCAGAAGATT
              M  A  K  F  V  A  A  W  T  L  K  A  A  A  M  S  L  L>

80         90        100        110        120        130        140
    *     *    *     *    *     *    *     *    *     *    *     *    *     *
CCGAGGTCGAAACGTACGTTCTCTCTATCATCCCATCAGGCCCCCTCAAAGCCGAGATCGCGCAGAGACT
GGCTCCAGCTTTGCATGCAAGAGAGATAGTAGGGTAGTCCGGGGGAGTTTCGGCTCTAGCGCGTCTCTGA
  T  E  V  E  T  Y  V  L  S  I  I  P  S  G  P  L  K  A  E  I  A  Q  R  L>

150        160        170        180        190        200        210
    *     *    *     *    *     *    *     *    *     *    *     *    *     *
TGAGGATGTTTTTGCAGGGAAGAACACAGATCTTGAGGCTCTCATGGAATGGCTAAAGACAAGACCAATC
ACTCCTACAAAAACGTCCCTTCTTGTGTCTAGAACTCCGAGAGTACCTTACCGATTTCTGTTCTGGTTAG
   E  D  V  F  A  G  K  N  T  D  L  E  A  L  M  E  W  L  K  T  R  P  I>

220        230        240        250        260        270        280
    *     *    *     *    *     *    *     *    *     *    *     *    *     *
CTGTCACCTCTGACTAAGGGAATTTTAGGGTTTGTGTTCACGCTCACCGTGCCCAGTGAGCGAGGACTGC
GACAGTGGAGACTGATTCCCTTAAAATCCCAAACACAAGTGCGAGTGGCACGGGTCACTCGCTCCTGACG
    L  S  P  L  T  K  G  I  L  G  F  V  F  T  L  T  V  P  S  E  R  G  L>

290        300        310        320        330        340        350
    *     *    *     *    *     *    *     *    *     *    *     *    *     *
AGCGTAGACGATTTGTCCAAAATGCCCTAAATGGGAATGGAGACCCAAACAACATGGACAGGGCAGTTAA
TCGCATCTGCTAAACAGGTTTTACGGGATTTACCCTTACCTCTGGGTTTGTTGTACCTGTCCCGTCAATT
   Q  R  R  R  F  V  Q  N  A  L  N  G  N  G  D  P  N  N  M  D  R  A  V  K>

360        370        380        390        400        410        420
    *     *    *     *    *     *    *     *    *     *    *     *    *     *
ACTATACAAGAAGCTGAAGAGGGAAATGACATTCCATGGAGCAAAGGAAGTTGCACTCAGTTACTCAACT
TGATATGTTCTTCGACTTCTCCCTTTACTGTAAGGTACCTCGTTTCCTTCAACGTGAGTCAATGAGTTGA
    L  Y  K  K  L  K  R  E  M  T  F  H  G  A  K  E  V  A  L  S  Y  S  T>

430        440        450        460        470        480        490
    *     *    *     *    *     *    *     *    *     *    *     *    *     *
GGTGCGCTTGCCAGTTGCATGGGTCTCATATACAACCGGATGGGAACAGTGACCACAGAAGTGGCTCTTG
CCACGCGAACGGTCAACGTACCCAGAGTATATGTTGGCCTACCCTTGTCACTGGTGTCTTCACCGAGAAC
   G  A  L  A  S  C  M  G  L  I  Y  N  R  M  G  T  V  T  T  E  V  A  L>

500        510        520        530        540        550        560
    *     *    *     *    *     *    *     *    *     *    *     *    *     *
GCCTAGTATGTGCCACTTGTGAGCAGATTGCTGATGCCCAACATCGGTCCCACAGGCAGATGGCGACTAC
CGGATCATACACGGTGAACACTCGTCTAACGACTACGGGTTGTAGCCAGGGTGTCCGTCTACCGCTGATG
   G  L  V  C  A  T  C  E  Q  I  A  D  A  Q  H  R  S  H  R  Q  M  A  T  T>

570        580        590        600        610        620        630
    *     *    *     *    *     *    *     *    *     *    *     *    *     *
CACCAACCCACTAATCAGGCATGAGAACAGAATGGTACTAGCCAGCACTACGGCTAAGGCCATGGAGCAA
GTGGTTGGGTGATTAGTCCGTACTCTTGTCTTACCATGATCGGTCGTGATGCCGATTCCGGTACCTCGTT
    T  N  P  L  I  R  H  E  N  R  M  V  L  A  S  T  T  A  K  A  M  E  Q>

640        650        660        670        680        690        700
    *     *    *     *    *     *    *     *    *     *    *     *    *     *
ATGGCTGGATCAAGTGAGCAGGCAGCAGAGGCCATGGAAGTCGCAAGTCAGGCTAGACAAATGGTGCAGG
TACCGACCTAGTTCACTCGTCCGTCGTCTCCGGTACCTTCAGCGTTCAGTCCGATCTGTTTACCACGTCC
   M  A  G  S  S  E  Q  A  A  E  A  M  E  V  A  S  Q  A  R  Q  M  V  Q>
```

FIG.7A

```
        710       720       730       740       750       760       770
     *    *    *    *    *    *    *    *    *    *    *    *    *    *
CAATGAGGACAATTGGGACTCACCCTAGCTCCAGTGCAGGTCTAAAAGATGATCTTATTGAAAATTTGCA
GTTACTCCTGTTAACCCTGAGTGGGATCGAGGTCACGTCCAGATTTTCTACTAGAATAACTTTTAAACGT
 A  M  R  T  I  G  T  H  P  S  S  A  G  L  K  D  D  L  I  E  N  L  Q>

780       790       800       810
     *    *    *    *    *    *    *    *    *
GGCTTACCAGAAACGGATGGGGGTGCAGATGCAGCGATTCAAGTGA
CCGAATGGTCTTTGCCTACCCCCACGTCTACGTCGCTAAGTTCACT
 A  Y  Q  K  R  M  G  V  Q  M  Q  R  F  K  *>
```

FIG. 7B

```
         10        20        30        40        50        60        70
    *    *    *    *    *    *    *    *    *    *    *    *    *    *
GCTAGCGCCGCCACCATGGCCAAGTTCGTGGCTGCCTGGACCCTGAAGGCTGCCGCTCTCGAGATTGGGG
CGATCGCGGCGGTGGTACCGGTTCAAGCACCGACGGACCTGGGACTTCCGACGGCGAGAGCTCTAACCCC
             M  A  K  F  V  A  A  W  T  L  K  A  A  A  L  E  I  G>

80        90        100       110       120       130       140
    *    *    *    *    *    *    *    *    *    *    *    *    *    *
GACCCTGCCTGAACGCCGAGAACATCACATCAGGATTCCTAGGACCCCTTCTCGTGTTACAGGCGGGGTT
CTGGGACGGACTTGCGGCTCTTGTAGTGTAGTCCTAAGGATCCTGGGGAAGAGCACAATGTCCGCCCCAA
 G  P  C  L  N  A  E  N  I  T  S  G  F  L  G  P  L  L  V  L  Q  A  G  F>

150       160       170       180       190       200       210
    *    *    *    *    *    *    *    *    *    *    *    *    *    *
TTTCTTGTTGACAAGAATCCTCACAATACCGCAGAGTCTAGACTCGTGGTGGACTTCTCTCAATTTTCTA
AAAGAACAACTGTTCTTAGGAGTGTTATGGCGTCTCAGATCTGAGCACCACCTGAAGAGAGTTAAAAGAT
  F  L  L  T  R  I  L  T  I  P  Q  S  L  D  S  W  W  T  S  L  N  F  L>

220       230       240       250       260       270       280
    *    *    *    *    *    *    *    *    *    *    *    *    *    *
GGGGGAACTACCGTGTGTCTTGGCCAAAATTCGCAGTCCCCAACCTCCAATCACTCACCAACCTCTTGTC
CCCCCTTGATGGCACACAGAACCGGTTTTAAGCGTCAGGGGTTGGAGGTTAGTGAGTGGTTGGAGAACAG
  G  G  T  T  V  C  L  G  Q  N  S  Q  S  P  T  S  N  H  S  P  T  S  C>

290       300       310       320       330       340       350
    *    *    *    *    *    *    *    *    *    *    *    *    *    *
CTCCAACTTGTCCTGGTTATCGCTGGATGTGTCTGCGGCGTTTTATCATCTTCCTCTTCATCCTGCTGCT
GAGGTTGAACAGGACCAATAGCGACCTACACAGACGCCGCAAAATAGTAGAAGGAGAAGTAGGACGACGA
  P  P  T  C  P  G  Y  R  W  M  C  L  R  R  F  I  I  F  L  F  I  L  L>

360       370       380       390       400       410       420
    *    *    *    *    *    *    *    *    *    *    *    *    *    *
ATGCCTCATCTTCTTGTTGGTTCTTCTGGACTATCAAGGTATGTTGCCCGTTTGTCCTCTAATTCCAGGA
TACGGAGTAGAAGAACAACCAAGAAGACCTGATAGTTCCATACAACGGGCAAACAGGAGATTAAGGTCCT
  C  L  I  F  L  L  V  L  L  D  Y  Q  G  M  L  P  V  C  P  L  I  P  G>

430       440       450       460       470       480       490
    *    *    *    *    *    *    *    *    *    *    *    *    *    *
TCCTCAACAACCAGCACGGGACCATGCCGGACCTGCATGACTACTGCTCAAGGAACCTCTATGTATCCCT
AGGAGTTGTTGGTCGTGCCCTGGTACGGCCTGGACGTACTGATGACGAGTTCCTTGGAGATACATAGGGA
  S  S  T  T  S  T  G  P  C  R  T  C  M  T  T  A  Q  G  T  S  M  Y  P>

500       510       520       530       540       550       560
    *    *    *    *    *    *    *    *    *    *    *    *    *    *
CCTGTTGCTGTACCAAACCTTCGGACGGAAATTGCACCTGTATTCCCATCCCATCATCCTGGGCTTTCGG
GGACAACGACATGGTTTGGAAGCCTGCCTTTAACGTGGACATAAGGGTAGGGTAGTAGGACCCGAAAGCC
  S  C  C  C  T  K  P  S  D  G  N  C  T  C  I  P  I  P  S  S  W  A  F  G>

570       580       590       600       610       620       630
    *    *    *    *    *    *    *    *    *    *    *    *    *    *
AAAATTCCTATGGGAGTGGGCCTCAGCCCGTTTCTCCTGGCTCAGTTTACTAGTGCCATTTGTTCAGTGG
TTTTAAGGATACCCTCACCCGGAGTCGGGCAAAGAGGACCGAGTCAAATGATCACGGTAAACAAGTCACC
  K  F  L  W  E  W  A  S  A  R  F  S  W  L  S  L  L  V  P  F  V  Q  W>
```

FIG.8A

```
       640       650       660       670       680       690       700
    *    *    *    *    *    *    *    *    *    *    *    *    *    *
TTCGTAGGGCTTTCCCCCACTGTTTGGCTTTCAGTTATATGGATGATGTGGTATTGGGGGCCAAGTCTGT
AAGCATCCCGAAAGGCGGTGACAAACCGAAAGTCAATATACCTACTACACCATAACCCCCGGTTCAGACA
  F   V   G   L   S   P   T   V   W   L   S   V   I   W   M   M   W   Y   W   G   P   S   L>

710       720       730       740       750       760       770
    *    *    *    *    *    *    *    *    *    *    *    *    *    *
ACAGCATCTTGAGTCCCTTTTTTACCGCTGTTACCAATTTTCTTTTGTCTTTGGGTATACATTTAAACCCT
TGTCGTAGAACTCAGGGAAAAATGGCGACAATGGTTAAAAGAAAACAGAAACCCATATGTAAATTTGGGA
  Y   S   I   L   S   P   F   L   P   L   L   P   I   F   F   C   L   W   V   Y   I   *>

780       790       800
    *    *    *    *    *    *
AACAAAACAAAGAGATGGGGTTACTCTCTAA
TTGTTTTGTTTCTCTACCCCAATGAGAGATT
```

FIG.8B

```
        10        20        30        40        50        60        70
    *    *    *    *    *    *    *    *    *    *    *    *    *    *
GCTAGCGCCGCCACCATGCCAGGGGGTCTAGAAGCCCTCAGAGCCCTGCCTCTCCTCCTCTTCTTGTCAT
CGATCGCGGCGGTGGTACGGTCCCCCAGATCTTCGGGAGTCTCGGGACGGAGAGGAGGAGAAGAACAGTA
              M  P  G  G  L  E  A  L  R  A  L  P  L  L  L  F  L  S>

80        90       100       110       120       130       140
    *    *    *    *    *    *    *    *    *    *    *    *    *    *
ACGCCTGTTTGGGTCCCGGATGCCAGGCCATCAGCCAGGCTGTGCACGCCGCTCACGCCGAAATCAACGA
TGCGGACAAACCCAGGGCCTACGGTCCGGTAGTCGACACGACACGTGCGGCGAGTGCGGCTTTAGTTGCT
 Y  A  C  L  G  P  G  C  Q  A  I  S  Q  A  V  H  A  A  H  A  E  I  N  E>

150       160       170       180       190       200       210
    *    *    *    *    *    *    *    *    *    *    *    *    *    *
AGCTGGAAGAACCCCTCCAGCTTATCGCCCTCCAAACGCTCCTATCCTGTTCTTTCTGCTGACCAGAATC
TCGACCTTCTTGGGGAGGTCGAATAGCGGGAGGTTTGCGAGGATAGGACAAGAAAGACGACTGGTCTTAG
 A  G  R  T  P  P  A  Y  R  P  P  N  A  P  I  L  F  F  L  L  T  R  I>

220       230       240       250       260       270       280
    *    *    *    *    *    *    *    *    *    *    *    *    *    *
CTGACAATCCCCCAGTCCCTGGACGCCAAGTTCGTGGCTGCCTGGACCCTGAAGGCTGCCGCTGGGATCA
GACTGTTAGGGGGTCAGGGACCTGCGGTTCAAGCACCGACGGACCTGGGACTTCCGACGGCGACCCTAGT
 L  T  I  P  Q  S  L  D  A  K  F  V  A  A  W  T  L  K  A  A  A  G  I>

290       300       310       320       330       340       350
    *    *    *    *    *    *    *    *    *    *    *    *    *    *
TCTTGCTGTTCTGTGCAGTGGTGCCAGGGACGCTGCTGCTATTCAGGAAACGGTGGCAAAATGAGAAGTT
AGAACGACAAGACACGTCACCACGGTCCCTGCGACGACGATAAGTCCTTTGCCACCGTTTTACTCTTCAA
 I  L  L  F  C  A  V  V  P  G  T  L  L  L  F  R  K  R  W  Q  N  E  K  F>

360       370       380       390       400       410       420
    *    *    *    *    *    *    *    *    *    *    *    *    *    *
TGGGGTGGACATGCCAGATGACTATGAAGATGAAAATCTCTATGAGGGCCTGAACCTTGATGACTGTTCT
ACCCCACCTGTACGGTCTACTGATACTTCTACTTTTAGAGATACTCCCGGACTTGGAACTACTGACAAGA
 G  V  D  M  P  D  D  Y  E  D  E  N  L  Y  E  G  L  N  L  D  D  C  S>

430       440       450       460       470       480       490
    *    *    *    *    *    *    *    *    *    *    *    *    *    *
ATGTATGAGGACATCTCCAGGGGACTCCAGGGCACCTACCAGGATGTGGGCAACCTCCACATTGGAGATG
TACATACTCCTGTAGAGGTCCCCTGAGGTCCCGTGGATGGTCCTACACCCGTTGGAGGTGTAACCTCTAC
 M  Y  E  D  I  S  R  G  L  Q  G  T  Y  Q  D  V  G  N  L  H  I  G  D>

500       510
    *    *    *    *    *
CCCAGCTGGAAAAGCCATGAGGTACC
GGGTCGACCTTTTCGGTACTCCATGG
 A  Q  L  E  K  P  *>
```

FIG.9

```
         10        20        30        40        50        60        70
    *    *    *    *    *    *    *    *    *    *    *    *    *    *
GCTAGCGCCGCCACCATGGCCACACTGGTGCTGTCTTCCATGCCCTGCCACTGGCTGTTGTTCCTGCTGC
CGATCGCGGCGGTGGTACCCGTGTGACCACGACAGAAGGTACGGGACGGTGACCGACAACAAGGACGACG
              M  A  T  L  V  L  S  S  M  P  C  H  W  L  L  F  L  L>

80        90       100       110       120       130       140
    *    *    *    *    *    *    *    *    *    *    *    *    *    *
TGCTCTTCTCAGGTGAGCCGATCAGCCAGGCTGTGCACGCCGCTCACGCCGAAATCAACGAAGCTGGAAG
ACGAGAAGAGTCCACTCGGCTAGTCGGTCCGACACGTGCGGCGAGTGCGGCTTTAGTTGCTTCGACCTTC
 L  L  F  S  G  E  P  I  S  Q  A  V  H  A  A  H  A  E  I  N  E  A  G  R>

150       160       170       180       190       200       210
    *    *    *    *    *    *    *    *    *    *    *    *    *    *
AACCCCTCCAGCTTATCGCCCTCCAAACGCTCCTATCCTGTTCTTTCTGCTGACCAGAATCCTGACAATC
TTGGGGAGGTCGAATAGCGGGAGGTTTGCGAGGATAGGACAAGAAAGACGACTGGTCTTAGGACTGTTAG
  T  P  P  A  Y  R  P  P  N  A  P  I  L  F  F  L  L  T  R  I  L  T  I>

220       230       240       250       260       270       280
    *    *    *    *    *    *    *    *    *    *    *    *    *    *
CCCCAGTCCCTGGACGCCAAGTTCGTGGCTGCCTGGACCCTGAAGGCTGCCGCTATTATCTTGATCCAGA
GGGGTCAGGGACCTGCGGTTCAAGCACCGACGGACCTGGGACTTCCGACGGCGATAATAGAACTAGGTCT
  P  Q  S  L  D  A  K  F  V  A  A  W  T  L  K  A  A  A  I  I  L  I  Q>

290       300       310       320       330       340       350
    *    *    *    *    *    *    *    *    *    *    *    *    *    *
CCCTCCTCATCATCCTCTTCATCATTGTGCCCATCTTCCTGCTACTTGACAAGGATGACGGCAAGGCTGG
GGGAGGAGTAGTAGGAGAAGTAGTAACACGGGTAGAAGGACGATGAACTGTTCCTACTGCCGTTCCGTTC
  T  L  L  I  I  L  F  I  I  V  P  I  F  L  L  L  D  K  D  D  G  K  A  G>

360       370       380       390       400       410       420
    *    *    *    *    *    *    *    *    *    *    *    *    *    *
GATGGAGGAAGATCACACCTATGAGGGCTTGAACATTGACCAGACAGCCACCTATGAAGACATAGTGACT
CTACCTCCTTCTAGTGTGGATACTCCCGAACTTGTAACTGGTCTGTCGGTGGATACTTCTGTATCACTGA
  M  E  E  D  H  T  Y  E  G  L  N  I  D  Q  T  A  T  Y  E  D  I  V  T>

430       440       450       460       470       480
    *    *    *    *    *    *    *    *    *    *    *    *
CTTCGGACAGGGGGAGGTAAAGTGGTCGGTAGGAGAGCATCCAGGCCAGGAATGAGGTACC
GAAGCCTGTCCCCTCCATTTCACCAGCCATCCTCTCGTAGGTCCGGTCGTTACTCCATGG
  L  R  T  G  E  V  K  W  S  V  G  E  H  P  G  Q  E  *>
```

FIG.10

```
         10        20        30        40        50        60        70
    *    *    *    *    *    *    *    *    *    *    *    *    *    *
GCTAGCGCCGCCACCATGGGAATGCAGGTGCAGATCCAGAGCCTGTTTCTGCTCCTCCTGTGGGTGCCCG
CGATCGCGGCGGTCGTACCCTTACGTCCACGTCTAGGTCTCGGACAAAGACGAGGAGGACACCCACGGGC
               M  G  M  Q  V  Q  I  Q  S  L  F  L  L  L  W  V  P>

80        90       100       110       120       130       140
    *    *    *    *    *    *    *    *    *    *    *    *    *    *
GGTCCCGAGGAATCAGCCAGGCTGTGCACGCCGCTCACGCCGAAATCAACGAAGCTGGAAGAACCCCTCC
CCAGGGCTCCTTAGTCGGTCCGACACGTGCGGCGAGTGCGGCTTTAGTTGCTTCGACCTTCTTGGGGAGG
 G  S  R  G  I  S  Q  A  V  H  A  A  H  A  E  I  N  E  A  G  R  T  P  P>

150       160       170       180       190       200       210
    *    *    *    *    *    *    *    *    *    *    *    *    *    *
AGCTTATCGCCCTCCAAACGCTCCTATCCTGTTCTTTCTGCTGACCAGAATCCTGACAATCCCCCAGTCC
TCGAATAGCGGGAGGTTTGCGAGGATAGGACAAGAAAGACGACTGGTCTTAGGACTGTTAGGGGGTCAGG
  A  Y  R  P  P  N  A  P  I  L  F  F  L  L  T  R  I  L  T  I  P  Q  S>

220       230       240       250       260       270       280
    *    *    *    *    *    *    *    *    *    *    *    *    *    *
CTGGACGCCAAGTTCGTGGCTGCCTGGACCCTGAAGGCTGCCGCTTGAGGTACC
GACCTGCGGTTCAAGCACCGACGGACCTGGGACTTCCGACGGCGAACTCCATGG
  L  D  A  K  F  V  A  A  W  T  L  K  A  A  A  *>
```

FIG.11

| | |
|---|---:|
| TTCCCAG ATG CAC AGG AGG AGA AGC AGG AGC TGT CGG GAA GAT CAG AAG<br>         Met His Arg Arg Arg Ser Arg Ser Cys Arg Glu Asp Gln Lys<br>          1               5                      10 | 49 |
| CCA GTC ATG GAT GAC CAG CGC GAC CTT ATC TCC AAC AAT GAG CAA CTG<br>Pro Val Met Asp Asp Gln Arg Asp Leu Ile Ser Asn Asn Glu Gln Leu<br> 15                 20                25               30 | 97 |
| CCC ATG CTG GGC CGG CGC CCT GGG GCC CCG GAG AGC AAG TGC AGC CGC<br>Pro Met Leu Gly Arg Arg Pro Gly Ala Pro Glu Ser Lys Cys Ser Arg<br>               35                   40               45 | 145 |
| GGA GCC CTG TAC ACA GGC TTT TCC ATC CTG GTG ACT CTG CTC CTC GCT<br>Gly Ala Leu Tyr Thr Gly Phe Ser Ile Leu Val Thr Leu Leu Leu Ala<br>         50                   55                   60 | 193 |
| GGC CAG GCC ACC ACC GCC TAC TTC CTG TAC CAG CAG CAG GGC CGG CTG<br>Gly Gln Ala Thr Thr Ala Tyr Phe Leu Tyr Gln Gln Gln Gly Arg Leu<br>       65                   70                  75 | 241 |
| GAC AAA CTG ACA GTC ACC TCC CAG AAC CTG CAG CTG GAG AAC CTG CGC<br>Asp Lys Leu Thr Val Thr Ser Gln Asn Leu Gln Leu Glu Asn Leu Arg<br>  80                  85                  90 | 289 |
| ATG AAG CTT CCC AAG CCT CCC AAG CCT GTG AGC AAG ATG CGC ATG GCC<br>Met Lys Leu Pro Lys Pro Pro Lys Pro Val Ser Lys Met Arg Met Ala<br> 95                100              105            110 | 337 |
| ACC CCG CTG CTG ATG CAG GCG CTG CCC ATG GGA GCC CTG CCC CAG GGG<br>Thr Pro Leu Leu Met Gln Ala Leu Pro Met Gly Ala Leu Pro Gln Gly<br>               115               120             125 | 385 |
| CCC ATG CAG AAT GCC ACC AAG TAT GGC AAC ATG ACA GAG GAC CAT GTG<br>Pro Met Gln Asn Ala Thr Lys Tyr Gly Asn Met Thr Glu Asp His Val<br>         130                135             140 | 433 |
| ATG CAC CTG CTC CAG AAT GCT GAC CCC CTG AAG GTG TAC CCG CCA CTG<br>Met His Leu Leu Gln Asn Ala Asp Pro Leu Lys Val Tyr Pro Pro Leu<br>       145                150             155 | 481 |
| AAG GGG AGC TTC CCG GAG AAC CTG AGA CAC CTT AAG AAC ACC ATG GAG<br>Lys Gly Ser Phe Pro Glu Asn Leu Arg His Leu Lys Asn Thr Met Glu<br>      160               165              170 | 529 |
| ACC ATA GAC TGG AAG GTC TTT GAG AGC TGG ATG CAC CAT TGG CTC CTG<br>Thr Ile Asp Trp Lys Val Phe Glu Ser Trp Met His His Trp Leu Leu<br>175                 180               185            190 | 577 |

FIG.12A

```
TTT GAA ATG AGC AGG CAC TCC TTG GAG CAA AAG CCC ACT GAC GCT CCA              625
Phe Glu Met Ser Arg His Ser Leu Glu Gln Lys Pro Thr Asp Ala Pro
                195                 200                 205

CCG AAA GAG TCA CTG GAA CTG GAG GAC CCG TCT TCT GGG CTG GGT GTG              673
Pro Lys Glu Ser Leu Glu Leu Glu Asp Pro Ser Ser Gly Leu Gly Val
                210                 215                 220

ACC AAG CAG GAT CTG GGC CCA GTC CCC ATG TGAGAGCAGC AGAGGCGGTC                723
Thr Lys Gln Asp Leu Gly Pro Val Pro Met
                225                 230
```

FIG.12B

```
CCGCCTCGGC ATG GCG CCC CGC AGC GCC CGG CGA CCC CTG CTG CTG CTA      229
           Met Ala Pro Arg Ser Ala Arg Arg Pro Leu Leu Leu Leu
            1               5                  10

CTG CCT GTT GCT GCT GCT CGG CCT CAT GCA TTG TCG TCA GCA GCC ATG      277
Leu Pro Val Ala Ala Ala Arg Pro His Ala Leu Ser Ser Ala Ala Met
        15              20                  25

TTT ATG GTG AAA AAT GGC AAC GGG ACC GCG TGC ATA ATG GCC AAC TTC      325
Phe Met Val Lys Asn Gly Asn Gly Thr Ala Cys Ile Met Ala Asn Phe
 30              35                  40                  45

TCT GCT GCC TTC TCA GTG AAC TAC GAC ACC AAG AGT GGC CCC AAG AAC      373
Ser Ala Ala Phe Ser Val Asn Tyr Asp Thr Lys Ser Gly Pro Lys Asn
            50                  55                  60

ATG ACC TTT GAC CTG CCA TCA GAT GCC ACA GTG GTG CTC AAC CGC AGC      421
Met Thr Phe Asp Leu Pro Ser Asp Ala Thr Val Val Leu Asn Arg Ser
             65                  70                  75

TCC TGT GGA AAA GAG AAC ACT TCT GAC CCC AGT CTC GTG ATT GCT TTT      469
Ser Cys Gly Lys Glu Asn Thr Ser Asp Pro Ser Leu Val Ile Ala Phe
         80                  85                  90

GGA AGA GGA CAT ACA CTC ACT CTC AAT TTC ACG AGA AAT GCA ACA CGT      517
Gly Arg Gly His Thr Leu Thr Leu Asn Phe Thr Arg Asn Ala Thr Arg
         95              100                 105

TAC AGC GTT CAG CTC ATG AGT TTT GTT TAT AAC TTG TCA GAC ACA CAC      565
Tyr Ser Val Gln Leu Met Ser Phe Val Tyr Asn Leu Ser Asp Thr His
110                 115                 120                 125

CTT TTC CCC AAT GCG AGC TCC AAA GAA ATC AAG ACT GTG GAA TCT ATA      613
Leu Phe Pro Asn Ala Ser Ser Lys Glu Ile Lys Thr Val Glu Ser Ile
                130                 135                 140

ACT GAC ATC AGG GCA GAT ATA GAT AAA AAA TAC AGA TGT GTT AGT GGC      661
Thr Asp Ile Arg Ala Asp Ile Asp Lys Lys Tyr Arg Cys Val Ser Gly
            145                 150                 155

ACC CAG GTC CAC ATG AAC AAC GTG ACC GTA ACG CTC CAT GAT GCC ACC      709
Thr Gln Val His Met Asn Asn Val Thr Val Thr Leu His Asp Ala Thr
        160                 165                 170

ATC CAG GCG TAC CTT TCC AAC AGC AGC TTC AGC AGG GGA GAG ACA CGC      757
Ile Gln Ala Tyr Leu Ser Asn Ser Ser Phe Ser Arg Gly Glu Thr Arg
175                 180                 185
```

FIG.13A

```
TGT GAA CAA GAC AGG CCT TCC CCA ACC ACA GCG CCC CCT GCG CCA CCC        805
Cys Glu Gln Asp Arg Pro Ser Pro Thr Thr Ala Pro Pro Ala Pro Pro
190             195             200             205

AGC CCC TCG CCC TCA CCC GTG CCC AAG AGC CCC TCT GTG GAC AAG TAC        853
Ser Pro Ser Pro Ser Pro Val Pro Lys Ser Pro Ser Val Asp Lys Tyr
                210             215             220

AAC GTG AGC GGC ACC AAC GGG ACC TGC CTG CTG GCC AGC ATG GGG CTG        901
Asn Val Ser Gly Thr Asn Gly Thr Cys Leu Leu Ala Ser Met Gly Leu
            225             230             235

CAG CTG AAC CTC ACC TAT GAG AGG AAG GAC AAC ACG ACG GTG ACA AGG        949
Gln Leu Asn Leu Thr Tyr Glu Arg Lys Asp Asn Thr Thr Val Thr Arg
        240             245             250

CTT CTC AAC ATC AAC CCC AAC AAG ACC TCG GCC AGC GGG AGC TGC GGC        997
Leu Leu Asn Ile Asn Pro Asn Lys Thr Ser Ala Ser Gly Ser Cys Gly
    255             260             265

GCC CAC CTG GTG ACT CTG GAG CTG CAC AGC GAG GGC ACC ACC GTC CTG       1045
Ala His Leu Val Thr Leu Glu Leu His Ser Glu Gly Thr Thr Val Leu
270             275             280             285

CTC TTC CAG TTC GGG ATG AAT GCA AGT TCT AGC CGG TTT TTC CTA CAA       1093
Leu Phe Gln Phe Gly Met Asn Ala Ser Ser Ser Arg Phe Phe Leu Gln
                290             295             300

GGA ATC CAG TTG AAT ACA ATT CTT CCT GAC GCC AGA GAC CCT GCC TTT       1141
Gly Ile Gln Leu Asn Thr Ile Leu Pro Asp Ala Arg Asp Pro Ala Phe
            305             310             315

AAA GCT GCC AAC GGC TCC CTG CGA GCG CTG CAG GCC ACA GTC GGC AAT       1189
Lys Ala Ala Asn Gly Ser Leu Arg Ala Leu Gln Ala Thr Val Gly Asn
        320             325             330

TCC TAC AAG TGC AAC GCG GAG GAG CAC GTC CGT GTC ACG AAG GCG TTT       1237
Ser Tyr Lys Cys Asn Ala Glu Glu His Val Arg Val Thr Lys Ala Phe
    335             340             345

TCA GTC AAT ATA TTC AAA GTG TGG GTC CAG GCT TTC AAG GTG GAA GGT       1285
Ser Val Asn Ile Phe Lys Val Trp Val Gln Ala Phe Lys Val Glu Gly
350             355             360             365

GGC CAG TTT GGC TCT GTG GAG GAG TGT CTG CTG GAC GAG AAC AGC ACG       1333
Gly Gln Phe Gly Ser Val Glu Glu Cys Leu Leu Asp Glu Asn Ser Thr
                370             375             360
```

FIG.13B

```
CTG ATC CCC ATC GCT GTG GGT GGT GGC CTG GCG GGG CTG GTC CTC ATC          1381
Leu Ile Pro Ile Ala Val Gly Gly Gly Leu Ala Gly Leu Val Leu Ile
            385                 390                 395

GTC CTC ATC GCC TAC CTC GTC GGC AGG AAG AGG AGT CAC GCA GGC TAC          1429
Val Leu Ile Ala Tyr Leu Val Gly Arg Lys Arg Ser His Ala Gly Tyr
            400                 405                 410

CAG ACT ATC TAGCCTGGTG CACGCAGGCA CAGCAGCTGC AGGGGCCTCT                  1478
Gln Thr Ile
    415
```

FIG.13C

```
          10        20        30        40        50        60        70
     *    *    *    *    *    *    *    *    *    *    *    *    *    *
ATGATCACATTCCTGCCGCTGCTGCTGGGGCTCAGCCTGGGCTGCACAGGAGCAGGTGGCTTCGTGGCCC
TACTAGTGTAAGGACGGCGACGACGACCCCGAGTCGGACCCGACGTGTCCTCGTCCACCGAAGCACCGGG
  M  I  T  F  L  P  L  L  G  L  S  L  G  C  T  G  A  G  G  F  V  A>

80        90       100       110       120       130       140
     *    *    *    *    *    *    *    *    *    *    *    *    *    *
ATGTGGAAAGCACCTGTCTGTTGGATGATGCTGGGACTCCAAAGGATTTCACATACTGCATCTCCTTCAA
TACACCTTTCGTGGACAGACAACCTACTACGACCCTGAGGTTTCCTAAAGTGTATGACGTAGAGGAAGTT
  H  V  E  S  T  C  L  L  D  D  A  G  T  P  K  D  F  T  Y  C  I  S  F  N>

150       160       170       180       190       200       210
     *    *    *    *    *    *    *    *    *    *    *    *    *    *
CAAGGATCTGCTGACCTGCTGGGATCCAGAGGAGAATAAGATGGCCCCTTGCGAATTTGGGGTGCTGAAT
GTTCCTAGACGACTGGACGACCCTAGGTCTCCTCTTATTCTACCGGGGAACGCTTAAACCCCACGACTTA
   K  D  L  L  T  C  W  D  P  E  E  N  K  M  A  P  C  E  F  G  V  L  N>

220       230       240       250       260       270       280
     *    *    *    *    *    *    *    *    *    *    *    *    *    *
AGCTTGGCGAATGTCCTCTCACAGCACCTCAACCAAAAAGACACCCTGATGCAGCGCTTGCGCAATGGGC
TCGAACCGCTTACAGGAGAGTGTCGTGGAGTTGGTTTTTCTGTGGGACTACGTCGCGAACGCGTTACCCG
  S  L  A  N  V  L  S  Q  H  L  N  Q  K  D  T  L  M  Q  R  L  R  N  G>

290       300       310       320       330       340       350
     *    *    *    *    *    *    *    *    *    *    *    *    *    *
TTCAGAATTGTGCCACACACACCCAGCCCTTCTGGGGATCACTGACCAACAGGACACGGCCACCATCTGT
AAGTCTTAACACGGTGTGTGTGGGTCGGGAAGACCCCTAGTGACTGGTTGTCCTGTGCCGGTGGTAGACA
  L  Q  N  C  A  T  H  T  Q  P  F  W  G  S  L  T  N  R  T  R  P  P  S  V>

360       370       380       390       400       410       420
     *    *    *    *    *    *    *    *    *    *    *    *    *    *
GCAAGTAGCCAAAACCACTCCTTTTAACACGAGGGAGCCTGTGATGCTGGCCTGCTATGTGTGGGGCTTC
CGTTCATCGGTTTTGGTGAGGAAAATTGTGCTCCCTCGGACACTACGACCGGACGATACACACCCCGAAG
  Q  V  A  K  T  T  P  F  N  T  R  E  P  V  M  L  A  C  Y  V  W  G  F>

430       440       450       460       470       480       490
     *    *    *    *    *    *    *    *    *    *    *    *    *    *
TATCCAGCAGAAGTGACTATCACGTGGAGGAAGAACGGGAAGCTTGTCATGCCTCACAGCAGTGCGCACA
ATAGGTCGTCTTCACTGATAGTGCACCTCCTTCTTGCCCTTCGAACAGTACGGAGTGTCGTCACGCGTGT
  Y  P  A  E  V  T  I  T  W  R  K  N  G  K  L  V  M  P  H  S  S  A  H>

500       510       520       530       540       550       560
     *    *    *    *    *    *    *    *    *    *    *    *    *    *
AGACTGCCCAGCCCAATGGAGACTGGACATACCAGACCCTCTCCCATTTAGCCTTAACCCCCTCTTACGG
TCTGACGGGTCGGGTTACCTCTGACCTGTATGGTCTGGGAGAGGGTAAATCGGAATTGGGGGAGAATGCC
  K  T  A  Q  P  N  G  D  W  T  Y  Q  T  L  S  H  L  A  L  T  P  S  Y  G>
```

FIG.14A

```
        570       580       590       600       610       620       630
    *    *    *    *    *    *    *    *    *    *    *    *    *    *
GGACACTTACACCTGTGTGGTAGAGCACATTGGGGCTCCTGAGCCCATCCTTCGGGACTGGACACCTGGG
CCTGTGAATGTGGACACACCATCTCGTGTAACCCCGAGGACTCGGGTAGGAAGCCCTGACCTGTGGACCC
     D  T  Y  T  C  V  V  E  H  I  G  A  P  E  P  I  L  R  D  W  T  P  G>

640       650       660       670       680       690       700
    *    *    *    *    *    *    *    *    *    *    *    *    *    *
CTGTCCCCCATGCAGACCCTGAAGGTTTCTGTGTCTGCAGTGACTCTGGGCCTGGGCCTCATCATCTTCT
GACAGGGGGTACGTCTGGGACTTCCAAAGACACAGACGTCACTGAGACCCGGACCCGGAGTAGTAGAAGA
     L  S  P  M  Q  T  L  K  V  S  V  S  A  V  T  L  G  L  G  L  I  I  F>

710       720       730       740       750       760       770
    *    *    *    *    *    *    *    *    *    *    *    *    *    *
CTCTTGGTGTGATCAGCTGGCGGAGAGCTGGCCACTCTAGTTACACTCCTCTTCCTGGGTCCAATTATTC
GAGAACCACACTAGTCGACCGCCTCTCGACCGGTGAGATCAATGTGAGGAGAAGGACCCAGGTTAATAAG
     S  L  G  V  I  S  W  R  R  A  G  H  S  S  Y  T  P  L  P  G  S  N  Y  S>

780       790
    *    *    *    *
AGAAGGATGGCACATTTCCTAG
TCTTCCTACCGTGTAAAGGATC
     E  G  W  H  I  S  *>
```

FIG.14B

```
            10        20        30        40        50        60        70
    *     *     *     *     *     *     *     *     *     *     *     *     *     *
ATGGGTTCTGGGTGGGTCCCCTGGGTGGTGGCTCTGCTAGTGAATCTGACCCAACTGGATTCCTCCATGA
TACCCAAGACCCACCCAGGGGACCCACCACCGAGACGATCACTTAGACTGGGTTGACCTAAGGAGGTACT
 M   G   S   G   W   V   P   W   V   V   A   L   L   V   N   L   T   Q   L   D   S   S   M>

80        90        100       110       120       130       140
    *     *     *     *     *     *     *     *     *     *     *     *     *     *
CTCAAGGCACAGACTCTCCAGAAGATTTTGTGATTCAGGCAAAGGCTGACTGTTACTTCACCAACGGGAC
GAGTTCCGTGTCTGAGAGGTCTTCTAAAACACTAAGTCCGTTTCCGACTGACAATGAAGTGGTTGCCCTG
 T   Q   G   T   D   S   P   E   D   F   V   I   Q   A   K   A   D   C   Y   F   T   N   G   T>

150       160       170       180       190       200       210
    *     *     *     *     *     *     *     *     *     *     *     *     *     *
AGAAAAGGTGCAGTTTGTGGTCAGATTCATCTTTAACTTGGAGGAGTATGTACGTTTCGACAGTGATGTG
TCTTTTCCACGTCAAACACCAGTCTAAGTAGAAATTGAACCTCCTCATACATGCAAAGCTGTCACTACAC
 E   K   V   Q   F   V   V   R   F   I   F   N   L   E   E   Y   V   R   F   D   S   D   V>

220       230       240       250       260       270       280
    *     *     *     *     *     *     *     *     *     *     *     *     *     *
GGGATGTTTGTGGCATTGACCAAGCTGGGGCAGCCAGATGCTGAGCAGTGGAACAGCCGGCTGGATCTCT
CCCTACAAACACCGTAACTGGTTCGACCCCGTCGGTCTACGACTCGTCACCTTGTCGGCCGACCTAGAGA
 G   M   F   V   A   L   T   K   L   G   Q   P   D   A   E   Q   W   N   S   R   L   D   L>

290       300       310       320       330       340       350
    *     *     *     *     *     *     *     *     *     *     *     *     *     *
TGGAGAGGAGCAGACAGGCCGTGGATGGGGTCTGTAGACACAACTACAGGCTGGGCGCACCCTTCACTGT
ACCTCTCCTCGTCTGTCCGGCACCTACCCCAGACATCTGTGTTGATGTCCGACCCGCGTGGGAAGTGACA
 L   E   R   S   R   Q   A   V   D   G   V   C   R   H   N   Y   R   L   G   A   P   F   T   V>

360       370       380       390       400       410       420
    *     *     *     *     *     *     *     *     *     *     *     *     *     *
GGGGAGAAAAGTGCAACCAGAGGTGACAGTGTACCCAGAGAGGACCCCACTCCTGCACCAGCATAATCTG
CCCCTCTTTTCACGTTGGTCTCCACTGTCACATGGGTCTCTCCTGGGGTGAGGACGTGGTCGTATTAGAC
 G   R   K   V   Q   P   E   V   T   V   Y   P   E   R   T   P   L   L   H   Q   H   N   L>

430       440       450       460       470       480       490
    *     *     *     *     *     *     *     *     *     *     *     *     *     *
CTGCACTGCTCTGTGACAGGCTTCTATCCAGGGGATATCAAGATCAAGTGGTTCCTGAATGGGCAGGAGG
GACGTGACGAGACACTGTCCGAAGATAGGTCCCCTATAGTTCTAGTTCACCAAGGACTTACCCGTCCTCC
 L   H   C   S   V   T   G   F   Y   P   G   D   I   K   I   K   W   F   L   N   G   Q   E>

```
AGAGAGCTGGGGTCATGTCCACTGGCCCTATCAGGAATGGAGACTGGACCTTTCAGACTGTGGTGATGCT
TCTCTCGACCCCAGTACAGGTGACCGGGATAGTCCTTACCTCTGACCTGGAAAGTCTGACACCACTACGA
  E   R   A   G   V   M   S   T   G   P   I   R   N   G   D   W   T   F   Q   T   V   V   M   L>

570       580       590       600       610       620       630
         *    *    *    *    *    *    *    *    *    *    *    *    *    *
AGAAATGACTCCTGAACTTGGACATGTCTACACCTGCCTTGTCGATCACTCCAGCCTGCTGAGCCCTGTT
TCTTTACTGAGGACTTGAACCTGTACAGATGTGGACGGAACAGCTAGTGAGGTCGGACGACTCGGGACAA
   E   M   T   P   E   L   G   H   V   Y   T   C   L   V   D   H   S   S   L   L   S   P   V>

640       650       660       670       680       690       700
         *    *    *    *    *    *    *    *    *    *    *    *    *    *
TCTGTGGAGTGGAGAGCTCAGTCTGAATATTCTTGGAGAAAGATGCTGAGTGGCATTGCAGCCTTCCTAC
AGACACCTCACCTCTCGAGTCAGACTTATAAGAACCTCTTTCTACGACTCACCGTAACGTCGGAAGGATG
   S   V   E   W   R   A   Q   S   E   Y   S   W   R   K   M   L   S   G   I   A   A   F   L>

710       720       730       740       750       760       770
         *    *    *    *    *    *    *    *    *    *    *    *    *    *
TTGGGCTAATCTTCCTTCTGGTGGGAATCGTCATCCAGCTAAGGGCTCAGAAAGGATATGTGAGGACGCA
AACCCGATTAGAAGGAAGACCACCCTTAGCAGTAGGTCGATTCCCGAGTCTTTCCTATACACTCCTGCGT
   L   G   L   I   F   L   L   V   G   I   V   I   Q   L   R   A   Q   K   G   Y   V   R   T   Q>

780       790       800       810       820
         *    *    *    *    *    *    *    *    *    *
GATGTCTGGTAATGAGGTCTCAAGAGCTGTTCTGCTCCCTCAGTCATGCTAA
CTACAGACCATTACTCCAGAGTTCTCGACAAGACGAGGGAGTCAGTACGATT
    M   S   G   N   E   V   S   R   A   V   L   L   P   Q   S   C   *>
```

FIG. 15B

```
         10        20        30        40        50        60        70
    *    *    *    *    *    *    *    *    *    *    *    *    *    *
ATGCCTGGGGGTCCAGGAGTCCTCCAAGCTCTGCCTGCCACCATCTTCCTCCTCTTCCTGCTGTCTGCTG
TACGGACCCCCAGGTCCTCAGGAGGTTCGAGACGGACGGTGGTAGAAGGAGGAGAAGGACGACAGACGAC
  M  P  G  G  P  G  V  L  Q  A  L  P  A  T  I  F  L  L  F  L  L  S  A>

80        90       100       110       120       130       140
    *    *    *    *    *    *    *    *    *    *    *    *    *    *
TCTACCTGGGCCCTGGGTGCCAGGCCCTGTGGATGCACAAGGTCCCAGCATCATTGATGGTGAGCCTGGG
AGATGGACCCGGGACCCACGGTCCGGGACACCTACGTGTTCCAGGGTCGTAGTAACTACCACTCGGACCC
  V  Y  L  G  P  G  C  Q  A  L  W  M  H  K  V  P  A  S  L  M  V  S  L  G>

150       160       170       180       190       200       210
    *    *    *    *    *    *    *    *    *    *    *    *    *    *
GGAAGACGCCCACTTCCAATGCCCGCACAATAGCAGCAACAACGCCAACGTCACCTGGTGGCGCGTCCTC
CCTTCTGCGGGTGAAGGTTACGGGCGTGTTATCGTCGTTGTTGCGGTTGCAGTGGACCACCGCGCAGGAG
   E  D  A  H  F  Q  C  P  H  N  S  S  N  N  A  N  V  T  W  W  R  V  L>

220       230       240       250       260       270       280
    *    *    *    *    *    *    *    *    *    *    *    *    *    *
CATGGCAACTACACGTGGCCCCCTGAGTTCTTGGGCCCGGGCGAGGACCCCAATGGTACGCTGATCATCC
GTACCGTTGATGTGCACCGGGGGACTCAAGAACCCGGGCCCGCTCCTGGGGTTACCATGCGACTAGTAGG
  H  G  N  Y  T  W  P  P  E  F  L  G  P  G  E  D  P  N  G  T  L  I  I>

290       300       310       320       330       340       350
    *    *    *    *    *    *    *    *    *    *    *    *    *    *
AGAATGTGAACAAGAGCCATGGGGGCATATACGTGTGCCGGGTCCAGGAGGGCAACGAGTCATACCAGCA
TCTTACACTTGTTCTCGGTACCCCCGTATATGCACACGGCCCAGGTCCTCCCGTTGCTCAGTATGGTCGT
  Q  N  V  N  K  S  H  G  G  I  Y  V  C  R  V  Q  E  G  N  E  S  Y  Q  Q>

360       370       380       390       400       410       420
    *    *    *    *    *    *    *    *    *    *    *    *    *    *
GTCCTGCGGCACCTACCTCCGCGTGCGCCAGCCGCCCCCCAGGCCCTTCCTGGACATGGGGGAGGGCACC
CAGGACGCCGTGGATGGAGGCGCACGCGGTCGGCGGGGGGTCCGGGAAGGACCTGTACCCCCTCCCGTGG
    S  C  G  T  Y  L  R  V  R  Q  P  P  P  R  P  F  L  D  M  G  E  G  T>

430       440       450       460       470       480       490
    *    *    *    *    *    *    *    *    *    *    *    *    *    *
AAGAACCGAATCATCACAGCCGAGGGGATCATCCTCCTGTTCTGCGCGGTGGTGCCTGGGACGCTGCTGC
TTCTTGGCTTAGTAGTGTCGGCTCCCCTAGTAGGAGGACAAGACGCGCCACCACGGACCCTGCGACGACG
   K  N  R  I  I  T  A  E  G  I  I  L  L  F  C  A  V  V  P  G  T  L  L>
```

FIG.16A

```
            500       510       520       530       540       550       560
         *    *    *    *    *    *    *    *    *    *    *    *    *    *
         TGTTCAGGAAACGATGGCAGAACGAGAAGCTCGGGTTGGATGCCGGGGATGAATATGAAGATGAAAACCT
         ACAAGTCCTTTGCTACCGTCTTGCTCTTCGAGCCCAACCTACGGCCCCTACTTATACTTCTACTTTTGGA
          L  F  R  K  R  W  Q  N  E  K  L  G  L  D  A  G  D  E  Y  E  D  E  N  L>

570       580       590       600       610       620       630
         *    *    *    *    *    *    *    *    *    *    *    *    *    *
         TTATGAAGGCCTGAACCTGGACGACTGCTCCATGTATGAGGACATCTCCCGGGGCCTCCAGGGCACCTAC
         AATACTTCCGGACTTGGACCTGCTGACGAGGTACATACTCCTGTAGAGGGCCCCGGAGGTCCCGTGGATG
           Y  E  G  L  N  L  D  D  C  S  M  Y  E  D  I  S  R  G  L  Q  G  T  Y>

640       650       660       670       680       690       700
         *    *    *    *    *    *    *    *    *    *    *    *    *    *
         CAGGATGTGGGCAGCCTCAACATAGGAGATGTCCAGCTGGAGAAGCCGTGACACCCCTACTCCTGCCAGG
         GTCCTACACCCGTCGGAGTTGTATCCTCTACAGGTCGACCTCTTCGGCACTGTGGGGATGAGGACGGTCC
          Q  D  V  G  S  L  N  I  G  D  V  Q  L  E  K  P  *>
```

FIG.16B

```
GAATTCCGCG GTGACC ATG GCC AGG CTG GCG TTG TCT CCT GTG CCC AGC           49
              Met Ala Arg Leu Ala Leu Ser Pro Val Pro Ser
               1               5                  10

CAC TGG ATG GTG GCG TTG CTG CTG CTC TCA GCT GAG CCA GTA CCA             97
His Trp Met Val Ala Leu Leu Leu Leu Ser Ala Glu Pro Val Pro
             15                  20                  25

GCA GCC AGA TCG GAG GAC CGG TAC CGG AAT CCC AAA GGT AGT GCT TGT        145
Ala Ala Arg Ser Glu Asp Arg Tyr Arg Asn Pro Lys Gly Ser Ala Cys
             30                  35                  40

TCG CGG ATC TGG CAG AGC CCA CGT TTC ATA GCC AGG AAA CGG CGC TTC        193
Ser Arg Ile Trp Gln Ser Pro Arg Phe Ile Ala Arg Lys Arg Arg Phe
             45                  50                  55

ACG GTG AAA ATG CAC TGC TAC ATG AAC AGC GCC TCC GGC AAT GTG AGC        241
Thr Val Lys Met His Cys Tyr Met Asn Ser Ala Ser Gly Asn Val Ser
 60              65                  70                  75

TGG CTC TGG AAG CAG GAG ATG GAC GAG AAT CCC CAG CAG CTG AAG CTG        289
Trp Leu Trp Lys Gln Glu Met Asp Glu Asn Pro Gln Gln Leu Lys Leu
                 80                  85                  90

GAA AAG GGC CGC ATG GAA GAG TCC CAG AAC GAA TCT CTC GCC ACC CTC        337
Glu Lys Gly Arg Met Glu Glu Ser Gln Asn Glu Ser Leu Ala Thr Leu
                 95                 100                 105

ACC ATC CAA GGC ATC CGG TTT GAG GAC AAT GGC ATC TAC TTC TGC CAG        385
Thr Ile Gln Gly Ile Arg Phe Glu Asp Asn Gly Ile Tyr Phe Cys Gln
            110                 115                 120

CAG AAG TGC AAC AAC ACC TCG GAG GTC TAC CAG GGC TGC GGC ACA GAG        433
Gln Lys Cys Asn Asn Thr Ser Glu Val Tyr Gln Gly Cys Gly Thr Glu
            125                 130                 135

CTG CGA GTC ATG GGA TTC AGC ACC TTG GCA CAG CTG AAG CAG AGG AAC        481
Leu Arg Val Met Gly Phe Ser Thr Leu Ala Gln Leu Lys Gln Arg Asn
140                 145                 150                 155

ACG CTG AAG GAT GGT ATC ATC ATG ATC CAG ACG CTG CTG ATC ATC CTC        529
Thr Leu Lys Asp Gly Ile Ile Met Ile Gln Thr Leu Leu Ile Ile Leu
                160                 165                 170
```

FIG.17A

```
TTC ATC ATC GTG CCT ATC TTC CTG CTG CTG GAC AAG GAT GAC AGC AAG      577
Phe Ile Ile Val Pro Ile Phe Leu Leu Leu Asp Lys Asp Asp Ser Lys
            175                 180                 185

GCT GGC ATG GAG GAA GAT CAC ACC TAC GAG GGC CTG GAC ATT GAC CAG      625
Ala Gly Met Glu Glu Asp His Thr Tyr Glu Gly Leu Asp Ile Asp Gln
            190                 195                 200

ACA GCC ACC TAT GAG GAC ATA GTG ACG CTG CGG ACA GGG GAA GTG AAG      673
Thr Ala Thr Tyr Glu Asp Ile Val Thr Leu Arg Thr Gly Glu Val Lys
            205                 210                 215

TGG TCT GTA GGT GAG CAC CCA GGC CAG GAG TGAGAGCCAG GTCGCCCCAT        723
Trp Ser Val Gly Glu His Pro Gly Gln Glu
220                 225                 230
```

FIG.17B

```
          10        20        30        40        50        60        70
     *    *    *    *    *    *    *    *    *    *    *    *    *    *
GACGGATCGGGAGATCTCCCGATCCCTATGGTCGACTCTCAGTACAATCTGCTCTGATGCCGCATAGTT
CTGCCTAGCCCTCTAGAGGGCTAGGGGATACCAGCTGAGAGTCATGTTAGACGAGACTACGGCGTATCAA 80        90       100       110       120       130       140
     *    *    *    *    *    *    *    *    *    *    *    *    *    *
AAGCCAGTATCTGCTCCCTGCTTGTGTGTTGGAGGTCGCTGAGTAGTGCGCGAGCAAAATTTAAGCTACA
TTCGGTCATAGACGAGGGACGAACACACAACCTCCAGCGACTCATCACGCGCTCGTTTTAAATTCGATGT 150       160       170       180       190       200       210
     *    *    *    *    *    *    *    *    *    *    *    *    *    *
ACAAGGCAAGGCTTGACCGACAATTGCATGAAGAATCTGCTTAGGGTTAGGCGTTTTGCGCTGCTTCGCG
TGTTCCGTTCCGAACTGGCTGTTAACGTACTTCTTAGACGAATCCCAATCCGCAAAACGCGACGAAGCGC 220       230       240       250       260       270       280
     *    *    *    *    *    *    *    *    *    *    *    *    *    *
ATGTACGGGCCAGATATACGCGTTGACATTGATTATTGACTAGTTATTAATAGTAATCAATTACGGGGTC
TACATGCCCGGTCTATATGCGCAACTGTAACTAATAACTGATCAATAATTATCATTAGTTAATGCCCCAG 290       300       310       320       330       340       350
     *    *    *    *    *    *    *    *    *    *    *    *    *    *
ATTAGTTCATAGCCCATATATGGAGTTCCGCGTTACATAACTTACGGTAAATGGCCCGCCTGGCTGACCG
TAATCAAGTATCGGGTATATACCTCAAGGCGCAATGTATTGAATGCCATTTACCGGGCGGACCGACTGGC 360       370       380       390       400       410       420
     *    *    *    *    *    *    *    *    *    *    *    *    *    *
CCCAACGACCCCCGCCCATTGACGTCAATAATGACGTATGTTCCCATAGTAACGCCAATAGGGACTTTCC
GGGTTGCTGGGGGCGGGTAACTGCAGTTATTACTGCATACAAGGGTATCATTGCGGTTATCCCTGAAAGG 430       440       450       460       470       480       490
     *    *    *    *    *    *    *    *    *    *    *    *    *    *
ATTGACGTCAATGGGTGGACTATTTACGGTAAACTGCCCACTTGGCAGTACATCAAGTGTATCATATGCC
TAACTGCAGTTACCCACCTGATAAATGCCATTTGACGGGTGAACCGTCATGTAGTTCACATAGTATACGG 500       510       520       530       540       550       560
     *    *    *    *    *    *    *    *    *    *    *    *    *    *
AAGTACGCCCCCTATTGACGTCAATGACGGTAAATGGCCCGCCTGGCATTATGCCCAGTACATGACCTTA
TTCATGCGGGGGATAACTGCAGTTACTGCCATTTACCGGGCGGACCGTAATACGGGTCATGTACTGGAAT 570       580       590       600       610       620       630
     *    *    *    *    *    *    *    *    *    *    *    *    *    *
TGGGACTTTCCTACTTGGCAGTACATCTACGTATTAGTCATCGCTATTACCATGGTGATGCGGTTTTGGC
ACCCTGAAAGGATGAACCGTCATGTAGATGCATAATCAGTAGCGATAATGGTACCACTACGCCAAAACCG 640       650       660       670       680       690       700
     *    *    *    *    *    *    *    *    *    *    *    *    *    *
AGTACATCAATGGGCGTGGATAGCGGTTTGACTCACGGGGATTTCCAAGTCTCCACCCCATTGACGTCAA
TCATGTAGTTACCCGCACCTATCGCCAAACTGAGTGCCCCTAAAGGTTCAGAGGTGGGGTAACTGCAGTT
```

FIG. 19A

```
          710       720       730       740       750       760       770
       *    *    *    *    *    *    *    *    *    *    *    *    *    *
     TGGGAGTTTGTTTTGGCACCAAAATCAACGGGACTTTCCAAAATGTCGTAACAACTCCGCCCCATTGACG
     ACCCTCAAACAAAACCGTGGTTTTAGTTGCCCTGAAAGGTTTTACAGCATTGTTGAGGCGGGGTAACTGC 780       790       800       810       820       830       840
       *    *    *    *    *    *    *    *    *    *    *    *    *    *
     CAAATGGGCGGTAGGCGTGTACGGTGGGAGGTCTATATAAGCAGAGCTCTCTGGCTAACTAGAGAACCCA
     GTTTACCCGCCATCCGCACATGCCACCCTCCAGATATATTCGTCTCGAGAGACCGATTGATCTCTTGGGT 850       860       870       880       890       900       910
       *    *    *    *    *    *    *    *    *    *    *    *    *    *
     CTGCTTACTGGCTTATCGAAATTAATACGACTCACTATAGGGAGACCCAAGCTGGCTAGAGTAAGTACCG
     GACGAATGACCGAATAGCTTTAATTATGCTGAGTGATATCCCTCTGGGTTCGACCGATCTCATTCATGGC 920       930       940       950       960       970       980
       *    *    *    *    *    *    *    *    *    *    *    *    *    *
     CCTATAGAGTCTATAGGCCCACCCCCTTGGCTTCTTATGCATGCTATACTGTTTTTGGCTTGGGGTCTAT
     GGATATCTCAGATATCCGGGTGGGGGAACCGAAGAATACGTACGATATGACAAAAACCGAACCCCAGATA 990      1000      1010      1020      1030      1040      1050
       *    *    *    *    *    *    *    *    *    *    *    *    *    *
     ACACCCCCGCTTCCTCATGTTATAGGTGATGGTATAGCTTAGCCTATAGGTGTGGGTTATTGACCATTAT
     TGTGGGGGCGAAGGAGTACAATATCCACTACCATATCGAATCGGATATCCACACCCAATAACTGGTAATA 1060      1070      1080      1090      1100      1110      1120
       *    *    *    *    *    *    *    *    *    *    *    *    *    *
     TGACCACTCCCCTATTGGTGACGATACTTTCCATTACTAATCCATAACATGGCTCTTTGCCACAACTCTC
     ACTGGTGAGGGGATAACCACTGCTATGAAAGGTAATGATTAGGTATTGTACCGAGAAACGGTGTTGAGAG 1130      1140      1150      1160      1170      1180      1190
       *    *    *    *    *    *    *    *    *    *    *    *    *    *
     TTTATTGGCTATATGCCAATACACTGTCCTTCAGAGACTGACACGGACTCTGTATTTTTACAGGATGGGG
     AAATAACCGATATACGGTTATGTGACAGGAAGTCTCTGACTGTGCCTGAGACATAAAAATGTCCTACCCC 1200      1210      1220      1230      1240      1250      1260
       *    *    *    *    *    *    *    *    *    *    *    *    *    *
     TCTCATTTATTATTTACAAATTCACATATACAACACCACCGTCCCCAGTGCCCGCAGTTTTTATTAAACA
     AGAGTAAATAATAAATGTTTAAGTGTATATGTTGTGGTGGCAGGGGTCACGGGCGTCAAAAATAATTTGT 1270      1280      1290      1300      1310      1320      1330
       *    *    *    *    *    *    *    *    *    *    *    *    *    *
     TAACGTGGGATCTCCACGCGAATCTCGGGTACGTGTTCCGGACATGGGCTCTTCTCCGGTAGCGGCGGAG
     ATTGCACCCTAGAGGTGCGCTTAGAGCCCATGCACAAGGCCTGTACCCGAGAAGAGGCCATCGCCGCCTC 1340      1350      1360      1370      1380      1390      1400
       *    *    *    *    *    *    *    *    *    *    *    *    *    *
     CTTCTACATCCGAGCCCTGCTCCCATGCCTCCAGCGACTCATGGTCGCTCGGCAGCTCCTTGCTCCTAAC
     GAAGATGTAGGCTCGGGACGAGGGTACGGAGGTCGCTGAGTACCAGCGAGCCGTCGAGGAACGAGGATTG
```

FIG. 19B

```
       1410      1420      1430      1440      1450      1460      1470
    *    *    *    *    *    *    *    *    *    *    *    *    *    *
AGTGGAGGCCAGACTTAGGCACAGCACGATGCCCACCACCACCAGTGTGCCGCACAAGGCCGTGGCGGTA
TCACCTCCGGTCTGAATCCGTGTCGTGCTACGGGTGGTGGTGGTCACACGGCGTGTTCCGGCACCGCCAT 1480      1490      1500      1510      1520      1530      1540
    *    *    *    *    *    *    *    *    *    *    *    *    *    *
GGGTATGTGTCTGAAAATGAGCTCGGGGAGCGGGCTTGCACCGCTGACGCATTTGGAAGACTTAAGGCAG
CCCATACACAGACTTTTACTCGAGCCCCTCGCCCGAACGTGGCGACTGCGTAAACCTTCTGAATTCCGTC 1550      1560      1570      1580      1590      1600      1610
    *    *    *    *    *    *    *    *    *    *    *    *    *    *
CGGCAGAAGAAGATGCAGGCAGCTGAGTTGTTGTGTTCTGATAAGAGTCAGAGGTAACTCCCGTTGCGGT
GCCGTCTTCTTCTACGTCCGTCGACTCAACAACACAAGACTATTCTCAGTCTCCATTGAGGGCAACGCCA 1620      1630      1640      1650      1660      1670      1680
    *    *    *    *    *    *    *    *    *    *    *    *    *    *
GCTGTTAACGGTGGAGGGCAGTGTAGTCTGAGCAGTACTCGTTGCTGCCGCGCGCGCCACCAGACATAAT
CGACAATTGCCACCTCCCGTCACATCAGACTCGTCATGAGCAACGACGGCGCGCGCGGTGGTCTGTATTA 1690      1700      1710      1720      1730      1740      1750
    *    *    *    *    *    *    *    *    *    *    *    *    *    *
AGCTGACAGACTAACAGACTGTTCCTTTCCATGGGTCTTTTCTGCAGGCTAGCCGGCCTGAATTCGGATA
TCGACTGTCTGATTGTCTGACAAGGAAAGGTACCCAGAAAAGACGTCCGATCGGCCGGACTTAAGCCTAT 1760      1770      1780      1790      1800      1810      1820
    *    *    *    *    *    *    *    *    *    *    *    *    *    *
TCCAAGCTTGATGAATAAAAGATCAGAGCTCTAGTGATCTGTGTGTTGGTTTTTTGTGTGCTCGAGCCCC
AGGTTCGAACTACTTATTTTCTAGTCTCGAGATCACTAGACACACAACCAAAAAACACACGAGCTCGGGG 1830      1840      1850      1860      1870      1880      1890
    *    *    *    *    *    *    *    *    *    *    *    *    *    *
AGCTGGTTCTTTTCCGCCTCAGAAGCCATAGAGCCCACCGCATCCCCAGCATGCCTGCTATTGTCTTCCCA
TCGACCAAGAAAGGCGGAGTCTTCGGTATCTCGGGTGGCGTAGGGGTCGTACGGACGATAACAGAAGGGT 1900      1910      1920      1930      1940      1950      1960
    *    *    *    *    *    *    *    *    *    *    *    *    *    *
ATCCTCCCCCTTGCTGTCCTGCCCCACCCCACCCCCCAGAATAGAATGACACCTACTCAGACAATGCGAT
TAGGAGGGGGAACGACAGGACGGGGTGGGGTGGGGGGTCTTATCTTACTGTGGATGAGTCTGTTACGCTA 1970      1980      1990      2000      2010      2020      2030
    *    *    *    *    *    *    *    *    *    *    *    *    *    *
GCAATTTCCTCATTTTATTAGGAAAGGACAGTGGGAGTGGCACCTTCCAGGGTCAAGGAAGGCACGGGGG
CGTTAAAGGAGTAAAATAATCCTTTCCTGTCACCCTCACCGTGGAAGGTCCCAGTTCCTTCCGTGCCCCC 2040      2050      2060      2070      2080      2090      2100
    *    *    *    *    *    *    *    *    *    *    *    *    *    *
AGGGGCAAACAACAGATGGCTGGCAACTAGAAGGCACAGTCGAGGCTGATCAGCGAGCTCTAGCGGTACC
TCCCCGTTTGTAGTCTACCGACCGTTGATCTTCCGTGTCAGCTCCGACTAGTCGCTCGAGATCGCCATGG
```

FIG.19C

```
          2110      2120      2130      2140      2150      2160      2170
            *    *    *    *    *    *    *    *    *    *    *    *    *    *
GGCATTAGTCTATGGCCGACTCTAGATTTTCTCCTTGCGGCCGCCCTAGATGCATGCTCGATCGACCTGC
CCGTAATCAGATACCGGCTGAGATCTAAAAGAGGAACGCCGGCGGGATCTACGTACGAGCTAGCTGGACG 2180      2190      2200      2210      2220      2230      2240
            *    *    *    *    *    *    *    *    *    *    *    *    *    *
AGTTGGACCTGGGAGTGGACACCTGTGGAGAGAAAGGCAAAGTGGATGTCATTGTCACTCAAGTGTATGG
TCAACCTGGACCCTCACCTGTGGACACCTCTCTTTCCGTTTCACCTACAGTAACAGTGAGTTCACATACC 2250      2260      2270      2280      2290      2300      2310
            *    *    *    *    *    *    *    *    *    *    *    *    *    *
CCAGATCTCAAGCCTGCCACACCTCAAGCTAGCTTGACAACAAAAAGATTGTCTTTTCTGACCAGATGGA
GGTCTAGAGTTCGGACGGTGTGGAGTTCGATCGAACTGTTGTTTTTCTAACAGAAAAGACTGGTCTACCT 2320      2330      2340      2350      2360      2370      2380
            *    *    *    *    *    *    *    *    *    *    *    *    *    *
CGCGGCCACCCTCAAAGGCATCACCGCGGGCCAGGTGAATATCAAATCCTCCTCGTTTTTGGAAACTGAC
GCGCCGGTGGGAGTTTCCGTAGTGGCGCCCGGTCCACTTATAGTTTAGGAGGAGCAAAAACCTTTGACTG 2390      2400      2410      2420      2430      2440      2450
            *    *    *    *    *    *    *    *    *    *    *    *    *    *
AATCTTAGCGCAGAAGTCATGCCCGCTTTTGAGAGGGAGTACTCACCCCAACAGCTGGCCCTCGCAGACA
TTAGAATCGCGTCTTCAGTACGGGCGAAAACTCTCCCTCATGAGTGGGGTTGTCGACCGGGAGCGTCTGT 2460      2470      2480      2490      2500      2510      2520
            *    *    *    *    *    *    *    *    *    *    *    *    *    *
GCGAATTAATTCCAGCACACTGGCGGCCGTTACTAGTGGATCCGAGCTCGCAAGCTAGCTTGGGTCTCCC
CGCTTAATTAAGGTCGTGTGACCGCCGGCAATGATCACCTAGGCTCGAGCGTTCGATCGAACCCAGAGGG 2530      2540      2550      2560      2570      2580      2590
            *    *    *    *    *    *    *    *    *    *    *    *    *    *
TATAGTGAGTCGTATTAATTTCGATAAGCCAGTAAGCAGTGGGTTCTCTAGTTAGCCAGAGAGCTCTGCT
ATATCACTCAGCATAATTAAAGCTATTCGGTCATTCGTCACCCAAGAGATCAATCGGTCTCTCGAGACGA 2600      2610      2620      2630      2640      2650      2660
            *    *    *    *    *    *    *    *    *    *    *    *    *    *
TATATAGACCTCCCACCGTACACGCCTACCGCCCATTTGCGTCAATGGGGCGGAGTTGTTACGACATTTT
ATATATCTGGAGGGTGGCATGTGCGGATGGCGGGTAAACGCAGTTACCCCGCCTCAACAATGCTGTAAAA 2670      2680      2690      2700      2710      2720      2730
            *    *    *    *    *    *    *    *    *    *    *    *    *    *
GGAAAGTCCCGTTGATTTTGGTGCCAAAACAAACTCCCATTGACGTCAATGGGGTGGAGACTTGGAAATC
CCTTTCAGGGCAACTAAAACCACGGTTTTGTTTGAGGGTAACTGCAGTTACCCCACCTCTGAACCTTTAG 2740      2750      2760      2770      2780      2790      2800
            *    *    *    *    *    *    *    *    *    *    *    *    *    *
CCCGTGAGTCAAACCGCTATCCACGCCCATTGATGTACTGCCAAAACCGCATCACCATGGTAATAGCGAT
GGGCACTCAGTTTGGCGATAGGTGCGGGTAACTACATGACGGTTTTGGCGTAGTGGTACCATTATCGCTA
```

FIG.19D

```
        2810      2820      2830      2840      2850      2860      2870
    *    *    *    *    *    *    *    *    *    *    *    *    *    *
GACTAATACGTAGATGTACTGCCAAGTAGGAAAGTCCCATAAGGTCATGTACTGGGCATAATGCCAGGCG
CTGATTATGCATCTACATGACGGTTCATCCTTTCAGGGTATTCCAGTACATGACCCGTATTACGGTCCGC 2880      2890      2900      2910      2920      2930      2940
    *    *    *    *    *    *    *    *    *    *    *    *    *    *
GGCCATTTACCGTCATTGACGTCAATAGGGGGCGTACTTGGCATATGATACACTTGATGTACTGCCAAGT
CCGGTAAATGGCAGTAACTGCAGTTATCCCCCGCATGAACCGTATACTATGTGAACTACATGACGGTTCA 2950      2960      2970      2980      2990      3000      3010
    *    *    *    *    *    *    *    *    *    *    *    *    *    *
GGGCAGTTTACCGTAAATAGTCCACCCATTGACGTCAATGGAAAGTCCCTATTGGCGTTACTATGGGAAC
CCCGTCAAATGGCATTTATCAGGTGGGTAACTGCAGTTACCTTTCAGGGATAACCGCAATGATACCCTTG 3020      3030      3040      3050      3060      3070      3080
    *    *    *    *    *    *    *    *    *    *    *    *    *    *
ATACGTCATTATTGACGTCAATGGGCGGGGGTCGTTGGGCGGTCAGCCAGGCGGGCCATTTACCGTAAGT
TATGCAGTAATAACTGCAGTTACCCGCCCCCAGCAACCCGCCAGTCGGTCCGCCCGGTAAATGGCATTCA 3090      3100      3110      3120      3130      3140      3150
    *    *    *    *    *    *    *    *    *    *    *    *    *    *
TATGTAACGCGGAACTCCATATATGGGCTATGAACTAATGACCCCGTAATTGATTACTATTAATAACTAG
ATACATTGCGCCTTGAGGTATATACCCGATACTTGATTACTGGGGCATTAACTAATGATAATTATTGATC 3160      3170      3180      3190      3200      3210      3220
    *    *    *    *    *    *    *    *    *    *    *    *    *    *
TCAATAATCAATGTCCTGCATTAATGAATCGGCCAACGCGCGGGGAGAGGCGGTTTGCGTATTGGGCGCT
AGTTATTAGTTACAGGACGTAATTACTTAGCCGGTTGCGCGCCCCTCTCCGCCAAACGCATAACCCGCGA 3230      3240      3250      3260      3270      3280      3290
    *    *    *    *    *    *    *    *    *    *    *    *    *    *
CTTCCGCTTCCTCGCTCACTGACTCGCTGCGCTCGGTCGTTCGGCTGCGGCGAGCGGTATCAGCTCACTC
GAAGGCGAAGGAGCGAGTGACTGAGCGACGCGAGCCAGCAAGCCGACGCCGCTCGCCATAGTCGAGTGAG 3300      3310      3320      3330      3340      3350      3360
    *    *    *    *    *    *    *    *    *    *    *    *    *    *
AAAGGCGGTAATACGGTTATCCACAGAATCAGGGGATAACGCAGGAAAGAACATGTGAGCAAAAGGCCAG
TTTCCGCCATTATGCCAATAGGTGTCTTAGTCCCCTATTGCGTCCTTTCTTGTACACTCGTTTTCCGGTC 3370      3380      3390      3400      3410      3420      3430
    *    *    *    *    *    *    *    *    *    *    *    *    *    *
CAAAAGGCCAGGAACCGTAAAAAGGCCGCGTTGCTGGCGTTTTTCCATAGGCTCCGCCCCCCTGACGAGC
GTTTTCCGGTCCTTGGCATTTTTCCGGCGCAACGACCGCAAAAAGGTATCCGAGGCGGGGGGACTGCTCG 3440      3450      3460      3470      3480      3490      3500
    *    *    *    *    *    *    *    *    *    *    *    *    *    *
ATCACAAAAATCGACGCTCAAGTCAGAGGTGGCGAAACCCGACAGGACTATAAAGATACCAGGCGTTTCC
TAGTGTTTTTAGCTGCGAGTTCAGTCTCCACCGCTTTGGGCTGTCCTGATATTTCTATGGTCCGCAAAGG
```

FIG. 19E

```
         3510      3520      3530      3540      3550      3560      3570
           *    *    *    *    *    *    *    *    *    *    *    *    *    *
CCCTGGAAGCTCCCTCGTGCGCTCTCCTGTTCCGACCCTGCCGCTTACCGGATACCTGTCCGCCTTTCTC
GGGACCTTCGAGGGAGCACGCGAGAGGACAAGGCTGGGACGGCGAATGGCCTATGGACAGGCGGAAAGAG 3580      3590      3600      3610      3620      3630      3640
           *    *    *    *    *    *    *    *    *    *    *    *    *    *
CCTTCGGGAAGCGTGGCGCTTTCTCAATGCTCACGCTGTAGGTATCTCAGTTCGGTGTAGGTCGTTCGCT
GGAAGCCCTTCGCACCGCGAAAGAGTTACGAGTGCGACATCCATAGAGTCAAGCCACATCCAGCAAGCGA 3650      3660      3670      3680      3690      3700      3710
           *    *    *    *    *    *    *    *    *    *    *    *    *    *
CCAAGCTGGGCTGTGTGCACGAACCCCCCGTTCAGCCCGACCGCTGCGCCTTATCCGGTAACTATCGTCT
GGTTCGACCCGACACACGTGCTTGGGGGGCAAGTCGGGCTGGCGACGCGGAATAGGCCATTGATAGCAGA 3720      3730      3740      3750      3760      3770      3780
           *    *    *    *    *    *    *    *    *    *    *    *    *    *
TGAGTCCAACCCGGTAAGACACGACTTATCGCCACTGGCAGCAGCCACTGGTAACAGGATTAGCAGAGCG
ACTCAGGTTGGGCCATTCTGTGCTGAATAGCGGTGACCGTCGTCGGTGACCATTGTCCTAATCGTCTCGC 3790      3800      3810      3820      3830      3840      3850
           *    *    *    *    *    *    *    *    *    *    *    *    *    *
AGGTATGTAGGCGGTGCTACAGAGTTCTTGAAGTGGTGGCCTAACTACGGCTACACTAGAAGGACAGTAT
TCCATACATCCGCCACGATGTCTCAAGAACTTCACCACCGGATTGATGCCGATGTGATCTTCCTGTCATA 3860      3870      3880      3890      3900      3910      3920
           *    *    *    *    *    *    *    *    *    *    *    *    *    *
TTGGTATCTGCGCTCTGCTGAAGCCAGTTACCTTCGGAAAAAGAGTTGGTAGCTCTTGATCCGGCAAACA
AACCATAGACGCGAGACGACTTCGGTCAATGGAAGCCTTTTTCTCAACCATCGAGAACTAGGCCGTTTGT 3930      3940      3950      3960      3970      3980      3990
           *    *    *    *    *    *    *    *    *    *    *    *    *    *
AACCACCGCTGGTAGCGGTGGTTTTTTTGTTTGCAAGCAGCAGATTACGCGCAGAAAAAAAGGATCTCAA
TTGGTGGCGACCATCGCCACCAAAAAAACAAACGTTCGTCGTCTAATGCGCGTCTTTTTTTTCCTAGAGTT 4000      4010      4020      4030      4040      4050      4060
           *    *    *    *    *    *    *    *    *    *    *    *    *    *
GAAGATCCTTTGATCTTTTCTACGGGGTCTGACGCTCAGTGGAACGAAAACTCACGTTAAGGGATTTTGG
CTTCTAGGAAACTAGAAAAGATGCCCCAGACTGCGAGTCACCTTGCTTTTGAGTGCAATTCCCTAAAACC 4070      4080      4090      4100      4110      4120      4130
           *    *    *    *    *    *    *    *    *    *    *    *    *    *
TCATGAACAATAAAACTGTCTGCTTACATAAACAGTAATACAAGGGGTGTTATGAGCCATATTCAACGGG
AGTACTTGTTATTTTGACAGACGAATGTATTTGTCATTATGTTCCCCACAATACTCGGTATAAGTTGCCC 4140      4150      4160      4170      4180      4190      4200
           *    *    *    *    *    *    *    *    *    *    *    *    *    *
AAACGTCTTGCTCGAGGCCGCGATTAAATTCCAACATGGATGCTGATTTATATGGGTATAAATGGGCTCG
TTTGCAGAACGAGCTCCGGCGCTAATTTAAGGTTGTACCTACGACTAAATATACCCATATTTACCCGAGC
```

FIG. 19F

```
      4210      4220      4230      4240      4250      4260      4270
   *    *    *    *    *    *    *    *    *    *    *    *    *    *
CGATAATGTCGGGCAATCAGGTGCGACAATCTATCGATTGTATGGGAAGCCCGATGCGCCAGAGTTGTTT
GCTATTACAGCCCGTTAGTCCACGCTGTTAGATAGCTAACATACCCTTCGGGCTACGCGGTCTCAACAAA 4280      4290      4300      4310      4320      4330      4340
   *    *    *    *    *    *    *    *    *    *    *    *    *    *
CTGAAACATGGCAAAGGTAGCGTTGCCAATGATGTTACAGATGAGATGGTCAGACTAAACTGGCTGACGG
GACTTTGTACCGTTTCCATCGCAACGGTTACTACAATGTCTACTCTACCAGTCTGATTTGACCGACTGCC 4350      4360      4370      4380      4390      4400      4410
   *    *    *    *    *    *    *    *    *    *    *    *    *    *
AATTTATGCCTCTTCCGACCATCAAGCATTTTATCCGTACTCCTGATGATGCATGGTTACTCACCACTGC
TTAAATACGGAGAAGGCTGGTAGTTCGTAAAATAGGCATGAGGACTACTACGTACCAATGAGTGGTGACG 4420      4430      4440      4450      4460      4470      4480
   *    *    *    *    *    *    *    *    *    *    *    *    *    *
GATCCCCGGGAAAACAGCATTCCAGGTATTAGAAGAATATCCTGATTCAGGTGAAAATATTGTTGATGCG
CTAGGGGCCCTTTTGTCGTAAGGTCCATAATCTTCTTATAGGACTAAGTCCACTTTTATAACAACTACGC 4490      4500      4510      4520      4530      4540      4550
   *    *    *    *    *    *    *    *    *    *    *    *    *    *
CTGGCAGTGTTCCTGCGCCGGTTGCATTCGATTCCTGTTTGTAATTGTCCTTTTAACAGCGATCGCGTAT
GACCGTCACAAGGACGCGGCCAACGTAAGCTAAGGACAAACATTAACAGGAAAATTGTCGCTAGCGCATA 4560      4570      4580      4590      4600      4610      4620
   *    *    *    *    *    *    *    *    *    *    *    *    *    *
TTCGTCTCGCTCAGGCGCAATCACGAATGAATAACGGTTTGGTTGATGCGAGTGATTTTGATGACGAGCG
AAGCAGAGCGAGTCCGCGTTAGTGCTTACTTATTGCCAAACCAACTACGCTCACTAAAACTACTGCTCGC 4630      4640      4650      4660      4670      4680      4690
   *    *    *    *    *    *    *    *    *    *    *    *    *    *
TAATGGCTGGCCTGTTGAACAAGTCTGGAAAGAAATGCATAAACTTTTGCCATTCTCACCGGATTCAGTC
ATTACCGACCGGACAACTTGTTCAGACCTTTCTTTACGTATTTGAAAACGGTAAGAGTGGCCTAAGTCAG 4700      4710      4720      4730      4740      4750      4760
   *    *    *    *    *    *    *    *    *    *    *    *    *    *
GTCACTCATGGTGATTTCTCACTTGATAACCTTATTTTTTGACGAGGGGAAATTAATAGGTTGTATTGATG
CAGTGAGTACCACTAAAGAGTGAACTATTGGAATAAAAACTGCTCCCCTTTAATTATCCAACATAACTAC 4770      4780      4790      4800      4810      4820      4830
   *    *    *    *    *    *    *    *    *    *    *    *    *    *
TTGGACGAGTCGGAATCGCAGACCGATACCAGGATCTTGCCATCCTATGGAACTGCCTCGGTGAGTTTTC
AACCTGCTCAGCCTTAGCGTCTGGCTATGGTCCTAGAACGGTAGGATACCTTGACGGAGCCACTCAAAAG 4840      4850      4860      4870      4880      4890      4900
   *    *    *    *    *    *    *    *    *    *    *    *    *    *
TCCTTCATTACAGAAACGGCTTTTTCAAAAATATGGTATTGATAATCCTGATATGAATAAAATTGCAGTTT
AGGAAGTAATGTCTTTGCCGAAAAAGTTTTTATACCATAACTATTAGGACTATACTTATTTAACGTCAAA
```

FIG.19G

```
         4910      4920      4930      4940      4950      4960      4970
          *    *    *    *    *    *    *    *    *    *    *    *    *    *
CATTTGATGCTCGATGAGTTTTTCTAATCAGAATTGGTTAATTGGTTGTAACACTGGCAGAGCATCATGA
GTAAACTACGAGCTACTCAAAAAGATTAGTCTTAACCAATTAACCAACATTGTGACCGTCTCGTAGTACT 4980      4990      5000      5010      5020      5030      5040
          *    *    *    *    *    *    *    *    *    *    *    *    *    *
GCGGATACATATTTGAATGTATTTAGAAAAATAAACAAATAGGGGTTCCGCGCACATTTCCCCGAAAAGT
CGCCTATGTATAAACTTACATAAATCTTTTTATTTGTTTATCCCCAAGGCGCGTGAAAAGGGGCTTTTCA

5050
          *    *
GCCACCTGACGTC
CGGTGGACTGCAG
```

FIG.19H

```
          10        20        30        40        50        60        70
    *    *    *    *    *    *    *    *    *    *    *    *    *    *
GCTAGCGCCGCCACCATGGGAATGCAGGTGCAGATCCAGAGCCTGTTTCTGCTCCTCCTGTGGGTGCCCG
CGATCGCGGCGGTGGTACCCTTACGTCCACGTCTAGGTCTCGGACAAAGACGAGGAGGACACCCACGGGC
              M  G  M  Q  V  Q  I  Q  S  L  F  L  L  L  W  V  P>

80        90       100       110       120       130       140
    *    *    *    *    *    *    *    *    *    *    *    *    *    *
GGTCCAGAGGACACACCCTGTGGAAGGCCGGAATCCTGTATAAGGCCAAGTTCGTGGCTGCCTGGACCCT
CCAGGTCTCCTGTGTGGGACACCTTCCGGCCTTAGGACATATTCCGGTTCAAGCACCGACGGACCTGGGA
   G  S  R  G  H  T  L  W  K  A  G  I  L  Y  K  A  K  F  V  A  A  W  T  L>

150       160       170       180       190       200       210
    *    *    *    *    *    *    *    *    *    *    *    *    *    *
GAAGGCTGCCGCTTTCCTGCCTAGCGATTTCTTTCCTAGCGTGAAGCTGACCCCACTGTGCGTGACCCTG
CTTCCGACGGCGAAAGGACGGATCGCTAAAGAAAGGATCGCACTTCGACTGGGGTGACACGCACTGGGAC
    K  A  A  A  F  L  P  S  D  F  F  P  S  V  K  L  T  P  L  C  V  T  L>

220       230       240       250       260       270       280
    *    *    *    *    *    *    *    *    *    *    *    *    *    *
TATATGGATGACGTGGTGCTGGGAGCCAGCATCATCAACTTCGAGAAGCTGGGACTGTCCAGATACGTGG
ATATACCTACTGCACCACGACCCTCGGTCGTAGTAGTTGAAGCTCTTCGACCCTGACAGGTCTATGCACC
    Y  M  D  D  V  V  L  G  A  S  I  I  N  F  E  K  L  G  L  S  R  Y  V>

290       300       310       320       330       340       350
    *    *    *    *    *    *    *    *    *    *    *    *    *    *
CTAGGCTGATCCTGAAGGAGCCTGTGCACGGCGTGTCCACCCTGCCAGAGACCACCGTGGTGAGGAGGAC
GATCCGACTAGGACTTCCTCGGACACGTGCCGCACAGGTGGGACGGTCTCTGGTGGCACCACTCCTCCTG
    A  R  L  I  L  K  E  P  V  H  G  V  S  T  L  P  E  T  T  V  V  R  R  T>

360       370       380       390       400       410
    *    *    *    *    *    *    *    *    *    *    *    *
CGTGTACTATGGAGTGCCTGTGTGGAAGTGGCTGAGCCTGCTGGTGCCCTTTGTGGGTACC
GCACATGATACCTCACGGACACACCTTCACCGACTCGGACGACCACGGGAAACACCCATGG
    V  Y  Y  G  V  P  V  W  K  W  L  S  L  L  V  P  F  V  G  T>
```

FIG.20

```
         10        20        30        40        50        60        70
     *    *    *    *    *    *    *    *    *    *    *    *    *    *
GCTAGCGCCGCCACCATGGGAATGCAGGTGCAGATCCAGAGCCTGTTTCTGCTCCTCCTGTGGGTGCCCG
CGATCGCGGCGGTGGTACCCTTACGTCCACGTCTAGGTCTCGGACAAAGACGAGGAGGACACCCACGGGC
              M  G  M  Q  V  Q  I  Q  S  L  F  L  L  L  W  V  P>

80        90       100       110       120       130       140
     *    *    *    *    *    *    *    *    *    *    *    *    *    *
GGTCCAGAGGACACACCCTGTGGAAGGCCGGAATCCTGTATAAGGCCAAGTTCGTGGCTGCCTGGACCCT
CCAGGTCTCCTGTGTGGGACACCTTCCGGCCTTAGGACATATTCCGGTTCAAGCACCGACGGACCTGGGA
  G  S  R  G  H  T  L  W  K  A  G  I  L  Y  K  A  K  F  V  A  A  W  T  L>

150       160       170       180       190       200       210
     *    *    *    *    *    *    *    *    *    *    *    *    *    *
GAAGGCTGCCGCTTTCCTGCCTAGCGATTTCTTTCCTAGCGTGAAGCTGACCCCACTGTGCGTGACCCTG
CTTCCGACGGCGAAAGGACGGATCGCTAAAGAAAGGATCGCACTTCGACTGGGGTGACACGCACTGGGAC
  K  A  A  A  F  L  P  S  D  F  F  P  S  V  K  L  T  P  L  C  V  T  L>

220       230       240       250       260       270       280
     *    *    *    *    *    *    *    *    *    *    *    *    *    *
TATATGGATGACGTGGTGCTGGGAGTGGGACTGTCCAGGTACGTGGCTAGGCTGATCCTGAAGGAGCCTG
ATATACCTACTGCACCACGACCCTCACCCTGACAGGTCCATGCACCGATCCGACTAGGACTTCCTCGGAC
  Y  M  D  D  V  V  L  G  V  G  L  S  R  Y  V  A  R  L  I  L  K  E  P>

290       300       310       320       330       340       350
     *    *    *    *    *    *    *    *    *    *    *    *    *    *
TGCACGGCGTGTCCACCCTGCCAGAGACCACCGTGGTGAGGAGGACCGTGTACTATGGAGTGCCTGTGTG
ACGTGCCGCACAGGTGGGACGGTCTCTGGTGGCACCACTCCTCCTGGCACATGATACCTCACGGACACAC
  V  H  G  V  S  T  L  P  E  T  T  V  V  R  R  T  V  Y  Y  G  V  P  V  W>

360       370       380       390
     *    *    *    *    *    *    *    *
GAAGTGGCTGAGCCTGCTGGTGCCCTTTGTGTGAGGTACC
CTTCACCGACTCGGACGACCACGGGAAACACACTCCATGG
  K  W  L  S  L  L  V  P  F  V  *>
```

FIG.21

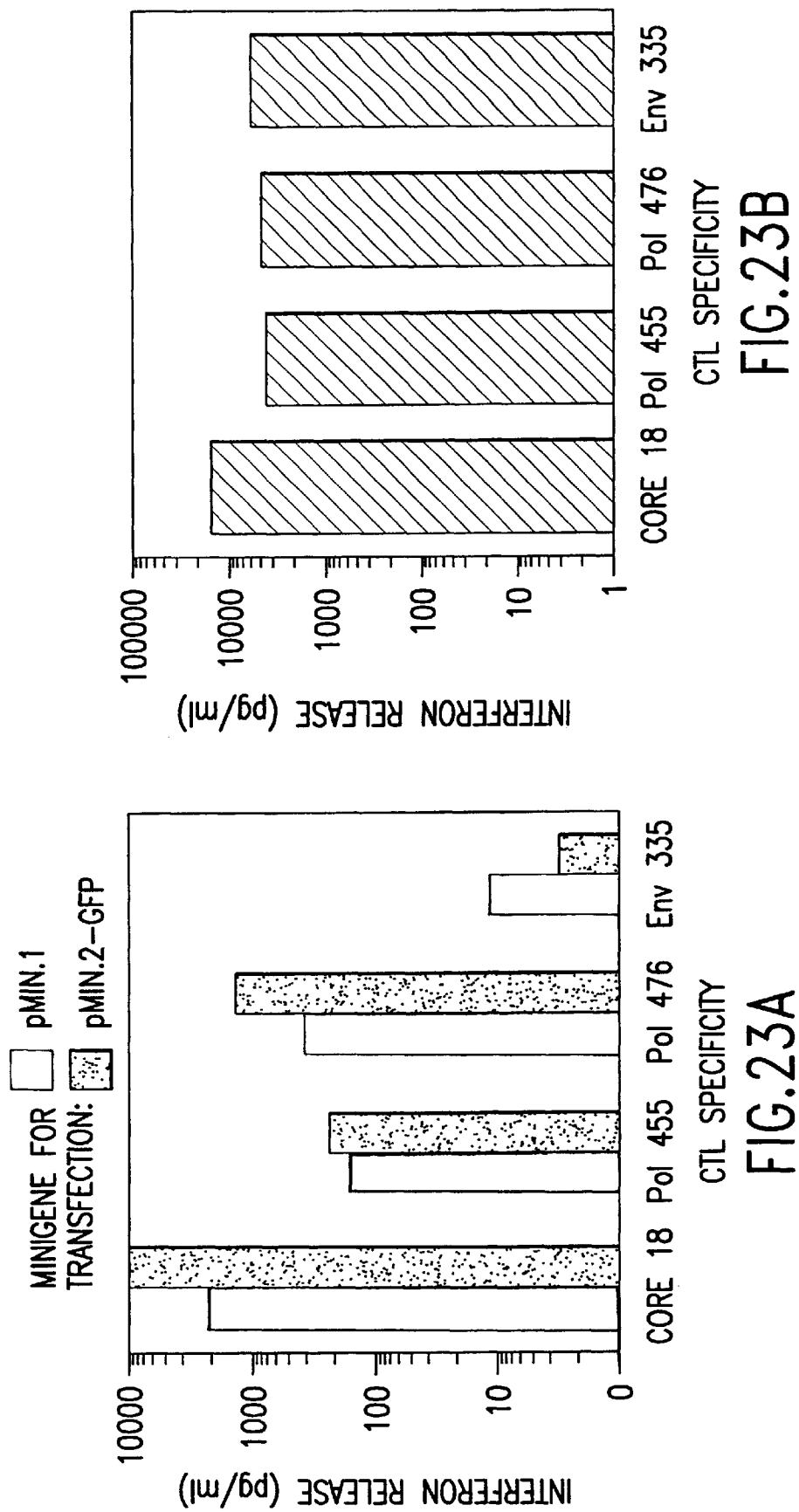

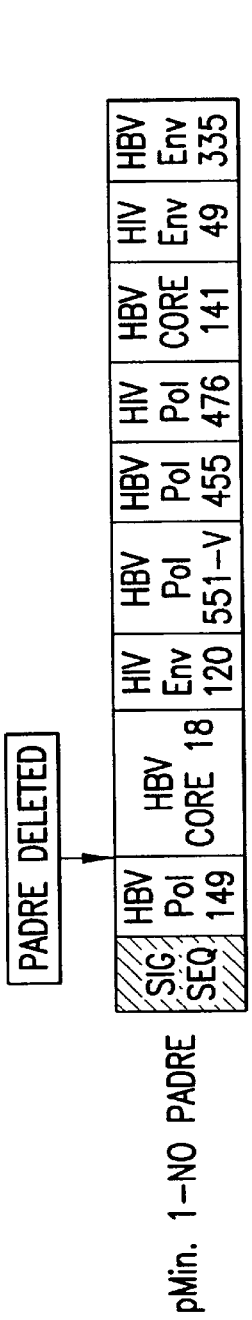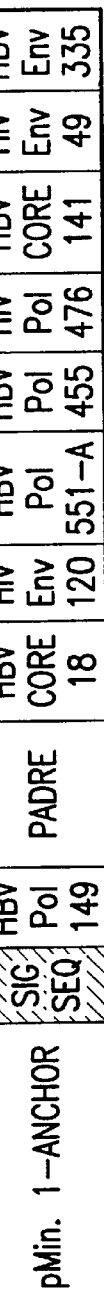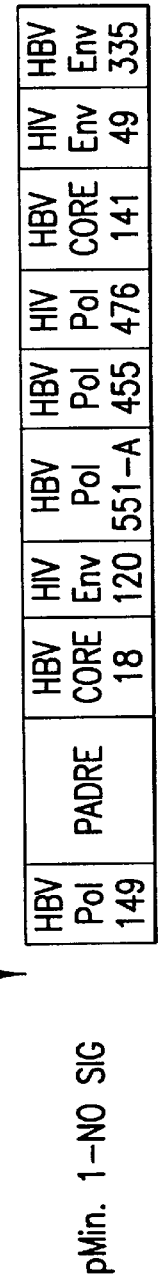

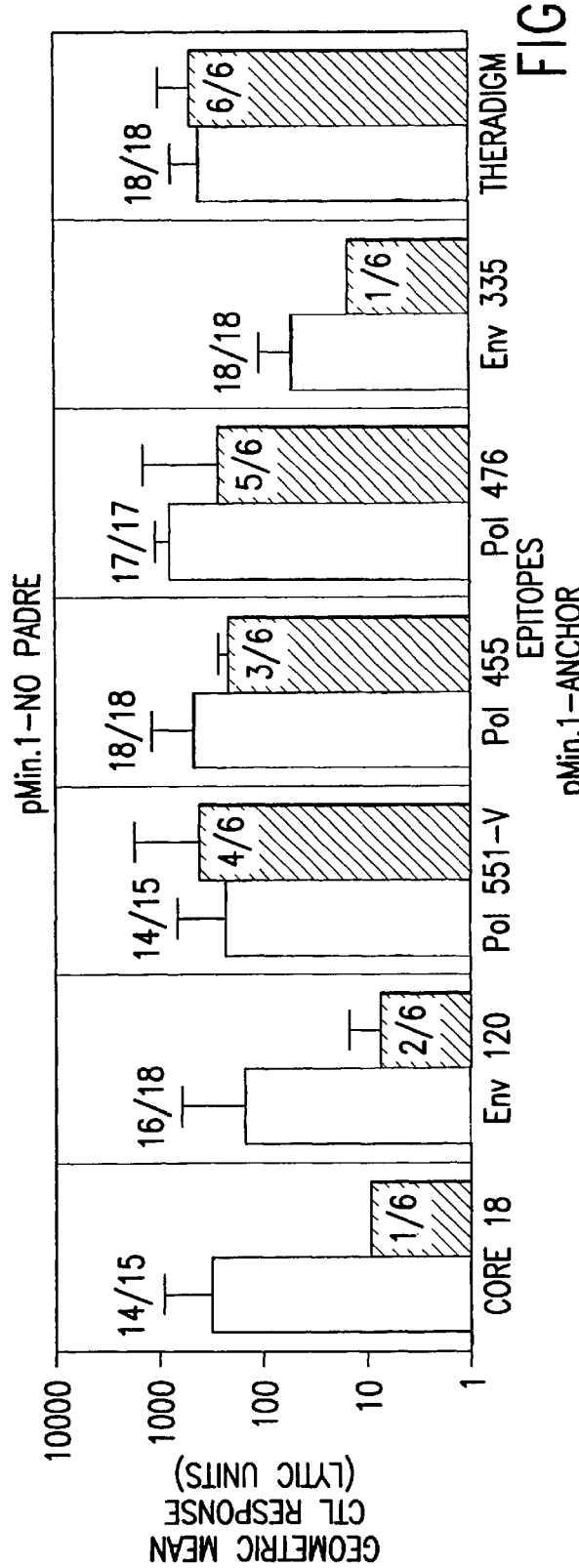
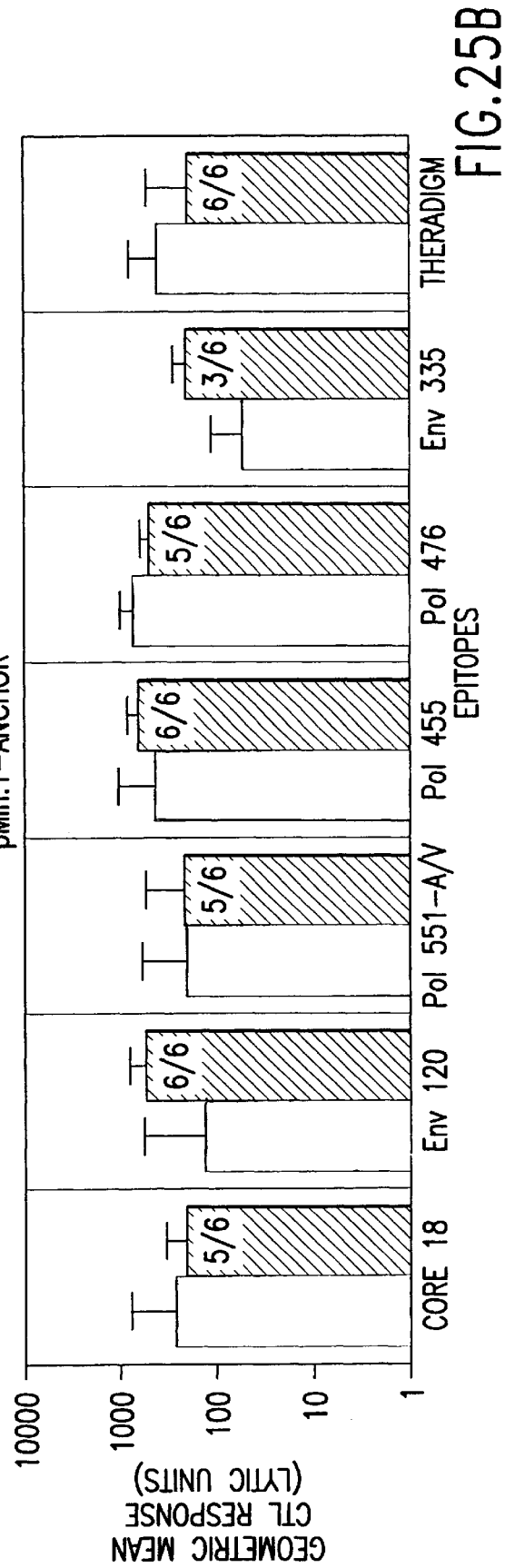

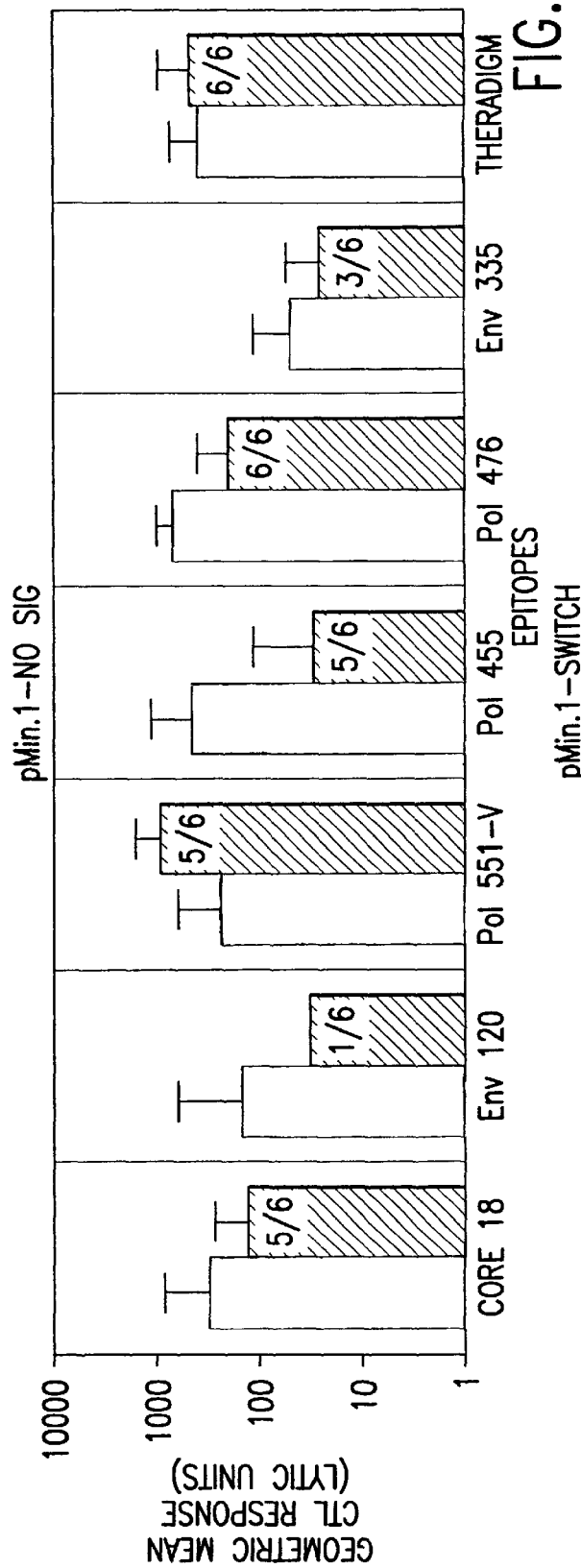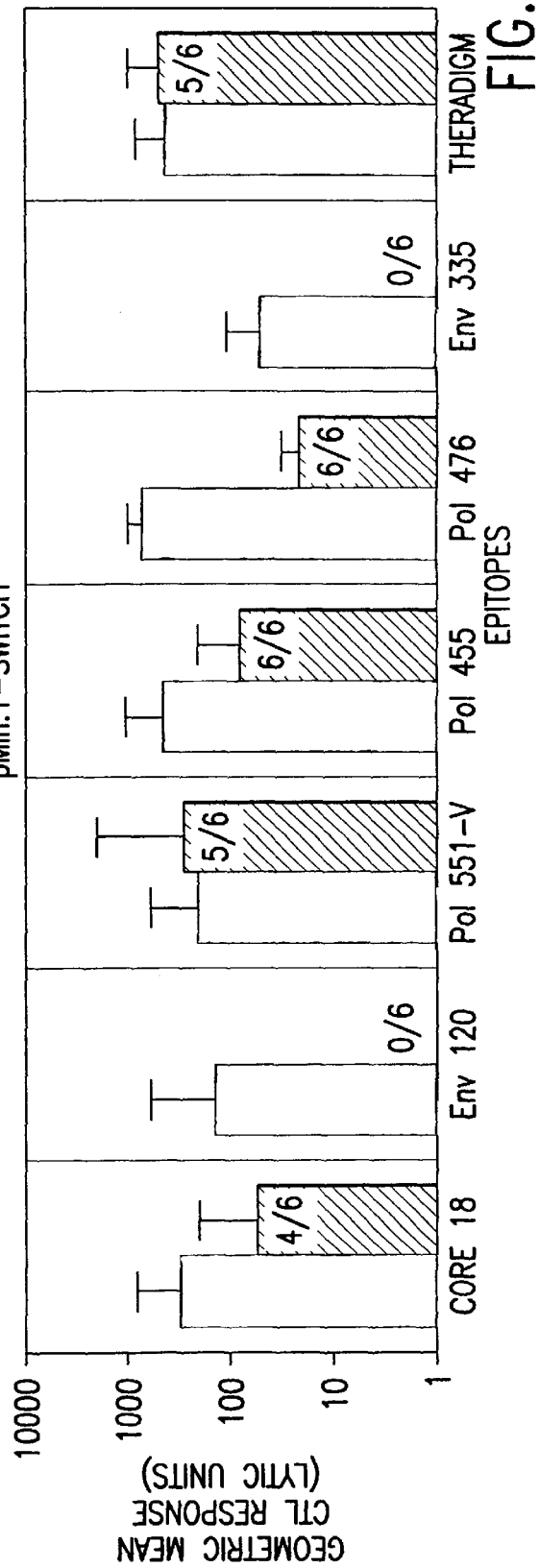

# EXPRESSION VECTORS FOR STIMULATING AN IMMUNE RESPONSE AND METHODS OF USING THE SAME

CROSS-REFERENCE TO RELATED APPLICATIONS

This application is a continuation and claims the benefit of Ser. No. 09/078,904, filed May 13, 1998, now abandoned, and 60/085,751, filed May 15, 1998;, now abandoned, both herein incorporated by reference in their entirety.

STATEMENT AS TO RIGHTS TO INVENTIONS MADE UNDER FEDERALLY SPONSORED RESEARCH AND DEVELOPMENT

This invention was made with government support under NIH Grant No. AI-42699-01, NIH Grant No. AI38584-03, and NIH Contract No. N01-AI-45241. The Government has certain rights in this invention.

FIELD OF THE INVENTION

SUBMISSION ON COMPACT DISC

The contents of the following submission on compact discs are incorporated herein by reference in its entirety: A compact disc copy of the substitute Sequence Listing (COPY 1) (file name: 3996320022.txt, date recorded: Jan. 4, 2002, size:199 KB); a duplicate compact disc copy of the substitute Sequence Listing (COPY 2) (file name: 3996320022.txt, date recorded: Jan. 4, 2002, size: 199 KB); a computer readable form copy of the substitute Sequence Listing (CRF COPY) (file name: 3996320022.txt, date recorded: Jan. 4, 2002, size: 199 KB).

The present invention relates to nucleic acid vaccines encoding multiple CTL and HTL epitopes and MHC targeting sequences.

BACKGROUND OF THE INVENTION

Vaccines are of fundamental importance in modern medicine and have been highly effective in combating certain human diseases. However, despite the successful implementation of vaccination programs that have greatly limited or virtually eliminated several debilitating human diseases, there are a number of diseases that affect millions worldwide for which effective vaccines have not been developed.

Major advances in the field of immunology have led to a greater understanding of the mechanisms involved in the immune response and have provided insights into developing new vaccine strategies (Kuby, *Immunology*, 443–457 (3rd ed., 1997), which is incorporated herein by reference). These new vaccine strategies have taken advantage of knowledge gained regarding the mechanisms by which foreign material, termed antigen, is recognized by the immune system and eliminated from the organism. An effective vaccine is one that elicits an immune response to an antigen of interest.

Specialized cells of the immune system are responsible for the protective activity required to combat diseases. An immune response involves two major groups of cells, lymphocytes, or white blood cells, and antigen-presenting cells. The purpose of these immune response cells is to recognize foreign material, such as an infectious organism or a cancer cell, and remove that foreign material from the organism.

Two major types of lymphocytes mediate different aspects of the immune response. B cells display on their cell surface specialized proteins, called antibodies, that bind specifically to foreign material, called antigens. Effector B cells produce soluble forms of the antibody, which circulate throughout the body and function to eliminate antigen from the organism. This branch of the immune system is known as the humoral branch. Memory B cells function to recognize the antigen in future encounters by continuing to express the membrane-bound form of the antibody.

A second major type of lymphocyte is the T cell. T cells also have on their cell surface specialized proteins that recognize antigen but, in contrast to B cells, require that the antigen be bound to a specialized membrane protein complex, the major histocompatibility complex (MHC), on the surface of an antigen-presenting cell. Two major classes of T cells, termed helper T lymphocytes ("HTL") and cytotoxic T lymphocytes ("CTL"), are often distinguished based on the presence of either CD4 or CD8 protein, respectively, on the cell surface. This branch of the immune system is known as the cell-mediated branch.

The second major class of immune response cells are cells that function in antigen presentation by processing antigen for binding to MHC molecules expressed in the antigen presenting cells. The processed antigen bound to MHC molecules is transferred to the surface of the cell, where the antigen-MHC complex is available to bind to T cells.

MHC molecules can be divided into MHC class I and class II molecules and are recognized by the two classes of T cells. Nearly all cells express MHC class I molecules, which function to present antigen to cytotoxic T lymphocytes. Cytotoxic T lymphocytes typically recognize antigen bound to MHC class I. A subset of cells called antigen-presenting cells express MHC class II molecules. Helper T lymphocytes typically recognize antigen bound to MHC class II molecules. Antigen-presenting cells include dendritic cells, macrophages, B cells, fibroblasts, glial cells, pancreatic beta cells, thymic epithelial cells, thyroid epithelial cells and vascular endothelial cells. These antigen-presenting cells generally express both MHC class I and class II molecules. Also, B cells function as both antibody-producing and antigen-presenting cells.

Once a helper T lymphocyte recognizes an antigen-MHC class II complex on the surface of an antigen-presenting cell, the helper T lymphocyte becomes activated and produces growth factors that activate a variety of cells involved in the immune response, including B cells and cytotoxic T lymphocytes. For example, under the influence of growth factors expressed by activated helper T lymphocytes, a cytotoxic T lymphocyte that recognizes an antigen-MHC class I complex becomes activated. CTLs monitor and eliminate cells that display antigen specifically recognized by the CTL, such as infected cells or tumor cells. Thus, activation of helper T lymphocytes stimulates the activation of both the humoral and cell-mediated branches of the immune system.

An important aspect of the immune response, in particular as it relates to vaccine efficacy, is the manner in which antigen is processed so that it can be recognized by the specialized cells of the immune system. Distinct antigen processing and presentation pathways are utilized. The one is a cytosolic pathway, which results in the antigen being bound to MHC class I molecules. An alternative pathway is an endoplasmic reticulum pathway, which bypasses the cytosol. Another is an endocytic pathway, which results in the antigen being bound to MHC class II molecules. Thus, the cell surface presentation of a particular antigen by a MHC class II or class I molecule to a helper T lymphocyte or a cytotoxic T lymphocyte, respectively, is dependent on the processing pathway for that antigen.

The cytosolic pathway processes endogenous antigens that are expressed inside the cell. The antigen is degraded by a specialized protease complex in the cytosol of the cell, and the resulting antigen peptides are transported into the endoplasmic reticulum, an organelle that processes cell surface molecules. In the endoplasmic reticulum, the antigen peptides bind to MHC class I molecules, which are then transported to the cell surface for presentation to cytotoxic T lymphocytes of the immune system.

Antigens that exist outside the cell are processed by the endocytic pathway. Such antigens are taken into the cell by endocytosis, which brings the antigens into specialized vesicles called endosomes and subsequently to specialized vesicles called lysosomes, where the antigen is degraded by proteases into antigen peptides that bind to MHC class II molecules. The antigen peptide-MHC class II molecule complex is then transported to the cell surface for presentation to helper T lymphocytes of the immune system.

A variety of factors must be considered in the development of an effective vaccine. For example, the extent of activation of either the humoral or cell-mediated branch of the immune system can determine the effectiveness of a vaccine against a particular disease. Furthermore, the development of immunologic memory by inducing memory-cell formation can be important for an effective vaccine against a particular disease (Kuby, supra). For example, protection from infectious diseases caused by pathogens with short incubation periods, such as influenza virus, requires high levels of neutralizing antibody generated by the humoral branch because disease symptoms are already underway before memory cells are activated. Alternatively, protection from infectious diseases caused by pathogens with long incubation periods, such as polio virus, does not require neutralizing antibodies at the time of infection but instead requires memory B cells that can generate neutralizing antibodies to combat the pathogen before it is able to infect target tissues. Therefore, the effectiveness of a vaccine at preventing or ameliorating the symptoms of a particular disease depends on the type of immune response generated by the vaccine.

Many traditional vaccines have relied on intact pathogens such as attenuated or inactivated viruses or bacteria to elicit an immune response. However, these traditional vaccines have advantages and disadvantages, including reversion of an attenuated pathogen to a virulent form. The problem of reversion of an attenuated vaccine has been addressed by the use of molecules of the pathogen rather than the whole pathogen. For example, immunization approaches have begun to incorporate recombinant vector vaccines and synthetic peptide vaccines (Kuby, supra). Recently, DNA vaccines have also been used (Donnelly et al., *Annu. Rev. Immunol.* 15:617–648 (1997), which is incorporated herein by reference). The use of molecules of a pathogen provides safe vaccines that circumvent the potential for reversion to a virulent form of the vaccine.

The targeting of antigens to MHC class II molecules to activate helper T lymphocytes has been described using lysosomal targeting sequences, which direct antigens to lysosomes, where the antigen is digested by lysosomal proteases into antigen peptides that bind to MHC class II molecules (U.S. Pat. No. 5,633,234; Thomson et al., *J. Virol.* 72:2246–2252 (1998)). It would be advantageous to develop vaccines that deliver multiple antigens while exploiting the safety provided by administering individual epitopes of a pathogen rather than a whole organism. In particular, it would be advantageous to develop vaccines that effectively target antigens to MHC class II molecules for activation of helper T lymphocytes.

Several studies also point to the crucial role of cytotoxic T cells in both production and eradication of infectious diseases and cancer by the immune system (Byrne et al., *J. Immunol.* 51:682 (1984); McMichael et al., *N. Engl. J. Med.* 309:13 (1983)). Recombinant protein vaccines do not reliably induce CTL responses, and the use of otherwise immunogenic vaccines consisting of attenuated pathogens in humans is hampered, in the case of several important diseases, by overriding safety concerns. In the case of diseases such as HIV, HBV, HCV, and malaria, it appears desirable not only to induce a vigorous CTL response, but also to focus the response against highly conserved epitopes in order to prevent escape by mutation and overcome variable vaccine efficacy against different isolates of the target pathogen.

Induction of a broad response directed simultaneously against multiple epitopes also appears to be crucial for development of efficacious vaccines. HIV infection is perhaps the best example where an infected host may benefit from a multispecific response. Rapid progression of HIV infection has been reported in cases where a narrowly focused CTL response is induced whereas nonprogressors tend to show a broader specificity of CTLs (Goulder et al., *Nat. Med.* 3:212 (1997); Borrow et al., *Nat. Med.* 3:205 (1997)). The highly variable nature of HIV CTL epitopes resulting from a highly mutating genome and selection by CTL responses directed against only a single or few epitopes also supports the need for broad epitope CTL responses (McMichael et al., *Annu. Rev. Immunol.* 15:271 (1997)).

One potential approach to induce multispecific responses against conserved epitopes is immunization with a minigene plasmid encoding the epitopes in a string-of-beads fashion. Induction of CTL, HTL, and B cell responses in mice by minigene plasmids have been described by several laboratories using constructs encoding as many as 11 epitopes (An et al., *J. Virol.* 71:2292 (1997); Thomson et al., *J. Immunol.* 157:822 (1996); Whitton et al., *J. Virol.* 67:348 (1993); Hanke et al., *Vaccine* 16:426 (1998); Vitiello et al., *Eur. J. Immunol.* 27:671–678 (1997)). Minigenes have been delivered in vivo by infection with recombinant adenovirus or vaccinia, or by injection of purified DNA via the intramuscular or intradermal route (Thomson et al., *J. Immunol:* 160:1717 (1998); Toes et al., *Proc. Natl. Acad. Sci. USA* 94:14660 (1997)).

Successful development of minigene DNA vaccines for human use will require addressing certain fundamental questions dealing with epitope MHC affinity, optimization of constructs for maximum in vivo immunogenicity, and development of assays for testing in vivo potency of multi-epitope minigene constructs. Regarding MHC binding affinity of epitopes, it is not currently known whether both high and low affinity epitopes can be included within a single minigene construct, and what ranges of peptide affinity are permissible for CTL induction in vivo. This is especially important because dominant epitopes can vary in their affinity and because it might be important to be able to deliver mixtures of dominant and subdominant epitopes that are characterized by high and low MHC binding affinities.

With respect to minigene construct optimization for maximum immunogenicity in vivo, conflicting data exists regarding whether the exact position of the epitopes in a given construct or the presence of flanking regions, helper T cell epitopes, and signal sequences might be crucial for CTL induction (Del Val et al., *Cell* 66:1145 (1991); Bergmann et al., *J. Virol.* 68:5306 (1994); Thomson et al., *Proc. Natl. Acad. Sci. USA* 92:5845 (1995); Shirai et al., *J. Infect. Dis.* 173:24 (1996); Rahemtulla et al., *Nature* 353:180 (1991);

Jennings et al., *Cell. Immunol.* 133:234 (1991); Anderson et al., *J. Exp. Med.* 174:489 (1991); Uger et al., *J. Immunol.* 158:685 (1997)). Finally, regarding development of assays that allow testing of human vaccine candidates, it should be noted that, to date, all in vivo immunogenicity data of multi-epitope minigene plasmids have been performed with murine class I MHC-restricted epitopes. It would be advantageous to be able to test the in vivo immunogenicity of minigenes containing human CTL epitopes in a convenient animal model system.

Thus, there exists a need to develop methods to effectively deliver a variety of HTL (helper T lymphocyte) and CTL (cytotoxic T lymphocyte) antigens to stimulate an immune response. The present invention satisfies this need and provides related advantages as well.

SUMMARY OF THE INVENTION

The invention therefore provides expression vectors encoding two or more HTL epitopes fused to a MHC class II targeting sequence, as well as expression vectors encoding a CTL epitope and a universal HTL epitope fused to an MHC class I targeting sequence. The HTL epitope can be a universal HTL epitope (also referred to as a universal MHC class II epitope). The invention also provides expression vectors encoding two or more HTL epitopes fused to a MHC class II targeting sequence and encoding one or more CTL epitopes. The invention additionally provides methods of stimulating an immune response by administering an expression vector of the invention in vivo, as well as methods of assaying the human immunogenicity of a human T cell peptide epitope in vivo in a non-human mammal.

In one aspect, the present invention provides an expression vector comprising a promoter operably linked to a first nucleotide sequence encoding a major histocompatibility (MHC) targeting sequence fused to a second nucleotide sequence encoding two or more heterologous peptide epitopes, wherein the heterologous peptide epitopes comprise two HTL peptide epitopes or a CTL peptide epitope and a universal HTL peptide epitope.

In another aspect, the present invention provides a method of inducing an immune response in vivo comprising administering to a mammalian subject an expression vector comprising a promoter operably linked to a first nucleotide sequence encoding a major histocompatibility (MHC) targeting sequence fused to a second nucleotide sequence encoding two or more heterologous peptide epitopes, wherein the heterologous peptide epitopes comprise two HTL peptide epitopes or a CTL peptide epitope and a universal HTL peptide epitope.

In another aspect, the present invention provides a method of inducing an immune response in vivo comprising administering to a mammalian subject an expression vector comprising a promoter operably linked to a first nucleotide sequence encoding a major histocompatibility (MHC) targeting sequence fused to a second nucleotide sequence encoding a heterologous human HTL peptide epitope.

In another aspect, the present invention provides a method of assaying the human immunogenicity of a human T cell peptide epitope in vivo in a non-human mammal, comprising the step of administering to the non-human mammal an expression vector comprising a promoter operably linked to a first nucleotide sequence encoding a heterologous human CTL or HTL peptide epitope.

In one embodiment, the heterologous peptide epitopes comprise two or more heterologous HTL peptide epitopes. In another embodiment, the heterologous peptide epitopes comprise a CTL peptide epitope and a universal HTL peptide epitope. In another embodiment, the heterologous peptide epitopes further comprise one to two or more heterologous CTL peptide epitopes. In another embodiment, the expression vector comprises both HTL and CTL peptide epitopes.

In one embodiment, one of the HTL peptide epitopes is a universal HTL epitope. In another embodiment, the universal HTL epitope is a pan DR epitope. In another embodiment, the pan DR epitope has the sequence Ala-LysPheValAlaAlaTrpThrLeuLysAlaAlaAla (SEQ ID NO:52)

In one embodiment, the peptide epitopes are hepatitis B virus epitopes, hepatitis C virus epitopes, human immunodeficiency virus epitopes, human papilloma virus epitopes, MAGE epitopes, PSA epitopes, PSM epitopes, PAP epitopes, p53 epitopes, CEA epitopes, Her2/neu epitopes, or Plasmodium epitopes. In another embodiment, the peptide epitopes each have a sequence selected from the group consisting of the peptides depicted in Tables 1–8. In another embodiment, at least one of the peptide epitopes is an analog of a peptide depicted in Tables 1–8.

In one embodiment, the MHC targeting sequence comprises a region of a polypeptide selected from the group consisting of the Ii protein, LAMP-I, HLS-DM, HLA-DO, H2-DO, influenza matrix protein, hepatitis B surface antigen, hepatitis B virus core antigen, Ty particle, Ig-α protein, Ig-β protein, and Ig kappa chain signal sequence.

In one embodiment, the expression vector further comprises a second promoter sequence operably linked to a third nucleotide sequence encoding one or more heterologous HTL or CTL peptide epitopes. In another embodiment, the CTL peptide epitope comprises a structural motif for an HLA supertype, whereby the peptide CTL epitope binds to two or more members of the supertype with an affinity of greater that 500 nM. In another embodiment, the CTL peptide epitopes have structural motifs that provide binding affinity for more than one HLA allele supertype.

In one embodiment, the non-human mammal is a transgenic mouse that expresses a human HLA allele. In another embodiment, the human HLA allele is selected from the group consisting of AI I and A2. 1. In another embodiment, the non-human mammal is a macaque that expresses a human HLA allele.

BRIEF DESCRIPTION OF THE DRAWINGS

FIG. 1 shows the nucleotide and amino acid sequences (SEQ ID NOS: 1 and 2, respectively) of the IiPADRE construct encoding a fusion of the murine Ii gene with a pan DR epitope sequence substituted for the CLIP sequence of the Ii protein.

FIG. 2 shows the nucleotide and amino acid sequences (SEQ ID NOS:3 and 4, respectively) of the I80T construct encoding a fusion of the cytoplasmic domain, the transmembrane domain and part of the luminal domain of the Ii protein fused to multiple MHC class II epitopes.

FIG. 3 shows the nucleotide and amino acid sequences (SEQ ID NOS:5 and 6, respectively) of the IiThfull construct encoding a fusion of the cytoplasmic domain, transmembrane domain and a portion of the luminal domain of the Ii protein fused to multiple T helper epitopes and amino acid residues 101 to 215 of the Ii protein, which encodes the trimerization region of the Ii protein.

FIG. 4 shows the nucleotide and amino acid sequences (SEQ ID NOS:7 and 8, respectively) of the KappaLAMP-Th construct encoding a fusion of the murine immunoglobulin kappa signal sequence fused to multiple T helper epitopes and the transmembrane and cytoplasmic domains of LAMP-1.

FIG. 5 shows the nucleotide and amino acid sequences (SEQ ID NOS:9 and 10, respectively) of the H2M-Th construct encoding a fusion of the signal sequence of H2-M fused to multiple MHC class II epitopes and the transmembrane and cytoplasmic domains of H2-M.

FIG. 6 shows the nucleotide and amino acid sequences (SEQ ID NOS:11 and 12, respectively) of the H2O-Th construct encoding a fusion of the signal sequence of H2-DO fused to multiple MHC class II epitopes and the transmembrane and cytoplasmic domains of H2-DO.

FIG. 7 shows the nucleotide and amino acid sequences (SEQ ID NOS:13 and 14, respectively) of the PADRE-Influenza matrix construct encoding a fusion of a pan DR epitope sequence fused to the amino-terminus of influenza matrix protein.

FIG. 8 shows the nucleotide and amino acid sequences (SEQ ID NOS:15 and 16, respectively) of the PADRE-HBV-s construct encoding a fusion of a pan DR epitope sequence fused to the amino-terminus of hepatitis B virus surface antigen.

FIG. 9 shows the nucleotide and amino acid sequences (SEQ ID NOS:17 and 18, respectively) of the Ig-alphaTh construct encoding a fusion of the signal sequence of the Ig-a protein fused to multiple MHC class II epitopes and the transmembrane and cytoplasmic domains of the Ig-α protein.

FIG. 10 shows the nucleotide and amino acid sequences (SEQ ID NOS:19 and 20, respectively) of the Ig-betaTh construct encoding a fusion of the signal sequence of the Ig-β protein fused to multiple MHC class II epitopes and the transmembrane and cytoplasmic domains of the Ig-β protein.

FIG. 11 shows the nucleotide and amino acid sequences (SEQ ID NOS:21 and 22, respectively) of the SigTh construct encoding a fusion of the signal sequence of the kappa immunoglobulin fused to multiple MHC class II epitopes.

FIG. 12 shows the nucleotide and amino acid sequences (SEQ ID NOS:23 and 24, respectively) of human HLA-DR, the invariant chain (Ii) protein.

FIG. 13 shows the nucleotide and amino acid sequences (SEQ ID NOS:25 and 26, respectively) of human lysosomal membrane glycoprotein-1 (LAMP-1).

FIG. 14 shows the nucleotide and amino acid sequences (SEQ ID NOS:27 and 28, respectively) of human HLA-DMB.

FIG. 15 shows the nucleotide and amino acid sequences (SEQ ID NOS:29 and 30, respectively) of human HLA-DO beta.

FIG. 16 shows the nucleotide and amino acid sequences (SEQ ID NOS:31 and 32, respectively) of the human MB-1 Ig-α.

FIG. 17 shows the nucleotide and amino acid sequences (SEQ ID NOS:33 and 34, respectively) of human Ig-β protein.

FIG. 19 shows the nucleotide sequence of the vector pEP2 (SEQ ID NO:35).

FIG. 20 shows the nucleotide and amino acid sequences of the vector pMIN.0 (SEQ ID NO:36 and 37, respectively).

FIG. 21 shows the nucleotide and amino acid sequences of the vector pMIN.0 (SEQ ID NO:38 and 39, respectively).

FIG. 24. Summary of modified minigene constructs used to address variables critical for in vivo immunogenicity. The following modifications were incorporated into the prototype pMin. 1 construct; A, deletion of PADRE HTL epitope; B, incorporation of the native HBV Pol 551 epitope that contains an alanine in position 9; C, deletion of the Ig kappa signal sequence; and D, switching position of the HBV Env 335 and HBV Pol 455 epitopes.

FIG. 25. Examination of variables that may influence pMin. 1 immunogenicity. In vivo CTL-inducing activity of pMin.1 is compared to modified constructs. For ease of comparison, the CTL response induced by each of the modified DNA minigene constructs (shaded bars) is compared separately in each of the four panels to the response induced by the prototype pMin.1 construct (solid bars). The geometric mean response of CTL-positive cultures from two to five independent experiments are shown. Numbers shown with each bar indicate the number of positive cultures/total number tested for that particular epitope. The ratio of positive cultures/total tested for the pMin. 1 group is shown in panel A and is the same for the remaining Figure panels (see Example V, Materials and Methods, in vitro CTL cultures, for the definition of a positive CTL culture). Theradigm responses were obtained by immunizing animals with the lipopeptide and stimulating and testing splenocyte cultures with the HBV Core 18-27 peptide.

DEFINITIONS

Figure 18:
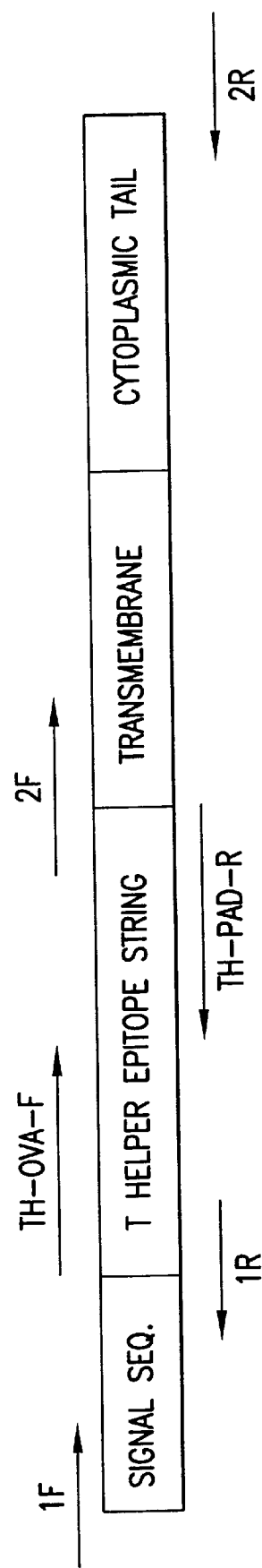
FIG. 18 shows a schematic diagram depicting the method of generating some of the constructs encoding a MHC class II targeting sequence fused to multiple MHC class II epitopes.
Figure 22A:
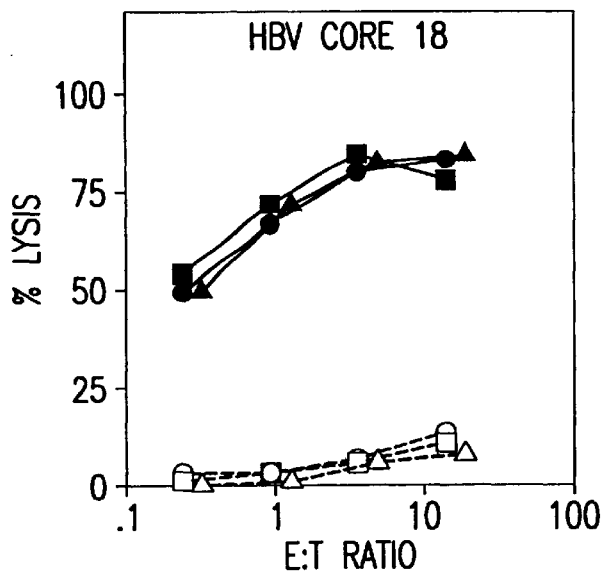
FIG. 22. Representative CTL responses in HLA-A2.1/$K^b$-H-$2^{bxs}$ mice immunized with pMin.1 DNA. Splenocytes from primed animals were cultured in triplicate flasks and stimulated twice in vitro with each peptide epitope. Cytotoxicity of each culture was assayed in a $^{51}$Cr release assay against Jurkat-A2.1/$K^b$ target cells in the presence (filled symbols, solid lines) or absence (open symbols, dotted lines) of peptide. Each symbol represents the response of a single culture.
Figure 22B:
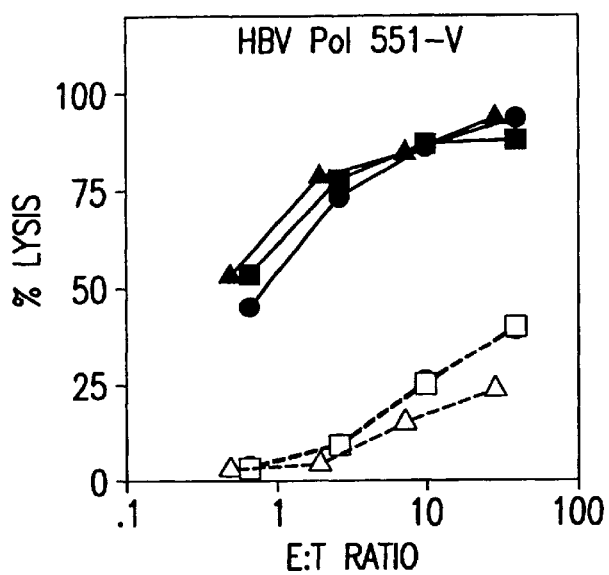
Figure 22C:
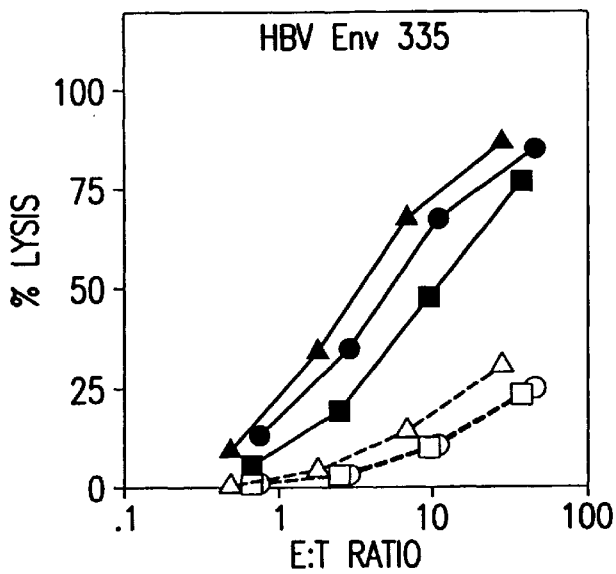
Figure 22D:
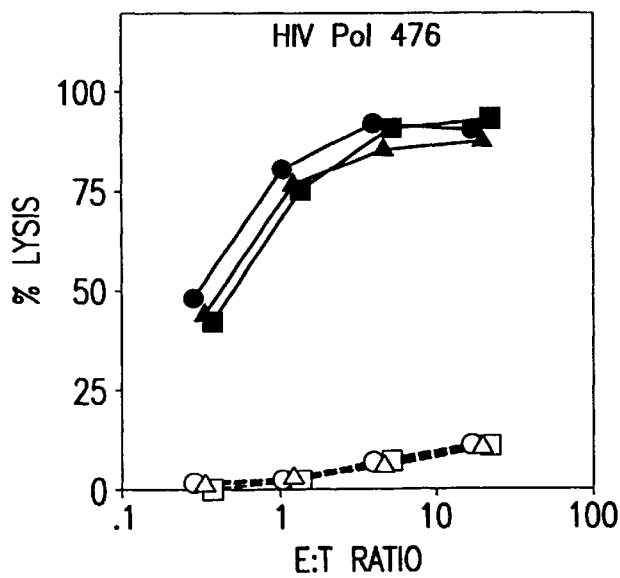
Figure 22E:
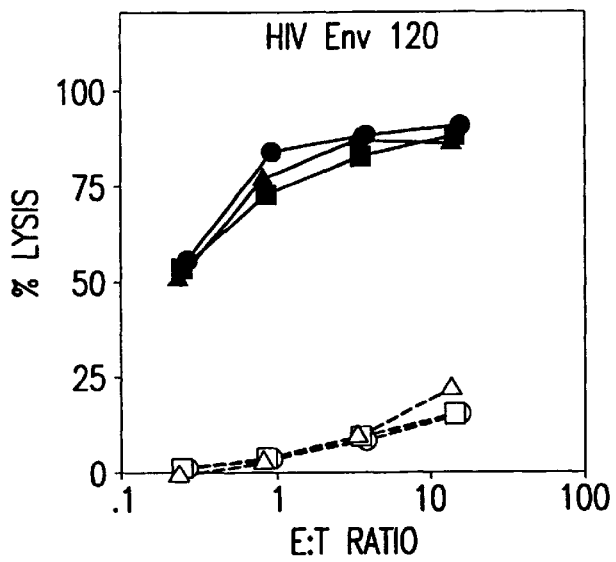
Figure 22F:
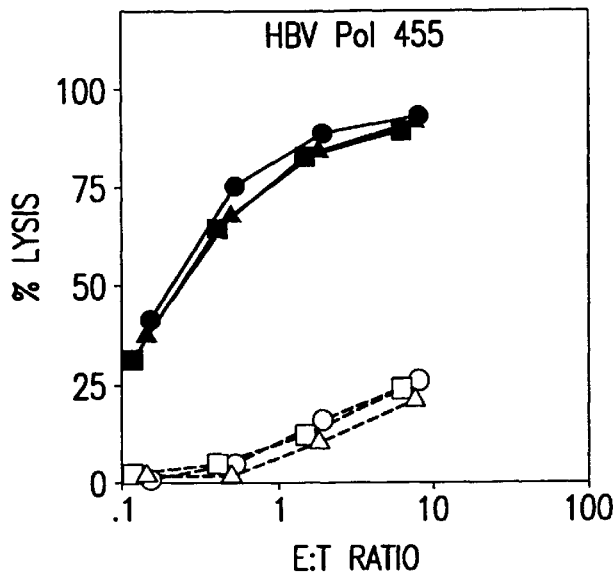

An "HTL" peptide epitopeor an "MHC II epitope" is an MHC class II restricted epitope, i.e., one that is bound by an MHC class II molecule.

A "CTL" peptide epitope or an "MHC I epitope" is an MHC class I restricted epitope, i.e., one that is bound by an MHC class I molecule.

An "MHC targeting sequence" refers to a peptide sequence that targets a polypeptide, e.g., comprising a peptide epitope, to a cytosolic pathway (e.g., an MHC class I antigen processing pathway), en endoplasmic reticulum pathwasy, or an endocytic pathway (e.g., an MHC class II antigen processing pathway).

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature, e.g., a fusion polypeptide comprising subsequence from different polypeptides, peptide epitopes from the same polypeptide that are not naturally in an adjacent position, or repeats of a single peptide epitope.

As used herein, the term "universal MHC class II epitope" or a "universal HTL epitope" refers to a MHC class II peptide epitope that binds to gene products of multiple MHC class II alleles. For example, the DR, DP and DQ alleles are human MHC II alleles. Generally, a unique set of peptides binds to a particular gene product of a MHC class II allele. In contrast, a universal MHC class II epitope is able to bind to gene products of multiple MHC class II alleles. A universal MHC class II epitope binds to 2 or more MHC class II alleles, generally 3 or more MHC class II alleles, and particularly 5 or more MHC class II alleles. Thus, the presence of a universal MHC class II epitope in an expression vector is advantageous in that it functions to increase the number of allelic MHC class II molecules that can bind to the peptide and, consequently, the number of Helper T lymphocytes that are activated.

Universal MHC class II epitopes are well known in the art and include, for example, epitopes such as the "pan DR epitopes," also referred to as "PADRE" (Alexander et al., *Immunity* 1:751–761 (1994); WO 95/07707, U.S. Ser. No. 60/036,713, U.S. Ser. No. 60/037,432, PCT/US98/01373, 09/009,953, and U.S. Ser. No. 60/087,192 each of which is incorporated herein by reference). A "pan DR binding peptide" or a "PADRE" peptide of the invention is a peptide capable of binding at least about 7 different DR molecules, preferably 7 of the 12 most common DR molecules, most preferably 9 of the 12 most common DR molecules (DR1, 2w2b, 2w2a, 3, 4w4, 4w14, 5, 7, 52a, 52b, 52c, and 53), alternatively, 50% of a panel of DR molecules representative of greater than or equal to 75% of the human population, preferably greater than or equal to 80% of the human population. Pan DR epitopes can bind to a number of DR alleles and are strongly immunogenic for T cells. For example, pan DR epitopes were found to be more effective at inducing an immune response than natural MHC class II epitopes (Alexander, supra). An example of a PADRE epitope is the peptide AlaLysPheValAlaAlaTrpThrLeuLysAlaAlaAla (SEQ ID NO:52)

With regard to a particular amino acid sequence, an "epitope" is a set of amino acid residues which is involved in recognition by a particular immunoglobulin, or in the context of T cells, those residues necessary for recognition by T cell receptor proteins and/or Major Histocompatibility Complex (MHC) receptors. In an immune system setting, in vivo or in vitro, an epitope is the collective features of a molecule, such as primary, secondary and tertiary peptide structure, and charge, that together form a site recognized by an immunoglobulin, T cell receptor or HLA molecule. Throughout this disclosure epitope and peptide are often used interchangeably. It is to be appreciated, however, that isolated or purified protein or peptide molecules larger than and comprising an epitope of the invention are still within the bounds of the invention.

As used herein, "high affinity" with respect to HLA class I molecules is defined as binding with an IC50 (or $K_D$) of less than 50 nM. "Intermediate affinity" is binding with an IC50 (or $K_D$) of between about 50 and about 500 nM. "High affinity" with respect to binding to HLA class II molecules is defined as binding with an $K_D$ of less than 100 nM. "Intermediate affinity" is binding with a $K_D$ of between about 100 and about 1000 nM. Assays for determining binding are described in detail, e.g., in PCT publications WO 94/20127 and WO 94/03205. Alternatively, binding is expressed relative to a reference peptide. As a particular assay becomes more, or less, sensitive, the IC50s of the peptides tested may change somewhat. However, the binding relative to the reference peptide will not significantly change. For example, in an assay run under conditions such that the IC50 of the reference peptide increases 10-fold, the IC50 values of the test peptides will also shift approximately 10-fold. Therefore, to avoid ambiguities, the assessment of whether a peptide is a good, intermediate, weak, or negative binder is generally based on its IC50, relative to the IC50 of a standard peptide. Throughout this disclosure, results are expressed in terms of "IC50s." IC50 is the concentration of peptide in a binding assay at which 50% inhibition of binding of a reference peptide is observed. Given the conditions in which the assays are run (i.e., limiting HLA proteins and labeled peptide concentrations), these values approximate KD values. It should be noted that IC50 values can change, often dramatically, if the assay conditions are varied, and depending on the particular reagents used (e.g., HLA preparation, etc.). For example, excessive concentrations of HLA molecules will increase the apparent measured IC50 of a given ligand.

The terms "identical" or percent "identity," in the context of two or more peptide sequences, refer to two or more sequences or subsequences that are the same or have a specified percentage of amino acid residues that are the same, when compared and aligned for maximum correspondence over a comparison window, as measured using a sequence comparison algorithms using default program parameters or by manual alignment and visual inspection.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment.

"Major histocompatibility complex" or "MHC" is a cluster of genes that plays a role in control of the cellular interactions responsible for physiologic immune responses. In humans, the MHC complex is also known as the HLA complex. For a detailed description of the MHC and HLA complexes, see Paul, *Fundamental Immunology* (3rd ed. 1993).

"Human leukocyte antigen" or "HLA" is a human class I or class II major histocompatibility complex (MHC) protein (see, e.g., Stites, et al., *Immunology,* (8th ed., 1994).

An "HLA supertype or family", as used herein, describes sets of HLA molecules grouped on the basis of shared peptide-binding specificities. HLA class I molecules that share somewhat similar binding affinity for peptides bearing certain amino acid motifs are grouped into HLA supertypes. The terms HLA superfamily, HLA supertype family, HLA family, and HLA xx-like supertype molecules (where xx denotes a particular HLA type), are synonyms.

The term "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs are typically different for each protein encoded by each human HLA allele and differ in the pattern of the primary and secondary anchor residues.

A "supermotif" is a peptide binding specificity shared by HLA molecules encoded by two or more HLA alleles. Thus, a preferably is recognized with high or intermediate affinity (as defined herein) by two or more HLA antigens.

"Cross-reactive binding" indicates that a peptide is bound by more than one HLA molecule; a synonym is degenerate binding.

The term "peptide" is used interchangeably with "oligopeptide" in the present specification to designate a series of residues, typically L-amino acids, connected one to the other, typically by peptide bonds between the α-amino and carboxyl groups of adjacent amino acids. The preferred CTL-inducing oligopeptides of the invention are 13 residues or less in length and usually consist of between about 8 and about 11 residues, preferably 9 or 10 residues. The preferred HTL-inducing oligopeptides are less than about 50 residues in length and usually consist of between about 6 and about 30 residues, more usually between about 12 and 25, and often between about 15 and 20 residues.

An "immunogenic peptide" or "peptide epitope" is a peptide which comprises an allele-specific motif or supermotif such that the peptide will bind an HLA molecule and induce a CTL and/or HTL response. Thus, immunogenic peptides of the invention are capable of binding to an appropriate HLA molecule and thereafter inducing a cytotoxic T cell response, or a helper T cell response, to the antigen from which the immunogenic peptide is derived.

A "protective immune response" refers to a CTL and/or an HTL response to an antigen derived from an infectious agent or a tumor antigen, which prevents or at least partially arrests disease symptoms or progression. The immune response may also include an antibody response which has been facilitated by the stimulation of helper T cells.

The term "residue" refers to an amino acid or amino acid mimetic incorporated into an oligopeptide by an amide bond or amide bond mimetic.

"Synthetic peptide" refers to a peptide that is not naturally occurring, but is man-made using such methods as chemical synthesis or recombinant DNA technology.

The nomenclature used to describe peptide compounds follows the conventional practice wherein the amino group is presented to the left (the N-terminus) and the carboxyl group to the right (the C-terminus) of each amino acid residue. When amino acid residue positions are referred to in a peptide epitope they are numbered in an amino to carboxyl direction with position one being the position closest to the amino terminal end of the epitope, or the peptide or protein of which it may be a part. In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three letter or single letter designations. The L-form of an amino acid residue is represented by a capital single letter or a capital first letter of a three-letter symbol, and the D-form for those amino acids having D-forms is represented by a lower case single letter or a lower case three letter symbol. Glycine has no asymmetric carbon atom and is simply referred to as "Gly" or G.

As used herein, the term "expression vector" is intended to refer to a nucleic acid molecule capable of expressing an antigen of interest such as a MHC class I or class II epitope in an appropriate target cell. An expression vector can be, for example, a plasmid or virus, including DNA or RNA viruses. The expression vector contains such a promoter element to express an antigen of interest in the appropriate cell or tissue in order to stimulate a desired immune response.

DETAILED DESCRIPTION OF THE INVENTION

Cytotoxic T lymphocytes (CTLs) and helper T lymphocytes (HTLs) are critical for immunity against infectious pathogens; such as viruses, bacteria, and protozoa; tumor cells; autoimmunne diseases and the like. The present invention provides minigenes that encode peptide epitopes which induce a CTL and/or HTL response. The minigenes of the invention also include an MHC targeting sequence. A variety of minigenes encoding different epitopes can be tested for immunogenicity using an HLA transgenic mouse. The epitopes are typically a combination of at least two or more HTL epitopes, or a CTL epitope plus a universal HTL epitope, and optinally include additional HTl and/or CTL epitopes. Two, three, four, five, six, seven, eight, nine, ten, twenty, thirty, forty or about fifty different epitopes, either HTL and/or CTL, can be included in the minigene, along with the MHC targeting sequence. The epitopes can have different HLA restriction. Epitopes to be tested include those derived from viruses such as HIV, HBV, HCV, HSV, CMV, HPV, and HTLV; cancer antigens such as p53, Her2/Neu, MAGE, PSA, human papilloma virus, and CEA; parasites such as Trypanosoma, Plasmodium, Leishmania, Giardia, Entamoeba; autoimmune diseases such as rheumatoid arthritis, myesthenia gravis, and lupus erythematosus; fungi such as Aspergillus and Candida; and bacteria such as *Escherichia coli*, Staphylococci, Chlamydia, Mycobacteria, Streptococci, and Pseudomonas. The epitopes to be encoded by the minigene are selected and tested using the methods described in published PCT applications WO 93/07421, WO 94/02353, WO 95/01000, WO 97/04451, and WO 97/05348, herein incorporated by reference.

HTL and CTL Epitopes

The expression vectors of the invention encode one or more MHC class II and/or class I epitopes and an MHC targeting sequence. Multiple MHC class II or class I epitopes present in an expression vector can be derived from the same antigen, or the MHC epitopes can be derived from different antigens. For example, an expression vector can contain one or more MHC epitopes that can be derived from two different antigens of the same virus or from two different antigens of different viruses. Furthermore, any MHC epitope can be used in the expression vectors of the invention. For example, any single MHC epitope or a combination of the MHC epitopes shown in Tables 1 to 8 can be used in the expression vectors of the invention. Other peptide epitopes can be selected by one of skill in the art, e.g., by using a computer to select epitopes that contain HLA allele-specific motifs or supermotifs. The expression vectors of the invention can also encode one or more universal MHC class II epitopes, e.g., PADRE (see, e.g., SEQ ID NO:52

Universal MHC class II epitopes can be advantageously combined with other MHC class I and class II epitopes to increase the number of cells that are activated in response to a given antigen and provide broader population coverage of MHC-reactive alleles. Thus, the expression vectors of the invention can encode MHC epitopes specific for an antigen, universal MHC class II epitopes, or a combination of specific MHC epitopes and at least one universal MHC class II epitope.

MHC class I epitopes are generally about 5 to 15 amino acids in length, in particular about 8 to 11 amino acids in length. MHC class II epitopes are generally about 10 to 25 amino acids in length, in particular about 13 to 21 amino acids in length. A MHC class I or II epitope can be derived from any desired antigen of interest. The antigen of interest can be a viral antigen, surface receptor, tumor antigen, oncogene, enzyme, or any pathogen, cell or molecule for which an immune response is desired. Epitopes can be selected based on their ability to bind one or multiple HLA alleles, and can also be selected using the "analog" technique described below.

Targeting Sequences

The expression vectors of the invention encode one or more MHC epitopes operably linked to a MHC targeting sequence. The use of a MHC targeting sequence enhances the immune response to an antigen, relative to delivery of antigen alone, by directing the peptide epitope to the site of MHC molecule assembly and transport to the cell surface, thereby providing an increased number of MHC molecule-peptide epitope complexes available for binding to and activation of T cells.

MHC class I targeting sequences are used in the present invention, e.g., those sequences that target an MHC class I epitope peptide to a cytosolic pathway or to the endoplasmic reticulum (see, e.g., Rammensee et al., *Immunogenetics* 41:178–228 (1995)). For example, the cytosolic pathway processes endogenous antigens that are expressed inside the cell. Although not wishing to be bound by any particular theory, cytosolic proteins are thought to be at least partially degraded by an endopeptidase activity of a proteasome and then transported to the endoplasmic reticulum by the TAP molecule (transporter associated with processing). In the endoplasmic reticulum, the antigen binds to MHC class I molecules. Endoplasmic reticulum signal sequences bypass the cytosolic processing pathway and directly target endogenous antigens to the endoplasmic reticulum, where proteolytic degradation into peptide fragments occurs. Such MHC class I targeting sequences are well known in the art, and include, e.g., signal sequences such as those from Ig kappa ,tissue plasminogen activator or insulin. A preferred signal peptide is the human Ig kappa chain sequence. Endoplasmic reticulum signal sequences can also be used to target MHC class II epitopes to the endoplasmic reticulum, the site of MHC class I molecule assembly.

MHC class II targeting sequences are also used in the invention, e.g., those that target a peptide to the endocytic pathway. These targeting sequences typically direct extracellular antigens to enter the endocytic pathway, which results in the antigen being transferred to the lysosomal compartment where the antigen is proteolytically cleaved into antigen peptides for binding to MHC class II molecules. As with the normal processing of exogenous antigen, a sequence that directs a MHC class II epitope to the endosomes of the endocytic pathway and/or subsequently to lysosomes, where the MHC class II epitope can bind to a MHC class II molecule, is a MHC class II targeting sequence. For example, group of MHC class II targeting sequences useful in the invention are lysosomal targeting sequences, which localize polypeptides to lysosomes. Since MHC class II molecules typically bind to antigen peptides derived from proteolytic processing of endocytosed antigens in lysosomes, a lysosomal targeting sequence can function as a MHC class II targeting sequence. Lysosomal targeting sequences are well known in the art and include sequences found in the lysosomal proteins LAMP-1 and LAMP-2 as described by August et al. (U.S. Pat. No. 5,633,234, issued May 27, 1997), which is incorporated herein by reference.

Other lysosomal proteins that contain lysosomal targeting sequences include HLA-DM. HLA-DM is an endosomal/lysosomal protein that functions in facilitating binding of antigen peptides to MHC class II molecules. Since it is located in the lysosome, HLA-DM has a lysosomal targeting sequence that can function as a MHC class II molecule targeting sequence (Copier et al., *J. Immunol.* 157:1017–1027 (1996), which is incorporated herein by reference).

The resident lysosomal protein HLA-DO can also function as a lysosomal targeting sequence. In contrast to the above described resident lysosomal proteins LAMP-1 and HLA-DM, which encode specific Tyr-containing motifs that target proteins to lysosomes, HLA-DO is targeted to lysosomes by association with HLA-DM (Liljedahl et al., *EMBO J.* 15:4817–4824 (1996)), which is incorporated herein by reference. Therefore, the sequences of HLA-DO that cause association with HLA-DM and, consequently, translocation of HLA-DO to lysosomes can be used as MHC class II targeting sequences. Similarly, the murine homolog of HLA-DO, H2-DO, can be used to derive a MHC class II targeting sequence. A MHC class II epitope can be fused to HLA-DO or H2-DO and targeted to lysosomes.

In another example, the cytoplasmic domains of B cell receptor subunits Ig-$\alpha$ and Ig-$\beta$ mediate antigen internalization and increase the efficiency of antigen presentation (Bonnerot et al., *Immunity* 3:335–347 (1995)), which is incorporated herein by reference. Therefore, the cytoplasmic domains of the Ig-$\alpha$ and Ig-$\beta$ proteins can function as MHC class II targeting sequences that target a MHC class II epitope to the endocytic pathway for processing and binding to MHC class II molecules.

Another example of a MHC class II targeting sequence that directs MHC class II epitopes to the endocytic pathway is a sequence that directs polypeptides to be secreted, where the polypeptide can enter the endosomal pathway. These MHC class II targeting sequences that direct polypeptides to be secreted mimic the normal pathway by which exogenous, extracellular antigens are processed into peptides that bind to MHC class II molecules. Any signal sequence that functions to direct a polypeptide through the endoplasmic reticulum and ultimately to be secreted can function as a MHC class II targeting sequence so long as the secreted polypeptide can enter the endosomal/lysosomal pathway and be cleaved into peptides that can bind to MHC class II molecules. An example of such a fusion is shown in FIG. 11, where the signal sequence of kappa immunoglobulin is fused to multiple MHC class II epitopes.

In another example, the Ii protein binds to MHC class II molecules in the endoplasmic reticulum, where it functions to prevent peptides present in the endoplasmic reticulum from binding to the MHC class II molecules. Therefore, fusion of a MHC class II epitope to the Ii protein targets the MHC class II epitope to the endoplasmic reticulum and a MHC class II molecule. For example, the CLIP sequence of the Ii protein can be removed and replaced with a MHC class II epitope sequence so that the MHC class II epitope is directed to the endoplasmic reticulum, where the epitope binds to a MHC class II molecule.

In some cases, antigens themselves can serve as MHC class II or I targeting sequences and can be fused to a universal MHC class II epitope to stimulate an immune response. Although cytoplasmic viral antigens are generally processed and presented as complexes with MHC class I molecules, long-lived cytoplasmic proteins such as the influenza matrix protein can enter the MHC class II molecule processing pathway (Guéguen & Long, Proc. Natl. Acad. Sci. USA 93:14692–14697 (1996)), which is incorporated herein by reference. Therefore, long-lived cytoplasmic proteins can function as a MHC class II targeting sequence. For example, an expression vector encoding influenza matrix protein fused to a universal MHC class II epitope can be advantageously used to target influenza antigen and the universal MHC class II epitope to the MHC class II pathway for stimulating an immune response to influenza.

Other examples of antigens functioning as MHC class II targeting sequences include polypeptides that spontaneously form particles. The polypeptides are secreted from the cell that produces them and spontaneously form particles, which are taken up into an antigen-presenting cell by endocytosis such as receptor-mediated endocytosis or are engulfed by phagocytosis. The particles are proteolytically cleaved into antigen peptides after entering the endosomal/lysosomal pathway.

One such polypeptide that spontaneously forms particles is HBV surface antigen (HBV-S) (Diminsky et al., Vaccine 15:637–647 (1997); Le Borgne et al., Virology 240:304–315 (1998)), each of which is incorporated herein by reference. Another polypeptide that spontaneously forms particles is HBV core antigen (Kuhröber et al., International Immunol. 9:1203–1212 (1997)), which is incorporated herein by reference. Still another polypeptide that spontaneously forms particles is the yeast Ty protein (Weber et al., Vaccine 13:831–834 (1995)), which is incorporated herein by reference. For example, an expression vector containing HBV-S antigen fused to a universal MHC class II epitope can be advantageously used to target HBV-S antigen and the universal MHC class II epitope to the MHC class II pathway for stimulating an immune response to HBV.

Binding Affinity of Peptide Epitopes for HLA Molecules

The large degree of HLA polymorphism is an important factor to be taken into account with the epitope-based approach to vaccine development. To address this factor, epitope selection encompassing identification of peptides capable of binding at high or intermediate affinity to multiple HLA molecules is preferably utilized, most preferably these epitopes bind at high or intermediate affinity to two or more allele specific HLA molecules.

CTL-inducing peptides of interest for vaccine compositions preferably include those that have a binding affinity for class I HLA molecules of less than 500 nM. HTL-inducing peptides preferably include those that have a binding affinity for class II HLA molecules of less than 1000 nM. For example, peptide binding is assessed by testing the capacity of a candidate peptide to bind to a purified HLA molecule in vitro. Peptides exhibiting high or intermediate affinity are then considered for further analysis. Selected peptides are tested on other members of the supertype family. In preferred embodiments, peptides that exhibit cross-reactive binding are then used in vaccines or in cellular screening analyses.

Higher HLA binding affinity is typically correlated with greater immunogenicity. Greater immunogenicity can be manifested in several different ways. Immunogenicity corresponds to whether an immune response is elicited at all, and to the vigor of any particular response, as well as to the extent of a population in which a response is elicited. For example, a peptide might elicit an immune response in a diverse array of the population, yet in no instance produce a vigorous response. In accordance with these principles, close to 90% of high binding peptides have been found to be immunogenic, as contrasted with about 50% of the peptides which bind with intermediate affinity. Moreover, higher binding affinity peptides leads to more vigorous immunogenic responses. As a result, less peptide is required to elicit a similar biological effect if a high affinity binding peptide is used. Thus, in preferred embodiments of the invention, high binding epitopes are particularly useful.

The relationship between binding affinity for HLA class I molecules and immunogenicity of discrete peptide epitopes on bound antigens has been determined for the first time in the art by the present inventors. The correlation between binding affinity and immunogenicity was analyzed in two different experimental approaches (Sette el al., J. Immunol. 153:5586–5592 (1994)). In the first approach, the immunogenicity of potential epitopes ranging in HLA binding affinity over a 10,000-fold range was analyzed in HLA-A*0201 transgenic mice. In the second approach, the antigenicity of approximately 100 different hepatitis B virus (HBV)-derived potential epitopes, all carrying A*0201 binding motifs, was assessed by using PBL (peripheral blood lymphocytes) from acute hepatitis patients. Pursuant to these approaches, it was determined that an affinity threshold of approximately 500 nM (preferably 50 nM or less) determines the capacity of a peptide epitope to elicit a CTL response. These data are true for class I binding affinity measurements for naturally processed peptides and for synthesized T cell epitopes. These data also indicate the important role of determinant selection in the shaping of T cell responses (see, e.g., Schaeffer et al. Proc. Natl. Acad. Sci. USA 86:4649–4653, 1989).

An affinity threshold associated with immunogenicity in the context of HLA class II DR molecules has also been delineated (see, e.g., Southwood et al. J. Immunology 160:3363–3373 (1998), and U.S. Ser. No. 60/087192, filed May 29, 1998). In order to define a biologically significant threshold of DR binding affinity, a database of the binding affinities of 32 DR-restricted epitopes for their restricting element (i.e., the HLA molecule that binds the motif) was compiled. In approximately half of the cases (15 of 32 epitopes), DR restriction was associated with high binding affinities, i.e. binding affinities of less than 100 nM. In the other half of the cases (16 of 32), DR restriction was associated with intermediate affinity (binding affinities in the 100–1000 nM range). In only one of 32 cases was DR restriction associated with an IC50 of 1000 nM or greater. Thus, 1000 nM can be defined as an affinity threshold associated with immunogenicity in the context of DR molecules.

Peptide Epitope Binding Motifs and Supermotifs

In the past few years evidence has accumulated to demonstrate that a large fraction of HLA class I and class II molecules can be classified into a relatively few supertypes, each characterized by largely overlapping peptide binding repertoires, and consensus structures of the main peptide binding pockets.

For HLA molecule pocket analyses, the residues comprising the B and F pockets of HLA class I molecules as described in crystallographic studies were analyzed (Guo et al., *Nature* 360:364 (1992); Saper et al., *J. Mol. Biol.* 219:277 (1991); Madden et al., *Cell* 75:693 (1993); Parham et al., *Immunol. Rev.* 143:141 (1995)). In these analyses, residues 9, 45, 63, 66, 67, 70, and 99 were considered to make up the B pocket; and the B pocket was deemed to determine the specificity for the amino acid residue in the second position of peptide ligands. Similarly, residues 77, 80, 81, and 116 were considered to determine the specificity of the F pocket; the F pocket was deemed to determine the specificity for the C-terminal residue of a peptide ligand bound by the HLA class I molecule.

Through the study of single amino acid substituted antigen analogs and the sequencing of endogenously bound, naturally processed peptides, critical residues required for allele-specific binding to HLA molecules have been identified. The presence of these residues correlates with binding affinity for HLA molecules. The identification of motifs and/or supermotifs that correlate with high and intermediate affinity binding is an important issue with respect to the identification of immunogenic peptide epitopes for the inclusion in a vaccine. Kast et al. (*J. Immunol.* 152:3904–3912 (1994)) have shown that motif-bearing peptides account for 90% of the epitopes that bind to allele-specific HLA class I molecules. In this study all possible peptides of 9 amino acids in length and overlapping by eight amino acids (240 peptides), which cover the entire sequence of the E6 and E7 proteins of human papillomavirus type 16, were evaluated for binding to five allele-specific HLA molecules that are expressed at high frequency among different ethnic groups. This unbiased set of peptides allowed an evaluation of the predictive value of HLA class I motifs. From the set of 240 peptides, 22 peptides were identified that bound to an allele-specific HLA molecules with high or intermediate affinity. Of these 22 peptides, 20, (i.e., 91%), were motif-bearing. Thus, this study demonstrates the value of motifs for the identification of peptide epitopes for inclusion in a vaccine: application of motif-based identification techniques eliminates screening of 90% of the potential epitopes in a target antigen protein sequence.

Peptides of the present invention may also include epitopes that bind to MHC class II DR molecules. There is a significant difference between class I and class II HLA molecules. This difference corresponds to the fact that, although a stringent size restriction and motif position relative to the binding pocket exists for peptides that bind to class I molecules, a greater degree of heterogeneity in both size and binding frame position of the motif, relative to the N and C termini of the peptide, exists for class II peptide ligands.

This increased heterogeneity of HLA class II peptide ligands is due to the structure of the binding groove of the HLA class II molecule which, unlike its class I counterpart, is open at both ends. Crystallographic analysis of HLA class II DRB*0101-peptide complexes showed that the residues occupying position I and position 6 of peptides complexed with DRB*0101 engage two complementary pockets on the DRBa*0101 molecules, with the P1 position corresponding to the most crucial anchor residue and the deepest hydrophobic pocket (see, e.g., Madden, *Ann. Rev. Immunol.* 13:587 (1995)). Other studies have also pointed to the P6 position as a crucial anchor residue for binding to various other DR molecules.

Thus, peptides of the present invention are identified by any one of several HLA class I or II -specific amino acid motifs (see, e.g., Tables I–III of U.S. Ser. No. 09/226,775, and 09/239,043, herein incorporated by reference in their entirety). If the presence of the motif corresponds to the ability to bind several allele-specific HLA antigens it is referred to as a supernotif. The allele-specific HLA molecules that bind to peptides that possess a particular amino acid supermotif are collectively referred to as an HLA "supertype."

Immune Response-Stimulating Peptide Analogs

In general, CTL and HTL responses are not directed against all possible epitopes. Rather, they are restricted to a few "immunodominant" determinants (Zinkernagel et al., *Adv. Immunol.* 27:5159 (1979); Bennink et al., *J. Exp. Med.* 168:1935–1939 (1988); Rawle et al., *J. Immunol.* 146:3977–3984 (1991)). It has been recognized that immunodominance (Benacerraf et al., *Science* 175:273–279 (1972)) could be explained by either the ability of a given epitope to selectively bind a particular HLA protein (determinant selection theory) (Vitiello et al., *J. Immunol.* 131:1635 (1983)); Rosenthal et al., *Nature* 267:156–158 (1977)), or being selectively recognized by the existing TCR (T cell receptor) specificity (repertoire theory) (Klein, *Immunology, The Science of Self on self Discrimination*, pp. 270–310 (1982)). It has been demonstrated that additional factors, mostly linked to processing events, can also play a key role in dictating, beyond strict immunogenicity, which of the many potential determinants will be presented as immunodominant (Sercarz et al., *Annu. Rev. Immunol.* 11:729–766 (1993)).

The concept of dominance and subdominance is relevant to immunotherapy of both infectious diseases and cancer. For example, in the course of chronic viral disease, recruitment of subdominant epitopes can be important for successful clearance of the infection, especially if dominant CTL or HTL specificities have been inactivated by functional tolerance, suppression, mutation of viruses and other mechanisms (Franco et al., *Curr. Opin. Immunol.* 7:524–531 (1995)). In the case of cancer and tumor antigens, CTLs recognizing at least some of the highest binding affinity peptides might be functionally inactivated. Lower binding affinity peptides are preferentially recognized at these times, and may therefore be preferred in therapeutic or prophylactic anti-cancer vaccines.

In particular, it has been noted that a significant number of epitopes derived from known non-viral tumor associated antigens (TAA) bind HLA class I with intermediate affinity (IC50 in the 50–500 nM range). For example, it has been found that 8 of 15 known TAA peptides recognized by tumor infiltrating lymphocytes (TIL) or CTL bound in the 50–500 nM range. (These data are in contrast with estimates that 90% of known viral antigens were bound by HLA class I molecules with IC50 of 50 nM or less, while only approximately 10% bound in the 50–500 nM range (Sette et al., *J. Immunol.*, 153:558–5592 (1994)). In the cancer setting this phenomenon is probably due to elimination, or functional inhibition of the CTL recognizing several of the highest binding peptides, presumably because of T cell tolerization events.

Without intending to be bound by theory, it is believed that because T cells to dominant epitopes may have been clonally deleted, selecting subdominant epitopes may allow extant T cells to be recruited, which will then lead to a therapeutic or prophylactic response. However, the binding of HLA molecules to subdominant epitopes is often less vigorous than to dominant ones. Accordingly, there is a need to be able to modulate the binding affinity of particular immunogenic epitopes for one or more HLA molecules, and thereby to modulate the immune response elicited by the peptide, for example to prepare analog peptides which elicit a more vigorous response. This ability would greatly enhance the usefulness of peptide-based vaccines and therapeutic agents.

Thus, although peptides with suitable cross-reactivity among all alleles of a superfamily are identified by the screening procedures described above, cross-reactivity is not always as complete as possible, and in certain cases procedures to further increase cross-reactivity of peptides can be useful; moreover, such procedures can also be used to modify other properties of the peptides such as binding affinity or peptide stability. Having established the general rules that govern cross-reactivity of peptides for HLA alleles within a given motif or supermotif, modification (i.e., analoging) of the structure of peptides of particular interest in order to achieve broader (or otherwise modified) HLA binding capacity can be performed. More specifically, peptides which exhibit the broadest cross-reactivity patterns, can be produced in accordance with the teachings herein. The present concepts related to analog generation are set forth in greater detail in co-pending U.S. Ser. No. 09/226,775.

In brief, the strategy employed utilizes the motifs or supermotifs which correlate with binding to certain HLA class I and II molecules. The motifs or supermotifs are defined by having primary anchors, and in many cases secondary anchors (see Tables I–III of U.S. Ser. No. 09/226, 775). Analog peptides can be created by substituting amino acids residues at primary anchor, secondary anchor, or at primary and secondary anchor positions. Generally, analogs are made for peptides that already bear a motif or supermotif. Preferred secondary anchor residues of supermotifs and motifs that have been defined for HLA class I and class II binding peptides are shown in Tables II and III, respectively, of U.S. Ser. No. 09/226,775.

For a number of the motifs or supermotifs in accordance with the invention, residues are defined which are deleterious to binding to allele-specific HLA molecules or members of HLA supertypes that bind to the respective motif or supermotif (see Tables II and III of U.S. Ser. No. 09/226, 775). Accordingly, removal of such residues that are detrimental to binding can be performed in accordance with the methods described therein. For example, in the case of the A3 supertype, when all peptides that have such deleterious residues are removed from the population of analyzed peptides, the incidence of cross-reactivity increases from 22% to 37% (I., Sidney et al., *Hu. Immunol.* 45:79 (1996)). Thus, one strategy to improve the cross-reactivity of peptides within a given supermotif is simply to delete one or more of the deleterious residues present within a peptide and substitute a small "neutral" residue such as Ala (that may not influence T cell recognition of the peptide). An enhanced likelihood of cross-reactivity is expected if, together with elimination of detrimental residues within a peptide, "preferred" residues associated with high affinity binding to an allele-specific HLA molecule or to multiple HLA molecules within a superfamily are inserted.

To ensure that an analog peptide, when used as a vaccine, actually elicits a CTL response to the native epitope in vivo (or, in the case of class II epitopes, a failure to elicit helper T cells that cross-react with the wild type peptides), the analog peptide may be used to immunize T cells in vitro from individuals of the appropriate HLA allele. Thereafter, the immunized cells' capacity to induce lysis of wild type peptide sensitized target cells is evaluated. In both class I and class II systems it will be desirable to use as targets, cells that have been either infected or transfected with the appropriate genes to establish whether endogenously produced antigen is also recognized by the relevant T cells.

Another embodiment of the invention is to create analogs of weak binding peptides, to thereby ensure adequate numbers of cross-reactive cellular binders. Class I peptides exhibiting binding affinities of 500–50000 nM, and carrying an acceptable but suboptimal primary anchor residue at one or both positions can be "fixed" by substituting preferred anchor residues in accordance with the respective supertype. The analog peptides can then be tested for crossbinding activity.

Another embodiment for generating effective peptide analogs involves the substitution of residues that have an adverse impact on peptide stability or solubility in, e.g., a liquid environment. This substitution may occur at any position of the peptide epitope. For example, a cysteine (C) can be substituted out in favor of gamma-amino butyric acid. Due to its chemical nature, cysteine has the propensity to form disulfide bridges and sufficiently alter the peptide structurally so as to reduce binding capacity. Substituting gamma-amino butyric acid for C not only alleviates this problem, but actually improves binding and crossbinding capability in certain instances (Sette et al, *In: Persistent Viral Infections* (Ahmed & Chen, eds., 1998)). Substitution of cysteine with gamma-amino butyric acid may occur at any residue of a peptide epitope, i.e., at either anchor or non-anchor positions.

Expression Vectors and Construction of a Minigene

The expression vectors of the invention contain at least one promoter element that is capable of expressing a transcription unit encoding the antigen of interest, for example, a MHC class I epitope or a MHC class II epitope and an MHC targeting sequence in the appropriate cells of an organism so that the antigen is expressed and targeted to the appropriate MHC molecule. For example, if the expression vector is administered to a mammal such as a human, a promoter element that functions in a human cell is incorporated into the expression vector. An example of an expression vector useful for expressing the MHC class II epitopes fused to MHC class II targeting sequences and the MHC class I epitopes described herein is the pEP2 vector described in Example IV.

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994); *Oligonucleotide Synthesis: A Practical Approach* (Gait, ed., 1984); Kuijpers, *Nucleic Acids Research* 18(17):5197 (1994); Dueholm, *J. Org. Chem.* 59:5767–5773 (1994); *Methods in Molecular Biology*, volume (Agrawal, ed.); and Tijssen, *Laboratory Techniques in Biochemistry and Molecular Biology—Hybridization with Nucleic Acid Probes*, e.g., Part I, chapter 2 "Overview of principles of hybridization and the strategy of nucleic acid probe assays" (1993)).

The minigenes are comprised of two or many different epitopes (see, e.g., Tables 1–8). The nucleic acid encoding the epitopes are assembled in a minigene according to standard techniques. In general, the nucleic acid sequences encoding minigene epitopes are isolated using amplification techniques with oligonucleotide primers, or are chemically synthesized. Recombinant cloning techniques can also be used when appropriate. Oligonucleotide sequences are selected which either amplify (when using PCR to assemble the minigene) or encode (when using synthetic oligonucleotides to assemble the minigene) the desired epitopes.

Amplification techniques using primers are typically used to amplify and isolate sequences encoding the epitopes of choice from DNA or RNA (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify epitope nucleic acid sequences directly from mRNA, from cDNA, from genomic libraries or cDNA libraries. Restriction endonuclease sites can be incorporated into the primers. Minigenes amplified by the PCR reaction can be purified from agarose gels and cloned into an appropriate vector.

Synthetic oligonucleotides can also be used to construct minigenes. This method is performed using a series of overlapping oligonucleotides, representing both the sense and non-sense strands of the gene. These DNA fragments are then annealed, ligated and cloned. Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The epitopes of the minigene are typically subcloned into an expression vector that contains a strong promoter to direct transcription, as well as other regulatory sequences such as enhancers and polyadenylation sites. Suitable promoters are well known in the art and described, e.g., in Sambrook et al. and Ausubel et al. Eukaryotic expression systems for mammalian cells are well known in the art and are commercially available. Such promoter elements include, for example, cytomegalovirus (CMV), Rous sarcoma virus LTR and SV40.

The expression vector typically contains a transcription unit or expression cassette that contains all the additional elements required for the expression of the minigene in host cells. A typical expression cassette thus contains a promoter operably linked to the minigene and signals required for efficient polyadenylation of the transcript. Additional elements of the cassette may include enhancers and introns with functional splice donor and acceptor sites.

In addition to a promoter sequence, the expression cassette can also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic cells may be used. Expression vectors containing regulatory elements from eukaryotic viruses are typically used in eukaryotic expression vectors, e.g., SV40 vectors, papilloma virus vectors, and vectors derived from Epstein Bar virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells. In one embodiment, the vector pEP2 is used in the present invention.

Other elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Administration In Vivo

The invention also provides methods for stimulating an immune response by administering an expression vector of the invention to an individual. Administration of an expression vector of the invention for stimulating an immune response is advantageous because the expression vectors of the invention target MHC epitopes to MHC molecules, thus increasing the number of CTL and HTL activated by the antigens encoded by the expression vector.

Initially, the expression vectors of the invention are screened in mouse to determine the expression vectors having optimal activity in stimulating a desired immune response. Initial studies are therefore carried out, where possible, with mouse genes of the MHC targeting sequences. Methods of determining the activity of the expression vectors of the invention are well known in the art and include, for example, the uptake of $^3$H-thymidine to measure T cell activation and the release of $^{51}$Cr to measure CTL activity as described below in Examples II and III. Experiments similar to those described in Example IV are performed to determine the expression vectors having activity at stimulating an immune response. The expression vectors having activity are further tested in human. To circumvent potential adverse immunological responses to encoded mouse sequences, the expression vectors having activity are modified so that the MHC class II targeting sequences are derived from human genes. For example, substitution of the analogous regions of the human homologs of genes containing various MHC class II targeting sequences are substituted into the expression vectors of the invention. Examples of such human homologs of genes containing MHC class II targeting sequences are shown in FIGS. 12 to 17. Expression vectors containing human MHC class II targeting sequences, such as those described in Example I below, are tested for activity at stimulating an immune response in human.

The invention also relates to pharmaceutical compositions comprising a pharmaceutically acceptable carrier and an expression vector of the invention. Pharmaceutically acceptable carriers are well known in the art and include aqueous or non-aqueous solutions, suspensions and emulsions, including physiologically buffered saline, alcohol/aqueous solutions or other solvents or vehicles such as glycols, glycerol, oils such as olive oil or injectable organic esters.

A pharmaceutically acceptable carrier can contain physiologically acceptable compounds that act, for example, to stabilize the expression vector or increase the absorption of the expression vector. Such physiologically acceptable compounds include, for example, carbohydrates, such as glucose, sucrose or dextrans, antioxidants such as ascorbic acid or glutathione, chelating agents, low molecular weight polypeptides, antimicrobial agents, inert gases or other stabilizers or excipients. Expression vectors can additionally be complexed with other components such as peptides, polypeptides and carbohydrates. Expression vectors can also be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The invention further relates to methods of administering a pharmaceutical composition comprising an expression vector of the invention to stimulate an immune response. The expression vectors are administered by methods well known in the art as described in Donnelly et al. (*Ann. Rev. Immunol.* 15:617–648 (1997)); Felgner et al. (U.S. Pat. No. 5,580,859, issued Dec. 3, 1996); Felgner (U.S. Pat. No. 5,703,055, issued Dec. 30, 1997); and Carson et al. U.S. Pat. No. 5,679,647, issued Oct. 21, 1997), each of which is incorporated herein by reference. In one embodiment, the minigene is administered as naked nucleic acid.

A pharmaceutical composition comprising an expression vector of the invention can be administered to stimulate an immune response in a subject by various routes including, for example, orally, intravaginally, rectally, or parenterally, such as intravenously, intramuscularly, subcutaneously, intraorbitally, intracapsularly, intraperitoneally, intracisternally or by passive or facilitated absorption through the skin using, for example, a skin patch or transdermal iontophoresis, respectively. Furthermore, the composition can be administered by injection, intubation or topically, the latter of which can be passive, for example, by direct application of an ointment or powder, or active, for example, using a nasal spray or inhalant. An expression vector also can be administered as a topical spray, in which case one component of the composition is an appropriate propellant. The pharmaceutical composition also can be incorporated, if desired, into liposomes, microspheres or other polymer matrices (Felgner et al., U.S. Pat. No. 5,703,055; Gregoriadis, *Liposome Technology*, Vols. I to III (2nd ed. 1993), each of which is incorporated herein by reference). Liposomes, for example, which consist of phospholipids or other lipids, are nontoxic, physiologically acceptable and metabolizable carriers that are relatively simple to make and administer.

The expression vectors of the invention can be delivered to the interstitial spaces of tissues of an animal body (Feigner et al., U.S. Pat. Nos. 5,580,859 and 5,703,055). Administration of expression vectors of the invention to muscle is a particularly effective method of administration, including intradermal and subcutaneous injections and transdermal administration. Transdermal administration, such as by iontophoresis, is also an effective method to deliver expression vectors of the invention to muscle. Epidermal administration of expression vectors of the invention can also be employed. Epidermal administration involves mechanically or chemically irritating the outermost layer of epidermis to stimulate an immune response to the irritant (Carson et al., U.S. Pat. No. 5,679,647).

Other effective methods of administering an expression vector of the invention to stimulate an immune response include mucosal administration (Carson et al., U.S. Pat. No. 5,679,647). For mucosal administration, the most effective method of administration includes intranasal administration of an appropriate aerosol containing the expression vector and a pharmaceutical composition. Suppositories and topical preparations are also effective for delivery of expression vectors to mucosal tissues of genital, vaginal and ocular sites. Additionally, expression vectors can be complexed to particles and administered by a vaccine gun.

The dosage to be administered is dependent on the method of administration and will generally be between about 0.1 $\mu$g up to about 200 $\mu$g. For example, the dosage can be from about 0.05 $\mu$g/kg to about 50 mg/kg, in particular about 0.005–5 mg/kg. An effective dose can be determined, for example, by measuring the immune response after administration of an expression vector. For example, the production of antibodies specific for the MHC class II epitopes or MHC class I epitopes encoded by the expression vector can be measured by methods well known in the art, including ELISA or other immunological assays. In addition, the activation of T helper cells or a CTL response can be measured by methods well known in the art including, for example, the uptake of $^3$H-thymidine to measure T cell activation and the release of $^{51}$Cr to measure CTL activity (see Examples II and III below).

The pharmaceutical compositions comprising an expression vector of the invention can be administered to mammals, particularly humans, for prophylactic or therapeutic purposes. Examples of diseases that can be treated or prevented using the expression vectors of the invention include infection with HBV, HCV, HIV and CMV as well as prostate cancer, renal carcinoma, cervical carcinoma, lymphoma, condyloma acuminatum and acquired immunodeficiency syndrome (AIDS).

In therapeutic applications, the expression vectors of the invention are administered to an individual already suffering from cancer, autoimmune disease or infected with a virus. Those in the incubation phase or acute phase of the disease can be treated with expression vectors of the invention, including those expressing all universal MHC class II epitopes, separately or in conjunction with other treatments, as appropriate.

In therapeutic and prophylactic applications, pharmaceutical compositions comprising expression vectors of the invention are administered to a patient in an amount sufficient to elicit an effective immune response to an antigen and to ameliorate the signs or symptoms of a disease. The amount of expression vector to administer that is sufficient to ameliorate the signs or symptoms of a disease is termed a therapeutically effective dose. The amount of expression vector sufficient to achieve a therapeutically effective dose will depend on the pharmaceutical composition comprising an expression vector of the invention, the manner of administration, the state and severity of the disease being treated, the weight and general state of health of the patient and the judgment of the prescribing physician.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following example is provided by way of illustration only and not by way of limitation. Those of skill in the art will readily recognize a variety of noncritical parameters that could be changed or modified to yield essentially similar results.

Example 1

Construction of Expression Vectors Containing MHC Class II Epitopes

This example shows construction of expression vectors containing MHC class II epitopes that can be used to target antigens to MHC class II molecules.

Expression vectors comprising DNA constructs were prepared using overlapping oligonucleotides, polymerase chain reaction (PCR) and standard molecular biology techniques (Dieffenbach & Dveksler, *PCR Primer: A Laboratory Manual* (1995); Sambrook et al., *Molecular Cloning: A Laboratory Manual* (2nd ed., 1989), each of which is incorporated herein by reference).

To generate full length wild type Ii, the full length invariant chain was amplified, cloned, and sequenced and used in the construction of the three invariant chain constructs. Except where noted, the source of cDNA for all the constructs listed below was Mouse Spleen Marathon-Ready cDNA made from Balb/c males (Clontech; Palo Alto Calif.). The primer pairs were the oligonucleotide GCTAGCGCCGCCACCATGGATGACCAACGCGACCTC (SEQ ID NO:40), which is designated murIi-F and contains an NheI site followed by the consensus Kozak sequence and the 5' end of the Ii cDNA; and the oligonucleotide GGTACCTCACAGGGTGACTTGACCCAG (SEQ ID NO:41), which is designated murIi-R and contains a KpnI site and the 3' end of the Ii coding sequence.

For the PCR reaction, 5 μl of spleen cDNA and 250 nM of each primer were combined in a 100 μl reaction with 0.25 mM each dNTP and 2.5 units of Pfu polymerase in Pfu polymerase buffer containing 10 mM KCl, 10 mM $NM_4)_2SO_4$, 20 mM Tris-chloride, pH 8.75, 2 MM $MgSO_4$, 0.1% TRITON X-100 and 100 μg/ml bovine serum albumin (BSA). A Perkin/Elmer 9600 PCR machine (Perkin Elmer; Foster City Calif.) was used and the cycling conditions were: 1 cycle of 95° C. for 5 minutes, followed by 30 cycles of 95° C. for 15 seconds, 52° C. for 30 seconds, and 72° C. for 1 minute. The PCR reaction was run on a 1% agarose gel, and the 670 base pair product was cut out, purified by spinning through a Millipore Ultrafree-MC filter (Millipore; Bedford Mass.) and cloned into pCR-Blunt from Invitrogen (San Diego, Calif.). Individual clones were screened by sequencing, and a correct clone (named bIi#3) was used as a template for the helper constructs.

DNA constructs containing pan DR epitope sequences and MHC II targeting sequences derived from the Ii protein were prepared. The Ii murine protein has been previously described (Zhu & Jones, *Nucleic Acids Res.* 17:447–448 (1989)), which is incorporated herein by reference. Briefly, the IiPADRE construct contains the full length Ii sequence with PADRE precisely replacing the CLIP region. The DNA construct encodes amino acids 1 through 87 of invariant chain, followed with the 13 amino acid PADRE sequence (SEQ ID NO.52) and the rest of the invariant chain DNA sequence (amino acids 101–215). The construct was amplified in 2 overlapping halves that were joined to produce the final construct. The two primers used to amplify the 5' half were murIi-F and the oligonucleotide CAGGGTCCAGGCAGCCACGAACTTGGCCACAGGTTTGGCAGA (SEQ ID NO:42), which is designated IiPADRE-R. The IiPADRE-R primer includes nucleotides 303–262 of IiPADRE. The 3' half was amplified with the primer GGCTGCCTGGACCCTGAAGGCTGCCGCTATGTCCATGGATAAC (SEQ ID NO:43), which is designated IiPADRE-F and includes nucleotides 288–330 of IiPADRE; and murIi-R. The PCR conditions were the same as described above, and the two halves were isolated by agarose gel electrophoresis as described above.

Ten microliters of each PCR product was combined in a 100 μl PCR reaction with an annealing temperature of 50° C. for five cycles to generate a full length template. Primers murIi-F and murIi-R were added and 25 more cycles carried out. The full length IiPADRE product was isolated, cloned, and sequenced as described above. This construct contains the murine Ii gene with a pan DR epitope sequence substituted for the CLIP sequence of Ii (FIG. 1).

A DNA construct, designated I80T, containing the cytoplasmic domain, the transmembrane domain and part of the luminal domain of Ii fused to a string of multiple MHC class II epitopes was constructed (FIG. 2). Briefly, the string of multiple MHC class II epitopes was constructed with three overlapping oligonucleotides (oligos). Each oligo overlapped its neighbor by 15 nucleotides and the final MHC class II epitope string was assembled by extending the overlapping oligonucleotides in three sets of reactions using PCR. The three oligonucleotides were: oligo 1, nucleotides 241–310, CTTCGCATGAAGCTTATCAGCCAGGCTGTGCACGCCGCTCACGCCGAAATCAA CGAAGCTGGAAGAACCC (SEQ ID NO:44);

oligo 2, nucleotides 364–295, TTCTGGTCAGCAGAAAGAACAGGATAGGAGCGTTTGGAGGGCGATAAGCTGG AGGGGTTCTTCCAGCTTC (SEQ ID NO:45); and oligo 3, nucleotides 350–42, TTCTGCTGACCAGAATCCTGACAATCCCCCAGTCCCTGGACGCCAAGTTCGTG GCTGCCTGGACCCTGAAG (SEQ ID NO:46).

For the first PCR reaction, 5 μg of oligos 1 and 2 were combined in a 100 μl reaction containing Pfu polymerase. A Perkin/Elmer 9600 PCR machine was used and the annealing temperature used was 45° C. The PCR product was gel-purified, and a second reaction containing the PCR product of oligos 1 and 2 with oligo 3 was annealed and extended for 10 cycles before gel purification of the full length product to be used as a "mega-primer."

The I80T construct was made by amplifying bIi#3 with murIi-F and the mega-primer. The cycling conditions were: 1 cycle of 95° C. for 5 minutes, followed by 5 cycles of 95° C. for 15 seconds, 37° C. for 30 seconds, and 72° C. for 1 minute. Primer Help-epR was added and an additional 25 cycles were carried out with the annealing temperature raised to 47° C. The Help-epR primer GGTACCTCAAGCGGCAGCCTTCAGGGTCCAGGCA (SEQ ID NO:47) corresponds to nucleotides 438–405. The full length I80T product was isolated, cloned, and sequenced as above.

The I80T construct (FIG. 2) encodes amino acid residues 1 through 80 of Ii, containing the cytoplasmic domain, the transmembrane domain and part of the luminal domain, fused to a string of multiple MHC class II epitopes corresponding to: amino acid residues 323–339 of ovalbumin (IleSerGlnAlaValHisAlaAlaHisAlaGluIleAsnGluAlaGlyArg; SEQ ID NO:48); amino acid residues 128 to 141 of HBV core antigen (amino acids ThrProProAlaTyrArgProProAsnAlaProIleLeu; SEQ ID NO:49); amino acid residues 182 to 196 of HBV env (amino acids PhePheLeuLeuThrArgIleLeuThrIleProGlnSerLeuAsp; SEQ ID NO:50); and the pan DR sequence designated SEQ ID NO:52)

A DNA construct containing the cytoplasmic domain, transmembrane domain and a portion of the luminal domain of Ii fused to the MHC class II epitope string shown in FIG. 2 and amino acid residues 101 to 215 of Ii encoding the trimerization region of Ii was generated (FIG. 3). This construct, designated IiThfull, encodes the first 80 amino acids of invariant chain followed by the MHC class II epitope string (replacing CLIP) and the rest of the invariant chain (amino acids 101–215). Briefly, the construct was generated as two overlapping halves that were annealed and extended by PCR to yield the final product.

The 5' end of IiThfull was made by amplifying I80T with murIi-F (SEQ ID NO:40) and Th-Pad-R. The Th-Pad-R primer AGCGGCAGCCTTCAGGGTC (SEQ ID NO:51) corresponds to nucleotides 429–411. The 3' half was made by amplifying bIi#3 with IiPADRE-F and murIi-R (SEQ ID NO:41). The IiPADRE-F primer GGCTGCCTGGACCCT-GAAGGCTGCCGCTATGTCCATGGATAAC (SEQ ID NO:43) corresponds to nucleotides 402–444. Each PCR product was gel purified and mixed, then denatured, annealed, and extended by five cycles of PCR. Primers murIi-F (SEQ ID NO:40) and murIi-R (SEQ ID NO:41) were added and another 25 cycles performed. The full length product was gel purified, cloned, and sequenced.

All of the remaining constructs described below were made essentially according to the scheme shown in FIG. 18. Briefly, primer pairs 1F plus 1R, designated below for each specific construct, were used to amplify the specific signal sequence and contained an overlapping 15 base pair tail identical to the 5' end of the MHC class II epitope string. Primer pair Th-ova-F, ATCAGCCAGGCTGTGCACGC (SEQ ID NO:53), plus Th-Pad-R (SEQ ID NO:51) were used to amplify the MHC class II epitope string. A 15 base pair overlap and the specific transmembrane and cytoplasmic tail containing the targeting signals were amplified with primer pairs 2F plus 2R.

All three pieces of each cDNA were amplified using the following conditions: 1 cycle of 95° C. for 5 minutes, followed by 30 cycles of 95° C. for 15 seconds, 52° C. for 30 seconds, and 72° C. for 1 minute. Each of the three fragments was agrose-gel purified, and the signal sequence and MHC class II string fragments were combined and joined by five cycles in a second PCR. After five cycles, primers 1F and Th-Pad-R were added for 25 additional cycles and the PCR product was gel purified. This signal sequence plus MHC class II epitope string fragment was combined with the transmembrane plus cytoplasmic tail fragment for the final PCR. After five cycles, primers 1F plus 2R were added for 25 additional cycles and the product was gel purified, cloned and sequenced.

A DNA construct containing the murine immunoglobulin kappa signal sequence fused to the T helper epitope string shown in FIG. 2 and the transmembrane and cytoplasmic domains of LAMP-1 was generated (FIG. 4) (Granger et al., *J. Biol. Chem.* 265:12036–12043 (1990)), which is incorporated by reference (mouse LAMP-1 GenBank accession No. M32015). This construct, designated kappaLAMP-Th, contains the consensus mouse immunoglobulin kappa signal sequence and was amplified from a plasmid containing full length immunoglobulin kappa as depicted in FIG. 18. The primer 1F used was the oligonucleotide designated KappaSig-F, GCTAGCGCCGCCACCATGGGAATGCAG (SEQ ID NO:54).

The primer 1R used was the oligonucleotide designated Kappa-Th-R, CACAGCCTGGCTGATTCCTCTGGACCC (SEQ ID NO:55).

The primer 2F used was the oligonucleotide designated PAD/LAMP-F, CTGAAGGCTGCCGCTAACAACATGT-TGATCCCC (SEQ ID NO:56). The primer 2R used was the oligonucleotide designated LAMP-CYTOR, GGTAC-CCTAGATGGTCTGATAGCC (SEQ ID NO:57).

A DNA construct containing the signal sequence of H2-M fused to the MHC class II epitope string shown in FIG. 2 and the transmembrane and cytoplasmic domains of H2-M was generated (FIG. 5). The mouse H2-M gene has been described previously, Peleraux et al., *Immunogenetics* 43:204–214 (1996)), which is incorporated herein by reference. This construct was designated H2M-Th and was constructed as depicted in FIG. 18. The primer 1F used was the oligonucleotide designated H2-Mb-1F, GCC GCT AGC GCC GCC ACC ATG GCT GCA CTC TGG (SEQ ID NO:58). The primer 1R used was the oligonucleotide designated H2-Mb-1R, CAC AGC CTG GCT GAT CCC CAT ACA GTG CAG (SEQ ID NO:59). The primer 2F used was the oligonucleotide designated H2-Mb-2F, CTG AAG GCT GCC GCT AAG GTC TCT GTG TCT (SEQ ID NO:60). The primer 2R used was the oligonucleotide designated H2-Mb-2R, GCG GGTACC CTAATG CCG TCC TTC (SEQ ID NO:61).

A DNA construct containing the signal sequence of H2-DO fused to the MHC class II epitope string shown in FIG. 2 and the transmembrane and cytoplasmic domains of H2-DO was generated (FIG. 6). The mouse H2-DO gene has been described previously (Larhammar et al., *J. Biol. Chem.* 260:14111–14119 (1985)), which is incorporated herein by reference (GenBank accession No. M19423). This construct, designated HBO-Th, was constructed as depicted in FIG. 18. The primer 1F used was the oligonucleotide designated H2-Ob-1F, GCG GCT AGC GCC GCC ACC ATG GGC GCT GGG AGG (SEQ ID NO:62). The primer 1R used was the oligonucleotide designated H2-Ob-1R, TGC ACA GCC TGG CTG ATG GAA TCC AGC CTC (SEQ ID NO:63). The primer 2F used was the oligonucleotide designated H2-Ob-2F, CTG AAG GCT GCC GCT ATA CTG AGT GGA GCT (SEQ ID NO:64). The primer 2R used was the oligonucleotide designated H2-Ob-2R, GCC GGT ACC TCA TGT GAC ATG TCC CG (SEQ ID NO:65).

A DNA construct containing a pan DR epitope sequence (SEQ ID NO:52) fused to the amino-terminus of influenza matrix protein is generated (FIG. 7). This construct, designated PADRE-Influenza matrix, contains the universal MHC class II epitope PADRE attached to the amino terminus of the influenza matrix coding sequence. The construct is made using a long primer on the 5' end primer. The 5' primer is the oligonucleotide GCTAGCGCCGCCACCATGGCCAAGT-TCGTGGCTGCCTGGACCCTGAAGGCTGC CGCTAT-GAGTCTTCTAACCGAGGTCGA (SEQ ID NO:66). The 3' primer is the oligonucleotide TCACTTGAATCGCTG-CATCTGCACCCCCAT (SEQ ID NO:67). Influenza virus from the America Type Tissue Collection (ATCC) is used as a source for the matrix coding region (Perdue et al. *Science* 279:393–396 (1998)), which is incorporated herein by reference (GenBank accession No. AF036358).

A DNA construct containing a pan DR epitope sequence (SEQ ID NO:52.) fused to the amino-terminus of HBV-S antigen was generated (FIG. 8). This construct is designated PADRE-HBV-s and was generated by annealing two overlapping oligonucleotides to add PADRE onto the amino terminus of hepatitis B surface antigen (Michel et al., *Proc. Natl. Acad. Sci. USA* 81:7708–7712 (1984); Michel et al., *Proc. Natl. Acad. Sci. USA* 92:5307–5311 (1995)), each of which is incorporated herein by reference. One oligonucleotide was GCTAGCGCCGCCACCATGGCCAAGT- TCGTGGCTGCCTGGACCCTGAAGGCTGC CGCTC (SEQ ID NO:68). The second oligonucleotide was CTC-GAGAGCGGCAGCCTTCAGGGTCCAG-GCAGCCACGAACTTGGCCATGGTG GCGGCG (SEQ ID NO:69). When annealed, the oligos have NheI and XhoI cohesive ends. The oligos were heated to 100° C. and slowly cooled to room temperature to anneal. A three part ligation joined PADRE with an XhoI-KpnI fragment containing HBV-s antigen into the NheI plus KpnI sites of the expression vector.

A DNA construct containing the signal sequence of Ig-α fused to the MHC class II epitope string shown in FIG. 2 and the transmembrane and cytoplasmic domains of Ig-α was generated (FIG. 9). The mouse Ig-α gene has been described previously (Kashiwamura et al., *J. Immunol.* 145:337–343 (1990)), which is incorporated herein by reference (GenBank accession No. M31773). This construct, designated Ig-alphaTh, was constructed as depicted in FIG. 18. The primer 1F used was the oligonucleotide designated Ig alpha-1F, GCG GCT AGC GCC GCC ACC ATG CCA GGG GGT CTA (SEQ ID NO:70). The primer 1R used was the oligonucleotide designated Igalpha-1R, GCA CAG CCT ATG TGA TCG CCT GGC ATC CGG (SEQ ID NO:71). The primer 2F used was the oligonucleotide designated Igalpha-2F, CTG AAG GCT GCC GCT GGG ATC ATC TTG CTG (SEQ ID NO:72). The primer 2R used was the oligonucleotide designated Igalpha-2R, GCG GGT ACC TCA TGG CTT TTC CAG CTG (SEQ ID NO:73).

A DNA construct containing the signal sequence of Ig-β fused to the MHC class II string shown in FIG. 2 and the transmembrane and cytoplasmic domains of Igβ was generated (FIG. 10). The Ig-β sequence is the B29 gene of mouse and has been described previously (Hermanson et al., *Proc. Natl. Acad. Sci. USA* 85:6890–6894 (1988)), which is incorporated herein by reference (GenBank accession No. J03857). This construct, designated Ig-betaTh, was constructed as depicted in FIG. 18. The primer 1F used was the oligonucleotide designated B29-1F (33mer) GCG GCT AGC GCC GCC ACC ATG GCC ACA CTG GTG (SEQ ID NO:74). The primer 1R used was the oligonucleotide designated B29-1R (30mer) CAC AGC CTG GCT GAT CGG CTC ACC TGA GAA (SEQ ID NO:75). The primer 2F used was the oligonucleotide designated B292F (30mer) CTG AAG GCT GCC GCT ATT ATC TTG ATC CAG (SEQ ID NO:76). The primer 2R used was the oligonucleotide designated B29–2R (27mer), GCC GGT ACC TCA TTC CTG GCC TGG ATG (SEQ ID NO:77).

A DNA construct containing the signal sequence of the kappa immunoglobulin signal sequence fused to the MHC class II epitope string shown in FIG. 2 was constructed (FIG. 11). This construct is designated SigTh and was generated by using the kappaLAMP-Th construct (shown in FIG. 4) and amplifying with the primer pair KappaSig-F (SEQ ID NO:54) plus Help-epR (SEQ ID NO:47) to create SigTh. SigTh contains the kappa immunoglobulin signal sequence fused to the T helper epitope string and terminated with a translational stop codon.

Constructs encoding human sequences corresponding to the above described constructs having mouse sequences are prepared by substituting human sequences for the mouse sequences. Briefly, for the IiPADRE construct, corresponding to FIG. 1, amino acid residues 1–80 from the human Ii gene HLA-DR sequence (FIG. 12) (GenBank accession No. X00497 M14765) is substituted for the mouse Ii sequences, which is fused to PADRE, followed by human invariant chain HLA-DR amino acid residues 114–223. For the I80T construct, corresponding to FIG. 2, amino acid residues 1–80 from the human sequence of Ii is followed by a MHC class II epitope string. For the IiThfull construct, corresponding to FIG. 3, amino acid residues 1–80 from the human sequence of Ii, which is fused to a MHC class II epitope string, is followed by human invariant chain amino acid residues 114–223.

For the LAMP-Th construct, similar to FIG. 4, the signal sequence encoded by amino acid residues 11 19 (nucleotides 11–67) of human LAMP-1(FIG. 13) (GenBank accession No. J04182), which is fused to the MHC class II epitope string, is followed by the transmembrane (nucleotides 1163–1213) and cytoplasmic tail (nucleotides 1214–1258) region encoded by amino acid residues 380–416 of human LAMP-1.

For the HLA-DM-Th construct, corresponding to FIG. 5, the signal sequence encoded by amino acid residues 1–17 (nucleotides 1–51) of human HLA-DMB (FIG. 14) (GenBank accession No. U15085), which is fused to the MHC class II epitope string, is followed by the transmembrane (nucleotides 646–720) and cytoplasmic tail (nucleotides 721–792) region encoded by amino acid residues 216–263 of human HLA-DMB.

For the HLA-DO-Th construct, corresponding to FIG. 6, the signal sequence encoded by amino acid residues 1–21 (nucleotides 1–63) of human HLA-DO (FIG. 15) (GenBank accession No. L29472 J02736 N00052), which is fused to the MHC class II epitope string, is followed by the transmembrane (nucleotides 685–735) and cytoplasmic tail (nucleotides 736–819) region encoded by amino acid residues 223–273 of human HLA-DO.

For the Ig-alphaTh construct, corresponding to FIG. 9, the signal sequence encoded by amino acid residues 1–29 (nucleotides 1–87) of human Ig-α MB-1 (FIG. 16) (GenBank accession No. U05259), which is fused to the MHC class II epitope string, is followed by the transmembrane (nucleotides 424–498) and cytoplasmic tail (nucleotides 499–678) region encoded by amino acid residues 142–226 of human Ig-α MB-1.

For the Ig-betaTh construct, corresponding to FIG. 10, the signal sequence encoded by amino acid residues 1–28 (nucleotides 17–100) of human Ig-β 29 (FIG. 17) (GenBank accession No. M80461), which is fused to the MHC class II epitope string, is followed by the transmembrane (nucleotides 500–547) and cytoplasmic tail (nucleotides 548–703) region encoded by amino acid residues 156–229 of human Ig-β.

The SigTh construct shown in FIG. 11 can be used in mouse and human. Alternatively, a signal sequence derived from an appropriate human gene containing a signal sequence can be substituted for the mouse kappa immunoglobulin sequence in the Sig Th construct.

The PADRE-Influenza matrix construct shown in FIG. 7 and the PADRE-HBVs construct shown in FIG. 8 can be used in mouse and human.

Some of the DNA constructs described above were cloned into the vector pEP2 (FIG. 19; SEQ ID NO:35). The pEP2 vector was constructed to contain dual CMV promoters. The pEP2 vector used the backbone of pcDNA3.1(−)Myc-His A from Invitrogen and pIRES1hyg from Clontech. Changes were made to both vectors before the CMV transcription unit from pIRES 1 hyg was moved into the modified pcDNA vector.

The pcDNA3.1(−)Myc-His A vector (http://www.invitrogen.com) was modified. Briefly, the PvuII fragment (nucleotides 1342–3508) was deleted. A BspHI fragment that contains the Ampicillin resistance gene (nucleotides 4404–5412) was cut out. The Ampicillin resistance gene was replaced with the kanamycin resistance gene from pUC4K (GenBank Accession #X06404). pUC4K was amplified with the primer set: TCTGATGTTACATTGCA-CAAG (SEQ ID NO:78) (nucleotides 1621–1601) and GCGCACTCATGATGCTCTGCCAGTGTTACAACC (SEQ ID NO:79) (nucleotides 682–702 plus the addition of a BspHI restriction site on the 5' end). The PCR product was digested with BspHI and ligated into the vector digested with BspHI. The region between the PmeI site at nucleotide 905 and the EcoRV site at nucleotide 947 was deleted. The vector was then digested with PmeI (cuts at nucleotide 1076) and ApaI (cuts at nucleotide 1004), Klenow filled in at the cohesive ends and ligated. The KpnI site at nucleotide 994 was deleted by digesting with KpnI and filling in the ends with Klenow DNA polymerase, and ligating. The intron A sequence from CMV (GenBank accession M21295, nucleotides 635–1461) was added by amplifying CMV DNA with the primer set: GCGTCTAGAGTAAGTACCGCCTATA-GACTC (SEQ ID NO:80) (nucleotides 635–655 plus an XbaI site on the 5' end) and CCGGCTAGCCTGCA-GAAAAGACCCATGGAA (SEQ ID NO:81) (nucleotides 1461–1441 plus an NheI site on the 3' end). The PCR product was digested with XbaI and NheI and ligated into the NheI site of the vector (nucleotide 895 of the original pcDNA vector) so that the NheI site was on the 3' end of the intron.

To modify the pIRES1hyg vector (GenBank Accession U89672, Clontech), the KpnI site (nucleotide 911) was deleted by cutting and filling in with Klenow. The plasmid was cut with NotI (nucleotide 1254) and XbaI (nucleotide 3196) and a polylinker oligo was inserted into the site. The polylinker was formed by annealing the following two oligos:
GGCCGCAAGGAAAAAATCTAGAGTCGGC-CATAGACTAATGCCGGTACCG (SEQ ID NO:82) and CTAGCGGTACCGGCATTAGTCTATGGC-CCGACTCTAGATTTTTTCCTTGC (SEQ ID NO:83). The resulting plasmid was cut with HincII and the fragment between HincII sites 234 and 3538 was isolated and ligated into the modified pcDNA vector. This fragment contains a CMV promoter, intron, polylinker, and polyadenylation signal.

The pIREShyg piece and the pcDNA piece were combined to form pEP2. The modified pcDNA3.1 (–)Myc-His A vector was partially digested with PvuII to isolate a linear fragment with the cut downstream of the pcDNA polyadenylation signal (the other PvuII site is the CMV intron). The HincII fragment from the modified pIRES1hyg vector was ligated into the PvuII cut vector. The polyadenylation signal from the pcDNA derived transcription unit was deleted by digesting with EcoRI (pcDNA nucleotide 955) and XhoI (pIRES1hyg nucleotide 3472) and replaced with a synthetic polyadenylation sequence. The synthetic polyadenylation signal was described in Levitt et al., *Genes and Development* 3:1019–1025 (1989)).

Two oligos were annealed to produce a fragment that contained a polylinker and polyadenylation signal with EcoRI and XhoI cohesive ends. The oligos were:
AATTCGGATATCCAAGCTTGAT-GAATAAAAGATCAGAGCTCTAGTGATCTGTGT GTTGGTTTTTTTGTGTGC (SEQ ID NO:84) and TCGAGCACACAAAAAACCAACACACA-GATCACTAGAGCTCTGATCTTTTTATT CATCAAGCT-TGGATATCCG (SEQ ID NO:85).

The resulting vector is named pEP2 and contains two separate transcription units. Both transcription units use the same CMV promoter but each contains different intron, polylinker, and polyadenylation sequences.

The pEP2 vector contains two transcription units. The first transcription unit contains the CMV promoter initially from pcDNA (nucleotides 210–862 in FIG. 19), CMV intron A sequence (nucleotides 900–1728 in FIG. 19), polylinker cloning site (nucleotides 1740–1760 in FIG. 19) and synthetic polyadenylation signal (nucleotides 1764–1769 in FIG. 19). The second transcription unit, which was initially derived from pIRES I hyg, contains the CMV promoter (nucleotides 3165–2493 in FIG. 19), intron sequence (nucleotides 2464–2173 in FIG. 19), polylinker clone site (nucleotides 2126–2095 in FIG. 19) and bovine growth hormone polyadenylation signal (nucleotides 1979–1974 in FIG. 19). The kanamycin resistance gene is encoded in nucleotides 4965–4061 (FIG. 19).

The DNA constructs described above were digested with NheI and KpnI and cloned into the XbaI and KpnI sites of pEP2 (the second transcription unit).

Additional vectors were also constructed. To test for the effect of co-expression of MHC class I epitopes with MHC class II epitopes, an insert was generated, designated AOS, that contains nine MHC class I epitopes. The AOS insert was initially constructed in the vector pMIN.0 (FIG. 20; SEQ ID NO:36). Briefly, the AOS insert contains nine MHC class I epitopes, six restricted by HLA-A2 and three restricted by HLA-A11, and the universal MHC class II epitope PADRE. The vector pMIN.0 contains epitopes from HBV, HIV and a mouse ovalbumin epitope. The MHC class I epitopes appear in pMIN.0 in the following order:

consensus mouse Ig Kappa signal sequence (pMIN.0 amino acid residues 1–20, nucleotides 16–81) MQVQIQS-LFLLLLWVPGSRG (SEQ ID NO:86) encoded by nucleotides ATG CAG GTG CAG ATC CAG AGC CTG TTT CTG CTC CTC CTG TGG GTG CCC GGG TCC AGA GGA (SEQ ID NO:87);

HBV pol 149–159 (A11 restricted)
(pMIN.0 amino acid residues 21–31, nucleotides 82–114) HTLWKAGILYK (SEQ ID NO:88) encoded by nucleotides CAC ACC CTG TGG AAG GCC GGAATC CTG TAT AAG (SEQ ID NO:89);

PADRE-universal MHC class II epitope (pMIN.0 amino acid residues 32–45, nucleotides 115–153) AKFVAAWTL-KAAA (SEQ ID NO:52) encoded by nucleotides GCC AAG TTC GTG GCT GCC TGG ACC CTG AAG GCT GCC GCT (SEQ ID NO:90);

HBV core 18-27 (A2 restricted) (pMIN.0 amino acid residues 46–55, nucleotides 154–183) FLPSDFFPSV (SEQ ID NO:91) encoded by nucleotides TTC CTG CCT AGC GAT TTC TTT CCT AGC GTG (SEQ ID NO:92);

HIV env 120–128 (A2 restricted) (pMIN.0 amino acid residues 56–64, nucleotides 184–210) KLTPLCVTL (SEQ ID NO:93) encoded by nucleotides AAG CTG ACC CCA CTG TGC GTG ACC CTG (SEQ ID NO:94);

HBV pol 551–559 (A2 restricted) (pMIN.0 amino acid residues 65–73, nucleotides 211–237) YMDDVVLGA (SEQ ID NO:95) encoded by nucleotides TAT ATG GAT GAC GTG GTG CTG GGA GCC (SEQ ID NO:96);

mouse ovalbumin 257–264 ($K^b$ restricted) (pMIN.0 amino acid residues 74–81, nucleotides 238–261) SIIN-FEKL (SEQ ID NO:97) encoded by nucleotides AGC ATC ATC AAC TTC GAG AAG CTG (SEQ ID NO:98);

HBV pol 455–463 (A2 restricted) (pMIN.0 amino acid residues 82–90, nucleotides 262–288) GLSRYVARL (SEQ ID NO:99) encoded by nucleotides GGA CTG TCC AGA TAC GTG GCT AGG CTG (SEQ ID NO:100);

HIV pol 476–84 (A2 restricted) (pMIN.0 amino acid residues 91–99, nucleotides 289–315) ILKEPVHGV (SEQ ID NO:101) encoded by nucleotides ATC CTG AAG GAG CCT GTG CAC GGC GTG (SEQ ID NO:102);

HBV core 141–151 (All restricted) (pMIN.0 amino acid residues 100–110, nucleotides 316–348) STLPETTVVRR (SEQ ID NO:103) encoded by nucleotides TCC ACC CTG CCA GAG ACC ACC GTG GTG AGG AGA (SEQ ID NO:104);

HIV env 49–58 (All restricted) (pMIN.0 amino acid residues 111–120, nucleotides 349–378) TVYYGVPVWK (SEQ ID NO:105) encoded by nucleotides ACC GTG TAC TAT GGA GTG CCT GTG TGG AAG (SEQ ID NO:106); and HBV env 335–343 (A2 restricted) (pMIN.0 amino acid residues 121–129, nucleotides 378–405) WLSLLVPFV (SEQ ID NO:107) encoded by nucleotides TGG CTG AGC CTG CTG GTG CCC TTT GTG (SEQ ID NO:108).

The pMIN.0 vector contains a KpnI restriction site (pMIN.0 nucleotides 406–411) and a NheI restriction site (pMIN.0 nucleotides 1–6). The pMIN.0 vector contains a consensus Kozak sequence (nucleotides 7–18) (GCCGCCACCATG; SEQ ID NO:109) and murine Kappa Ig-light chain signal sequence followed by a string of 10 MHC class I epitopes and one universal MHC class II epitope. The pMIN.0 sequence encodes an open reading frame fused to the Myc and His antibody epitope tag coded for by the pcDNA 3.1 Myc-His vector. The pMIN.0 vector was constructed with eight oligonucleotides:

Min1 oligo
GAGGAGCAGAAACAGGCTCTGGATCTG-CACCTGCATTCCCATGGTGGCGGCGC TAGCAAGCT-TCTTGCGC (SEQ ID NO:110);

Min2 oligo
CCTGTTTCTGCTCCTCCTGTGGGTGC-CCGGGTCCAGAGGACACACCCTGTGGA AGGCCG-GAATCCTGTATA (SEQ ID NO:11);

Min3 oligo
TCGCTAGGCAGGAAAGCGGCAGCCT-TCAGGGTCCAGGCAGCCACGAACTTGG CCTTATA-CAGGATTCCGG (SEQ ID NO:112);

Min4 oligo
CTTTCCTGCCTAGCGATTTCTTTC-CTAGCGTGAAGCTGACCCCACTGTGCGTGA CCCT-GTATATGGATGAC (SEQ ID NO:113);

Min5 oligo
CGTACCTGGACAGTCCCAGCTTCTC-GAAGTTGATGATGCTGGCT CCCAGCACCACGT-CATCCATATACAG (SEQ ID NO:114);

Min6 oligo
GGACTGTCCAGATACGTGGCTAGGCT-GATCCTGAAGGAGCCTGTGCACGGCGT GTCCAC-CCTGCCAGAGAC (SEQ ID NO:115);

Min7 oligo
GCTCAGCCACTTCCACACAGGCACTC-CATAGTACACGGTCCTCCTCACCACGG TGGTCTCTGGCAGGGTG (SEQ ID NO:116);

Min8 oligo
GTGGAAGTGGCTGAGCCTGCTGGTGC-CCTTTGTGGGTACCTGATCTAGAGC (SEQ ID NO:117).

Additional primers were flanking primer 5', GCG CAA GAA GCT TGC TAG CG (SEQ ID NO:118) and flanking primer 3', GCT CTA GAT CAG GTA CCC CAC (SEQ ID NO:119).

The original pMIN.0 minigene construction was carried out using eight overlapping oligos averaging approximately 70 nucleotides in length, which were synthesized and HPLC purified by Operon Technologies Inc. Each oligo overlapped its neighbor by 15 nucleotides, and the final multi-epitope minigene was assembled by extending the overlapping oligos in three sets of reactions using PCR (Ho et al., *Gene* 77:51–59 (1989).

For the first PCR reaction, 5 μg of each of two oligos were annealed and extended: 1+2, 3+4, 5+6, and 7+8 were combined in 100 μl reactions containing 0.25 mM each dNTP and 2.5 units of Pfu polymerase in Pfu polymerase buffer containing 10 mM KCl, 10 mM $(NH_4)_2SO_4$, 20 mM Tris-chloride, pH 8.75, 2 mM $MgSO_4$, 0.1% TRITON X-100 and 100 mg/ml BSA. A Perkin/Elmer 9600 PCR machine was used and the annealing temperature used was 5° C. below the lowest calculated $T_m$ of each primer pair. The full length dimer products were gel-purified, and two reactions containing the product of 1–2 and 3–4, and the product of 5–6 and 7–8 were mixed, annealed and extended for 10 cycles. Half of the two reactions were then mixed, and 5 cycles of annealing and extension carried out before flanking primers were added to amplify the full length product for 25 additional cycles. The full length product was gel purified and cloned into pCR-blunt (Invitrogen) and individual clones were screened by sequencing. The Min insert was isolated as an NheI-KpnI fragment and cloned into the same sites of pcDNA3.1(−)/Myc-His A (Invitrogen) for expression. The Min protein contains the Myc and His antibody epitope tags at its carboxyl-terminal end.

For all the PCR reactions described, a total of 30 cycles were performed using Pfu polymerase and the following conditions: 95° C. for 15 seconds, annealing temperature for 30 seconds, 72° C. for one minute. The annealing temperature used was 5° C. below the lowest calculated Tm of each primer pair.

Three changes to pMIN.0 were made to produce pMIN.1 (FIG. 21; SEQ ID NO:37, also referred to as pMIN-AOS). The mouse ova epitope was removed, the position 9 alanine anchor residue (#547) of HBV pol 551–560 was converted to a valine which increased the in vitro binding affinity 40-fold, and a translational stop codon was introduced at the end of the multi-epitope coding sequence. The changes were made by amplifying two overlapping fragments and combining them to yield the full length product.

The first reaction used the 5' pcDNA vector primer T7 and the primer Min-ovaR (nucleotides 247–218) TGGA-CAGTCCCACTCCCAGCACCACGTCAT (SEQ ID NO:120). The 3' half was amplified with the primers: Min-ovaF (nucleotides 228–257) GCTGGGAGTGGGACT-GTCCAGGTACGTGGC (SEQ ID NO:121) and Min-StopR (nucleotides 390–361) GGTACCTCACACAAAGGGCAC-CAGCAGGC (SEQ ID NO:122)

The two fragments were gel purified, mixed, denatured, annealed, and filled in with five cycles of PCR. The full length fragment was amplified with the flanking primers T7 and Min-Stop for 25 more cycles. The product was gel purified, digested with NheI and KpnI and cloned into pcDNA3.1 for sequencing and expression. The insert from pMin.1 was isolated as an NheI-KpnI fragment and cloned into pEP2 to make pEP2-AOS.

Example II

Assay for T Helper Cell Activation

This example shows methods for assaying T helper cell activity. One method for assaying T helper cell activity uses spleen cells of an immunized organism. Briefly, a spleen cell pellet is suspended with 2–3 ml of red blood cell lysis buffer containing 8.3 g/liter ammonium chloride in 0.001 M Tris-HCl, pH 7.5. The cells are incubated in lysis buffer for 3–5 min at room temperature with occasional vortexing. An excess volume of 50 ml of R10 medium is added to the cells, and the cells are pelleted. The cells are resuspended and pelleted one or two more times in R2 medium or R10 medium.

The cell pellet is suspended in R10 medium and counted. If the cell suspension is aggregated, the aggregates are removed by filtration or by allowing the aggregates to settle by gravity. The cell concentration is brought to $10^7$/ml, and 100 μl of spleen cells are added to 96 well flat bottom plates.

Dilutions of the appropriate peptide, such as pan DR epitope (SEQ ID NO:145), are prepared in R10 medium at 100, 10, 1, 0.1 and 0.01 μg/ml, and 100 μl of peptide are added to duplicate or triplicate wells of spleen cells. The final peptide concentration is 50, 5, 0.5, 0.05 and 0.005 μg/ml. Control wells receive 100 μl R10 medium.

The plates are incubated for 3 days at 37° C. After 3 days, 20 μl of 50 μCi/ml $^3$H-thymidine is added per well. Cells are incubated for 18–24 hours and then harvested onto glass fiber filters. The incorporation of $^3$H-thymidine into DNA of proliferating cells is measured in a beta counter.

A second assay for T helper cell activity uses peripheral blood mononuclear cells (PBMC) that are stimulated in vitro as described in Alexander et al., supra and Sette (WO 95/07,707), as adapted from Manca et al., *J. Immunol.* 146:1964–1971 (1991), which is incorporated herein by reference. Briefly, PBMC are collected from healthy donors and purified over Ficoll-Plaque (Pharmacia Biotech; Piscataway, N.J.). PBMC are plated in a 24 well tissue culture plate at $4 \times 10^6$ cells/ml. Peptides are added at a final concentration of 10 μg/ml. Cultures are incubated at 37° C. in 5% $CO_2$.

On day 4, recombinant interleukin-2 (IL-2) is added at a final concentration of 10 ng/ml. Cultures are fed every 3 days by aspirating 1 ml of medium and replacing with fresh medium containing IL-2. Two additional stimulations of the T cells with antigen are performed on approximately days 14 and 28. The T cells ($3 \times 10^5$/well) are stimulated with peptide (10 μg/ml) using autologous PBMC cells ($2 \times 10^6$ irradiated cells/well) (irradiated with 7500 rads) as antigen-presenting cells in a total of three wells of a 24 well tissue culture plate. In addition, on day 14 and 28, T cell proliferative responses are determined under the following conditions: $2 \times 10^4$ T cells/well; $1 \times 10^5$ irradiated PBMC/well as antigen-presenting cells; peptide concentration varying between 0.01 and 10 μg/ml final concentration. The proliferation of the T cells is measured 3 days later by the addition of $^3$H-thymidine (1 μCi/well) 18 hr prior to harvesting the cells. Cells are harvested onto glass filters and $^3$H-thymidine incorporation is measured in a beta plate counter. These results demonstrate methods for assaying T helper cell activity by measuring $^3$H-thymidine incorporation.

Example III

Assay for Cytotoxic T Lymphocyte Response

This example shows a method for assaying cytotoxic T lymphocyte (CTL) activity. A CTL response is measured essentially as described previously (Vitiello et al., *Eur. J. Immunol.* 27:671–678 (1997), which is incorporated herein by reference). Briefly, after approximately 10–35 days following DNA immunization, splenocytes from an animal are isolated and co-cultured at 37° C. with syngeneic, irradiated (3000 rad) peptide-coated LPS blasts ($1 \times 10^6$ to $1.5 \times 10^6$ cells/ml) in 10 ml R10 in T25 flasks. LPS blasts are obtained by activating splenocytes ($1 \times 10^6$ to $1.5 \times 10^6$ cells/ml) with 25 μg/ml lipopolysaccharides (LPS) (Sigma cat. no. L-2387; St. Louis, Mo.) and 7 μg/ml dextran sulfate (Pharmacia Biotech) in 30 ml R10 medium in T75 flasks for 3 days at 37° C. The lymphoblasts are then resuspended at a concentration of $2.5 \times 10^7$ to $3.0 \times 10^7$/ml, irradiated (3000 rad), and coated with the appropriate peptides (100 μg/ml) for 1 h at 37° C. Cells are washed once, resuspended in R10 medium at the desired concentration and added to the responder cell preparation. Cultures are assayed for cytolytic activity on day 7 in a $^{51}$Cr-release assay.

For the $^{51}$Cr-release assay, target cells are labeled for 90 min at 37° C. with 150 μsodium $^{51}$chromate ($^{51}$Cr) (New England Nuclear; Wilmington Del.), washed three times and resuspended at the appropriate concentration in R10 medium. For the assay, $10^4$ target cells are incubated in the presence of different concentrations of effector cells in a final volume of 200 μl in U-bottom 96 well plates in the presence or absence of 10 μg/ml peptide. Supernatants are removed after 6 h at 37° C., and the percent specific lysis is determined by the formula: percent specific lysis=100× (experimental release−spontaneous release)/(maximum release−spontaneous release). To facilitate comparison of responses from different experiments, the percent release data is transformed to lytic units 30 per $10^6$ cells (LU30/$10^6$), with 1 LU30 defined as the number of effector cells required to induce 30% lysis of $10^4$ target cells in a 6 h assay. LU values represent the LU30/$10^6$ obtained in the presence of peptide minus LU30/$10^6$ in the absence of peptide. These results demonstrate methods for assaying CTL activity by measuring $^{51}$Cr release from cells.

Example IV

T Cell Proliferation in Mice Immunized with Expression Vectors Encoding MHC Class II Epitopes and MHC Class II Targeting Sequences This example demonstrates that expression vectors encoding MHC class II epitopes and MHC class II targeting sequences are effective at activating T cells.

The constructs used in the T cell proliferation assay are described in Example I and were cloned into the vector pEP2, a CMV driven expression vector. The peptides used for T cell in vitro stimulation are: Ova 323–339, ISQAVHAAHAEINEAGR (SEQ ID NO:48); HBVcore128, TPPAYRPPNAPILF (SEQ ID NO:124); HBVenv182, FFLLTRILTIPQSLD (SEQ ID NO:-50); and PADRE, AKFVAAWTLKAAA (SEQ ID NO:52).

T cell proliferation was assayed essentially as described in Example II. Briefly, 12 to 16 week old B6D2 F1 mice (2 mice per construct) were injected with 100 μg of the indicated expression vector (50 μg per leg) in the anterior tibialis muscle. After eleven days, spleens were collected from the mice and separated into a single cell suspension by Dounce homogenization. The splenocytes were counted and one million splenocytes were plated per well in a 96-well plate. Each sample was done in triplicate. Ten μg/ml of the corresponding peptide encoded by the respective expression vectors was added to each well. One well contained splenocytes without peptide added for a negative control. Cells were cultured at 37° C., 5% $CO_2$ for three days.

After three days, one μCi of $^3$H-thymidine was added to each well. After 18 hours at 37° C., the cells were harvested onto glass filters and $^3$H incorporation was measured on an LKB β plate counter. The results of the T cell proliferation assay are shown in Table 9. Antigenspecific T cell proliferation is presented as the stimulation index (SI); this is defined as the ratio of the average ³H-thymidine incorporation in the presence of antigen divided by the ³H-thymidine incorporation in the absence of antigen.

The immunogen "PADRE+IFA" is a positive control where the PADRE peptide in incomplete Freund's adjuvant was injected into the mice and compared to the response seen by injecting the MHC class II epitope constructs containing a PADRE sequence. As shown in Table 9, most of the expression vectors tested were effective at activating T cell proliferation in response to the addition of PADRE peptide. The activity of several of the expression vectors was comparable to that seen with immunization with the PADRE peptide in incomplete Freund's adjuvant. The expression vectors containing both MHC class I and MHC class II epitopes, pEP2-AOS and pcDNA-AOS, were also effective at activating T cell proliferation in response to the addition of PADRE peptide.

These results show that expression vectors encoding MHC class II epitopes fused to a MHC class II targeting sequence is effective at activating T cell proliferation and are useful for stimulating an immune response.

Example V

In vivo Assay Using Transgenic Mice

A. Materials and Methods

Peptides were synthesized according to standard F-moc solid phase synthesis methods which have been previously described (Ruppert et al., *Cell* 74:929 (1993); Sette et al., *Mol. Immunol.* 31:813 (1994)). Peptide purity was determined by analytical reverse-phase HPLC and purity was routinely>95%. Synthesis and purification of the Theradigm-HBV lipopeptide vaccine is described in (Vitiello et al., *J. Clin. Invest.* 95:341 (1995)).

Mice

HLA-A2.1 transgenic mice used in this study were the F1 generation derived by crossing transgenic mice expressing a chimeric gene consisting of the α1, α2 domains of HLA-A2.1 and α3 domain of H-2K$^b$ with SJL/J mice (Jackson Laboratory, Bar Harbor, Me.). This strain will be referred to hereafter as HLA-A2.1/K$^b$-H-2$^{bxs}$. The parental HLA-A2.1/K$^b$ transgenic strain was generated on a C57BL/6 background using the transgene and methods described in (Vitiello et al., *J. Exp. Med.* 173:1007 (1991)). HLA-A11/K$^b$ transgenic mice used in the current study were identical to those described in (Alexander et al., *J. Immunol.* 159:4753 (1997)).

Cell lines. MHC Purification, and Peptide Binding Assay

Target cells for peptide-specific cytotoxicity assays were Jurkat cells transfected with the HLA-A2.1/K$^b$ chimeric gene (Vitiello et al., *J. Exp. Med.* 173:1007 (1991)) and .221 tumor cells transfected with HLA-A11/K$^b$ (Alexander et al., *J. Immunol.* 159:4753 (1997)).

To measure presentation of endogenously processed epitopes, Jurkat-A2.1/K$^b$ cells were transfected with the pMin.1 or pMin.2-GFP minigenes then tested in a cytotoxicity assay against epitope-specific CTL lines. For transfection, Jurkat-A2.1/K$^b$ cells were resuspended at $10^7$ cells/ml and 30 μg of DNA was added to 600 μl of cell suspension. After electroporating cells in a 0.4 cm cuvette at 0.25 kV, 960 μFd, cells were incubated on ice for 10 min then cultured for 2 d in RPMI culture medium. Cells were then cultured in medium containing 200 U/ml hygromycin B (Calbiochem, San Diego Calif.) to select for stable transfectants. FACS was used to enrich the fraction of green fluorescent protein (GFP)-expressing cells from 15% to 60% (data not shown).

Methods for measuring the quantitative binding of peptides to purified HLA-A2.1 and -A11 molecules is described in Ruppert et al., *Cell* 74:929 (1993); Sette et al., *Mol. Immunol.* 31:813 (1994); Alexander et al., *J. Immunol.* 159:4753 (1997).

All tumor cell lines and splenic CTLs from primed mice were grown in culture medium (CM) that consisted of RPMI 1640 medium with Hepes (Life Technologies, Grand Island, N.Y.) supplemented with 10% FBS, 4 mM L-glutamine, $5\times10^{-5}$ M 2-ME, 0.5 mM sodium pyruvate, 100 μg/ml streptomycin, and 100 U/ml penicillin.

Construction of Minigene Multi-epitope DNA Plasmids pMIN.0 and pMIN.1 (i.e., pMIN-AOS) were constructed as described above and in U.S. Ser. No. 60/085,751.

pMin.1-No PADRE and pMin.1-Anchor. pMin.1 was amplified using two overlapping fragments which was then combined to yield the full length product. The first reaction used the 5' pcDNA vector primer T7 and either primer ATCGCTAGGCAGGAACTTATACAGGATTCC (SEQ ID NO:126) for pMin. 1-No PADRE or TGGACAGTCCG-GCTCCCAGCACCACGT (SEQ ID NO:127) for pMin. 1-Anchor. The 3' half was amplified with the primers TTC-CTGCCTAGCGATTTC (SEQ ID NO:128) (No PADRE) or GCTGGGAGCCGGACTGTCCAGGTACGT (SEQ ID NO:129) (Anchor) and Min-StopR. The two fragments generated from amplifying the 5' and 3' ends were gel purified, mixed, denatured, annealed, and filled in with five cycles of PCR. The full length fragment was further amplified with the flanking primers T7 and Min-StopR for 25 more cycles.

pMin.1-No Sig. The Ig signal sequence was deleted from pMin.1 by PCR amplification with primer GCTAGCGC-CGCCACCATGCACACCCTGTGGAAGGC CGGAATC (SEQ ID NO:130) and pcDNA rev (Invitrogen) primers. The product was cloned into pCR-blunt and sequenced.

pMin.1-Switch. Three overlapping fragments were amplified from pMin.1, combined, and extended. The 5' fragment was amplified with the vector primer T7 and primer GGGCACCAGCAGGCTCAGCCACACTC-CCAGCACCACGTC (SEQ ID NO:131). The second overlapping fragment was amplified with primers AGCCT-GCTGGTGCCCTTTGTGATCCTGAAGGAGCCTGTGC (SEQ ID NO:132) and AGCCACGTACCTGGACAGTC-CCTTCCACACAGGCACTCCAT (SEQ ID NO:133). Primer TGTCCAGGTACGTGGCTAGGCTGTGAGG-TACC (SEQ ID NO:134) and the vector primer pcDNA rev (Invitrogen) were used to amplify the third (3') fragment. Fragments 1, 2, and 3 were amplified and gel purified. Fragments 2 and 3 were mixed, annealed, amplified, and gel purified. Fragment 1 was combined with the product of 2 and 3, and extended, gel purified and cloned into pcDNA3.1 for expression.

pMin.2-GFP. The signal sequence was deleted from pMin.0 by PCR amplification with Min.0-No Sig-5' GCTAGCGCCGCCACCATGCACACCCT-GTGGAAGGCCGGAATC (SEQ ID NO:135) plus pcDNA rev (Invitrogen) primers. The product was cloned into pCR-blunt and sequenced. The insert containing the open reading frame of the signal sequence-deleted multi-epitope construct was cut out with NheI plus HindIII and ligated into the same sites of pEGFPN1 (Clontech). This construct fuses the coding region of the signal-deleted pMin.0 construct to the N-terminus of green fluorescent protein (GFP).

Immunization of Mice

For DNA immunization, mice were pretreated by injecting 50 µl of 10 µM cardiotoxin (Sigma Chem. Co., #C9759) bilaterally into the tibialis anterior muscle. Four or five days later, 100 µg of DNA diluted in PBS were injected in the same muscle.

Theradigm-HBV lipopeptide (10 mg/ml in DMSO) that was stored at−20° C., was thawed for 10 min at 45° C. before being diluted 1:10 (v/v) with room temperature PBS. Immediately upon addition of PBS, the lipopeptide suspension was vortexed vigorously and 100 µl was injected s.c. at the tail base (100 µg/mouse).

Immunogenicity of individual CTL epitopes was tested by mixing each CTL epitope (50 µg/mouse) with the HBV core 128–140 peptide (TPPAYRPPNAPIL (SEQ ID NO:49), 140 µg/mouse) which served to induce I-A$^b$-restricted Th cells. The peptide cocktail was then emuslifed in incomplete Freund's adjuvant (Sigma Chem. Co.) and 100 µl of peptide emulsion was injected s.c. at the tail base.

In vitro CTL Cultures and Cytotoxicity Assays

Eleven to 14 days after immunization, animals were sacrificed and a single cell suspension of splenocytes prepared. Splenocytes from cDNA-primed animals were stimulated in vitro with each of the peptide epitopes represented in the minigene. Splenocytes (2.5–3.0×10$^7$/flask) were cultured in upright 25 cm$^2$ flasks in the presence of 10 µg/ml peptide and 100 irradiated spleen cells that had been activated for 3 days with LPS (25 µg/ml) and dextran sulfate (7 µg/ml). Triplicate cultures were stimulated with each epitope. Five days later, cultures were fed with fresh CM. After 10 d of in vitro culture, 2–4×10$^6$ CTLs from each flask were restimulated with 10$^7$ LPS/dextran sulfate-activated splenocytes treated with 100 µg/ml peptide for 60–75 min at 37° C., then irradiated 3500 rads. CTLs were restimulated in 6-well plates in 8 ml of cytokine-free CM. Eighteen hr later, cultures received cytokines contained in con A-activated splenocyte supernatant (10–15% final concentration, v/v) and were fed or expanded on the third day with CM containing 10–15% cytokine supernate. Five days after restimulation, CTL activity of each culture was measured by incubating varying numbers of CTLs with 10$^4$ $^{51}$Cr-labelled target cells in the presence or absence of peptide. To decrease nonspecific cytotoxicity from NK cells, YAC-1 cells (ATCC) were also added at a YAC-1:$^{51}$Cr-labeled target cell ratio of 20:1. CTL activity against the HBV Pol 551 epitope was measured by stimulating DNA-primed splenocytes in vitro with the native A-containing peptide and testing for cytotoxic activity against the same peptide.

To more readily compare responses, the standard E:T ratio vs % cytotoxicity data curves were converted into LU per 10$^6$ effector cells with one LU defined as the lytic activity required to achieve 30% lysis of target cells at a 100:1 E:T ratio. Specific CTL activity (ΔLU) was calculated by subtracting the LU value obtained in the absence of peptide from the LU value obtained with peptide. A given culture was scored positive for CTL induction if all of the following criteria were met: 1) ΔLU>2;2) LU(+peptide)÷LU(−peptide)>3; and 3) a>10% difference in % cytotoxicity tested with and without peptide at the two highest E:T ratios (starting E:T ratios were routinely between 25–50:1).

CTL lines were generated from pMin.1-primed splenocytes through repeated weekly stimulations of CTLs with peptide-treated LPS/DxS-activated splenocytes using the 6-well culture conditions described above with the exception that CTLs were expanded in cytokine-containing CM as necessary during the seven day stimulation period.

Cytokine Assay

To measure IFN-γ production in response to minigene-transfected target cells, 4×10$^4$ CTLs were cultured with an equivalent number of minigene-transfected Jurkat-A2.1/K$^b$ cells in 96-well flat bottom plates. After overnight incubation at 37° C., culture supernatant from each well was collected and assayed for IFN-γ concentration using a sandwich ELISA. Immulon II microtiter wells (Dynatech, Boston, Mass.) were coated overnight at 4° C. with 0.2 µg of anti-mouse IFN-γ capture Ab, R4-6A2 (Pharmingen). After washing wells with PBS/0.1% Tween-20 and blocking with 1% BSA, Ab-coated wells were incubated with culture supernate samples for 2 hr at room temperature. A secondary anti-IFN-γ Ab, XMG1.2 (Pharmingen), was added to wells and allowed to incubate for 2 hr at room temperature. Wells were then developed by incubations with Avidin-DH and finally with biotinylated horseradish peroxidase H (Vectastain ABC kit, Vector Labs, Burlingame, Calif.) and TMB peroxidase substrate (Kirkegaard and Perry Labs, Gaithersberg, Md.). The amount of cytokine present in each sample was calculated using a rIFN-γ standard (Pharmingen).

b. Results

Selection of Epitopes and Minigene Construct Design

In the first series of experiments, the issue was whether a balanced multispecific CTL response could be induced by simple minigene cDNA constructs that encode several dominant HLA class I-restricted epitopes. Accordingly, nine CTL epitopes were chosen on the basis of their relevance in CTL immunity during HBV and HIV infection in humans, their sequence conservancy among viral subtypes, and their class I MHC binding affinity (Table 10). Of these nine epitopes, six are restricted by HLA-A2.1 and three showed HLA-Al 11-restriction. One epitope, HBV Pol 551, was studied in two alternative forms: either the wild type sequence or an analog (HBV Pol 551-V) engineered for higher binding affinity.

As referenced in Table 10, several independent laboratories have reported that these epitopes are part of the dominant CTL response during HBV or HIV infection. All of the epitopes considered showed greater than 75% conservancy in primary amino acid sequence among the different HBV subtypes and HIV clades. The MHC binding affinity of the peptides was also considered in selection of the epitopes. These experiment addressed the feasibility of immunizing with epitopes possessing a wide range of affinities and, as shown in Table 10, the six HBV and three HIV HLA-restricted epitopes covered a spectrum of MHC binding affinities spanning over two orders of magnitude, with IC$_{50}$% concentrations ranging from 3 nM to 200 nM.

The immunogenicity of the six A2.1- and three A11-restricted CTL epitopes in transgenic mice was verified by co-immunization with a helper T cell peptide in an IFA formulation. All of the epitopes induced significant CTL responses in the 5 to 73 ΔLU range (Table 10). As mentioned above, to improve the MHC binding and immunogenicity of HBV Pol 551, the C-terminal A residue of this epitope was substituted with V resulting in a dramatic 40-fold increase in binding affinity to HLA-A2.1 (Table 10). While the parental sequence was weakly or nonimmunogenic in HLA transgenic mice, the HBV Pol 551-V analog induced significant levels of CTL activity when administered in IFA (Table 10). On the basis of these results, the V analog of the HBV Pol 551 epitope was selected for the initial minigene construct. In all of the experiments reported herein, CTL responses were measured with target cells coated with the native HBV Pol 551 epitope, irrespective of whether the V analog or native epitope was utilized for immunization.

Finally, since previous studies indicated that induction of T cell help significantly improved the magnitude and duration of CTL responses (Vitiello et al., *J. Clin. Invest.* 95.341 (1995); Livingston et al., *J. Immunol.* 159:1383 (1997)), the universal Th cell epitope PADRE was also incorporated into the minigene. PADRE has been shown previously to have high MHC binding affinity to a wide range of mouse and human MHC class II haplotypes (Alexander et al., *Immunity* 1:751 (1994)). In particular, it has been previously shown that PADRE is highly immunogenic in H-$2^b$ mice that are used in the current study (Alexander et al., *Immunity* 1:751 (1994)).

pMin. 1, the prototype cDNA minigene construct encoding nine CTL epitopes and PADRE, was synthesized and subcloned into the pcDNA3.1 vector. The position of each of the nine epitopes in the minigene was optimized to avoid junctional mouse H-$2^b$ and HLA-A2.1 class I MHC epitopes. The mouse Ig K signal sequence was also included at the 5' end of the construct to facilitate processing of the CTL epitopes in the endoplasmic reticulum (ER) as reported by others (Anderson et al., *J. Exp. Med.* 174:489 (1991)). To avoid further conformational structure in the translated polypeptide gene product that may affect processing of the CTL epitopes, an ATG stop codon was introduced at the 3' end of the minigene construct upstream of the coding region for c-myc and poly-his epitopes in the pcDNA3.1 vector.

Immunopenicity of pMin.1 in Transgenic Mice

To assess the capacity of the pMin.1 minigene construct to induce CTLs in vivo, HLA-A2.1/$K^b$-H-$2^{bxs}$ transgenic mice were immunized intramuscularly with 100 µg of naked cDNA. As a means of comparing the level of CTLs induced by cDNA immunization, a control group of animals was also immunized with Theradigm-HBV, a palmitolyated lipopeptide consisting of the HBV Core 18 CTL epitope linked to the tetanus toxin 830–843 Th cell epitope.

Splenocytes from immunized animals were stimulated twice with each of the peptide epitopes encoded in the minigene, then assayed for peptide-specific cytotoxic activity in a $^{51}$Cr release assay. A representative panel of CTL responses of pMin.1-primed splenocytes, shown in FIG. 22, clearly indicates that significant levels of CTL induction were generated by minigene immunization. The majority of the cultures stimulated with the different epitopes exceeded 50% specific lysis of target cells at an E:T ratio of 1:1. The results of four independent experiments, compiled in Table 11, indicate that the pMin.1 construct is indeed highly immunogenic in HLA-A2.1/$K^b$-H-$2^{bxs}$ transgenic mice, inducing a broad CTL response directed against each of its six A2.1-restricted epitopes.

To more conveniently compare levels of CTL induction among the different epitopes, the % cytotoxicity values for each splenocyte culture was converted to ΔLU and the mean ΔLU of CTL activity in positive cultures for each epitope was determined (see Example V, materials and methods, for positive criteria). The data, expressed in this manner in Table 11, confirms the breadth of CTL induction elicited by pMin.1 immunization since extremely high CTL responses, ranging between 50 to 700 ΔLU, were observed against the six A2.1-restricted epitopes. More significantly, the responses of several hundred ΔLU observed for five of the six epitopes approached or exceeded that of the Theradigm-HBV lipopeptide, a vaccine formulation known for its high CTL-inducing potency (Vitiello et al., *J. Clin. Invest.* 95:341 (1995); Livingston et al., *J. Immunol.* 159:1383 (1997)). The HBV Env 335 epitope was the only epitope showing a lower mean ΔLU response compared to lipopeptide (Table 11, 44 vs 349 ΔLU).

Processing of Minigene Epitopes by Transfected Cells

The decreased CTL response observed against HBV Env 335 was somewhat unexpected since this epitope had good A2.1 binding affinity (IC50%, 5 nM) and was also immunogenic when administered in IFA. The lower response may be due, at least in part, to the inefficient processing of this epitope from the minigene polypeptide by antigen presenting cells following in vivo cDNA immunization. To address this possibility, Jurkat-A2.1/$K^b$ tumor cells were transfected with pMin.1 cDNA and the presentation of the HBV Env 335 epitope by transfected cells was compared to more immunogenic A2.1-restricted epitopes using specific CTL lines. Epitope presentation was also studied using tumor cells transfected with a control cDNA construct, pMin.2-GFP, that encoded a similar multi-epitope minigene fused with GFP which allows detection of minigene expression in transfected cells by FACS.

Figure 23D:
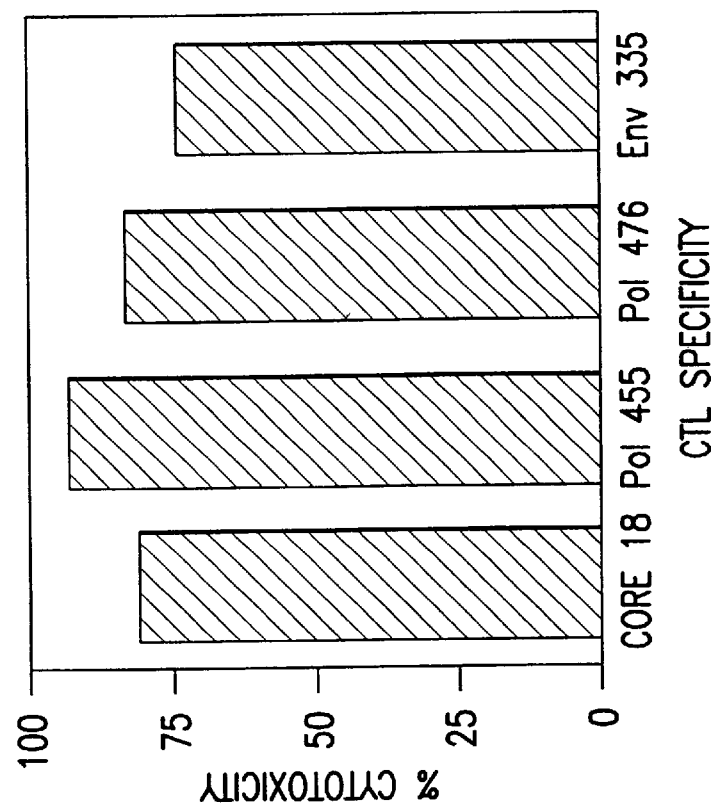
FIG. 23. Presentation of viral epitopes to specific CTLs by Jurkat-A2.1$K^b$ tumor cells transfected with DNA minigene. Two constructs were used for transfection, pMin.1 and pMin.2-GFP. pMin.2-GFP-transfected targets cells were sorted by FACS and the population used in this experiment contained 60% fluorescent cells. CTL stimulation was measured by quantitating the amount of IFN-γ release (A, B) or by lysis of $^{51}$Cr-labeled target cells (C, D, hatched bars). CTLs were stimulated with transfected cells (A, C) or with parental Jurkat-A2.1/$K^b$ cells in the presence of 1 μg/ml peptide (B, D). Levels of IFN-γ release and cytotoxicity for the different CTL lines in the absence of epitope ranged from 72–126 pg/ml and 2–6% respectively.
Figure 23C:
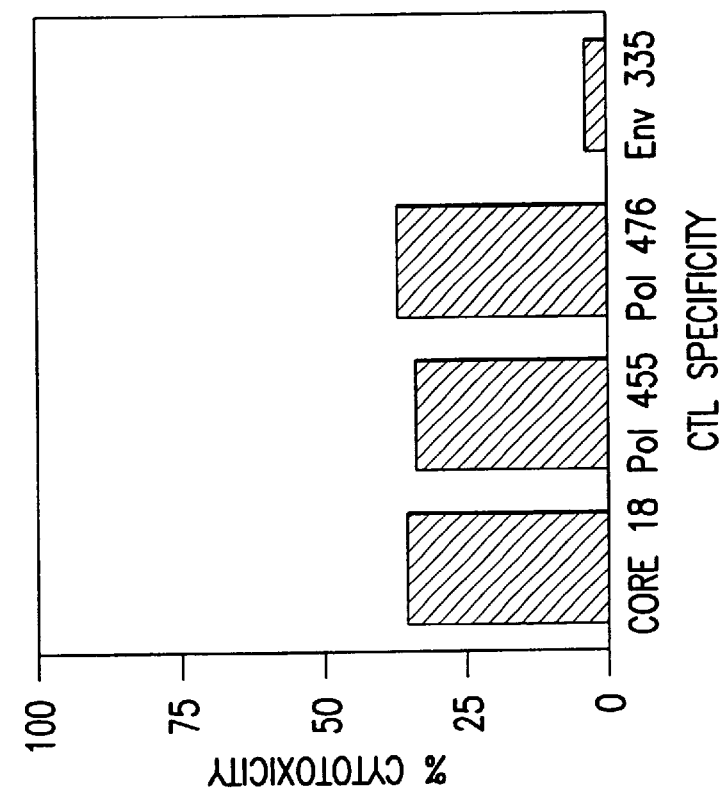

Epitope presentation of the transfected Jurkat cells was analyzed using specific CTL lines, with cytotoxicity or IFN-γ production serving as a read-out. It was found that the levels of CTL response correlated directly with the in vivo immunogenicity of the epitopes. Highly immunogenic epitopes in vivo, such as HBV Core 18, HIV Pol 476, and HBV Pol 455, were efficiently presented to CTL lines by pMin.1- or pMin.2-GFP-transfected cells as measured by IFN-γ production (FIG. 23A, >100 pg/ml for each epitope) or cytotoxic activity (FIG. 23C,>30% specific lysis). In contrast to these high levels of in vitro activity, the stimulation of the HBV Env 335-specific CTL line against both populations of transfected cells resulted in less than 12 pg/ml IFN-γ and 3% specific lysis. Although the HBV Env 335-specific CTL line did not recognize the naturally processed epitope efficiently, this line did show an equivalent response to peptide-loaded target cells, as compared to CTL lines specific for the other epitopes (FIG. 23B, D). Collectively, these results suggest that a processing and/or presentation defect associated with the HBV Env 335 epitope that may contribute to its diminished immunogenicity in vivo.

Effect of the Helper T Cell Epitope PADRE on Minigene Immunogenicity

Having obtained a broad and balanced CTL response in transgenic mice immunized with a minigene cDNA encoding multiple HLA-A2.1-restricted epitopes, next possible variables were examined that could influence the immunogenicity of the prototype construct. This type of analysis could lead to rational and rapid optimization of future constructs. More specifically, a cDNA construct based on the pMin.1 prototype was synthesized in which the PADRE epitope was deleted to examine the contribution of T cell help in minigene immunogenicity (FIG. 24A).

The results of the immunogenicity analysis indicated that deletion of the PADRE Th cell epitope resulted in significant decreases in the frequency of specific CTL precursors against four of the minigene epitopes (HBV Core 18, HIV Env 120, HBV Pol 455, and HBV Env 335) as indicated by the 17 to 50% CTL-positive cultures observed against these epitopes compared to the 90–100% frequency in animals immunized with the prototype pMin.1 construct (FIG. 25). Moreover, for two of the epitopes, HBV Core 18 and HIV Env 120, the magnitude of response in positive cultures induced by pMin.1-No PADRE was 20- to 30-fold less than that of the pMin. 1 construct (FIG. 25A).

Effect of Modulation of MHC Binding Affinity on Epitope Immunogenicity

Next a construct was synthesized in which the V anchor residue in HBV Pol 551 was replaced with alanine, the native residue, to address the effect of decreasing MHC binding on epitope immunogenicity (FIG. 24B).

Unlike deletion of the Th cell epitope, decreasing the MHC binding capacity of the HBV Pol 551 epitope by 40-fold through modification of the anchor residue did not appear to affect epitope immunogenicity (FIG. 25B). The CTL response against the HBV Pol 551 epitope, as well as to the other epitopes, measured either by LU or frequency of CTL-positive cultures, was very similar between the constructs containing the native A or improved V residue at the MHC binding anchor site. This finding reinforces the notion that minimal epitope minigenes can efficiently deliver epitopes of vastly different MHC binding affinities. Furthermore, this finding is particularly relevant to enhancing epitope immunogenicity via different delivery methods, especially in light of the fact that the wild type HBV Pol 551 epitope was essentially nonimmunogenic when delivered in a less potent IFA emulsion.

Effect of the Signal Sequence on Minigene Construct Immunogenicity

The signal sequence was deleted from the pMin.1 construct, thereby preventing processing of the minigene polypeptide in the ER (FIG. 24C). When the immunogenicity of the pMin.1-No Sig construct was examined, an overall decrease in response was found against four CTL epitopes. Two of these epitopes, HIV Env 120 and HBV Env 335, showed a decrease in frequency of CTL-positive cultures compared to pMin.1 while the remaining epitopes, HBV Pol 455 and HIV Pol 476, showed a 16-fold (from 424 to 27 ΔLU) and 3-fold decrease (709 to 236 ΔLU) in magnitude of the mean CTL response, respectively (FIG. 25C). These findings suggest that allowing ER-processing of some of the epitopes encoded in the pMin.1 prototype construct may improve immunogenicity, as compared with constructs that allow only cytoplasmic processing of the same panel of epitopes.

Effect of Epitope Rearrangement and Creation of New Junctional Epitopes

In the final construct tested, the immunogenicity of the HBV Env 335 epitope was analyzed to determine whether it may be influenced by its position at the 3' terminus of the minigene construct (FIG. 24D). Thus, the position of the Env epitope in the cDNA construct was switched with a more immunogenic epitope, HBV Pol 455, located in the center of the minigene. It should be noted that this modification also created two potentially new epitopes. As shown in FIG. 25D, the transposition of the two epitopes appeared to affect the immunogenicity of not only the transposed epitopes but also more globally of other epitopes. Switching epitopes resulted in obliteration of CTL induction against HBV Env 335 (no positive cultures detected out of six). The CTL response induced by the terminal HBV Pol 455 epitope was also decreased but only slightly (424 vs 78 mean ΔLU). In addition to the switched epitopes, CTL induction against other epitopes in the pMin. 1-Switch construct was also markedly reduced compared to the prototype construct. For example, a CTL response was not observed against the HIV Env 120 epitope and it was significantly diminished against the HBV Core 18 (4 of 6 positive cultures, decrease in mean ΔLU from 306 to 52) and HBV Pol 476 (decrease in mean ΔLU from 709 to 20) epitopes (FIG. 25D).

As previously mentioned, it should be noted that switching the two epitopes had created new junctional epitopes. Indeed, in the pMin.1-Switch construct, two new potential CTL epitopes were created from sequences of HBV Env 335-HIV Pol 476 (LLVPFVIL (SEQ ID NO:123), H-2$K^b$-restricted) and HBV Env 335-HBV Pol 551 (VLGVWLSLLV (SEQ ID NO:136), HLA-A2.1-restricted) epitopes. Although these junctional epitopes have not been examined to determine whether or not they are indeed immunogenic, this may account for the low immunogenicity of the HBV Env 335 and HIV Pol 476 epitopes. These findings suggest that avoiding junctional epitopes may be important in designing multi-epitope minigenes as is the ability to confirm their immunogenicity in vivo in a biological assay system such as HLA transgenic mice.

Induction of CTLs Against A11 Epitopes Encoded in pMin. 1

To further examine the flexibility of the minigene vaccine approach for inducing a broad CTL response against not only multiple epitopes but also against epitopes restricted by different HLA alleles, HLA-A11$K^b$ transgenic mice were immunized to determine whether the three Al I epitopes in the pMin.1 construct were immunogenic for CTLs, as was the case for the A2.1-restricted epitopes in the same construct. As summarized in Table 12, significant CTL induction was observed in a majority of cultures against all three of the HLA-A11-restricted epitopes and the level of CTL immunity induced for the three epitopes, in the range of 40 to 260 ΔLU, exceeded that of peptides delivered in IFA (Table 10). Thus,.nine CTL epitopes of varying HLA restrictions incorporated into a prototype minigene construct all demonstrated significant CTL induction in vivo, confirming that minigene DNA plasmids can serve as means of delivering multiple epitopes, of varying HLA restrictions and MHC binding affinities, to the immune system in an immunogenic fashion and that appropriate transgenic mouse strains can be used to measure DNA construct immunogenicity in vivo.

CTLs were also induced against three A11 epitopes in A11/$K^b$ transgenic mice. These responses suggest that minigene delivery of multiple CTL epitopes that confers broad population coverage may be possible in humans and that transgenic animals of appropriate haplotypes may be a useful tools in optimizing the in vivo immunogenicity of minigene DNA. In addition, animals such as monkeys having conserved HLA molecules with cross reactivity to CTL and HTL epitopes recognized by human MHC molecules can be used to determine human immunogenicity of HTL and CTL epitopes (Bertoni et al., *J. Immunol.*161:4447–4455 (1998)).

This study represents the first description of the use of HLA transgenic mice to quantitate the in vivo immunogenicity of DNA vaccines, by examining response to epitopes restricted by human HLA antigens. In vivo studies are required to address the variables crucial for vaccine development, that are not easily evaluated by in vitro assays, such as route of administration, vaccine formulation, tissue biodistribution, and involvement of primary and secondary lymphoid organs. Because of its simplicity and flexibility, HLA transgenic mice represent an attractive alternative, at least for initial vaccine development studies, compared to more cumbersome and expensive studies in higher animal species, such as nonhuman primates. The in vitro presentation studies described above further supports the use of HLA transgenic mice for screening DNA constructs containing human epitopes inasmuch as a direct correlation between in vivo immunogenicity and in vitro presentation was observed. Finally, strong CTL responses were observed against all six A 2.1 restricted viral epitopes and in three A11 restricted epitopes encoded in the prototype pMin.1 construct. For five of the A 2.1 restricted epitopes, the magnitude of CTL response approximated that observed with the lipopeptide, Theradigm-HBV, that previously was shown to induce strong CTL responses in humans (Vitiello et al., *J. Clin. Invest.* 95:341 (1995); Livingston et al., *J. Immunol.* 159:1383 (1997)).

TABLE 1

HBV derived HTL epitopes

| Peptide | Sequence | Source | SEQ ID NO: |
|---|---|---|---|
| 1298.06 | KQAFTFSPTYKAFLC | HBV POL 661 | 137 |
| F107.03 | LQSLTNLLSSNLSWL | RBV POL 412 | 138 |
| 1280.06 | AGFFLLTRILTlPQS | HBV ENV 180 | 139 |
| 1280.09 | GTSFVYVPSALNPAD | HBV POL 774 | 140 |
| CF-08 | VSFGVWIRTPPAYRPPNAPI | HBV NUC 120 | 141 |
| 27.0280 | GVWIRTPPAYRPPNA | HBV NUC 123 | 142 |
| 1186.25 | SFGVWIRTPPAYRPP | HBV NUC 121 | 143 |
| 27.0281 | RHYLHTLWKAGILYK | HBV POL 145 | 144 |
| F107.04 | PFLLAQFTSAICSVV | HBV POL 523 | 145 |
| 1186.15 | LVPFVQWFVGLSPTV | HBV ENV 339 | 146 |
| 1280.15 | LHLYSHPlILGFRKl | HBV POL 501 | 147 |
| 1298.04 | KQCFRKLPVNRPIDW | HBV POL 615 | 148 |
| 1298.07 | AANWILRGTSFVYVP | HBV POL 764 | 149 |
| 857.02 | PHHTALRQAILCWGELMTLA | HBV CORE 50 | 150 |
| 35.0100 | LCQVFADATPTGWGL | HBV POL 683 | 151 |
| 35.0096 | ESRLVVDFSQFSRGN | HBV POL 387 | 152 |
| 35.0093 | VGPLTVNEKRRLKLl | HBV POL 96 | 153 |
| 1186.18 | NLSWLSLDVSAAFYH | HBV POL 422 | 154 |

TABLE 2

HBV derived CTL epitopes

| Supertype | Peptide | Sequence | Source | SEQ ID NO: |
|---|---|---|---|---|
| A2 | 924.07 | FLPSDFFPSV | HBV core 18–27 | 91 |
|  | 1013.0102 | WLSLLVPFV | HBVadr-ENV (S Ag 335–343) | 107 |
|  | 777.03 | FLLTRILTI | HBV ENV ayw 183 | 155 |
|  | 927.15 | ALMPLYACI | HBV ayw pol 642 | 156 |
|  | 1168.02 | GLSRYVARL | HBV POL 455 | 99 |
|  | 927.11 | FLLSLGIHL | HBV pol 562 | 157 |
| A3 | 1147.16 | HTLWKAGILYK | HBV POL 149 | 88 |
|  | 1083.01 | STLPETTVVRR | HBV core 141 | 103 |
|  | 1090.11 | SAICSVVRR | HBV pol 531 | 158 |
|  | 1090.10 | QAFTFSPTYK | HBV pol 665 | 159 |
|  | 1069.16 | NVSIPWTHK | HBV pol 47 | 160 |
|  | 1069.20 | LVVDFSQFSR | HBV pol 388 | 161 |
|  | 1142.05 | KVGNFTGLY | HBV adr POL 629 | 162 |
|  | 1069.15 | TLWKAGILYK | HBV pol 150 | 163 |
| B7 | 1145.04 | IPIPISSWAF | HBV ENV 313 | 164 |
|  | 988.05 | LPSDFFPSV | HBV core 19–27 | 165 |
|  | 1147.04 | TPARVTGGVF | HBV POL 354 | 166 |
| A2 | 1069.06 | LLVPFVQWFV | HBV env 338–347 | 167 |
|  | 1147.13 | FLLAQFTSAI | HBV POL 513 | 168 |
|  | 1147.14 | VLLDYQGMLPV | HBV ENV 259 | 169 |
|  | 1132.01 | LVPFVQWFV | HBV ENV 339 | 170 |
|  | 1069.05 | LLAQFTSAI | HBV pol 504–512 | 171 |
|  | 927.42 | NLSWLSLD-V | HBV pol 411 | 172 |
|  | 927.41 | LLSSNLSWL | HBV pol 992 | 173 |
|  | 927.46 | KLHLYSHPI | HBV pol 489 | 174 |
|  | 1069.071 | FLLAQFRSA | HBV pol 503 | 175 |
|  | 1142.07 | GLLGWSPQA | HBV ENV 62 | 176 |
|  | 927.47 | HLYSHPIIL | HBV ayw pol 1076 | 177 |
|  | 1069.13 | PLLPIFFCL | HBV env 377–385 | 178 |
|  | 103.1402 | VLQAGFFLL | HBVadr-ENV 177 | 179 |
|  | 1090.14 | YMDDVVLGA | HBV pol 538–546 | 95 |
| A3 | 26.0539 | RLVVDFSQFSR | HBV pol 376 | 180 |
|  | 26.0535 | GVWIRTPPAYR | HBV X niuc fus 299 | 181 |
| A3 | 26.0153 | SSAGPCALR | HBV X 64 | 182 |
|  | 1.0993 | KVFVLGGCR | HBV adr "X" 1548 | 183 |
|  | 26.0149 | CALRFTSAR | HBV X 69 | 184 |
|  | 26.0023 | VSFGVWIR | HBV x nuc fus 296 | 185 |
|  | 26.0545 | TLPETUVVRRR | HBV x nuc fus 318 | 186 |
|  | 20.0131 | SVVRRAFPH | HBV POL 524 | 187 |
|  | 1.0219 | FVLGGCRHK | HBV adr "X" 1550 | 188 |
|  | 26.0008 | FTFSPTYK | HBV pol 656 | 189 |
|  | 20.0130 | AFTESPTYK | HBV POL 655 | 190 |

TABLE 2-continued

HBV derived CTL epitopes

| Supertype | Peptide | Sequence | Source | SEQ ID NO: |
|---|---|---|---|---|
| B7 | 1147.05 | FPHCLAFSYM | HBV POL 530 | 191 |
|  | 1147.08 | YPALMPLYA | HBV POL 640 | 192 |
|  | 1147.06 | LPVCAFSSA | HBV X 58 | 193 |
|  | 1147.02 | HPAAMPHLL | HBV POL 429 | 194 |
|  | 26.0570 | YPALMPLYACI | HBV pol 640 | 195 |
|  | 19.0014 | YPALMPLY | HBV POL 640 | 196 |
|  | 1145.08 | FPHCLAFSY | HBV POL 541 | 197 |
| Other | 1090.02 | AYRPPNAPI | HBV NUC 131 | 198 |
|  | 1.0519 | DLLDTASALY | HBV adr CORE 419 | 199 |
|  | 13.0129 | EYLVSFGVWI | HBV NUC 117 | 200 |
|  | 20.0254 | FAAPFTQCGY | HBV POL 631 | 201 |
|  | 2.0060 | GYPALMPLY | HBV ALL 1224 | 202 |
|  | 1069.04 | HTLWKAGILY | HBV pol 149 | 203 |
|  | 1069.08 | ILLLCLIFLL | HBV env 249–258 | 204 |
|  | 1.0166 | KVGNFTGLY | HBV adr POL 629 | 162 |
|  | 1069.23 | KYTSFPWLL | HBV POL 745 | 205 |
|  | 1069.01 | LLDTASALY | HBV core 59 | 26 |
|  | 2.0239 | LSLDVSAAFY | HBV ALL 1000 | 207 |
|  | 2.0181 | LYSRPIILGF | HBV POL 492 | 208 |
|  | 1039.01 | MMWYWGPSLY | HBV 360 | 209 |
|  | 2.0126 | MSTTDLEAY | HBV adr 1521 | 210 |
|  | 1069.03 | PLDKGIKPYY | HBV pol 124 | 211 |
|  | 1090.09 | PTTGRTSLY | HBV pol 808 | 212 |
|  | 20.0138 | PWTHKVGNF | HBV POL 51 | 213 |
|  | 20.0135 | RWMCLRRFI | HBV ENV 236 | 214 |
|  | 20.0269 | RWMCLRRFII | HBV ENV 236 | 215 |
|  | 20.0139 | SFCGSPYSW | HBV POL 167 | 216 |
| Other | 1069.02 | SLDVSAAFY | RBV pol 427 | 217 |
|  | 20.0136 | SWLSLLVPF | HBV ENV 334 | 218 |
|  | 20.0271 | SWPKFAVPNL | HBV POL 392 | 219 |
|  | 20.0137 | SWWTSLNFL | HBV ENV 197 | 220 |
|  | 2.0173 | SYQHFRKLLL | HBV POL 4 | 221 |
|  | 13.0073 | WFHISCLTF | HBV NUC 102 | 222 |
|  | 1.0774 | WLWGMDIDPY | HBV adw CORE 416 | 223 |
|  | 1039.06 | WMMWYWGPSLY | HBV env 359 | 224 |
|  | 924.14 | FLPSDFFPSI | HBv 18–27 $I_{10}$ var. | 225 |
|  | 1090.77 | YMDDVVLGV | HBV pol 538–546 sub | 462 |
|  | 941.01 | FLPSDYFPSV | HBc 18–27 analog | 226 |
|  | 1083.02 | STLPETYVVRR | HBV core 141–151 analog | 227 |
|  | 1145.05 | FPIPSSWAF | HBV ENV 313 analog | 228 |
|  | 1145.11 | FPHCLAFSL | HBV POL 541 analog | 229 |
|  | 1145.24 | FPHCLAFAL | HBV POL 541 analog | 230 |
|  | 1145.06 | IPITSSWAF | HBV ENV 313 analog | 231 |
|  | 145.23 | IPIPMSWAF | HBV ENV 313 analog | 232 |
|  | 1145.07 | IPILSSWAF | HBV ENV 313 analog | 233 |
|  | 1145.09 | FPVCLAFSY | HBV POL 541 analog | 234 |
|  | 1145.10 | FPHCLAFAY | HBV POL 541 analog | 235 |

TABLE 3

HCV derived HTL epitopes

| Peptide | Sequence | Source | SEQ ID NO: |
|---|---|---|---|
|  | AAYAAQGYKVLVLNPSVAATLGFGAY | HCV NS3 1242–1267 | 236 |
| P98.03 | AAYAAQGYKVLVLNPSVAAT | HCV NS3 1242 | 237 |
| P98.04 | GYKVLVLNPSVAATLGFGAY | HCV NS3 1248 | 238 |
| P98.05 | GYKVLVLNPSVAAT | HCV NS3 1248 | 239 |
| 1283.21 | GYKVLVLNPSVAATL | HCV NS3 1253 | 240 |
| 1283.20 | AQGYKVLVLNPSVAA | HCV NS3 1251 | 241 |
|  | GEGAVQWMNRLIAFASRGNHVS | HCV NS4 1914–1935 | 242 |
| F134.08 | GEGAVQWMNRLIAFASRGNHV | HCV NS4 1914 | 243 |
| 1283.44 | MNRLIAFASRGNHVS | HCV NS4 1921 | 244 |
| 1283.16 | SKGWRLLAPITAYAQ | HCV NS3 1025 | 245 |
| 1283.55 | GSSYGFQYSPGQRVE | HCV NS5 2641 | 246 |
| F134.05 | NFISGIQYLAGLSTLPGNPA | HCV NS4 1772 | 247 |
| 1283.61 | ASCLRKLGVPPLRVW | HCV NS5 2939 | 248 |
| 1283.25 | GRHLIFCHSKKKCDE | HCV NS3 1393 | 249 |
| 35.0107 | TVDFSLDPTFTIETT | HCV 1466 | 250 |
| 35.0106 | VVVVATDALMTGYTG | HCV 1437 | 251 |

TABLE 4

HCV derived CTL epitopes

| Super-type | Peptide | Sequence | Source | SEQ ID NO: |
|---|---|---|---|---|
| A2 | 1090.18 | FLLLADARV | HCV NS I/E2 728 | 252 |
| | 1073.05 | LLFNILGGWV | HCV NS4 1812 | 253 |
| | 1013.02 | YLVAYQATV | HCV NS3 1590 | 254 |
| | 1013.1002 | DLMGYIPLV | HCV Core 132 | 255 |
| | 1090.22 | RLIVFPDLGV | HCV NS5 2611 | 256 |
| | 24.0075 | VLVGGVLAA | HCV NS4 1666 | 257 |
| | 24.0073 | WMNRLIAFA | HCV NS4 1920 | 258 |
| | 1174.08 | HMWNFISGI | HCV NS4 1769 | 259 |
| | 1073.06 | ILAGYGAGV | HCV NS4 1851 | 260 |
| | 24.0071 | LLFLLLADA | HCV NS1/E2 726 | 261 |
| | 1073.07 | YLLPRRGPRL | HCV Core 35 | 262 |
| | 1.0119 | YLVTRHADV | HCV NS3 1136 | 263 |
| A3 | 1.0952 | KTSERSQPR | HCV Core 51 | 264 |
| | 1073.10 | GVAGALVAFR | HCV NS4 1863 | 265 |
| | 1.0123 | LIFCHSKKK | HCV NS3 1391 | 266 |
| | 1.0955 | QLFTFSPRR | HCV E1 290 | 267 |
| | 1073.11 | RLGVRATRK | HCV Core 43 | 268 |
| | 1073.13 | RMYVGGVEHR | HCV NS1/E2 635 | 269 |
| | 24.0090 | VAGALVAFK | HCV NS4 1864 | 270 |
| | F104.01 | VGIYLLPNR | HCV NS5 3036 | 271 |
| B7 | 1145.12 | LPGCSFSIF | HCV Core 168 | 272 |
| | 29.0035 | IPFYGKAI | HCV 1378 | 273 |
| Other | 1069.62 | CTCGSSDLY | HCV NS3 1128 | 274 |
| | 24.0092 | FWAKHMVNF | HCV NS4 1765 | 275 |
| | 13.0019 | LSAFSLRSY | HCV NS5 2922 | 276 |
| A3 | 24.0086 | LGFGAYMSK | HCV NS3 1267 | 277 |
| | 1174.21 | RVCEKMALY | HCV NS5 2621 | 278 |
| | 1174.16 | WMNSTGFTK | HCV NS1/E2 557 | 279 |
| | 1073.04 | TLHGPTPLLY | HCV NS3 1622 | 280 |
| B7 | 16.0012 | FPYLVAYQA | HCV NS3 1588 | 281 |
| | 15.0047 | YPCTVNFTI | HCV NS1/E2 623 | 282 |
| Other | 24.0093 | EVDGVRLHRY | HCV NS5 2129 | 283 |
| | 3.0417 | LTCGFADLMGY | HCV 126 | 284 |
| | 1073.01 | NIVDVQYLY | HCV E1 700 | 285 |
| | 1.0509 | GLSAFSLHSY | HCV NS5 2921 | 286 |
| | 1073.17 | MYVGDLCGSVF | HCV E1 275 | 287 |
| | 1073.18 | MYVGGVEHRL | HCV NS1/E2 633 | 288 |
| | 13.075 | QYLAGLSTL | HCV NS4 1778 | 289 |
| | 1145.13 | FPGCSFSIF | HCV Core 168 | 290 |
| | 1145.25 | LPGCMFSIF | HCV Core 168 | 291 |
| | 1292.24 | LPGCSFSII | HCV Core 169 | 292 |
| | 1145.14 | LPVCSFSIF | HCV Core 168 | 293 |
| | 1145.15 | LPGCSFSYF | HCV Core 168 | 294 |

TABLE 5

HIV derived HTL epitopes

| Peptide | Sequence | Source | SEQ ID NO: |
|---|---|---|---|
| | GEIYKRWIILGLNKIVRMYSPTSILD | HIV1 GAG 294–319 | 295 |
| | KRWIILGLNKIVRMYSPTSILD | HIV gag 298–319 | 296 |
| 27.0313 | KRWIILGLNKIVRMY | HIV1 GAG 298 | 297 |
| 27.0311 | GEIYKRWIILGLNKI | HIV1 GAG 294 | 298 |
| 27.0354 | WEFVNTPPLVKLWYQ | HIV1 POL 596 | 299 |
| 27.0377 | QKQITKIQNFRVYYR | HIV1 POL 956 | 300 |
| | EKVYLAWVPAHKGIGG | HIV1 POL 711–726 | 301 |
| 1280.03 | KVYLAWVPAHKGIGG | HIV POL 712 | 302 |
| 27.0361 | EKVYLAWVPAHKGIG | HIV1 POL 711 | 303 |
| | PIVQNIQGQMVHQAISPRTLNA | HIV1 gag 165–186 | 304 |
| 27.0304 | QGQMVHQAISPRTLN | HIV1 GAG 171 | 305 |
| 27.0297 | QHLLQLTVWGIKQLQ | HIV1 ENV 729 | 306 |
| 27.0344 | SPAIFQSSMTKILEP | HIV1 POL 335 | 307 |
| F091.15 | IKQFINMWQEVGKAMY | HIV1 ENV 566 | 308 |
| 27.0341 | FRKYTAFTIPSINNE | HIV1 POL 303 | 309 |
| 27.0364 | HSNWRAMASDFNLPP | HIV1 POL 758 | 310 |
| 27.0373 | KTAVQMAVFIHNFKR | HIV1 POL 915 | 311 |
| | DRVHPVHAGPIAPGQMREPRGS | HIV GAG 245 | 312 |
| | AFSPEVIPMFSALSEGATPQDLNTML | HIV gag 195–216 | 313 |
| | AFSPEVIPMFSALSEGATPQDL | HIV gag 195–216 | 314 |
| 200.06 | SALSEGATPQDLNIMLT | HIV gag 205 | 315 |
| 27.0307 | SPEVIPMFSALSEGA | HIV gag 197 | 316 |
| | LQEQIGWMTNNPPIPVGEIYKR | HIV gag 275 | 317 |
| 27.0310 | QEQIGWMTNNPPIPV | HIV gag 276 | 3218 |
| 35.0135 | YRKILRQRKIDRLID | HIV VPU 31 | 319 |
| 35.0131 | WAGIKQEFGIPYNPQ | HIV POL 874 | 320 |
| 35.0127 | EVNIVTDSQYALGII | HIV POL 674 | 321 |
| 35.0125 | AETFYVDGAANRETK | HIV POL 619 | 322 |
| 35.0133 | GAVVIQDNSDIKVVP | HIV POL 989 | 323 |

TABLE 6

HIV derived CTL epitopes

| Supertype | Peptide | Sequence | Source | SEQ ID NO: |
|---|---|---|---|---|
| A2 | 25.0148 | MASDFNLPPV | HIV1 POL 70 | 324 |
|  | 1069.32 | VLAEAMSQV | HIV gag 397 | 325 |
|  | 1211.04 | KLTPLCVTL | HIV ENV 134 | 326 |
|  | 25.0062 | KILVGKLNWA | HIV1 POL 87 | 463 |
|  | 25.0039 | LTFGWCFKL | HIV1 NEF 62 | 327 |
|  | 941.031 | ILKEPVHGV | HIVI pol 476–484 | 101 |
|  | 25.0035 | MTNNPPIPV | HIV1 GAG 34 | 328 |
|  | 25.0057 | RILQQLLFI | HIV1 VPR 72 | 329 |
| A3 | 1.0944 | AVFIHNFKR | HIV POL 1434 | 330 |
|  | 1.1056 | KIQNFRVYYR | HIV POL 1474 | 331 |
|  | 1069.49 | QMAVFIHNFK | HIV pol 1432 | 332 |
|  | 966.0102 | AIFQSSMTK | HIV pol 337 | 333 |
|  | 1150.14 | MAVFIHNFK | HIV pol 909 | 334 |
|  | 940.03 | QVPLRPMTYK | HIV nef 73–82 | 335 |
|  | 25.0175 | TTLFCASDAK | HIV1 ENV 81 | 336 |
|  | 1069.43 | TVYYGVPVWK | HIV env 49 | 105 |
|  | 25.0209 | VTIKIGGQLK | HIV1 POL 65 | 337 |
| B7 | 1146.01 | FPVRPQVPL | HIV nef 84–92 | 338 |
|  | 29.0060 | IPIHYCAPA | HIV env 293 | 339 |
|  | 15.0073 | FPISPIETV | HIV POL 171 | 340 |
|  | 29.0056 | CPKVSFEPI | HIV env 285 | 341 |
|  | 29.0107 | IPYNPQSQGVV | HIV pol 883 | 342 |
| A2 | 25.0151 | CTLNFPISPI | HIV1 POL 96 | 343 |
|  | 25.0143 | LTPGWCFKLV | HIV1 NEFP 62 | 344 |
|  | 25.0043 | YTAFTIPSI | HIV1 POL 83 | 345 |
|  | 25.0055 | AIIRILQQL | HIV1 VPR 76 | 346 |
|  | 25.0049 | ALVEICTEM | HIV1 POL 52 | 347 |
|  | 25.0032 | LLQLTVWGI | HIV1 ENV 61 | 348 |
|  | 25.0050 | LVGPTPVNI | HIV1 POL 100 | 349 |
|  | 25.0047 | KAACWWAGI | HIV1 POL 65 | 350 |
|  | 25.0162 | KMIGGIGGFI | HIV1 POL 96 | 351 |
|  | 25.0052 | RAMASDFNL | HIV1 POL 78 | 352 |
|  | 1211.09 | SLLNATDIAV | HIV ENV 814 | 353 |
| A2 | 25.0041 | TLNFPISPI | HIV1 POL 96 | 354 |
| A3 | 1.0046 | IVIWGKTPK | HIV POL 1075 | 355 |
|  | 25.0064 | MVHQAISPR | HIV1 GAG 45 | 356 |
|  | 1.0062 | YLAWVPAHK | HIV POL 1227 | 357 |
|  | 1.0942 | MTKILEPFR | HIV POL 859 | 358 |
|  | 25.0184 | QMVHQAISPR | HIV1 GAG 45 | 359 |
|  | 1069.48 | AVFIHNFKRK | HIV pol 1434 | 360 |
|  | 1069.44 | KLAGRWPVK | HIV pol 1358 | 361 |
|  | 1069.42 | KVYLAWVPAHK | HIV pol 1225 | 362 |
|  | 1.0024 | NTPVFAIKK | HIV pol 752 | 363 |
|  | 25.0062 | RIVELLGRR | HIV1 ENV 53 | 364 |
|  | 25.0095 | TIKIGGQLK | HIV1 POL 65 | 365 |
|  | 25.0078 | TLFCASDAK | HIV1 ENV 82 | 366 |
|  | 25.0104 | VMIVWQVDR | HIV1 VIF 83 | 367 |
|  | 1069.47 | VTVYYGVPVWK | HIV env 48 | 368 |
| B7 | 15.0268 | YPLASLRSLF | HIV GAG 507 | 369 |
|  | 1292.13 | HPVHAGPIA | HIV GAG 248 | 370 |
|  | 19.0044 | VPLQLPPL | HJV con. REV 71 | 371 |
| Other | 1.0431 | EVNIVTDSQY | HIV POL 1187 | 372 |
|  | 1.0014 | FRDYVDRFY | HIV GAG 298 | 373 |
|  | 25.0113 | IWGCSGKLI | HIV1 ENV 69 | 374 |
|  | 25.0127 | IYETYGDTW | HIV1 VPR 92 | 375 |
|  | 1069.60 | IYQEPFKNL | HIV pol 1036 | 376 |
|  | 2.0129 | IYQYMDDLY | HIV pol 359 | 377 |
|  | 25.0128 | PYNEWTLEL | HIV1 VPR 56 | 378 |
|  | 25.0123 | PYNTPVFAI | HIV1 POL 74 | 379 |
|  | 1069.57 | RYLKDQQLL | HIV env 2778 | 380 |
|  | 1069.58 | RYLRDQQLL | HIV env 2778 | 381 |
|  | 1069.59 | TYQIYQEPF | HIV pol 1033 | 382 |
|  | 1069.27 | VIYQYMDDLY | HIV pol 358 | 383 |
|  | 1069.26 | VTVLDVGDAY | HIV pol 265 | 384 |
|  | 25.0115 | VWKEATTTL | HIV1 ENV 47 | 385 |
|  | 25.0218 | VWYEATITLF | HIV1 ENV 47 | 386 |
|  | 25.0219 | YMQATWIPEW | HIV1 POL 96 | 387 |
| A2 | 1211.4 | SLLNATAIAV | HIV MN gp 160 814(a) | 388 |

TABLE 6-continued

HIV derived CTL epitopes

| Supertype | Peptide | Sequence | Source | SEQ ID NO: |
|---|---|---|---|---|
| A3 | F105.21 | AIFQRSMTR | HIV pol 337(a) | 389 |
| | F105.17 | AIFQSSMTR | HIV pol 337(a) | 390 |
| | F105.02 | GIFQSSMTY | HIV pol 337(a) | 391 |
| | F105.03 | AAFQSSMTK | HIV pol 337(a) | 392 |
| | F105.04 | AIAQSSMTK | HIV pol 337(a) | 393 |
| | F105.05 | AIFASSMTK | HIV pol 337(a) | 394 |
| | F105.06 | AIFQASMTK | HIV pol 337(a) | 395 |
| | F105.07 | AIFQSAMTK | HIV pol 337(a) | 396 |
| | F105.08 | AIFQSSATK | HIV pol 337(a) | 397 |
| | F105.09 | AIFQSSMAK | HIV pol 337(a) | 398 |
| | F105.11 | FIFQSSMTK | HIV pol 337(a) | 399 |
| | F105.12 | SIFQSSMTK | HIV pol 337(a) | 400 |
| | F105.16 | AIFQCSMTK | HIV pol 337(a) | 401 |
| B7 | 1145.03 | FPVRPQFPL | HIV nef 84–92 analog | 402 |
| | 1181.03 | FPVRPQVPI | HIV nef 84–92(a) | 403 |
| | 1292.14 | HPVHAGPII | HIV GAG 248 | 404 |
| | 1292.09 | FPISPIETI | HIV POL 179 | 405 |
| | 1145.02 | FPVFQVPL | HIV nef 84–92 analog | 406 |
| | 1145.22 | TPVRMQVPL | HIV nef 84–92 analog | 407 |
| | 1181.04 | FPVRPQVPM | HIV nef 84–92(a) | 408 |
| | 1181.01 | FPVRPQVPA | HIV nef 84–92(a) | 409 |
| | 1181.02 | FPVRPQVPV | HIV nef 84–92(a) | 410 |
| | 1181.05 | FPVRPQVPF | HIV nef 84–92(a) | 411 |
| | 1181.06 | FPVRPQVPW | HIV nef 84–92(a) | 412 |

TABLE 7

P. falciparum derived HTL epitopes

| Peptide | Sequence | Source | SEQ ID NO: |
|---|---|---|---|
| F125.04 | RHNWVNHAVPLAMKLI | Pf SSP2 61 | 473 |
| 1188.34 | HNWVNHAVPLAMKLI | Pf SSP2 62 | 414 |
| 1188.16 | KSKYKLATSVLAGLL | Pf EXP1 71 | 415 |
| | LVNLLIFHINGKIIKNSE | Pf LSA1 13 | 416 |
| F125.02 | LVNLLIFHINGKIIKNS | Pf LSA1 13 | 417 |
| 27.0402 | LLIFHINGKIIKNSE | Pf LSA1 16 | 418 |
| 1188.32 | GLAYKFVVPGAATPY | Pf SSP2 512 | 419 |
| 27.0392 | SSVFNVVNSSIGLIM | Pf CSP 410 | 420 |
| 27.0417 | VKNVTGPFMKAVCVE | Pf SSP2 223 | 421 |
| 27.0388 | MRKLAILSVSSFLFV | Pf CSP 2 | 422 |
| 27.0387 | MNYYGKQENWYSLKK | Pf CSP 53 | 423 |
| 1188.38 | KYKIAGGIAGGLALL | Pf SSP2 494 | 424 |
| 1188.13 | AGLLGNVSTVLLGGV | Pf EXP1 82 | 425 |
| 27.0408 | QTNFKSLLRNLGVSE | Pf LSA1 94 | 426 |
| 35.0171 | PDSIQDSLKESRKLN | Pf SSP2 165 | 427 |
| 35.0172 | KCNLYADSAWENVKN | Pf SSP2 211 | 428 |

TABLE 8

P. falciparum derived CTL epitopes

| Supertype | Peptide | Sequence | Source | SEQ ID NO: |
|---|---|---|---|---|
| A2 | 1167.21 | FLIFFDLFLV | Pf SSP2 14 | 429 |
| | 1167.08 | GLIMVLSFL | Pf CSP 425 | 430 |
| | 1167.12 | VLAGLLGNV | Pf EXP1 80 | 431 |
| | 1167.13 | KILSVFFLA | Pf EXP1 2 | 432 |
| | 1167.10 | GLLGNVSTV | Pf EXP183 | 433 |
| | 1167.18 | ILSVSSFLFV | Pf CSP 7 | 434 |
| | 1167.19 | VLLGGVGLVL | Pf EXP 1 91 | 435 |
| A3 | 1167.36 | LACAGLAYK | Pf SSP2 511 | 436 |
| | 1167.32 | QTNFKSLLR | Pf LSA1 94 | 437 |
| | 1167.43 | VTCGNGIQVR | Pf CSP 375 | 438 |
| | 1167.24 | ALFFIINK | Pf EXP1 10 | 439 |
| | 167.28 | GVSENIFLK | Pf LSA 1 105 | 440 |
| | 1167.47 | HVLSHNSYEK | Pf LSA1 59 | 441 |
| | 1167.51 | LLACAGLAYK | Pf SSP2 510 | 442 |
| | 1167.46 | FILVNLLIFH | Pf LSA1 11 | 443 |
| B7 | 1101.03 | MPLETQLAI | Pf SHEBA 77 | 444 |
| | 1167.61 | TPYAGEPAPF | Pf SSP2 539 | 445 |

TABLE 8-continued

P. falciparum derived CTL epitopes

| Supertype | Peptide | Sequence | Source | SEQ ID NO: |
|---|---|---|---|---|
| A2 | 1167.14 | FLIFFDLFL | Pf SSP2 14 | 446 |
| | 1167.16 | FMKAVCVEV | Pf SSP2 230 | 447 |
| | 1167.15 | LIFFDLFLV | Pf SSP2 15 | 448 |
| | 1167.17 | LLMDCSGSI | Pf SSP2 51 | 449 |
| | 1167.09 | VLLGGVGLV | Pf EXP1 91 | 450 |
| B7 | 19.0051 | LPYGRTNL | Pf SSP2 126 | 451 |
| Other | 16.0245 | FQDEENIGIY | Pf LSA1 1794 | 452 |
| | 16.0040 | FVEALFQEY | Pf CSP 15 | 453 |
| | 1167.54 | FYFTLVNLL | Pf LSA1 9 | 454 |
| | 1167.53 | KYKLATSVL | Pf EXP1 73 | 455 |
| | 1167.56 | KYLVIVFLI | Pf SSP2 8 | 456 |
| | 15.0184 | LPSENERGY | Pf LSA1 1663 | 457 |
| | 16.0130 | PSDGKCNLY | Pf SSP2 207 | 458 |
| | 16.0077 | PSENERGYY | Pf LSA 1 1664 | 459 |
| | 1167.57 | PYAGEPAPF | Pf SSP2 528 | 460 |
| | 1167.55 | YYIPHQSSL | Pf LSA1 1671 | 461 |

TABLE 9

Activation of T Cell Proliferation by Expression Vectors Encoding MHC Class II Epitopes Fused to MHC Class II Targeting Sequences

| | Stimulating Peptide[1] | | |
|---|---|---|---|
| Immunogen | PADRE | OVA 323 | CORE 128 |
| peptide + CFA[2] | 3.0 (1.1) | 2.7 (1.2) | 3.2 (1.4) |
| pEP2.(PAOS).(-) | — | — | — |
| pEP2.(AOS).(-) | 5.6 (1.8) | — | — |
| pEP2.(PAOS).(sigTh) | 5.0 (2.9) | — | 2.6 (1.5) |
| pEP2.(PAOS).(IgαTh) | 5.6 (2.1) | — | 3.0 (1.6) |
| pEP2.(PAOS).(LampTh) | 3.8 (1.7) | — | 3 |
| pEP2.(PAOS).(IiTh) | 5.2 (2.0) | 3.2 (1.5) | 3.7 (1.5) |
| pEP2.(PAOS).(H2M) | 3.3 (1.3) | — | 2.8 |

[1]Geometric mean of cultures with SI ≥ 2.
[2]Proliferative response measured in the lymph node.

TABLE 10

CTL Epitopes in CDNA Minigene

| Epitope | Sequence | MHC Restrict. | MHC Binding Affinity [IC30% (nM)] | No. CTL-Positive Cultures | CTL Response (Geo. Mean ΔLU | SEQ ID NO: |
|---|---|---|---|---|---|---|
| HBV Core 18 | FLPSDFFPSV WLSLLVPFV | A2.1 | | 6/6 | 73.0 (1.1) | 91 |
| HBV Env 335 | GLSRYVARL KLTPLCVTL | A2.1 | 3 | 4/6 | 5.3 (1.6) | 107 |
| HBV Pol 455 | ILKEPVRGV YMDDVVLGA | A2.1 | 5 | ND$^c$ | ND | 99 |
| HIV Env 120 | YMDDVVLGV | A2.1 | 76 | 2/5 | 6.4 (1.3) | 93 |
| HIV Pol 476 | TVYYGVPVWK | A2.1 | 102 | 2/5 | 15.2 (2.9) | 101 |
| HBV Pol 55 1-A | STLPETRVVRR | A2.1 | 192 | 0/6 | — | 95 |
| HBV Pol 55 1-V | HTLWKAGILYK | A2.1 | 200 | 6/6 | 8.2 (2.3) | — |
| HIV Env 49 | | A11 | 5 | 28/33 | 13.4 (3.1) | 105 |
| HBV Core 141 | | A11 | 4 | 6/6 | 12.1 (2.6) | 103 |
| HBV Pol 149 | | A11 | 4 | 6/6 | 13.1 (1.2) | |
| | | | 14 | | | 8 |

$^a$Peptide tested in HLA-A2.1/K$^b$H-2$^{bxs}$ transgenic mice by co-immunizing with a T helper cell peptide in IFA.
$^b$Geometric mean CTL response of positive cultures.
$^c$ND, not done.

TABLE 11

Summary of Immunogenicity of pMin.1 DNA construct in HLA A2.l/K$^b$ transgenic mice

| Epitope | CTL Response$^a$ | |
|---|---|---|
| | No. Positive Cultures/Total$^b$ | Geo. Mean Response Positive Cultures [x/÷ SD] ΔLU |
| HBV Core 18 | 9/9 | 455.5 [2.2] |
| HIV Env 120 | 12/12 | 211.9 [3.7] |
| HBV Pol 551-V | 9/9 | 126.1 [2.8] |
| HBV Pol 455 | 12/12 | 738.6 [1.3] |
| HIV Pol 476 | 11/11 | 716.7 [1.5] |
| HBV Env 335 | 12/12 | 43.7 [1.8] |
| HBV Core 18 (Theradigm)$^c$ | 10/10 | 349.3 [1.8] |

$^a$Mice were immunized with pMin.1 DNA or Theradigm-HBV lipopeptide and CTL activity in splenocyte cultures was determined after in vitro stimulation with individual peptide epitopes. Results from four independent experiments are shown.
$^b$See Example V, Materials and Methods for definition of a CTL-positive culture.
$^c$Response of mice immunized with Theradigm-HBV lipopeptide containing the HBV Core 18 epitope.

TABLE 12

Summary of immunogenicity in HLA A11/K$^b$ transgenic mice

| Epitope | CTL Response$^a$ | |
|---|---|---|
| | No. Positive Cultures/Total$^b$ | Geo. Mean Response Positive Cultures [x/÷ SD] ΔLU |
| HBV Core 141 | 5/9 | 128.1 [1.6] |
| HBV Pol 149 | 6/9 | 267.1 [2.2] |
| HIV Env 43 | 9/9 | 40.1 [2.9] |

$^a$Mice were immunized with pMin.1 DNA and CTL activity in splenocyte cultures was determined after in vitro stimulation with individual A11-restricted epitopes. The geometric mean CTL response from three independent experiments are shown.
$^b$Definition of a CTL-positive culture is described in Example V, Materials and Methods.

SEQUENCE LISTING

```
<160> NUMBER OF SEQ ID NOS: 463

<210> SEQ ID NO 1
<211> LENGTH: 669
<212> TYPE: DNA
<213> ORGANISM: Artificial Sequence
<220> FEATURE:
<223> OTHER INFORMATION: IiPADRE construct encoding fusion of murine Ii
      gene with pan DR epitope sequences substituted for
      CLIP sequence
<221> NAME/KEY: CDS
<222> LOCATION: (16)...(663)
<223> OTHER INFORMATION: IiPADRE
```

```
<400> SEQUENCE: 1
gctagcgccg ccacc atg gat gac caa cgc gac ctc atc tct aac cat gag        51
                 Met Asp Asp Gln Arg Asp Leu Ile Ser Asn His Glu
                  1               5                  10 caa ttg ccc ata ctg ggc aac cgc cct aga gag cca gaa agg tgc agc        99
Gln Leu Pro Ile Leu Gly Asn Arg Pro Arg Glu Pro Glu Arg Cys Ser
         15                  20                  25 cgt gga gct ctg tac acc ggt gtt tct gtc ctg gtg gct ctg ctc ttg       147
Arg Gly Ala Leu Tyr Thr Gly Val Ser Val Leu Val Ala Leu Leu Leu
 30                  35                  40 gct ggg cag gcc acc act gct tac ttc ctg tac cag caa cag ggc cgc       195
Ala Gly Gln Ala Thr Thr Ala Tyr Phe Leu Tyr Gln Gln Gln Gly Arg
 45                  50                  55                  60 cta gac aag ctg acc atc acc tcc cag aac ctg caa ctg gag agc ctt       243
Leu Asp Lys Leu Thr Ile Thr Ser Gln Asn Leu Gln Leu Glu Ser Leu
                 65                  70                  75 cgc atg aag ctt ccg aaa tct gcc aaa cct gtg gcc aag ttc gtg gct       291
Arg Met Lys Leu Pro Lys Ser Ala Lys Pro Val Ala Lys Phe Val Ala
         80                  85                  90 gcc tgg acc ctg aag gct gcc gct atg tcc atg gat aac atg ctc ctt       339
Ala Trp Thr Leu Lys Ala Ala Ala Met Ser Met Asp Asn Met Leu Leu
 95                 100                 105 ggg cct gtg aag aac gtt acc aag tac ggc aac atg acc cag gac cat       387
Gly Pro Val Lys Asn Val Thr Lys Tyr Gly Asn Met Thr Gln Asp His
110                 115                 120 gtg atg cat ctg ctc acg agg tct gga ccc ctg gag tac ccg cag ctg       435
Val Met His Leu Leu Thr Arg Ser Gly Pro Leu Glu Tyr Pro Gln Leu
125                 130                 135                 140 aag ggg acc ttc cca gag aat ctg aag cat ctt aag aac tcc atg gat       483
Lys Gly Thr Phe Pro Glu Asn Leu Lys His Leu Lys Asn Ser Met Asp
                145                 150                 155 ggc gtg aac tgg aag atc ttc gag agc tgg atg aag cag tgg ctc ttg       531
Gly Val Asn Trp Lys Ile Phe Glu Ser Trp Met Lys Gln Trp Leu Leu
                160                 165                 170 ttt gag atg agc aag aac tcc ctg gag gag aag aag ccc acc gag gct       579
Phe Glu Met Ser Lys Asn Ser Leu Glu Glu Lys Lys Pro Thr Glu Ala
        175                 180                 185 cca cct aaa gag cca ctg gac atg gaa gac cta tct tct ggc ctg gga       627
Pro Pro Lys Glu Pro Leu Asp Met Glu Asp Leu Ser Ser Gly Leu Gly
        190                 195                 200 gtg acc agg cag gaa ctg ggt caa gtc acc ctg tgaggtacc                 669
Val Thr Arg Gln Glu Leu Gly Gln Val Thr Leu
205                 210                 215

<210> SEQ ID NO 2
<211> LENGTH: 215
<212> TYPE: PRT
<213> ORGANISM: Artificial Sequence
<220> FEATURE:
<223> OTHER INFORMATION: IiPADRE

<400> SEQUENCE: 2

Met Asp Asp Gln Arg Asp Leu Ile Ser Asn His Glu Gln Leu Pro Ile
 1               5                  10                  15

Leu Gly Asn Arg Pro Arg Glu Pro Glu Arg Cys Ser Arg Gly Ala Leu
             20                  25                  30

Tyr Thr Gly Val Ser Val Leu Val Ala Leu Leu Leu Ala Gly Gln Ala
         35                  40                  45

Thr Thr Ala Tyr Phe Leu Tyr Gln Gln Gln Gly Arg Leu Asp Lys Leu
     50                  55                  60
```

-continued

```
Thr Ile Thr Ser Gln Asn Leu Gln Leu Glu Ser Leu Arg Met Lys Leu
65                  70                  75                  80

Pro Lys Ser Ala Lys Pro Val Ala Lys Phe Val Ala Ala Trp Thr Leu
                85                  90                  95

Lys Ala Ala Met Ser Met Asp Asn Met Leu Leu Gly Pro Val Lys
            100                 105                 110

Asn Val Thr Lys Tyr Gly Asn Met Thr Gln Asp His Val Met His Leu
            115                 120                 125

Leu Thr Arg Ser Gly Pro Leu Glu Tyr Pro Gln Leu Lys Gly Thr Phe
        130                 135                 140

Pro Glu Asn Leu Lys His Leu Lys Asn Ser Met Asp Gly Val Asn Trp
145                 150                 155                 160

Lys Ile Phe Glu Ser Trp Met Lys Gln Trp Leu Leu Phe Glu Met Ser
                165                 170                 175

Lys Asn Ser Leu Glu Glu Lys Lys Pro Thr Glu Ala Pro Pro Lys Glu
            180                 185                 190

Pro Leu Asp Met Glu Asp Leu Ser Ser Gly Leu Gly Val Thr Arg Gln
            195                 200                 205

Glu Leu Gly Gln Val Thr Leu
        210                 215
```

<210> SEQ ID NO 3
<211> LENGTH: 438
<212> TYPE: DNA
<213> ORGANISM: Artificial Sequence
<220> FEATURE:
<223> OTHER INFORMATION: I80T construct encoding fusion of the
      cytoplasmic, transmembrane and part of the luminal domains of
      murine Ii protein gene fused to multiple MHC class
      II epitopes
<221> NAME/KEY: CDS
<222> LOCATION: (16)...(432)
<223> OTHER INFORMATION: I80T

<400> SEQUENCE: 3

```
gctagcgccg ccacc atg gat gac caa cgc gac ctc atc tct aac cat gag        51
                Met Asp Asp Gln Arg Asp Leu Ile Ser Asn His Glu
                 1               5                  10 caa ttg ccc ata ctg ggc aac cgc cct aga gag cca gaa agg tgc agc         99
Gln Leu Pro Ile Leu Gly Asn Arg Pro Arg Glu Pro Glu Arg Cys Ser
         15                  20                  25 cgt gga gct ctg tac acc ggt gtt tct gtc ctg gtg gct ctg ctc ttg        147
Arg Gly Ala Leu Tyr Thr Gly Val Ser Val Leu Val Ala Leu Leu Leu
     30                  35                  40 gct ggg cag gcc acc act gct tac ttc ctg tac cag caa cag ggc cgc        195
Ala Gly Gln Ala Thr Thr Ala Tyr Phe Leu Tyr Gln Gln Gln Gly Arg
 45                  50                  55                  60 cta gac aag ctg acc atc acc tcc cag aac ctg caa ctg gag agc ctt        243
Leu Asp Lys Leu Thr Ile Thr Ser Gln Asn Leu Gln Leu Glu Ser Leu
                 65                  70                  75 cgc atg aag ctt atc agc cag gct gtg cac gcc gct cac gcc gaa atc        291
Arg Met Lys Leu Ile Ser Gln Ala Val His Ala Ala His Ala Glu Ile
             80                  85                  90 aac gaa gct gga aga acc cct cca gct tat cgc cct cca aac gct cct        339
Asn Glu Ala Gly Arg Thr Pro Pro Ala Tyr Arg Pro Pro Asn Ala Pro
         95                 100                 105 atc ctg ttc ttt ctg ctg acc aga atc ctg aca atc ccc cag tcc ctg        387
Ile Leu Phe Phe Leu Leu Thr Arg Ile Leu Thr Ile Pro Gln Ser Leu
     110                 115                 120
```

```
gac gcc aag ttc gtg gct gcc tgg acc ctg aag gct gcc gct           429
Asp Ala Lys Phe Val Ala Ala Trp Thr Leu Lys Ala Ala Ala
125                 130                 135 tgaggtacc                                                          438

<210> SEQ ID NO 4
<211> LENGTH: 138
<212> TYPE: PRT
<213> ORGANISM: Artificial Sequence
<220> FEATURE:
<223> OTHER INFORMATION: I80T

<400> SEQUENCE: 4

Met Asp Asp Gln Arg Asp Leu Ile Ser Asn His Glu Gln Leu Pro Ile
1               5                   10                  15

Leu Gly Asn Arg Pro Arg Glu Pro Glu Arg Cys Ser Arg Gly Ala Leu
            20                  25                  30

Tyr Thr Gly Val Ser Val Leu Val Ala Leu Leu Leu Ala Gly Gln Ala
        35                  40                  45

Thr Thr Ala Tyr Phe Leu Tyr Gln Gln Gln Gly Arg Leu Asp Lys Leu
    50                  55                  60

Thr Ile Thr Ser Gln Asn Leu Gln Leu Glu Ser Leu Arg Met Lys Leu
65                  70                  75                  80

Ile Ser Gln Ala Val His Ala Ala His Ala Glu Ile Asn Glu Ala Gly
                85                  90                  95

Arg Thr Pro Pro Ala Tyr Arg Pro Asn Ala Pro Ile Leu Phe Phe
            100                 105                 110

Leu Leu Thr Arg Ile Leu Thr Ile Pro Gln Ser Leu Asp Ala Lys Phe
        115                 120                 125

Val Ala Ala Trp Thr Leu Lys Ala Ala Ala
    130                 135

<210> SEQ ID NO 5
<211> LENGTH: 783
<212> TYPE: DNA
<213> ORGANISM: Artificial Sequence
<220> FEATURE:
<223> OTHER INFORMATION: IiThfull construct encoding fusion of the
      cytoplasmic, transmembrane and part of the luminal
      domains of the murine Ii protein gene fused to
      multiple T helper epitopes and amino acid residues
      101-215 trimerization region of the Ii protein
<221> NAME/KEY: CDS
<222> LOCATION: (16)...(777)
<223> OTHER INFORMATION: IiThful

<400> SEQUENCE: 5
gctagcgccg ccacc atg gat gac caa cgc gac ctc atc tct aac cat gag      51
              Met Asp Asp Gln Arg Asp Leu Ile Ser Asn His Glu
              1               5                   10 caa ttg ccc ata ctg ggc aac cgc cct aga gag cca gaa agg tgc agc       99
Gln Leu Pro Ile Leu Gly Asn Arg Pro Arg Glu Pro Glu Arg Cys Ser
            15                  20                  25 cgt gga gct ctg tac acc ggt gtt tct gtc ctg gtg gct ctg ctc ttg      147
Arg Gly Ala Leu Tyr Thr Gly Val Ser Val Leu Val Ala Leu Leu Leu
        30                  35                  40 gct ggg cag gcc acc act gct tac ttc ctg tac cag cag cag ggc cgc      195
Ala Gly Gln Ala Thr Thr Ala Tyr Phe Leu Tyr Gln Gln Gln Gly Arg
    45                  50                  55                  60 cta gac aag ctg acc atc acc tcc cag aac ctg caa ctg gag agc ctt      243
Leu Asp Lys Leu Thr Ile Thr Ser Gln Asn Leu Gln Leu Glu Ser Leu
                65                  70                  75
```

```
cgc atg aag ctt atc agc cag gct gtg cac gcc gct cac gcc gaa atc      291
Arg Met Lys Leu Ile Ser Gln Ala Val His Ala Ala His Ala Glu Ile
            80                  85                  90 aac gaa gct gga aga acc cct cca gct tat cgc cct cca aac gct cct      339
Asn Glu Ala Gly Arg Thr Pro Pro Ala Tyr Arg Pro Pro Asn Ala Pro
        95                 100                 105 atc ctg ttc ttt ctg ctg acc aga atc ctg aca atc ccc cag tcc ctg      387
Ile Leu Phe Phe Leu Leu Thr Arg Ile Leu Thr Ile Pro Gln Ser Leu
        110                 115                 120 gac gcc aag ttc gtg gct gcc tgg acc ctg aag gct gcc gct atg tcc      435
Asp Ala Lys Phe Val Ala Ala Trp Thr Leu Lys Ala Ala Ala Met Ser
125                 130                 135                 140 atg gat aac atg ctc ctt ggg cct gtg aag aac gtt acc aag tac ggc      483
Met Asp Asn Met Leu Leu Gly Pro Val Lys Asn Val Thr Lys Tyr Gly
                145                 150                 155 aac atg acc cag gac cat gtg atg cat ctg ctc acg agg tct gga ccc      531
Asn Met Thr Gln Asp His Val Met His Leu Leu Thr Arg Ser Gly Pro
            160                 165                 170 ctg gag tac ccg cag ctg aag ggg acc ttc cca gag aat ctg aag cat      579
Leu Glu Tyr Pro Gln Leu Lys Gly Thr Phe Pro Glu Asn Leu Lys His
        175                 180                 185 ctt aag aac tcc atg gat ggc gtg aac tgg aag atc ttc gag agc tgg      627
Leu Lys Asn Ser Met Asp Gly Val Asn Trp Lys Ile Phe Glu Ser Trp
        190                 195                 200 atg aag cag tgg ctc ttg ttt gag atg agc aag aac tcc ctg gag gag      675
Met Lys Gln Trp Leu Leu Phe Glu Met Ser Lys Asn Ser Leu Glu Glu
205                 210                 215                 220 aag aag ccc acc gag gct cca cct aaa gag cca ctg gac atg gaa gac      723
Lys Lys Pro Thr Glu Ala Pro Pro Lys Glu Pro Leu Asp Met Glu Asp
                225                 230                 235 cta tct tct ggc ctg gga gtg acc agg cag gaa ctg ggt caa gtc acc      771
Leu Ser Ser Gly Leu Gly Val Thr Arg Gln Glu Leu Gly Gln Val Thr
            240                 245                 250 ctg tgaggtacc                                                        783
Leu

<210> SEQ ID NO 6
<211> LENGTH: 253
<212> TYPE: PRT
<213> ORGANISM: Artificial Sequence
<220> FEATURE:
<223> OTHER INFORMATION: IiThfull

<400> SEQUENCE: 6

Met Asp Asp Gln Arg Asp Leu Ile Ser Asn His Glu Gln Leu Pro Ile
 1               5                  10                  15

Leu Gly Asn Arg Pro Arg Glu Pro Glu Arg Cys Ser Arg Gly Ala Leu
            20                  25                  30

Tyr Thr Gly Val Ser Val Leu Val Ala Leu Leu Leu Ala Gly Gln Ala
        35                  40                  45

Thr Thr Ala Tyr Phe Leu Tyr Gln Gln Gln Gly Arg Leu Asp Lys Leu
    50                  55                  60

Thr Ile Thr Ser Gln Asn Leu Gln Leu Glu Ser Leu Arg Met Lys Leu
65                  70                  75                  80

Ile Ser Gln Ala Val His Ala Ala His Ala Glu Ile Asn Glu Ala Gly
                85                  90                  95

Arg Thr Pro Pro Ala Tyr Arg Pro Pro Asn Ala Pro Ile Leu Phe Phe
            100                 105                 110
```

-continued

```
Leu Leu Thr Arg Ile Leu Thr Ile Pro Gln Ser Leu Asp Ala Lys Phe
        115                 120                 125

Val Ala Ala Trp Thr Leu Lys Ala Ala Met Ser Met Asp Asn Met
130                 135                 140

Leu Leu Gly Pro Val Lys Asn Val Thr Lys Tyr Gly Asn Met Thr Gln
145                 150                 155                 160

Asp His Val Met His Leu Leu Thr Arg Ser Gly Pro Leu Glu Tyr Pro
                165                 170                 175

Gln Leu Lys Gly Thr Phe Pro Glu Asn Leu Lys His Leu Lys Asn Ser
            180                 185                 190

Met Asp Gly Val Asn Trp Lys Ile Phe Glu Ser Trp Met Lys Gln Trp
        195                 200                 205

Leu Leu Phe Glu Met Ser Lys Asn Ser Leu Glu Glu Lys Lys Pro Thr
    210                 215                 220

Glu Ala Pro Pro Lys Glu Pro Leu Asp Met Glu Asp Leu Ser Ser Gly
225                 230                 235                 240

Leu Gly Val Thr Arg Gln Glu Leu Gly Gln Val Thr Leu
                245                 250
```

<210> SEQ ID NO 7
<211> LENGTH: 378
<212> TYPE: DNA
<213> ORGANISM: Artificial Sequence
<220> FEATURE:
<223> OTHER INFORMATION: KappaLAMP-Th construct encoding fusion of
      murine immunoglobulin kappa signal sequence fused to
      multiple T helper epitopes and the cytoplasmic and
      transmembrane domains of human lysosomal membrane
      glycoprotein-1 (LAMP-1)
<221> NAME/KEY: CDS
<222> LOCATION: (16)...(372)
<223> OTHER INFORMATION: KappaLAMP-Th

<400> SEQUENCE: 7

```
gctagcgccg ccacc atg gga atg cag gtg cag atc cag agc ctg ttt ctg      51
                 Met Gly Met Gln Val Gln Ile Gln Ser Leu Phe Leu
                  1               5                   10 ctc ctc ctg tgg gtg ccc ggg tcc aga gga atc agc cag gct gtg cac       99
Leu Leu Leu Trp Val Pro Gly Ser Arg Gly Ile Ser Gln Ala Val His
        15                  20                  25 gcc gct cac gcc gaa atc aac gaa gct gga aga acc cct cca gct tat      147
Ala Ala His Ala Glu Ile Asn Glu Ala Gly Arg Thr Pro Pro Ala Tyr
    30                  35                  40 cgc cct cca aac gct cct atc ctg ttc ttt ctg ctg acc aga atc ctg      195
Arg Pro Pro Asn Ala Pro Ile Leu Phe Phe Leu Leu Thr Arg Ile Leu
45                  50                  55                  60 aca atc ccc cag tcc ctg gac gcc aag ttc gtg gct gcc tgg acc ctg      243
Thr Ile Pro Gln Ser Leu Asp Ala Lys Phe Val Ala Ala Trp Thr Leu
                65                  70                  75 aag gct gcc gct aac aac atg ttg atc ccc att gct gtg ggc ggt gcc      291
Lys Ala Ala Ala Asn Asn Met Leu Ile Pro Ile Ala Val Gly Gly Ala
            80                  85                  90 ctg gca ggg ctg gtc ctc atc gtc ctc att gcc tac ctc att ggc agg      339
Leu Ala Gly Leu Val Leu Ile Val Leu Ile Ala Tyr Leu Ile Gly Arg
        95                  100                 105 aag agg agt cac gcc ggc tat cag acc atc tagggtacc                    378
Lys Arg Ser His Ala Gly Tyr Gln Thr Ile
    110                 115
```

<210> SEQ ID NO 8
<211> LENGTH: 118

-continued

```
<212> TYPE: PRT
<213> ORGANISM: Artificial Sequence
<220> FEATURE:
<223> OTHER INFORMATION: KappaLAMP-Th

<400> SEQUENCE: 8

Met Gly Met Gln Val Gln Ile Gln Ser Leu Phe Leu Leu Leu Leu Trp
 1               5                  10                  15

Val Pro Gly Ser Arg Gly Ile Ser Gln Ala Val His Ala Ala His Ala
            20                  25                  30

Glu Ile Asn Glu Ala Gly Arg Thr Pro Pro Ala Tyr Arg Pro Pro Asn
        35                  40                  45

Ala Pro Ile Leu Phe Phe Leu Leu Thr Arg Ile Leu Thr Ile Pro Gln
    50                  55                  60

Ser Leu Asp Ala Lys Phe Val Ala Ala Trp Thr Leu Lys Ala Ala Ala
65                  70                  75                  80

Asn Asn Met Leu Ile Pro Ile Ala Val Gly Gly Ala Leu Ala Gly Leu
                85                  90                  95

Val Leu Ile Val Leu Ile Ala Tyr Leu Ile Gly Arg Lys Arg Ser His
            100                 105                 110

Ala Gly Tyr Gln Thr Ile
        115

<210> SEQ ID NO 9
<211> LENGTH: 381
<212> TYPE: DNA
<213> ORGANISM: Artificial Sequence
<220> FEATURE:
<223> OTHER INFORMATION: H2M-Th construct encoding fusion of signal
      sequence of H2-M fused to multiple MHC class II
      epitopes and the cytoplasmic and transmembrane
      domains of H2-M
<221> NAME/KEY: CDS
<222> LOCATION: (16)...(375)
<223> OTHER INFORMATION: H2M-Th

<400> SEQUENCE: 9
gctagcgccg ccacc atg gct gca ctc tgg ctg ctg ctg ctg gtc ctc agt      51
                 Met Ala Ala Leu Trp Leu Leu Leu Leu Val Leu Ser
                  1               5                  10 ctg cac tgt atg ggg atc agc cag gct gtg cac gcc gct cac gcc gaa       99
Leu His Cys Met Gly Ile Ser Gln Ala Val His Ala Ala His Ala Glu
        15                  20                  25 atc aac gaa gct gga aga acc cct cca gct tat cgc cct cca aac gct      147
Ile Asn Glu Ala Gly Arg Thr Pro Pro Ala Tyr Arg Pro Pro Asn Ala
     30                  35                  40 cct atc ctg ttc ttt ctg ctg acc aga atc ctg aca atc ccc cag tcc      195
Pro Ile Leu Phe Phe Leu Leu Thr Arg Ile Leu Thr Ile Pro Gln Ser
 45                  50                  55                  60 ctg gac gcc aag ttc gtg gct gcc tgg acc ctg aag gct gcc gct aag      243
Leu Asp Ala Lys Phe Val Ala Ala Trp Thr Leu Lys Ala Ala Ala Lys
                 65                  70                  75 gtc tct gtg tct gca gcc acc ctg ggc ctg ggc ttc atc atc ttc tgt      291
Val Ser Val Ser Ala Ala Thr Leu Gly Leu Gly Phe Ile Ile Phe Cys
             80                  85                  90 gtt ggc ttc ttc aga tgg cgc aag tct cat tcc tcc agc tac act cct      339
Val Gly Phe Phe Arg Trp Arg Lys Ser His Ser Ser Ser Tyr Thr Pro
         95                 100                 105 ctc cct gga tcc acc tac cca gaa gga cgg cat tagggtacc                381
Leu Pro Gly Ser Thr Tyr Pro Glu Gly Arg His
    110                 115
```

<210> SEQ ID NO 10
<211> LENGTH: 119
<212> TYPE: PRT
<213> ORGANISM: Artificial Sequence
<220> FEATURE:
<223> OTHER INFORMATION: H2M-Th

<400> SEQUENCE: 10

```
Met Ala Ala Leu Trp Leu Leu Leu Val Leu Ser Leu His Cys Met
 1               5                  10                  15

Gly Ile Ser Gln Ala Val His Ala Ala His Ala Glu Ile Asn Glu Ala
            20                  25                  30

Gly Arg Thr Pro Pro Ala Tyr Arg Pro Pro Asn Ala Pro Ile Leu Phe
            35                  40                  45

Phe Leu Leu Thr Arg Ile Leu Thr Ile Pro Gln Ser Leu Asp Ala Lys
 50                  55                  60

Phe Val Ala Ala Trp Thr Leu Lys Ala Ala Ala Lys Val Ser Val Ser
 65                  70                  75                  80

Ala Ala Thr Leu Gly Leu Gly Phe Ile Ile Phe Cys Val Gly Phe Phe
                85                  90                  95

Arg Trp Arg Lys Ser His Ser Ser Ser Tyr Thr Pro Leu Pro Gly Ser
                100                 105                 110

Thr Tyr Pro Glu Gly Arg His
            115
```

<210> SEQ ID NO 11
<211> LENGTH: 432
<212> TYPE: DNA
<213> ORGANISM: Artificial Sequence
<220> FEATURE:
<223> OTHER INFORMATION: H2O-Th construct encoding fusion of signal
      sequence of H2-DO fused to multiple MHC class II
      epitopes and the cytoplasmic and transmembrane
      domains of H2-DO
<221> NAME/KEY: CDS
<222> LOCATION: (16)...(426)
<223> OTHER INFORMATION: H2O-Th

<400> SEQUENCE: 11

```
gctagcgccg ccacc atg ggc gct ggg agg gcc ccc tgg gtg gtg gct ctg     51
                Met Gly Ala Gly Arg Ala Pro Trp Val Val Ala Leu
                 1               5                  10 ttg gtg aac ctc atg agg ctg gat tcc atc agc cag gct gtg cac gcc     99
Leu Val Asn Leu Met Arg Leu Asp Ser Ile Ser Gln Ala Val His Ala
            15                  20                  25 gct cac gcc gaa atc aac gaa gct gga aga acc cct cca gct tat cgc    147
Ala His Ala Glu Ile Asn Glu Ala Gly Arg Thr Pro Pro Ala Tyr Arg
        30                  35                  40 cct cca aac gct cct atc ctg ttc ttt ctg ctg acc aga atc ctg aca    195
Pro Pro Asn Ala Pro Ile Leu Phe Phe Leu Leu Thr Arg Ile Leu Thr
 45                  50                  55                  60 atc ccc cag tcc ctg gac gcc aag ttc gtg gct gcc tgg acc ctg aag    243
Ile Pro Gln Ser Leu Asp Ala Lys Phe Val Ala Ala Trp Thr Leu Lys
                65                  70                  75 gct gcc gct ata ctg agt gga gct gca gtg ttc ctg ctt ggg ctg att    291
Ala Ala Ala Ile Leu Ser Gly Ala Ala Val Phe Leu Leu Gly Leu Ile
                80                  85                  90 gtc ttc ctg gtg ggg gtt gtt atc cat ctc aag gct cag aaa gca tct    339
Val Phe Leu Val Gly Val Val Ile His Leu Lys Ala Gln Lys Ala Ser
                95                  100                 105 gtg gag act cag cct ggc aat gag agt agg tcc cgg atg atg gag cgg    387
```

-continued

```
Val Glu Thr Gln Pro Gly Asn Glu Ser Arg Ser Arg Met Met Glu Arg
    110                 115                 120 cta acc aag ttc aag gct gga ccg gga cat gtc aca tgaggtacc          432
Leu Thr Lys Phe Lys Ala Gly Pro Gly His Val Thr
125                 130                 135

<210> SEQ ID NO 12
<211> LENGTH: 136
<212> TYPE: PRT
<213> ORGANISM: Artificial Sequence
<220> FEATURE:
<223> OTHER INFORMATION: H2O-Th

<400> SEQUENCE: 12

Met Gly Ala Gly Arg Ala Pro Trp Val Val Ala Leu Leu Val Asn Leu
 1               5                  10                  15

Met Arg Leu Asp Ser Ile Ser Gln Ala Val His Ala Ala His Ala Glu
            20                  25                  30

Ile Asn Glu Ala Gly Arg Thr Pro Pro Ala Tyr Arg Pro Pro Asn Ala
        35                  40                  45

Pro Ile Leu Phe Phe Leu Leu Thr Arg Ile Leu Thr Ile Pro Gln Ser
    50                  55                  60

Leu Asp Ala Lys Phe Val Ala Ala Trp Thr Leu Lys Ala Ala Ala Ile
65                  70                  75                  80

Leu Ser Gly Ala Ala Val Phe Leu Leu Gly Leu Ile Val Phe Leu Val
                85                  90                  95

Gly Val Val Ile His Leu Lys Ala Gln Lys Ala Ser Val Glu Thr Gln
            100                 105                 110

Pro Gly Asn Glu Ser Arg Ser Arg Met Met Glu Arg Leu Thr Lys Phe
        115                 120                 125

Lys Ala Gly Pro Gly His Val Thr
    130                 135

<210> SEQ ID NO 13
<211> LENGTH: 816
<212> TYPE: DNA
<213> ORGANISM: Artificial Sequence
<220> FEATURE:
<223> OTHER INFORMATION: PADRE-Influenza matrix construct encoding
      fusion of pan DR epitope sequence to amino-terminus of
      influenza matrix protein gene
<221> NAME/KEY: CDS
<222> LOCATION: (16)...(816)
<223> OTHER INFORMATION: PADRE-Influenza matrix

<400> SEQUENCE: 13
gctagcgccg ccacc atg gcc aag ttc gtg gct gcc tgg acc ctg aag gct      51
                 Met Ala Lys Phe Val Ala Ala Trp Thr Leu Lys Ala
                  1               5                  10 gcc gct atg agt ctt cta acc gag gtc gaa acg tac gtt ctc tct atc       99
Ala Ala Met Ser Leu Leu Thr Glu Val Glu Thr Tyr Val Leu Ser Ile
        15                  20                  25 atc cca tca ggc ccc ctc aaa gcc gag atc gcg cag aga ctt gag gat      147
Ile Pro Ser Gly Pro Leu Lys Ala Glu Ile Ala Gln Arg Leu Glu Asp
     30                  35                  40 gtt ttt gca ggg aag aac aca gat ctt gag gct ctc atg gaa tgg cta      195
Val Phe Ala Gly Lys Asn Thr Asp Leu Glu Ala Leu Met Glu Trp Leu
 45                  50                  55                  60 aag aca aga cca atc ctg tca cct ctg act aag gga att tta ggg ttt      243
Lys Thr Arg Pro Ile Leu Ser Pro Leu Thr Lys Gly Ile Leu Gly Phe
                65                  70                  75
```

```
gtg ttc acg ctc acc gtg ccc agt gag cga gga ctg cag cgt aga cga      291
Val Phe Thr Leu Thr Val Pro Ser Glu Arg Gly Leu Gln Arg Arg Arg
            80                  85                  90 ttt gtc caa aat gcc cta aat ggg aat gga gac cca aac aac atg gac      339
Phe Val Gln Asn Ala Leu Asn Gly Asn Gly Asp Pro Asn Asn Met Asp
        95                 100                 105 agg gca gtt aaa cta tac aag aag ctg aag agg gaa atg aca ttc cat      387
Arg Ala Val Lys Leu Tyr Lys Lys Leu Lys Arg Glu Met Thr Phe His
110                 115                 120 gga gca aag gaa gtt gca ctc agt tac tca act ggt gcg ctt gcc agt      435
Gly Ala Lys Glu Val Ala Leu Ser Tyr Ser Thr Gly Ala Leu Ala Ser
125                 130                 135                 140 tgc atg ggt ctc ata tac aac cgg atg gga aca gtg acc aca gaa gtg      483
Cys Met Gly Leu Ile Tyr Asn Arg Met Gly Thr Val Thr Thr Glu Val
                145                 150                 155 gct ctt ggc cta gta tgt gcc act tgt gag cag att gct gat gcc caa      531
Ala Leu Gly Leu Val Cys Ala Thr Cys Glu Gln Ile Ala Asp Ala Gln
            160                 165                 170 cat cgg tcc cac agg cag atg gcg act acc acc aac cca cta atc agg      579
His Arg Ser His Arg Gln Met Ala Thr Thr Thr Asn Pro Leu Ile Arg
        175                 180                 185 cat gag aac aga atg gta cta gcc agc act acg gct aag gcc atg gag      627
His Glu Asn Arg Met Val Leu Ala Ser Thr Thr Ala Lys Ala Met Glu
190                 195                 200 caa atg gct gga tca agt gag cag gca gca gag gcc atg gaa gtc gca      675
Gln Met Ala Gly Ser Ser Glu Gln Ala Ala Glu Ala Met Glu Val Ala
205                 210                 215                 220 agt cag gct aga caa atg gtg cag gca atg agg aca att ggg act cac      723
Ser Gln Ala Arg Gln Met Val Gln Ala Met Arg Thr Ile Gly Thr His
                225                 230                 235 cct agc tcc agt gca ggt cta aaa gat gat ctt att gaa aat ttg cag      771
Pro Ser Ser Ser Ala Gly Leu Lys Asp Asp Leu Ile Glu Asn Leu Gln
            240                 245                 250 gct tac cag aaa cgg atg ggg gtg cag atg cag cga ttc aag              813
Ala Tyr Gln Lys Arg Met Gly Val Gln Met Gln Arg Phe Lys
        255                 260                 265 tga                                                                  816

<210> SEQ ID NO 14
<211> LENGTH: 266
<212> TYPE: PRT
<213> ORGANISM: Artificial Sequence
<220> FEATURE:
<223> OTHER INFORMATION: PADRE-Influenza matrix

<400> SEQUENCE: 14

Met Ala Lys Phe Val Ala Ala Trp Thr Leu Lys Ala Ala Ala Met Ser
1               5                   10                  15

Leu Leu Thr Glu Val Glu Thr Tyr Val Leu Ser Ile Ile Pro Ser Gly
            20                  25                  30

Pro Leu Lys Ala Glu Ile Ala Gln Arg Leu Glu Asp Val Phe Ala Gly
        35                  40                  45

Lys Asn Thr Asp Leu Glu Ala Leu Met Glu Trp Leu Lys Thr Arg Pro
    50                  55                  60

Ile Leu Ser Pro Leu Thr Lys Gly Ile Leu Gly Phe Val Phe Thr Leu
65                  70                  75                  80

Thr Val Pro Ser Glu Arg Gly Leu Gln Arg Arg Arg Phe Val Gln Asn
                85                  90                  95

Ala Leu Asn Gly Asn Gly Asp Pro Asn Asn Met Asp Arg Ala Val Lys
```

-continued

```
            100                 105                 110
Leu Tyr Lys Lys Leu Lys Arg Glu Met Thr Phe His Gly Ala Lys Glu
        115                 120                 125

Val Ala Leu Ser Tyr Ser Thr Gly Ala Leu Ala Ser Cys Met Gly Leu
    130                 135                 140

Ile Tyr Asn Arg Met Gly Thr Val Thr Thr Glu Val Ala Leu Gly Leu
145                 150                 155                 160

Val Cys Ala Thr Cys Glu Gln Ile Ala Asp Ala Gln His Arg Ser His
                165                 170                 175

Arg Gln Met Ala Thr Thr Thr Asn Pro Leu Ile Arg His Glu Asn Arg
            180                 185                 190

Met Val Leu Ala Ser Thr Thr Ala Lys Ala Met Glu Gln Met Ala Gly
        195                 200                 205

Ser Ser Glu Gln Ala Ala Glu Ala Met Glu Val Ala Ser Gln Ala Arg
    210                 215                 220

Gln Met Val Gln Ala Met Arg Thr Ile Gly Thr His Pro Ser Ser Ser
225                 230                 235                 240

Ala Gly Leu Lys Asp Asp Leu Ile Glu Asn Leu Gln Ala Tyr Gln Lys
                245                 250                 255

Arg Met Gly Val Gln Met Gln Arg Phe Lys
            260                 265

<210> SEQ ID NO 15
<211> LENGTH: 801
<212> TYPE: DNA
<213> ORGANISM: Artificial Sequence
<220> FEATURE:
<223> OTHER INFORMATION: PADRE-HBV-s construct encoding fusion of pan
      DR epitope sequence to amino-terminus of hepatitis B
      virus surface antigen gene
<221> NAME/KEY: CDS
<222> LOCATION: (16)...(765)
<223> OTHER INFORMATION: PADRE-HBV-s

<400> SEQUENCE: 15
gctagcgccg ccacc atg gcc aag ttc gtg gct gcc tgg acc ctg aag gct      51
                 Met Ala Lys Phe Val Ala Ala Trp Thr Leu Lys Ala
                 1               5                   10 gcc gct ctc gag att ggg gga ccc tgc ctg aac gcc gag aac atc aca       99
Ala Ala Leu Glu Ile Gly Gly Pro Cys Leu Asn Ala Glu Asn Ile Thr
        15                  20                  25 tca gga ttc cta gga ccc ctt ctc gtg tta cag gcg ggg ttt ttc ttg      147
Ser Gly Phe Leu Gly Pro Leu Leu Val Leu Gln Ala Gly Phe Phe Leu
     30                  35                  40 ttg aca aga atc ctc aca ata ccg cag agt cta gac tcg tgg tgg act      195
Leu Thr Arg Ile Leu Thr Ile Pro Gln Ser Leu Asp Ser Trp Trp Thr
 45                  50                  55                  60 tct ctc aat ttt cta ggg gga act acc gtg tgt ctt ggc caa aat tcg      243
Ser Leu Asn Phe Leu Gly Gly Thr Thr Val Cys Leu Gly Gln Asn Ser
                65                  70                  75 cag tcc cca acc tcc aat cac tca cca acc tct tgt cct cca act tgt      291
Gln Ser Pro Thr Ser Asn His Ser Pro Thr Ser Cys Pro Pro Thr Cys
            80                  85                  90 cct ggt tat cgc tgg atg tgt ctg cgg cgt ttt atc atc ttc ctc ttc      339
Pro Gly Tyr Arg Trp Met Cys Leu Arg Arg Phe Ile Ile Phe Leu Phe
        95                  100                 105 atc ctg ctg cta tgc ctc atc ttc ttg ttg gtt ctt ctg gac tat caa      387
Ile Leu Leu Leu Cys Leu Ile Phe Leu Leu Val Leu Leu Asp Tyr Gln
    110                 115                 120
```

-continued

```
ggt atg ttg ccc gtt tgt cct cta att cca gga tcc tca aca acc agc       435
Gly Met Leu Pro Val Cys Pro Leu Ile Pro Gly Ser Ser Thr Thr Ser
125                 130                 135                 140 acg gga cca tgc cgg acc tgc atg act act gct caa gga acc tct atg       483
Thr Gly Pro Cys Arg Thr Cys Met Thr Thr Ala Gln Gly Thr Ser Met
            145                 150                 155 tat ccc tcc tgt tgc tgt acc aaa cct tcg gac gga aat tgc acc tgt       531
Tyr Pro Ser Cys Cys Cys Thr Lys Pro Ser Asp Gly Asn Cys Thr Cys
        160                 165                 170 att ccc atc cca tca tcc tgg gct ttc gga aaa ttc cta tgg gag tgg       579
Ile Pro Ile Pro Ser Ser Trp Ala Phe Gly Lys Phe Leu Trp Glu Trp
    175                 180                 185 gcc tca gcc cgt ttc tcc tgg ctc agt tta cta gtg cca ttt gtt cag       627
Ala Ser Ala Arg Phe Ser Trp Leu Ser Leu Leu Val Pro Phe Val Gln
190                 195                 200 tgg ttc gta ggg ctt tcc ccc act gtt tgg ctt tca gtt ata tgg atg       675
Trp Phe Val Gly Leu Ser Pro Thr Val Trp Leu Ser Val Ile Trp Met
205                 210                 215                 220 atg tgg tat tgg ggg cca agt ctg tac agc atc ttg agt ccc ttt tta       723
Met Trp Tyr Trp Gly Pro Ser Leu Tyr Ser Ile Leu Ser Pro Phe Leu
                225                 230                 235 ccg ctg tta cca att ttc ttt tgt ctt tgg gta tac att taaaccctaa        772
Pro Leu Leu Pro Ile Phe Phe Cys Leu Trp Val Tyr Ile
            240                 245 caaaacaaag agatggggtt actctctaa                                       801
```

<210> SEQ ID NO 16
<211> LENGTH: 249
<212> TYPE: PRT
<213> ORGANISM: Artificial Sequence
<220> FEATURE:
<223> OTHER INFORMATION: PADRE-HBV-s

<400> SEQUENCE: 16

```
Met Ala Lys Phe Val Ala Ala Trp Thr Leu Lys Ala Ala Ala Leu Glu
1               5                   10                  15

Ile Gly Gly Pro Cys Leu Asn Ala Glu Asn Ile Thr Ser Gly Phe Leu
            20                  25                  30

Gly Pro Leu Leu Val Leu Gln Ala Gly Phe Phe Leu Leu Thr Arg Ile
        35                  40                  45

Leu Thr Ile Pro Gln Ser Leu Asp Ser Trp Trp Thr Ser Leu Asn Phe
    50                  55                  60

Leu Gly Gly Thr Thr Val Cys Leu Gly Gln Asn Ser Gln Ser Pro Thr
65                  70                  75                  80

Ser Asn His Ser Pro Thr Ser Cys Pro Pro Thr Cys Pro Gly Tyr Arg
                85                  90                  95

Trp Met Cys Leu Arg Arg Phe Ile Ile Phe Leu Phe Ile Leu Leu Leu
            100                 105                 110

Cys Leu Ile Phe Leu Leu Val Leu Leu Asp Tyr Gln Gly Met Leu Pro
        115                 120                 125

Val Cys Pro Leu Ile Pro Gly Ser Ser Thr Thr Ser Thr Gly Pro Cys
    130                 135                 140

Arg Thr Cys Met Thr Thr Ala Gln Gly Thr Ser Met Tyr Pro Ser Cys
145                 150                 155                 160

Cys Cys Thr Lys Pro Ser Asp Gly Asn Cys Thr Cys Ile Pro Ile Pro
                165                 170                 175

Ser Ser Trp Ala Phe Gly Lys Phe Leu Trp Glu Trp Ala Ser Ala Arg
            180                 185                 190
```

```
Phe Ser Trp Leu Ser Leu Leu Val Pro Phe Val Gln Trp Phe Val Gly
        195                 200                 205

Leu Ser Pro Thr Val Trp Leu Ser Val Ile Trp Met Met Trp Tyr Trp
        210                 215                 220

Gly Pro Ser Leu Tyr Ser Ile Leu Ser Pro Phe Leu Pro Leu Leu Pro
225                 230                 235                 240

Ile Phe Phe Cys Leu Trp Val Tyr Ile
                245

<210> SEQ ID NO 17
<211> LENGTH: 516
<212> TYPE: DNA
<213> ORGANISM: Artificial Sequence
<220> FEATURE:
<223> OTHER INFORMATION: Ig-alphaTh construct encoding fusion of the
      signal sequence of Ig-alpha protein fused to multiple MHC
      class II epitopes and the transmembrane and
      cytoplasmic domains of the Ig-alpha protein
<221> NAME/KEY: CDS
<222> LOCATION: (16)...(510)
<223> OTHER INFORMATION: Ig-alphaTh

<400> SEQUENCE: 17
gctagcgccg ccacc atg cca ggg ggt cta gaa gcc ctc aga gcc ctg cct       51
               Met Pro Gly Gly Leu Glu Ala Leu Arg Ala Leu Pro
                 1               5                  10 ctc ctc ctc ttc ttg tca tac gcc tgt ttg ggt ccc gga tgc cag gcc        99
Leu Leu Leu Phe Leu Ser Tyr Ala Cys Leu Gly Pro Gly Cys Gln Ala
             15                  20                  25 atc agc cag gct gtg cac gcc gct cac gcc gaa atc aac gaa gct gga       147
Ile Ser Gln Ala Val His Ala Ala His Ala Glu Ile Asn Glu Ala Gly
         30                  35                  40 aga acc cct cca gct tat cgc cct cca aac gct cct atc ctg ttc ttt       195
Arg Thr Pro Pro Ala Tyr Arg Pro Pro Asn Ala Pro Ile Leu Phe Phe
     45                  50                  55                  60 ctg ctg acc aga atc ctg aca atc ccc cag tcc ctg gac gcc aag ttc       243
Leu Leu Thr Arg Ile Leu Thr Ile Pro Gln Ser Leu Asp Ala Lys Phe
                 65                  70                  75 gtg gct gcc tgg acc ctg aag gct gcc gct ggg atc atc ttg ctg ttc       291
Val Ala Ala Trp Thr Leu Lys Ala Ala Ala Gly Ile Ile Leu Leu Phe
             80                  85                  90 tgt gca gtg gtg cca ggg acg ctg ctg cta ttc agg aaa cgg tgg caa       339
Cys Ala Val Val Pro Gly Thr Leu Leu Leu Phe Arg Lys Arg Trp Gln
         95                 100                 105 aat gag aag ttt ggg gtg gac atg cca gat gac tat gaa gat gaa aat       387
Asn Glu Lys Phe Gly Val Asp Met Pro Asp Asp Tyr Glu Asp Glu Asn
    110                 115                 120 ctc tat gag ggc ctg aac ctt gat gac tgt tct atg tat gag gac atc       435
Leu Tyr Glu Gly Leu Asn Leu Asp Asp Cys Ser Met Tyr Glu Asp Ile
125                 130                 135                 140 tcc agg gga ctc cag ggc acc tac cag gat gtg ggc aac ctc cac att       483
Ser Arg Gly Leu Gln Gly Thr Tyr Gln Asp Val Gly Asn Leu His Ile
                145                 150                 155 gga gat gcc cag ctg gaa aag cca tgaggtacc                             516
Gly Asp Ala Gln Leu Glu Lys Pro
            160

<210> SEQ ID NO 18
<211> LENGTH: 164
<212> TYPE: PRT
<213> ORGANISM: Artificial Sequence
<220> FEATURE:
```

<223> OTHER INFORMATION: Ig-alphaTh

<400> SEQUENCE: 18

```
Met Pro Gly Gly Leu Glu Ala Leu Arg Ala Leu Pro Leu Leu Leu Phe
 1               5                  10                  15

Leu Ser Tyr Ala Cys Leu Gly Pro Gly Cys Gln Ala Ile Ser Gln Ala
             20                  25                  30

Val His Ala Ala His Ala Glu Ile Asn Glu Ala Gly Arg Thr Pro Pro
         35                  40                  45

Ala Tyr Arg Pro Pro Asn Ala Pro Ile Leu Phe Phe Leu Leu Thr Arg
     50                  55                  60

Ile Leu Thr Ile Pro Gln Ser Leu Asp Ala Lys Phe Val Ala Ala Trp
 65                  70                  75                  80

Thr Leu Lys Ala Ala Gly Ile Ile Leu Leu Phe Cys Ala Val Val
                 85                  90                  95

Pro Gly Thr Leu Leu Leu Phe Arg Lys Arg Trp Gln Asn Glu Lys Phe
                100                 105                 110

Gly Val Asp Met Pro Asp Asp Tyr Glu Asp Glu Asn Leu Tyr Glu Gly
             115                 120                 125

Leu Asn Leu Asp Asp Cys Ser Met Tyr Glu Asp Ile Ser Arg Gly Leu
         130                 135                 140

Gln Gly Thr Tyr Gln Asp Val Gly Asn Leu His Ile Gly Asp Ala Gln
145                 150                 155                 160

Leu Glu Lys Pro
```

<210> SEQ ID NO 19
<211> LENGTH: 480
<212> TYPE: DNA
<213> ORGANISM: Artificial Sequence
<220> FEATURE:
<223> OTHER INFORMATION: Ig-betaTh construct encoding fusion of the
      signal sequence of Ig-beta protein fused to multiple MHC
      class II epitopes and the transmembrane and
      cytoplasmic domains of the Ig-beta protein
<221> NAME/KEY: CDS
<222> LOCATION: (16)...(474)
<223> OTHER INFORMATION: Ig-betaTh

<400> SEQUENCE: 19

```
gctagcgccg ccacc atg gcc aca ctg gtg ctg tct tcc atg ccc tgc cac         51
             Met Ala Thr Leu Val Leu Ser Ser Met Pro Cys His
              1               5                  10 tgg ctg ttg ttc ctg ctg ctc ttc tca ggt gag ccg atc agc cag              99
Trp Leu Leu Phe Leu Leu Leu Phe Ser Gly Glu Pro Ile Ser Gln
         15                  20                  25 gct gtg cac gcc gct cac gcc gaa atc aac gaa gct gga aga acc cct        147
Ala Val His Ala Ala His Ala Glu Ile Asn Glu Ala Gly Arg Thr Pro
             30                  35                  40 cca gct tat cgc cct cca aac gct cct atc ctg ttc ttt ctg ctg acc        195
Pro Ala Tyr Arg Pro Pro Asn Ala Pro Ile Leu Phe Phe Leu Leu Thr
         45                  50                  55                  60 aga atc ctg aca atc ccc cag tcc ctg gac gcc aag ttc gtg gct gcc        243
Arg Ile Leu Thr Ile Pro Gln Ser Leu Asp Ala Lys Phe Val Ala Ala
                 65                  70                  75 tgg acc ctg aag gct gcc gct att atc ttg atc cag acc ctc ctc atc        291
Trp Thr Leu Lys Ala Ala Ala Ile Ile Leu Ile Gln Thr Leu Leu Ile
             80                  85                  90 atc ctc ttc atc att gtg ccc atc ttc ctg cta ctt gac aag gat gac        339
Ile Leu Phe Ile Ile Val Pro Ile Phe Leu Leu Leu Asp Lys Asp Asp
         95                  100                 105
```

```
ggc aag gct ggg atg gag gaa gat cac acc tat gag ggc ttg aac att      387
Gly Lys Ala Gly Met Glu Glu Asp His Thr Tyr Glu Gly Leu Asn Ile
    110                 115                 120 gac cag aca gcc acc tat gaa gac ata gtg act ctt cgg aca ggg gag      435
Asp Gln Thr Ala Thr Tyr Glu Asp Ile Val Thr Leu Arg Thr Gly Glu
125                 130                 135                 140 gta aag tgg tcg gta gga gag cat cca ggc cag gaa tgaggtacc            480
Val Lys Trp Ser Val Gly Glu His Pro Gly Gln Glu
                145                 150
```

```
<210> SEQ ID NO 20
<211> LENGTH: 152
<212> TYPE: PRT
<213> ORGANISM: Artificial Sequence
<220> FEATURE:
<223> OTHER INFORMATION: Ig-betaTh

<400> SEQUENCE: 20

Met Ala Thr Leu Val Leu Ser Ser Met Pro Cys His Trp Leu Leu Phe
1               5                   10                  15

Leu Leu Leu Leu Phe Ser Gly Glu Pro Ile Ser Gln Ala Val His Ala
            20                  25                  30

Ala His Ala Glu Ile Asn Glu Ala Gly Arg Thr Pro Pro Ala Tyr Arg
        35                  40                  45

Pro Pro Asn Ala Pro Ile Leu Phe Phe Leu Leu Thr Arg Ile Leu Thr
    50                  55                  60

Ile Pro Gln Ser Leu Asp Ala Lys Phe Val Ala Ala Trp Thr Leu Lys
65                  70                  75                  80

Ala Ala Ala Ile Ile Leu Ile Gln Thr Leu Leu Ile Ile Leu Phe Ile
                85                  90                  95

Ile Val Pro Ile Phe Leu Leu Leu Asp Lys Asp Asp Gly Lys Ala Gly
            100                 105                 110

Met Glu Glu Asp His Thr Tyr Glu Gly Leu Asn Ile Asp Gln Thr Ala
        115                 120                 125

Thr Tyr Glu Asp Ile Val Thr Leu Arg Thr Gly Glu Val Lys Trp Ser
    130                 135                 140

Val Gly Glu His Pro Gly Gln Glu
145                 150
```

```
<210> SEQ ID NO 21
<211> LENGTH: 264
<212> TYPE: DNA
<213> ORGANISM: Artificial Sequence
<220> FEATURE:
<223> OTHER INFORMATION: SigTh construct encoding fusion of the signal
      sequence of kappa immunoglobulin fused to multiple
      MHC class II epitopes
<221> NAME/KEY: CDS
<222> LOCATION: (16)...(258)
<223> OTHER INFORMATION: SigTh

<400> SEQUENCE: 21
gctagcgccg ccacc atg gga atg cag gtg cag atc cag agc ctg ttt ctg    51
              Met Gly Met Gln Val Gln Ile Gln Ser Leu Phe Leu
                1               5                   10 ctc ctc ctg tgg gtg ccc ggg tcc cga gga atc agc cag gct gtg cac     99
Leu Leu Leu Trp Val Pro Gly Ser Arg Gly Ile Ser Gln Ala Val His
            15                  20                  25 gcc gct cac gcc gaa atc aac gaa gct gga aga acc cct cca gct tat    147
Ala Ala His Ala Glu Ile Asn Glu Ala Gly Arg Thr Pro Pro Ala Tyr
        30                  35                  40
```

| | | | | | | | | | | | | |
|---|---|---|---|---|---|---|---|---|---|---|---|---|
| cgc | cct | cca | aac | gct | cct | atc | ctg | ttc | ttt | ctg | ctg | acc | aga | atc | ctg | 195 |
| Arg | Pro | Pro | Asn | Ala | Pro | Ile | Leu | Phe | Phe | Leu | Leu | Thr | Arg | Ile | Leu | |
| 45 | | | | 50 | | | | | 55 | | | | | 60 | | |

| aca | atc | ccc | cag | tcc | ctg | gac | gcc | aag | ttc | gtg | gct | gcc | tgg | acc | ctg | 243 |
| Thr | Ile | Pro | Gln | Ser | Leu | Asp | Ala | Lys | Phe | Val | Ala | Ala | Trp | Thr | Leu | |
| | | | | 65 | | | | | 70 | | | | | 75 | | |

| aag | gct | gcc | gct | tgaggtacc | | | | | | | | | | | | 264 |
| Lys | Ala | Ala | Ala | | | | | | | | | | | | | |
| | | | 80 | | | | | | | | | | | | | |

<210> SEQ ID NO 22
<211> LENGTH: 80
<212> TYPE: PRT
<213> ORGANISM: Artificial Sequence
<220> FEATURE:
<223> OTHER INFORMATION: SigTh

<400> SEQUENCE: 22

Met Gly Met Gln Val Gln Ile Gln Ser Leu Phe Leu Leu Leu Leu Trp
 1               5                  10                  15

Val Pro Gly Ser Arg Gly Ile Ser Gln Ala Val His Ala Ala His Ala
             20                  25                  30

Glu Ile Asn Glu Ala Gly Arg Thr Pro Pro Ala Tyr Arg Pro Pro Asn
         35                  40                  45

Ala Pro Ile Leu Phe Phe Leu Leu Thr Arg Ile Leu Thr Ile Pro Gln
     50                  55                  60

Ser Leu Asp Ala Lys Phe Val Ala Ala Trp Thr Leu Lys Ala Ala Ala
65                  70                  75                  80

<210> SEQ ID NO 23
<211> LENGTH: 723
<212> TYPE: DNA
<213> ORGANISM: Homo sapiens
<220> FEATURE:
<221> NAME/KEY: CDS
<222> LOCATION: (8)...(706)
<223> OTHER INFORMATION: human HLA-DR invariant chain (Ii) protein

<400> SEQUENCE: 23

| ttcccag | atg | cac | agg | agg | aga | agc | agg | agc | tgt | cgg | gaa | gat | cag | aag | 49 |
|---|---|---|---|---|---|---|---|---|---|---|---|---|---|---|---|
| | Met | His | Arg | Arg | Arg | Ser | Arg | Ser | Cys | Arg | Glu | Asp | Gln | Lys | |
| | 1 | | | | 5 | | | | | 10 | | | | | |

| cca | gtc | atg | gat | gac | cag | cgc | gac | ctt | atc | tcc | aac | aat | gag | caa | ctg | 97 |
| Pro | Val | Met | Asp | Asp | Gln | Arg | Asp | Leu | Ile | Ser | Asn | Asn | Glu | Gln | Leu | |
| 15 | | | | | 20 | | | | | 25 | | | | | 30 | |

| ccc | atg | ctg | ggc | cgg | cgc | cct | ggg | gcc | ccg | gag | agc | aag | tgc | agc | cgc | 145 |
| Pro | Met | Leu | Gly | Arg | Arg | Pro | Gly | Ala | Pro | Glu | Ser | Lys | Cys | Ser | Arg | |
| | | | 35 | | | | | 40 | | | | | 45 | | | |

| gga | gcc | ctg | tac | aca | ggc | ttt | tcc | atc | ctg | gtg | act | ctg | ctc | ctc | gct | 193 |
| Gly | Ala | Leu | Tyr | Thr | Gly | Phe | Ser | Ile | Leu | Val | Thr | Leu | Leu | Leu | Ala | |
| | | 50 | | | | | 55 | | | | | 60 | | | | |

| ggc | cag | gcc | acc | acc | gcc | tac | ttc | ctg | tac | cag | cag | cag | ggc | cgg | ctg | 241 |
| Gly | Gln | Ala | Thr | Thr | Ala | Tyr | Phe | Leu | Tyr | Gln | Gln | Gln | Gly | Arg | Leu | |
| | 65 | | | | | 70 | | | | | 75 | | | | | |

| gac | aaa | ctg | aca | gtc | acc | tcc | cag | aac | ctg | cag | ctg | gag | aac | ctg | cgc | 289 |
| Asp | Lys | Leu | Thr | Val | Thr | Ser | Gln | Asn | Leu | Gln | Leu | Glu | Asn | Leu | Arg | |
| 80 | | | | | 85 | | | | | 90 | | | | | | |

| atg | aag | ctt | ccc | aag | cct | ccc | aag | cct | gtg | agc | aag | atg | cgc | atg | gcc | 337 |
| Met | Lys | Leu | Pro | Lys | Pro | Pro | Lys | Pro | Val | Ser | Lys | Met | Arg | Met | Ala | |
| 95 | | | | 100 | | | | | 105 | | | | | 110 | | |

| acc | ccg | ctg | ctg | atg | cag | gcg | ctg | ccc | atg | gga | gcc | ctg | ccc | cag | ggg | 385 |

```
                                                                              433
ccc atg cag aat gcc acc aag tat ggc aac atg aca gag gac cat gtg
Pro Met Gln Asn Ala Thr Lys Tyr Gly Asn Met Thr Glu Asp His Val
        130                 135                 140

481
atg cac ctg ctc cag aat gct gac ccc ctg aag gtc tac ccg cca ctg
Met His Leu Leu Gln Asn Ala Asp Pro Leu Lys Val Tyr Pro Pro Leu
145                 150                 155

529
aag ggg agc ttc ccg gag aac ctg aga cac ctt aag aac acc atg gag
Lys Gly Ser Phe Pro Glu Asn Leu Arg His Leu Lys Asn Thr Met Glu
        160                 165                 170

577
acc ata gac tgg aag gtc ttt gag agc tgg atg cac cat tgg ctc ctg
Thr Ile Asp Trp Lys Val Phe Glu Ser Trp Met His His Trp Leu Leu
175                 180                 185                 190

625
ttt gaa atg agc agg cac tcc ttg gag caa aag ccc act gac gct cca
Phe Glu Met Ser Arg His Ser Leu Glu Gln Lys Pro Thr Asp Ala Pro
                    195                 200                 205

673
ccg aaa gag tca ctg gaa ctg gag gac ccg tct tct ggg ctg ggt gtg
Pro Lys Glu Ser Leu Glu Leu Glu Asp Pro Ser Ser Gly Leu Gly Val
        210                 215                 220

723
acc aag cag gat ctg ggc cca gtc ccc atg tgagagcagc agaggcggtc
Thr Lys Gln Asp Leu Gly Pro Val Pro Met
        225                 230
```

<210> SEQ ID NO 24
<211> LENGTH: 232
<212> TYPE: PRT
<213> ORGANISM: Homo sapiens
<220> FEATURE:
<223> OTHER INFORMATION: human HLA-DR invariant chain (Ii) protein

<400> SEQUENCE: 24

```
Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
                20                  25                  30

Leu Gly Arg Arg Pro Gly Ala Pro Glu Ser Lys Cys Ser Arg Gly Ala
            35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
    115                 120                 125

Gln Asn Ala Thr Lys Tyr Gly Asn Met Thr Glu Asp His Val Met His
130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
    195                 200                 205
```

```
Glu Ser Leu Glu Leu Glu Asp Pro Ser Ser Gly Leu Gly Val Thr Lys
    210                 215                 220

Gln Asp Leu Gly Pro Val Pro Met
225                 230

<210> SEQ ID NO 25
<211> LENGTH: 1298
<212> TYPE: DNA
<213> ORGANISM: Homo sapiens
<220> FEATURE:
<221> NAME/KEY: CDS
<222> LOCATION: (11)...(1261)
<223> OTHER INFORMATION: human lysosomal membrane glycoprotein-1
      (LAMP-1)

<400> SEQUENCE: 25
ccgcctcggc atg gcg ccc cgc agc gcc cgg cga ccc ctg ctg ctg cta          49
           Met Ala Pro Arg Ser Ala Arg Arg Pro Leu Leu Leu Leu
             1               5                  10 ctg cct gtt gct gct gct cgg cct cat gca ttg tcg tca gca gcc atg         97
Leu Pro Val Ala Ala Ala Arg Pro His Ala Leu Ser Ser Ala Ala Met
        15                  20                  25 ttt atg gtg aaa aat ggc aac ggg acc gcg tgc ata atg gcc aac ttc        145
Phe Met Val Lys Asn Gly Asn Gly Thr Ala Cys Ile Met Ala Asn Phe
 30                  35                  40                  45 tct gct gcc ttc tca gtg aac tac gac acc aag agt ggc ccc aag aac        193
Ser Ala Ala Phe Ser Val Asn Tyr Asp Thr Lys Ser Gly Pro Lys Asn
                 50                  55                  60 atg acc ttt gac ctg cca tca gat gcc aca gtg gtg ctc aac cgc agc        241
Met Thr Phe Asp Leu Pro Ser Asp Ala Thr Val Val Leu Asn Arg Ser
             65                  70                  75 tcc tgt gga aaa gag aac act tct gac ccc agt ctc gtg att gct ttt        289
Ser Cys Gly Lys Glu Asn Thr Ser Asp Pro Ser Leu Val Ile Ala Phe
         80                  85                  90 gga aga gga cat aca ctc act ctc aat ttc acg aga aat gca aca cgt        337
Gly Arg Gly His Thr Leu Thr Leu Asn Phe Thr Arg Asn Ala Thr Arg
     95                 100                 105 tac agc gtt cag ctc atg agt ttt gtt tat aac ttg tca gac aca cac        385
Tyr Ser Val Gln Leu Met Ser Phe Val Tyr Asn Leu Ser Asp Thr His
110                 115                 120                 125 ctt ttc ccc aat gcg agc tcc aaa gaa atc aag act gtg gaa tct ata        433
Leu Phe Pro Asn Ala Ser Ser Lys Glu Ile Lys Thr Val Glu Ser Ile
                130                 135                 140 act gac atc agg gca gat ata gat aaa aaa tac aga tgt gtt agt ggc        481
Thr Asp Ile Arg Ala Asp Ile Asp Lys Lys Tyr Arg Cys Val Ser Gly
            145                 150                 155 acc cag gtc cac atg aac aac gtg acc gta acg ctc cat gat gcc acc        529
Thr Gln Val His Met Asn Asn Val Thr Val Thr Leu His Asp Ala Thr
        160                 165                 170 atc cag gcg tac ctt tcc aac agc agc ttc agc agg gga gag aca cgc        577
Ile Gln Ala Tyr Leu Ser Asn Ser Ser Phe Ser Arg Gly Glu Thr Arg
    175                 180                 185 tgt gaa caa gac agg cct tcc cca acc aca gcg ccc cct gcg cca ccc        625
Cys Glu Gln Asp Arg Pro Ser Pro Thr Thr Ala Pro Pro Ala Pro Pro
190                 195                 200                 205 agc ccc tcg ccc tca ccc gtg ccc aag agc ccc tct gtg gac aag tac        673
Ser Pro Ser Pro Ser Pro Val Pro Lys Ser Pro Ser Val Asp Lys Tyr
                210                 215                 220 aac gtg agc ggc acc aac ggg acc tgc ctg ctg gcc agc atg ggg ctg        721
Asn Val Ser Gly Thr Asn Gly Thr Cys Leu Leu Ala Ser Met Gly Leu
            225                 230                 235
```

```
cag ctg aac ctc acc tat gag agg aag gac aac acg acg gtg aca agg      769
Gln Leu Asn Leu Thr Tyr Glu Arg Lys Asp Asn Thr Thr Val Thr Arg
        240                 245                 250 ctt ctc aac atc aac ccc aac aag acc tcg gcc agc ggg agc tgc ggc      817
Leu Leu Asn Ile Asn Pro Asn Lys Thr Ser Ala Ser Gly Ser Cys Gly
        255                 260                 265 gcc cac ctg gtg act ctg gag ctg cac agc gag ggc acc acc gtc ctg      865
Ala His Leu Val Thr Leu Glu Leu His Ser Glu Gly Thr Thr Val Leu
270                 275                 280                 285 ctc ttc cag ttc ggg atg aat gca agt tct agc cgg ttt ttc cta caa      913
Leu Phe Gln Phe Gly Met Asn Ala Ser Ser Ser Arg Phe Phe Leu Gln
                290                 295                 300 gga atc cag ttg aat aca att ctt cct gac gcc aga gac cct gcc ttt      961
Gly Ile Gln Leu Asn Thr Ile Leu Pro Asp Ala Arg Asp Pro Ala Phe
            305                 310                 315 aaa gct gcc aac ggc tcc ctg cga gcg ctg cag gcc aca gtc ggc aat     1009
Lys Ala Ala Asn Gly Ser Leu Arg Ala Leu Gln Ala Thr Val Gly Asn
                320                 325                 330 tcc tac aag tgc aac gcg gag gag cac gtc cgt gtc acg aag gcg ttt     1057
Ser Tyr Lys Cys Asn Ala Glu Glu His Val Arg Val Thr Lys Ala Phe
        335                 340                 345 tca gtc aat ata ttc aaa gtg tgg gtc cag gct ttc aag gtg gaa ggt     1105
Ser Val Asn Ile Phe Lys Val Trp Val Gln Ala Phe Lys Val Glu Gly
350                 355                 360                 365 ggc cag ttt ggc tct gtg gag gag tgt ctg ctg gac gag aac agc acg     1153
Gly Gln Phe Gly Ser Val Glu Glu Cys Leu Leu Asp Glu Asn Ser Thr
                370                 375                 380 ctg atc ccc atc gct gtg ggt ggt gcc ctg gcg ggg ctg gtc ctc atc     1201
Leu Ile Pro Ile Ala Val Gly Gly Ala Leu Ala Gly Leu Val Leu Ile
            385                 390                 395 gtc ctc atc gcc tac ctc gtc ggc agg aag agg agt cac gca ggc tac     1249
Val Leu Ile Ala Tyr Leu Val Gly Arg Lys Arg Ser His Ala Gly Tyr
                400                 405                 410 cag act atc tagcctggtg cacgcaggca cagcagctgc agggcctct              1298
Gln Thr Ile
    415

<210> SEQ ID NO 26
<211> LENGTH: 416
<212> TYPE: PRT
<213> ORGANISM: Homo sapiens
<220> FEATURE:
<223> OTHER INFORMATION: human lysosomal membrane glycoprotein-1
      (LAMP-1)

<400> SEQUENCE: 26

Met Ala Pro Arg Ser Ala Arg Arg Pro Leu Leu Leu Leu Leu Pro Val
  1               5                  10                  15

Ala Ala Ala Arg Pro His Ala Leu Ser Ser Ala Ala Met Phe Met Val
                 20                  25                  30

Lys Asn Gly Asn Gly Thr Ala Cys Ile Met Ala Asn Phe Ser Ala Ala
             35                  40                  45

Phe Ser Val Asn Tyr Asp Thr Lys Ser Gly Pro Lys Asn Met Thr Phe
         50                  55                  60

Asp Leu Pro Ser Asp Ala Thr Val Val Leu Asn Arg Ser Ser Cys Gly
 65                  70                  75                  80

Lys Glu Asn Thr Ser Asp Pro Ser Leu Val Ile Ala Phe Gly Arg Gly
                 85                  90                  95

His Thr Leu Thr Leu Asn Phe Thr Arg Asn Ala Thr Arg Tyr Ser Val
```

```
                     100                 105                 110
          Gln Leu Met Ser Phe Val Tyr Asn Leu Ser Asp Thr His Leu Phe Pro
                 115                 120                 125

Asn Ala Ser Ser Lys Glu Ile Lys Thr Val Glu Ser Ile Thr Asp Ile
          130                 135                 140

Arg Ala Asp Ile Asp Lys Lys Tyr Arg Cys Val Ser Gly Thr Gln Val
          145                 150                 155                 160

His Met Asn Asn Val Thr Val Thr Leu His Asp Ala Thr Ile Gln Ala
                          165                 170                 175

Tyr Leu Ser Asn Ser Ser Phe Ser Arg Gly Glu Thr Arg Cys Glu Gln
                      180                 185                 190

Asp Arg Pro Ser Pro Thr Thr Ala Pro Pro Ala Pro Pro Ser Pro Ser
                  195                 200                 205

Pro Ser Pro Val Pro Lys Ser Pro Ser Val Asp Lys Tyr Asn Val Ser
              210                 215                 220

Gly Thr Asn Gly Thr Cys Leu Leu Ala Ser Met Gly Leu Gln Leu Asn
          225                 230                 235                 240

Leu Thr Tyr Glu Arg Lys Asp Asn Thr Thr Val Thr Arg Leu Leu Asn
                          245                 250                 255

Ile Asn Pro Asn Lys Thr Ser Ala Ser Gly Ser Cys Gly Ala His Leu
                      260                 265                 270

Val Thr Leu Glu Leu His Ser Glu Gly Thr Thr Val Leu Leu Phe Gln
                  275                 280                 285

Phe Gly Met Asn Ala Ser Ser Arg Phe Phe Leu Gln Gly Ile Gln
              290                 295                 300

Leu Asn Thr Ile Leu Pro Asp Ala Arg Asp Pro Ala Phe Lys Ala Ala
          305                 310                 315                 320

Asn Gly Ser Leu Arg Ala Leu Gln Ala Thr Val Gly Asn Ser Tyr Lys
                          325                 330                 335

Cys Asn Ala Glu Glu His Val Arg Val Thr Lys Ala Phe Ser Val Asn
                      340                 345                 350

Ile Phe Lys Val Trp Val Gln Ala Phe Lys Val Glu Gly Gly Gln Phe
                  355                 360                 365

Gly Ser Val Glu Glu Cys Leu Leu Asp Glu Asn Ser Thr Leu Ile Pro
              370                 375                 380

Ile Ala Val Gly Gly Ala Leu Ala Gly Leu Val Leu Ile Val Leu Ile
          385                 390                 395                 400

Ala Tyr Leu Val Gly Arg Lys Arg Ser His Ala Gly Tyr Gln Thr Ile
                          405                 410                 415

<210> SEQ ID NO 27
<211> LENGTH: 792
<212> TYPE: DNA
<213> ORGANISM: Homo sapiens
<220> FEATURE:
<221> NAME/KEY: CDS
<222> LOCATION: (1)...(792)
<223> OTHER INFORMATION: human HLA-DMB

<400> SEQUENCE: 27 atg atc aca ttc ctg ccg ctg ctg ctg ggg ctc agc ctg ggc tgc aca         48
Met Ile Thr Phe Leu Pro Leu Leu Leu Gly Leu Ser Leu Gly Cys Thr
 1               5                  10                  15 gga gca ggt ggc ttc gtg gcc cat gtg gaa agc acc tgt ctg ttg gat         96
Gly Ala Gly Gly Phe Val Ala His Val Glu Ser Thr Cys Leu Leu Asp
                20                  25                  30
```

-continued

```
gat gct ggg act cca aag gat ttc aca tac tgc atc tcc ttc aac aag      144
Asp Ala Gly Thr Pro Lys Asp Phe Thr Tyr Cys Ile Ser Phe Asn Lys
        35                  40                  45 gat ctg ctg acc tgc tgg gat cca gag gag aat aag atg gcc cct tgc      192
Asp Leu Leu Thr Cys Trp Asp Pro Glu Glu Asn Lys Met Ala Pro Cys
 50                  55                  60 gaa ttt ggg gtg ctg aat agc ttg gcg aat gtc ctc tca cag cac ctc      240
Glu Phe Gly Val Leu Asn Ser Leu Ala Asn Val Leu Ser Gln His Leu
 65                  70                  75                  80 aac caa aaa gac acc ctg atg cag cgc ttg cgc aat ggg ctt cag aat      288
Asn Gln Lys Asp Thr Leu Met Gln Arg Leu Arg Asn Gly Leu Gln Asn
                 85                  90                  95 tgt gcc aca cac acc cag ccc ttc tgg gga tca ctg acc aac agg aca      336
Cys Ala Thr His Thr Gln Pro Phe Trp Gly Ser Leu Thr Asn Arg Thr
            100                 105                 110 cgg cca cca tct gtg caa gta gcc aaa acc act cct ttt aac acg agg      384
Arg Pro Pro Ser Val Gln Val Ala Lys Thr Thr Pro Phe Asn Thr Arg
        115                 120                 125 gag cct gtg atg ctg gcc tgc tat gtg tgg ggc ttc tat cca gca gaa      432
Glu Pro Val Met Leu Ala Cys Tyr Val Trp Gly Phe Tyr Pro Ala Glu
130                 135                 140 gtg act atc acg tgg agg aag aac ggg aag ctt gtc atg cct cac agc      480
Val Thr Ile Thr Trp Arg Lys Asn Gly Lys Leu Val Met Pro His Ser
145                 150                 155                 160 agt gcg cac aag act gcc cag ccc aat gga gac tgg aca tac cag acc      528
Ser Ala His Lys Thr Ala Gln Pro Asn Gly Asp Trp Thr Tyr Gln Thr
                165                 170                 175 ctc tcc cat tta gcc tta acc ccc tct tac ggg gac act tac acc tgt      576
Leu Ser His Leu Ala Leu Thr Pro Ser Tyr Gly Asp Thr Tyr Thr Cys
            180                 185                 190 gtg gta gag cac att ggg gct cct gag ccc atc ctt cgg gac tgg aca      624
Val Val Glu His Ile Gly Ala Pro Glu Pro Ile Leu Arg Asp Trp Thr
        195                 200                 205 cct ggg ctg tcc ccc atg cag acc ctg aag gtt tct gtg tct gca gtg      672
Pro Gly Leu Ser Pro Met Gln Thr Leu Lys Val Ser Val Ser Ala Val
210                 215                 220 act ctg ggc ctg ggc ctc atc atc ttc tct ctt ggt gtg atc agc tgg      720
Thr Leu Gly Leu Gly Leu Ile Ile Phe Ser Leu Gly Val Ile Ser Trp
225                 230                 235                 240 cgg aga gct ggc cac tct agt tac act cct ctt cct ggg tcc aat tat      768
Arg Arg Ala Gly His Ser Ser Tyr Thr Pro Leu Pro Gly Ser Asn Tyr
                245                 250                 255 tca gaa gga tgg cac att tcc tag                                      792
Ser Glu Gly Trp His Ile Ser
            260
```

<210> SEQ ID NO 28
<211> LENGTH: 263
<212> TYPE: PRT
<213> ORGANISM: Homo sapiens
<220> FEATURE:
<223> OTHER INFORMATION: human HLA-DMB

<400> SEQUENCE: 28

```
Met Ile Thr Phe Leu Pro Leu Leu Gly Leu Ser Leu Gly Cys Thr
 1               5                  10                  15

Gly Ala Gly Gly Phe Val Ala His Val Glu Ser Thr Cys Leu Leu Asp
                 20                  25                  30

Asp Ala Gly Thr Pro Lys Asp Phe Thr Tyr Cys Ile Ser Phe Asn Lys
         35                  40                  45
```

```
Asp Leu Leu Thr Cys Trp Asp Pro Glu Glu Asn Lys Met Ala Pro Cys
     50                  55                  60
Glu Phe Gly Val Leu Asn Ser Leu Ala Asn Val Leu Ser Gln His Leu
 65                  70                  75                  80
Asn Gln Lys Asp Thr Leu Met Gln Arg Leu Arg Asn Gly Leu Gln Asn
                 85                  90                  95
Cys Ala Thr His Thr Gln Pro Phe Trp Gly Ser Leu Thr Asn Arg Thr
             100                 105                 110
Arg Pro Pro Ser Val Gln Val Ala Lys Thr Thr Pro Phe Asn Thr Arg
         115                 120                 125
Glu Pro Val Met Leu Ala Cys Tyr Val Trp Gly Phe Tyr Pro Ala Glu
    130                 135                 140
Val Thr Ile Thr Trp Arg Lys Asn Gly Lys Leu Val Met Pro His Ser
145                 150                 155                 160
Ser Ala His Lys Thr Ala Gln Pro Asn Gly Asp Trp Thr Tyr Gln Thr
                165                 170                 175
Leu Ser His Leu Ala Leu Thr Pro Ser Tyr Gly Asp Thr Tyr Thr Cys
            180                 185                 190
Val Val Glu His Ile Gly Ala Pro Glu Pro Ile Leu Arg Asp Trp Thr
        195                 200                 205
Pro Gly Leu Ser Pro Met Gln Thr Leu Lys Val Ser Val Ser Ala Val
    210                 215                 220
Thr Leu Gly Leu Gly Leu Ile Ile Phe Ser Leu Gly Val Ile Ser Trp
225                 230                 235                 240
Arg Arg Ala Gly His Ser Ser Tyr Thr Pro Leu Pro Gly Ser Asn Tyr
                245                 250                 255
Ser Glu Gly Trp His Ile Ser
            260

<210> SEQ ID NO 29
<211> LENGTH: 822
<212> TYPE: DNA
<213> ORGANISM: Homo sapiens
<220> FEATURE:
<221> NAME/KEY: CDS
<222> LOCATION: (1)...(822)
<223> OTHER INFORMATION: human HLA-DO beta

<400> SEQUENCE: 29 atg ggt tct ggg tgg gtc ccc tgg gtg gtg gct ctg cta gtg aat ctg       48
Met Gly Ser Gly Trp Val Pro Trp Val Val Ala Leu Leu Val Asn Leu
 1               5                  10                  15 acc caa ctg gat tcc tcc atg act caa ggc aca gac tct cca gaa gat       96
Thr Gln Leu Asp Ser Ser Met Thr Gln Gly Thr Asp Ser Pro Glu Asp
             20                  25                  30 ttt gtg att cag gca aag gct gac tgt tac ttc acc aac ggg aca gaa      144
Phe Val Ile Gln Ala Lys Ala Asp Cys Tyr Phe Thr Asn Gly Thr Glu
         35                  40                  45 aag gtg cag ttt gtg gtc aga ttc atc ttt aac ttg gag gag tat gta      192
Lys Val Gln Phe Val Val Arg Phe Ile Phe Asn Leu Glu Glu Tyr Val
     50                  55                  60 cgt ttc gac agt gat gtg ggg atg ttt gtg gca ttg acc aag ctg ggg      240
Arg Phe Asp Ser Asp Val Gly Met Phe Val Ala Leu Thr Lys Leu Gly
 65                  70                  75                  80 cag cca gat gct gag cag tgg aac agc cgg ctg gat ctc ttg gag agg      288
Gln Pro Asp Ala Glu Gln Trp Asn Ser Arg Leu Asp Leu Leu Glu Arg
                 85                  90                  95 agc aga cag gcc gtg gat ggg gtc tgt aga cac aac tac agg ctg ggc      336
```

```
Ser Arg Gln Ala Val Asp Gly Val Cys Arg His Asn Tyr Arg Leu Gly
            100                 105                 110 gca ccc ttc act gtg ggg aga aaa gtg caa cca gag gtg aca gtg tac      384
Ala Pro Phe Thr Val Gly Arg Lys Val Gln Pro Glu Val Thr Val Tyr
            115                 120                 125 cca gag agg acc cca ctc ctg cac cag cat aat ctg ctg cac tgc tct      432
Pro Glu Arg Thr Pro Leu Leu His Gln His Asn Leu Leu His Cys Ser
130                 135                 140 gtg aca ggc ttc tat cca ggg gat atc aag atc aag tgg ttc ctg aat      480
Val Thr Gly Phe Tyr Pro Gly Asp Ile Lys Ile Lys Trp Phe Leu Asn
145                 150                 155                 160 ggg cag gag gag aga gct ggg gtc atg tcc act ggc cct atc agg aat      528
Gly Gln Glu Glu Arg Ala Gly Val Met Ser Thr Gly Pro Ile Arg Asn
                165                 170                 175 gga gac tgg acc ttt cag act gtg gtg atg cta gaa atg act cct gaa      576
Gly Asp Trp Thr Phe Gln Thr Val Val Met Leu Glu Met Thr Pro Glu
            180                 185                 190 ctt gga cat gtc tac acc tgc ctt gtc gat cac tcc agc ctg ctg agc      624
Leu Gly His Val Tyr Thr Cys Leu Val Asp His Ser Ser Leu Leu Ser
        195                 200                 205 cct gtt tct gtg gag tgg aga gct cag tct gaa tat tct tgg aga aag      672
Pro Val Ser Val Glu Trp Arg Ala Gln Ser Glu Tyr Ser Trp Arg Lys
    210                 215                 220 atg ctg agt ggc att gca gcc ttc cta ctt ggg cta atc ttc ctt ctg      720
Met Leu Ser Gly Ile Ala Ala Phe Leu Leu Gly Leu Ile Phe Leu Leu
225                 230                 235                 240 gtg gga atc gtc atc cag cta agg gct cag aaa gga tat gtg agg acg      768
Val Gly Ile Val Ile Gln Leu Arg Ala Gln Lys Gly Tyr Val Arg Thr
                245                 250                 255 cag atg tct ggt aat gag gtc tca aga gct gtt ctc ctc cct cag tca      816
Gln Met Ser Gly Asn Glu Val Ser Arg Ala Val Leu Leu Pro Gln Ser
            260                 265                 270 tgc taa                                                               822
Cys

<210> SEQ ID NO 30
<211> LENGTH: 273
<212> TYPE: PRT
<213> ORGANISM: Homo sapiens
<220> FEATURE:
<223> OTHER INFORMATION: human HLA-DO beta

<400> SEQUENCE: 30

Met Gly Ser Gly Trp Val Pro Trp Val Val Ala Leu Leu Val Asn Leu
1               5                   10                  15

Thr Gln Leu Asp Ser Ser Met Thr Gln Gly Thr Asp Ser Pro Glu Asp
            20                  25                  30

Phe Val Ile Gln Ala Lys Ala Asp Cys Tyr Phe Thr Asn Gly Thr Glu
        35                  40                  45

Lys Val Gln Phe Val Val Arg Phe Ile Phe Asn Leu Glu Glu Tyr Val
    50                  55                  60

Arg Phe Asp Ser Asp Val Gly Met Phe Val Ala Leu Thr Lys Leu Gly
65                  70                  75                  80

Gln Pro Asp Ala Glu Gln Trp Asn Ser Arg Leu Asp Leu Leu Glu Arg
                85                  90                  95

Ser Arg Gln Ala Val Asp Gly Val Cys Arg His Asn Tyr Arg Leu Gly
            100                 105                 110

Ala Pro Phe Thr Val Gly Arg Lys Val Gln Pro Glu Val Thr Val Tyr
        115                 120                 125
```

```
Pro Glu Arg Thr Pro Leu Leu His Gln His Asn Leu Leu His Cys Ser
    130                 135                 140

Val Thr Gly Phe Tyr Pro Gly Asp Ile Lys Ile Lys Trp Phe Leu Asn
145                 150                 155                 160

Gly Gln Glu Glu Arg Ala Gly Val Met Ser Thr Gly Pro Ile Arg Asn
                165                 170                 175

Gly Asp Trp Thr Phe Gln Thr Val Val Met Leu Glu Met Thr Pro Glu
                180                 185                 190

Leu Gly His Val Tyr Thr Cys Leu Val Asp His Ser Ser Leu Leu Ser
                195                 200                 205

Pro Val Ser Val Glu Trp Arg Ala Gln Ser Glu Tyr Ser Trp Arg Lys
    210                 215                 220

Met Leu Ser Gly Ile Ala Ala Phe Leu Leu Gly Leu Ile Phe Leu Leu
225                 230                 235                 240

Val Gly Ile Val Ile Gln Leu Arg Ala Gln Lys Gly Tyr Val Arg Thr
                245                 250                 255

Gln Met Ser Gly Asn Glu Val Ser Arg Ala Val Leu Leu Pro Gln Ser
                260                 265                 270

Cys

<210> SEQ ID NO 31
<211> LENGTH: 700
<212> TYPE: DNA
<213> ORGANISM: Homo sapiens
<220> FEATURE:
<221> NAME/KEY: CDS
<222> LOCATION: (1)...(681)
<223> OTHER INFORMATION: human MB-1 Ig-alpha

<400> SEQUENCE: 31 atg cct ggg ggt cca gga gtc ctc caa gct ctg cct gcc acc atc ttc      48
Met Pro Gly Gly Pro Gly Val Leu Gln Ala Leu Pro Ala Thr Ile Phe
  1               5                  10                  15 ctc ctc ttc ctg ctg tct gct gtc tac ctg ggc cct ggg tgc cag gcc      96
Leu Leu Phe Leu Leu Ser Ala Val Tyr Leu Gly Pro Gly Cys Gln Ala
                 20                  25                  30 ctg tgg atg cac aag gtc cca gca tca ttg atg gtg agc ctg ggg gaa     144
Leu Trp Met His Lys Val Pro Ala Ser Leu Met Val Ser Leu Gly Glu
             35                  40                  45 gac gcc cac ttc caa tgc ccg cac aat agc agc aac aac gcc aac gtc     192
Asp Ala His Phe Gln Cys Pro His Asn Ser Ser Asn Asn Ala Asn Val
         50                  55                  60 acc tgg tgg cgc gtc ctc cat ggc aac tac acg tgg ccc cct gag ttc     240
Thr Trp Trp Arg Val Leu His Gly Asn Tyr Thr Trp Pro Pro Glu Phe
 65                  70                  75                  80 ttg ggc ccg ggc gag gac ccc aat ggt acg ctg atc atc cag aat gtg     288
Leu Gly Pro Gly Glu Asp Pro Asn Gly Thr Leu Ile Ile Gln Asn Val
                 85                  90                  95 aac aag agc cat ggg ggc ata tac gtg tgc cgg gtc cag gag ggc aac     336
Asn Lys Ser His Gly Gly Ile Tyr Val Cys Arg Val Gln Glu Gly Asn
                100                 105                 110 gag tca tac cag cag tcc tgc ggc acc tac ctc cgc gtg cgc cag ccg     384
Glu Ser Tyr Gln Gln Ser Cys Gly Thr Tyr Leu Arg Val Arg Gln Pro
            115                 120                 125 ccc ccc agg ccc ttc ctg gac atg ggg gag ggc acc aag aac cga atc     432
Pro Pro Arg Pro Phe Leu Asp Met Gly Glu Gly Thr Lys Asn Arg Ile
        130                 135                 140 atc aca gcc gag ggg atc atc ctc ctg ttc tgc gcg gtg gtg cct ggg     480
```

```
Ile Thr Ala Glu Gly Ile Ile Leu Leu Phe Cys Ala Val Val Pro Gly
145                 150                 155                 160 acg ctg ctg ctg ttc agg aaa cga tgg cag aac gag aag ctc ggg ttg      528
Thr Leu Leu Leu Phe Arg Lys Arg Trp Gln Asn Glu Lys Leu Gly Leu
                165                 170                 175 gat gcc ggg gat gaa tat gaa gat gaa aac ctt tat gaa ggc ctg aac      576
Asp Ala Gly Asp Glu Tyr Glu Asp Glu Asn Leu Tyr Glu Gly Leu Asn
            180                 185                 190 ctg gac gac tgc tcc atg tat gag gac atc tcc cgg ggc ctc cag ggc      624
Leu Asp Asp Cys Ser Met Tyr Glu Asp Ile Ser Arg Gly Leu Gln Gly
        195                 200                 205 acc tac cag gat gtg ggc agc ctc aac ata gga gat gtc cag ctg gag      672
Thr Tyr Gln Asp Val Gly Ser Leu Asn Ile Gly Asp Val Gln Leu Glu
    210                 215                 220 aag ccg tgacacccct actcctgcca gg                                     700
Lys Pro
225

<210> SEQ ID NO 32
<211> LENGTH: 226
<212> TYPE: PRT
<213> ORGANISM: Homo sapiens
<220> FEATURE:
<223> OTHER INFORMATION: human MB-1 Ig-alpha

<400> SEQUENCE: 32

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
                20                  25                  30

Leu Trp Met His Lys Val Pro Ala Ser Leu Met Val Ser Leu Gly Glu
            35                  40                  45

Asp Ala His Phe Gln Cys Pro His Asn Ser Ser Asn Ala Asn Val
        50                  55                  60

Thr Trp Trp Arg Val Leu His Gly Asn Tyr Thr Trp Pro Pro Glu Phe
65                  70                  75                  80

Leu Gly Pro Gly Glu Asp Pro Asn Gly Thr Leu Ile Ile Gln Asn Val
                85                  90                  95

Asn Lys Ser His Gly Gly Ile Tyr Val Cys Arg Val Gln Glu Gly Asn
                100                 105                 110

Glu Ser Tyr Gln Gln Ser Cys Gly Thr Tyr Leu Arg Val Arg Gln Pro
            115                 120                 125

Pro Pro Arg Pro Phe Leu Asp Met Gly Glu Gly Thr Lys Asn Arg Ile
        130                 135                 140

Ile Thr Ala Glu Gly Ile Ile Leu Leu Phe Cys Ala Val Val Pro Gly
145                 150                 155                 160

Thr Leu Leu Leu Phe Arg Lys Arg Trp Gln Asn Glu Lys Leu Gly Leu
                165                 170                 175

Asp Ala Gly Asp Glu Tyr Glu Asp Glu Asn Leu Tyr Glu Gly Leu Asn
            180                 185                 190

Leu Asp Asp Cys Ser Met Tyr Glu Asp Ile Ser Arg Gly Leu Gln Gly
        195                 200                 205

Thr Tyr Gln Asp Val Gly Ser Leu Asn Ile Gly Asp Val Gln Leu Glu
    210                 215                 220

Lys Pro
225
```

```
<210> SEQ ID NO 33
<211> LENGTH: 723
<212> TYPE: DNA
<213> ORGANISM: Homo sapiens
<220> FEATURE:
<221> NAME/KEY: CDS
<222> LOCATION: (17)...(706)
<223> OTHER INFORMATION: human Ig-beta protein

<400> SEQUENCE: 33
gaattccgcg gtgacc atg gcc agg ctg gcg ttg tct cct gtg ccc agc cac      52
                  Met Ala Arg Leu Ala Leu Ser Pro Val Pro Ser His
                   1               5                  10 tgg atg gtg gcg ttg ctg ctg ctc tca gct gag cca gta cca gca          100
Trp Met Val Ala Leu Leu Leu Leu Ser Ala Glu Pro Val Pro Ala
         15                  20                  25 gcc aga tcg gag gac cgg tac cgg aat ccc aaa ggt agt gct tgt tcg      148
Ala Arg Ser Glu Asp Arg Tyr Arg Asn Pro Lys Gly Ser Ala Cys Ser
         30                  35                  40 cgg atc tgg cag agc cca cgt ttc ata gcc agg aaa cgg cgc ttc acg      196
Arg Ile Trp Gln Ser Pro Arg Phe Ile Ala Arg Lys Arg Arg Phe Thr
 45                  50                  55                  60 gtg aaa atg cac tgc tac atg aac agc gcc tcc ggc aat gtg agc tgg      244
Val Lys Met His Cys Tyr Met Asn Ser Ala Ser Gly Asn Val Ser Trp
                 65                  70                  75 ctc tgg aag cag gag atg gac gag aat ccc cag cag ctg aag ctg gaa      292
Leu Trp Lys Gln Glu Met Asp Glu Asn Pro Gln Gln Leu Lys Leu Glu
             80                  85                  90 aag ggc cgc atg gaa gag tcc cag aac gaa tct ctc gcc acc ctc acc      340
Lys Gly Arg Met Glu Glu Ser Gln Asn Glu Ser Leu Ala Thr Leu Thr
         95                 100                 105 atc caa ggc atc cgg ttt gag gac aat ggc atc tac ttc tgc cag cag      388
Ile Gln Gly Ile Arg Phe Glu Asp Asn Gly Ile Tyr Phe Cys Gln Gln
     110                 115                 120 aag tgc aac aac acc tcg gag gtc tac cag ggc tgc ggc aca gag ctg      436
Lys Cys Asn Asn Thr Ser Glu Val Tyr Gln Gly Cys Gly Thr Glu Leu
125                 130                 135                 140 cga gtc atg gga ttc agc acc ttg gca cag ctg aag cag agg aac acg      484
Arg Val Met Gly Phe Ser Thr Leu Ala Gln Leu Lys Gln Arg Asn Thr
                145                 150                 155 ctg aag gat ggt atc atc atg atc cag acg ctg ctg atc atc ctc ttc      532
Leu Lys Asp Gly Ile Ile Met Ile Gln Thr Leu Leu Ile Ile Leu Phe
            160                 165                 170 atc atc gtg cct atc ttc ctg ctg ctg gac aag gat gac agc aag gct      580
Ile Ile Val Pro Ile Phe Leu Leu Leu Asp Lys Asp Asp Ser Lys Ala
        175                 180                 185 ggc atg gag gaa gat cac acc tac gag ggc ctg gac att gac cag aca      628
Gly Met Glu Glu Asp His Thr Tyr Glu Gly Leu Asp Ile Asp Gln Thr
    190                 195                 200 gcc acc tat gag gac ata gtg acg ctg cgg aca ggg gaa gtg aag tgg      676
Ala Thr Tyr Glu Asp Ile Val Thr Leu Arg Thr Gly Glu Val Lys Trp
205                 210                 215                 220 tct gta ggt gag cac cca ggc cag gag tgagagccag gtcgccccat            723
Ser Val Gly Glu His Pro Gly Gln Glu
                225

<210> SEQ ID NO 34
<211> LENGTH: 229
<212> TYPE: PRT
<213> ORGANISM: Homo sapiens
<220> FEATURE:
<223> OTHER INFORMATION: human Ig-beta protein
```

<400> SEQUENCE: 34

| | | | | | | | | | | | | | | |
|---|---|---|---|---|---|---|---|---|---|---|---|---|---|---|
|Met|Ala|Arg|Leu|Ala|Leu|Ser|Pro|Val|Pro|Ser|His|Trp|Met|Val|Ala|
|1| | | |5| | | | |10| | | | |15| |

Met Ala Arg Leu Ala Leu Ser Pro Val Pro Ser His Trp Met Val Ala
1               5                  10                 15

Leu Leu Leu Leu Leu Ser Ala Glu Pro Val Pro Ala Ala Arg Ser Glu
                20                  25                  30

Asp Arg Tyr Arg Asn Pro Lys Gly Ser Ala Cys Ser Arg Ile Trp Gln
            35                  40                  45

Ser Pro Arg Phe Ile Ala Arg Lys Arg Phe Thr Val Lys Met His
    50                  55                  60

Cys Tyr Met Asn Ser Ala Ser Gly Asn Val Ser Trp Leu Trp Lys Gln
65                  70                  75                  80

Glu Met Asp Glu Asn Pro Gln Gln Leu Lys Leu Glu Lys Gly Arg Met
                85                  90                  95

Glu Glu Ser Gln Asn Glu Ser Leu Ala Thr Leu Thr Ile Gln Gly Ile
                100                 105                 110

Arg Phe Glu Asp Asn Gly Ile Tyr Phe Cys Gln Gln Lys Cys Asn Asn
            115                 120                 125

Thr Ser Glu Val Tyr Gln Gly Cys Gly Thr Glu Leu Arg Val Met Gly
    130                 135                 140

Phe Ser Thr Leu Ala Gln Leu Lys Gln Arg Asn Thr Leu Lys Asp Gly
145                 150                 155                 160

Ile Ile Met Ile Gln Thr Leu Leu Ile Ile Leu Phe Ile Ile Val Pro
                165                 170                 175

Ile Phe Leu Leu Leu Asp Lys Asp Ser Lys Ala Gly Met Glu Glu
                180                 185                 190

Asp His Thr Tyr Glu Gly Leu Asp Ile Asp Gln Thr Ala Thr Tyr Glu
            195                 200                 205

Asp Ile Val Thr Leu Arg Thr Gly Glu Val Lys Trp Ser Val Gly Glu
    210                 215                 220

His Pro Gly Gln Glu
225

<210> SEQ ID NO 35
<211> LENGTH: 5053
<212> TYPE: DNA
<213> ORGANISM: Artificial Sequence
<220> FEATURE:
<223> OTHER INFORMATION: vector pEP2

<400> SEQUENCE: 35

```
gacggatcgg gagatctccc gatcccctat ggtcgactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacgggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggac tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
```

```
actcacgggg atttccaagt ctccacccca ttgacgtcaa tgggagtttg ttttggcacc      720
aaaatcaacg gactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctaga      900
gtaagtaccg cctatagagt ctataggccc accccttgg cttcttatgc atgctatact      960
gtttttggct tggggtctat acacccccgc ttcctcatgt tataggtgat ggtatagctt     1020
agcctatagg tgtgggttat tgaccattat tgaccactcc cctattggtg acgatacttt     1080
ccattactaa tccataacat ggctctttgc cacaactctc tttattggct atatgccaat     1140
acactgtcct tcagagactg acacggactc tgtatttta caggatgggg tctcatttat      1200
tatttacaaa ttcacatata caacaccacc gtccccagtg cccgcagttt ttattaaaca     1260
taacgtggga tctccacgcg aatctcgggt acgtgttccg gacatgggct cttctccggt     1320
agcggcggag cttctacatc cgagccctgc tcccatgcct ccagcgactc atggtcgctc     1380
ggcagctcct tgctcctaac agtggaggcc agacttaggc acagcacgat gcccaccacc     1440
accagtgtgc cgcacaaggc cgtggcggta gggtatgtgt ctgaaaatga gctcggggag     1500
cgggcttgca ccgctgacgc atttggaaga cttaaggcag cggcagaaga agatgcaggc     1560
agctgagttg ttgtgttctg ataagagtca gaggtaactc ccgttgcggt gctgttaacg     1620
gtggagggca gtgtagtctg agcagtactc gttgctgccg cgcgcgccac cagacataat     1680
agctgacaga ctaacagact gttcctttcc atgggtcttt tctgcaggct agccggcctg     1740
aattcggata tccaagcttg atgaataaaa gatcagagct ctagtgatct gtgtgttggt     1800 ttttgtgtg ctcgagcccc agctggttct ttccgcctca gaagccatag agcccaccgc      1860
atccccagca tgcctgctat tgtcttccca atcctccccc ttgctgtcct gccccacccc     1920
acccccagaa atagaatgac acctactcag acaatgcgat gcaatttcct catttattta     1980
ggaaaggaca gtgggagtgg caccttccag ggtcaaggaa ggcacggggg agggcaaac      2040 aacagatggc tggcaactag aaggcacagt cgaggctgat cagcgagctc tagcggtacc     2100
ggcattagtc tatggccgac tctagatttt ctccttgcgg ccgccctaga tgcatgctcg     2160
atcgacctgc agttggacct gggagtggac acctgtggag agaaaggcaa agtggatgtc     2220
attgtcactc aagtgtatgg ccagatctca agcctgccac acctcaagct agcttgacaa     2280
caaaaagatt gtcttttctg accagatgga cgcggccacc ctcaaaggca tcaccgcggg     2340
ccaggtgaat atcaaatcct cctcgttttt ggaaactgac aatcttagcg cagaagtcat     2400
gcccgctttt gagagggagt actcacccca acagctggcc ctcgcagaca gcgaattaat     2460
tccagcacac tggcggccgt tactagtgga tccgagctcg caagctagct tgggtctccc     2520
tatagtgagt cgtattaatt tcgataagcc agtaagcagt gggttctcta gttagccaga     2580
gagctctgct tatatagacc tcccaccgta cacgcctacc gcccatttgc gtcaatgggg     2640
cggagttgtt acgacatttt ggaaagtccc gttgattttg gtgccaaaac aaactcccat     2700
tgacgtcaat ggggtggaga cttggaaatc cccgtgagtc aaaccgctat ccacgcccat     2760
tgatgtactg ccaaaaccgc atcaccatgg taatagcgat gactaatacg tagatgtact     2820
gccaagtagg aaagtcccat aaggtcatgt actgggcata atgccaggcg ggccatttac     2880
cgtcattgac gtcaataggg ggcgtacttg gcatatgata cacttgatgt actgccaagt     2940
gggcagttta ccgtaaatag tccacccatt gacgtcaatg gaaagtccct attggcgtta     3000
ctatgggaac atacgtcatt attgacgtca atgggcgggg gtcgttgggc ggtcagccag     3060
```

-continued

```
gcgggccatt taccgtaagt tatgtaacgc ggaactccat atatgggcta tgaactaatg    3120 acccgtaat tgattactat taataactag tcaataatca atgtcctgca ttaatgaatc     3180
ggccaacgcg cggggagagg cggtttgcgt attgggcgct cttccgcttc ctcgctcact    3240
gactcgctgc gctcggtcgt tcggctgcgg cgagcggtat cagctcactc aaaggcggta    3300
atacggttat ccacagaatc aggggataac gcaggaaaga acatgtgagc aaaaggccag    3360
caaaaggcca ggaaccgtaa aaaggccgcg ttgctggcgt ttttccatag gctccgcccc    3420
cctgacgagc atcacaaaaa tcgacgctca agtcagaggt ggcgaaaccc gacaggacta    3480
taaagatacc aggcgtttcc ccctggaagc tccctcgtgc gctctcctgt tccgaccctg    3540
ccgcttaccg gatacctgtc cgcctttctc ccttcgggaa gcgtggcgct ttctcaatgc    3600
tcacgctgta ggtatctcag ttcggtgtag tcgttcgct ccaagctggg ctgtgtgcac    3660
gaaccccccg ttcagcccga ccgctgcgcc ttatccggta actatcgtct tgagtccaac    3720
ccggtaagac acgacttatc gccactggca gcagccactg gtaacaggat tagcagagcg    3780
aggtatgtag cggtgctac agagttcttg aagtggtggc ctaactacgg ctacactaga    3840
aggacagtat ttggtatctg cgctctgctg aagccagtta ccttcggaaa aagagttggt    3900
agctcttgat ccggcaaaca aaccaccgct ggtagcggtg ttttttgt ttgcaagcag     3960 cagattacgc gcagaaaaaa aggatctcaa gaagatcctt tgatctttc tacgggtct     4020 gacgctcagt ggaacgaaaa ctcacgttaa gggattttgg tcatgaacaa taaaactgtc    4080
tgcttacata acagtaata caagggtgt tatgagccat attcaacggg aaacgtcttg      4140
ctcgaggccg cgattaaatt ccaacatgga tgctgattta tatgggtata atgggctcg     4200 cgataatgtc gggcaatcag gtgcgacaat ctatcgattg tatgggaagc ccgatgcgcc    4260
agagttgttt ctgaaacatg gcaaaggtag cgttgccaat gatgttacag atgagatggt    4320
cagactaaac tggctgacgg aatttatgcc tcttccgacc atcaagcatt ttatccgtac    4380
tcctgatgat gcatggttac tcaccactgc gatccccggg aaaacagcat tccaggtatt    4440
agaagaatat cctgattcag gtgaaaatat tgttgatgcg ctggcagtgt tcctgcgccg    4500
gttgcattcg attcctgttt gtaattgtcc ttttaacagc gatcgcgtat ttcgtctcgc    4560
tcaggcgcaa tcacgaatga ataacggttt ggttgatgcg agtgattttg atgacgagcg    4620
taatggctgg cctgttgaac aagtctggaa agaaatgcat aaacttttgc cattctcacc    4680
ggattcagtc gtcactcatg gtgatttctc acttgataac cttatttttg acgaggggaa    4740
attaataggt tgtattgatg ttggacgagt cggaatcgca gaccgatacc aggatcttgc    4800
catcctatgg aactgcctcg gtgagttttc tccttcatta cagaaacggc ttttcaaaa    4860 atatggtatt gataatcctg atatgaataa attgcagttt catttgatgc tcgatgagtt    4920
tttctaatca gaattggtta attggttgta acactggcag agcatcatga gcggatacat    4980
atttgaatgt atttagaaaa ataaacaaat aggggttccg cgcacatttc cccgaaaagt    5040
gccacctgac gtc                                                      5053
```

<210> SEQ ID NO 36
<211> LENGTH: 411
<212> TYPE: DNA
<213> ORGANISM: Artificial Sequence
<220> FEATURE:
<223> OTHER INFORMATION: vector pMIN.0
<221> NAME/KEY: CDS
<222> LOCATION: (16)...(411)

-continued

```
<400> SEQUENCE: 36
gctagcgccg ccacc atg gga atg cag gtg cag atc cag agc ctg ttt ctg         51
                Met Gly Met Gln Val Gln Ile Gln Ser Leu Phe Leu
                  1               5                  10 ctc ctc ctg tgg gtg ccc ggg tcc aga gga cac acc ctg tgg aag gcc          99
Leu Leu Leu Trp Val Pro Gly Ser Arg Gly His Thr Leu Trp Lys Ala
         15                  20                  25 gga atc ctg tat aag gcc aag ttc gtg gct gcc tgg acc ctg aag gct         147
Gly Ile Leu Tyr Lys Ala Lys Phe Val Ala Ala Trp Thr Leu Lys Ala
     30                  35                  40 gcc gct ttc ctg cct agc gat ttc ttt cct agc gtg aag ctg acc cca         195
Ala Ala Phe Leu Pro Ser Asp Phe Phe Pro Ser Val Lys Leu Thr Pro
 45                  50                  55                  60 ctg tgc gtg acc ctg tat atg gat gac gtg gtg ctg gga gcc agc atc         243
Leu Cys Val Thr Leu Tyr Met Asp Asp Val Val Leu Gly Ala Ser Ile
                 65                  70                  75 atc aac ttc gag aag ctg gga ctg tcc aga tac gtg gct agg ctg atc         291
Ile Asn Phe Glu Lys Leu Gly Leu Ser Arg Tyr Val Ala Arg Leu Ile
             80                  85                  90 ctg aag gag cct gtg cac ggc gtg tcc acc ctg cca gag acc acc gtg         339
Leu Lys Glu Pro Val His Gly Val Ser Thr Leu Pro Glu Thr Thr Val
         95                 100                 105 gtg agg agg acc gtg tac tat gga gtg cct gtg tgg aag tgg ctg agc         387
Val Arg Arg Thr Val Tyr Tyr Gly Val Pro Val Trp Lys Trp Leu Ser
    110                 115                 120 ctg ctg gtg ccc ttt gtg ggt acc                                         411
Leu Leu Val Pro Phe Val Gly Thr
125                 130

<210> SEQ ID NO 37
<211> LENGTH: 132
<212> TYPE: PRT
<213> ORGANISM: Artificial Sequence
<220> FEATURE:
<223> OTHER INFORMATION: vector pMIN.0

<400> SEQUENCE: 37

Met Gly Met Gln Val Gln Ile Gln Ser Leu Phe Leu Leu Leu Leu Trp
  1               5                  10                  15

Val Pro Gly Ser Arg Gly His Thr Leu Trp Lys Ala Gly Ile Leu Tyr
                 20                  25                  30

Lys Ala Lys Phe Val Ala Ala Trp Thr Leu Lys Ala Ala Ala Phe Leu
             35                  40                  45

Pro Ser Asp Phe Phe Pro Ser Val Lys Leu Thr Pro Leu Cys Val Thr
         50                  55                  60

Leu Tyr Met Asp Asp Val Val Leu Gly Ala Ser Ile Ile Asn Phe Glu
 65                  70                  75                  80

Lys Leu Gly Leu Ser Arg Tyr Val Ala Arg Leu Ile Leu Lys Glu Pro
                 85                  90                  95

Val His Gly Val Ser Thr Leu Pro Glu Thr Thr Val Val Arg Arg Thr
            100                 105                 110

Val Tyr Tyr Gly Val Pro Val Trp Lys Trp Leu Ser Leu Leu Val Pro
        115                 120                 125

Phe Val Gly Thr
    130

<210> SEQ ID NO 38
<211> LENGTH: 390
<212> TYPE: DNA
```

```
<213> ORGANISM: Artificial Sequence
<220> FEATURE:
<223> OTHER INFORMATION: vector pMIN.1
<221> NAME/KEY: CDS
<222> LOCATION: (16)...(384)

<400> SEQUENCE: 38
gctagcgccg ccacc atg gga atg cag gtg cag atc cag agc ctg ttt ctg      51
                Met Gly Met Gln Val Gln Ile Gln Ser Leu Phe Leu
                1               5                   10 ctc ctc ctg tgg gtg ccc ggg tcc aga gga cac acc ctg tgg aag gcc       99
Leu Leu Leu Trp Val Pro Gly Ser Arg Gly His Thr Leu Trp Lys Ala
            15                  20                  25 gga atc ctg tat aag gcc aag ttc gtg gct gcc tgg acc ctg aag gct      147
Gly Ile Leu Tyr Lys Ala Lys Phe Val Ala Ala Trp Thr Leu Lys Ala
    30                  35                  40 gcc gct ttc ctg cct agc gat ttc ttt cct agc gtg aag ctg acc cca      195
Ala Ala Phe Leu Pro Ser Asp Phe Phe Pro Ser Val Lys Leu Thr Pro
45                  50                  55                  60 ctg tgc gtg acc ctg tat atg gat gac gtg gtg ctg gga gtg gga ctg      243
Leu Cys Val Thr Leu Tyr Met Asp Asp Val Val Leu Gly Val Gly Leu
                65                  70                  75 tcc agg tac gtg gct agg ctg atc ctg aag gag cct gtg cac ggc gtg      291
Ser Arg Tyr Val Ala Arg Leu Ile Leu Lys Glu Pro Val His Gly Val
            80                  85                  90 tcc acc ctg cca gag acc acc gtg gtg agg agg acc gtg tac tat gga      339
Ser Thr Leu Pro Glu Thr Thr Val Val Arg Arg Thr Val Tyr Tyr Gly
        95                  100                 105 gtg cct gtg tgg aag tgg ctg agc ctg ctg gtg ccc ttt gtg              381
Val Pro Val Trp Lys Trp Leu Ser Leu Leu Val Pro Phe Val
    110                 115                 120 tgaggtacc                                                            390

<210> SEQ ID NO 39
<211> LENGTH: 122
<212> TYPE: PRT
<213> ORGANISM: Artificial Sequence
<220> FEATURE:
<223> OTHER INFORMATION: vector pMIN.1

<400> SEQUENCE: 39

Met Gly Met Gln Val Gln Ile Gln Ser Leu Phe Leu Leu Leu Leu Trp
1               5                   10                  15

Val Pro Gly Ser Arg Gly His Thr Leu Trp Lys Ala Gly Ile Leu Tyr
            20                  25                  30

Lys Ala Lys Phe Val Ala Ala Trp Thr Leu Lys Ala Ala Ala Phe Leu
        35                  40                  45

Pro Ser Asp Phe Phe Pro Ser Val Lys Leu Thr Pro Leu Cys Val Thr
    50                  55                  60

Leu Tyr Met Asp Asp Val Val Leu Gly Val Gly Leu Ser Arg Tyr Val
65                  70                  75                  80

Ala Arg Leu Ile Leu Lys Glu Pro Val His Gly Val Ser Thr Leu Pro
                85                  90                  95

Glu Thr Thr Val Val Arg Arg Thr Val Tyr Tyr Gly Val Pro Val Trp
            100                 105                 110

Lys Trp Leu Ser Leu Leu Val Pro Phe Val
        115                 120

<210> SEQ ID NO 40
<211> LENGTH: 36
```

```
<212> TYPE: DNA
<213> ORGANISM: Artificial Sequence
<220> FEATURE:
<223> OTHER INFORMATION: primer oligonucleotide murIi-F

<400> SEQUENCE: 40
gctagcgccg ccaccatgga tgaccaacgc gacctc                              36

<210> SEQ ID NO 41
<211> LENGTH: 27
<212> TYPE: DNA
<213> ORGANISM: Artificial Sequence
<220> FEATURE:
<223> OTHER INFORMATION: primer oligonucleotide murIi-R

<400> SEQUENCE: 41
ggtacctcac agggtgactt gacccag                                        27

<210> SEQ ID NO 42
<211> LENGTH: 42
<212> TYPE: DNA
<213> ORGANISM: Artificial Sequence
<220> FEATURE:
<223> OTHER INFORMATION: primer oligonucleotide IiPADRE-R

<400> SEQUENCE: 42
cagggtccag gcagccacga acttggccac aggtttggca ga                       42

<210> SEQ ID NO 43
<211> LENGTH: 43
<212> TYPE: DNA
<213> ORGANISM: Artificial Sequence
<220> FEATURE:
<223> OTHER INFORMATION: primer oligonucleotide IiPADRE-F

<400> SEQUENCE: 43
ggctgcctgg accctgaagg ctgccgctat gtccatggat aac                      43

<210> SEQ ID NO 44
<211> LENGTH: 70
<212> TYPE: DNA
<213> ORGANISM: Artificial Sequence
<220> FEATURE:
<223> OTHER INFORMATION: oligo 1

<400> SEQUENCE: 44
cttcgcatga agcttatcag ccaggctgtg cacgccgctc acgccgaaat caacgaagct    60
ggaagaaccc                                                           70

<210> SEQ ID NO 45
<211> LENGTH: 70
<212> TYPE: DNA
<213> ORGANISM: Artificial Sequence
<220> FEATURE:
<223> OTHER INFORMATION: oligo 2

<400> SEQUENCE: 45
ttctggtcag cagaaagaac aggataggag cgtttggagg gcgataagct ggaggggttc    60
ttccagcttc                                                           70

<210> SEQ ID NO 46
<211> LENGTH: 71
<212> TYPE: DNA
<213> ORGANISM: Artificial Sequence
<220> FEATURE:
```

-continued

```
<223> OTHER INFORMATION: oligo 3

<400> SEQUENCE: 46
ttctgctgac cagaatcctg acaatccccc agtccctgga cgccaagttc gtggctgcct    60
ggaccctgaa g                                                         71

<210> SEQ ID NO 47
<211> LENGTH: 34
<212> TYPE: DNA
<213> ORGANISM: Artificial Sequence
<220> FEATURE:
<223> OTHER INFORMATION: Help-epR primer

<400> SEQUENCE: 47
ggtacctcaa gcggcagcct tcagggtcca ggca                                34

<210> SEQ ID NO 48
<211> LENGTH: 17
<212> TYPE: PRT
<213> ORGANISM: Artificial Sequence
<220> FEATURE:
<223> OTHER INFORMATION: residues 323-339 of ovalbumin (Ova323-339)

<400> SEQUENCE: 48

Ile Ser Gln Ala Val His Ala Ala His Ala Glu Ile Asn Glu Ala Gly
 1               5                  10                  15

Arg

<210> SEQ ID NO 49
<211> LENGTH: 13
<212> TYPE: PRT
<213> ORGANISM: Artificial Sequence
<220> FEATURE:
<223> OTHER INFORMATION: residues 128-141 of HBV core antigen
      (HBVcore 128)

<400> SEQUENCE: 49

Thr Pro Pro Ala Tyr Arg Pro Pro Asn Ala Pro Ile Leu
 1               5                  10

<210> SEQ ID NO 50
<211> LENGTH: 15
<212> TYPE: PRT
<213> ORGANISM: Artificial Sequence
<220> FEATURE:
<223> OTHER INFORMATION: residues 182-196 of HBV env (HBVenv182)

<400> SEQUENCE: 50

Phe Phe Leu Leu Thr Arg Ile Leu Thr Ile Pro Gln Ser Leu Asp
 1               5                  10                  15

<210> SEQ ID NO 51
<211> LENGTH: 19
<212> TYPE: DNA
<213> ORGANISM: Artificial Sequence
<220> FEATURE:
<223> OTHER INFORMATION: Th-Pad-R primer

<400> SEQUENCE: 51
agcggcagcc ttcagggtc                                                 19

<210> SEQ ID NO 52
<211> LENGTH: 43
<212> TYPE: DNA
<213> ORGANISM: Artificial Sequence
```

```
<220> FEATURE:
<223> OTHER INFORMATION: IiPADRE-F primer

<400> SEQUENCE: 52
ggctgcctgg accctgaagg ctgccgctat gtccatggat aac                    43

<210> SEQ ID NO 53
<211> LENGTH: 20
<212> TYPE: DNA
<213> ORGANISM: Artificial Sequence
<220> FEATURE:
<223> OTHER INFORMATION: primer Th-ova-F

<400> SEQUENCE: 53
atcagccagg ctgtgcacgc                                              20

<210> SEQ ID NO 54
<211> LENGTH: 27
<212> TYPE: DNA
<213> ORGANISM: Artificial Sequence
<220> FEATURE:
<223> OTHER INFORMATION: primer 1F oligonucleotide KappaSig-F

<400> SEQUENCE: 54
gctagcgccg ccaccatggg aatgcag                                      27

<210> SEQ ID NO 55
<211> LENGTH: 27
<212> TYPE: DNA
<213> ORGANISM: Artificial Sequence
<220> FEATURE:
<223> OTHER INFORMATION: primer 1R oligonucleotide Kappa-Th-R

<400> SEQUENCE: 55
cacagcctgg ctgattcctc tggaccc                                      27

<210> SEQ ID NO 56
<211> LENGTH: 33
<212> TYPE: DNA
<213> ORGANISM: Artificial Sequence
<220> FEATURE:
<223> OTHER INFORMATION: primer 2F oligonucleotide PAD/LAMP-F

<400> SEQUENCE: 56
ctgaaggctg ccgctaacaa catgttgatc ccc                               33

<210> SEQ ID NO 57
<211> LENGTH: 24
<212> TYPE: DNA
<213> ORGANISM: Artificial Sequence
<220> FEATURE:
<223> OTHER INFORMATION: primer 2R oligonucleotide LAMP-CYTOR

<400> SEQUENCE: 57
ggtaccctag atggtctgat agcc                                         24

<210> SEQ ID NO 58
<211> LENGTH: 33
<212> TYPE: DNA
<213> ORGANISM: Artificial Sequence
<220> FEATURE:
<223> OTHER INFORMATION: primer 1F oligonucleotide H2-Mb-1F

<400> SEQUENCE: 58
gccgctagcg ccgccaccat ggctgcactc tgg                               33
```

<210> SEQ ID NO 59
<211> LENGTH: 30
<212> TYPE: DNA
<213> ORGANISM: Artificial Sequence
<220> FEATURE:
<223> OTHER INFORMATION: primer 1R oligonucleotide H2-Mb-1R

<400> SEQUENCE: 59
cacagcctgg ctgatcccca tacagtgcag                                    30

<210> SEQ ID NO 60
<211> LENGTH: 30
<212> TYPE: DNA
<213> ORGANISM: Artificial Sequence
<220> FEATURE:
<223> OTHER INFORMATION: primer 2F oligonucleotide H2-Mb-2F

<400> SEQUENCE: 60
ctgaaggctg ccgctaaggt ctctgtgtct                                    30

<210> SEQ ID NO 61
<211> LENGTH: 24
<212> TYPE: DNA
<213> ORGANISM: Artificial Sequence
<220> FEATURE:
<223> OTHER INFORMATION: primer 2R oligonucleotide H2-Mb-2R

<400> SEQUENCE: 61
gcgggtaccc taatgccgtc cttc                                          24

<210> SEQ ID NO 62
<211> LENGTH: 33
<212> TYPE: DNA
<213> ORGANISM: Artificial Sequence
<220> FEATURE:
<223> OTHER INFORMATION: primer 1F oligonucleotide H2-Ob-1F

<400> SEQUENCE: 62
gcggctagcg ccgccaccat gggcgctggg agg                                33

<210> SEQ ID NO 63
<211> LENGTH: 30
<212> TYPE: DNA
<213> ORGANISM: Artificial Sequence
<220> FEATURE:
<223> OTHER INFORMATION: primer 1R oligonucleotide H2-Ob-1R

<400> SEQUENCE: 63
tgcacagcct ggctgatgga atccagcctc                                    30

<210> SEQ ID NO 64
<211> LENGTH: 30
<212> TYPE: DNA
<213> ORGANISM: Artificial Sequence
<220> FEATURE:
<223> OTHER INFORMATION: primer 2F oligonucleotide H2-Ob-2F

<400> SEQUENCE: 64
ctgaaggctg ccgctatact gagtggagct                                    30

<210> SEQ ID NO 65
<211> LENGTH: 26
<212> TYPE: DNA
<213> ORGANISM: Artificial Sequence
<220> FEATURE:
<223> OTHER INFORMATION: primer 2R oligonucleotide H2-Ob-2R

```
<400> SEQUENCE: 65
gccggtacct catgtgacat gtcccg                                              26

<210> SEQ ID NO 66
<211> LENGTH: 80
<212> TYPE: DNA
<213> ORGANISM: Artificial Sequence
<220> FEATURE:
<223> OTHER INFORMATION: PADRE-Influenza matrix 5' primer

<400> SEQUENCE: 66
gctagcgccg ccaccatggc caagttcgtg gctgcctgga ccctgaaggc tgccgctatg        60
agtcttctaa ccgaggtcga                                                    80

<210> SEQ ID NO 67
<211> LENGTH: 30
<212> TYPE: DNA
<213> ORGANISM: Artificial Sequence
<220> FEATURE:
<223> OTHER INFORMATION: PADRE-Influenza matrix 3' primer

<400> SEQUENCE: 67
tcacttgaat cgctgcatct gcaccccat                                          30

<210> SEQ ID NO 68
<211> LENGTH: 58
<212> TYPE: DNA
<213> ORGANISM: Artificial Sequence
<220> FEATURE:
<223> OTHER INFORMATION: PADRE-HBV-s one oligonucleotide

<400> SEQUENCE: 68
gctagcgccg ccaccatggc caagttcgtg gctgcctgga ccctgaaggc tgccgctc          58

<210> SEQ ID NO 69
<211> LENGTH: 58
<212> TYPE: DNA
<213> ORGANISM: Artificial Sequence
<220> FEATURE:
<223> OTHER INFORMATION: PADRE-HBV-s second oligonucleotide

<400> SEQUENCE: 69
ctcgagagcg gcagccttca gggtccaggc agccacgaac ttggccatgg tggcggcg          58

<210> SEQ ID NO 70
<211> LENGTH: 33
<212> TYPE: DNA
<213> ORGANISM: Artificial Sequence
<220> FEATURE:
<223> OTHER INFORMATION: primer 1F oligonucleotide Ig alpha-1F

<400> SEQUENCE: 70
gcggctagcg ccgccaccat gccagggggt cta                                     33

<210> SEQ ID NO 71
<211> LENGTH: 30
<212> TYPE: DNA
<213> ORGANISM: Artificial Sequence
<220> FEATURE:
<223> OTHER INFORMATION: primer 1R oligonucleotide Ig alpha-1R

<400> SEQUENCE: 71
gcacagcctg gctgatggcc tggcatccgg                                         30
```

<210> SEQ ID NO 72
<211> LENGTH: 30
<212> TYPE: DNA
<213> ORGANISM: Artificial Sequence
<220> FEATURE:
<223> OTHER INFORMATION: primer 2F oligonucleotide Ig alpha-2F

<400> SEQUENCE: 72
ctgaaggctg ccgctgggat catcttgctg    30

<210> SEQ ID NO 73
<211> LENGTH: 27
<212> TYPE: DNA
<213> ORGANISM: Artificial Sequence
<220> FEATURE:
<223> OTHER INFORMATION: primer 2R oligonucleotide Ig alpha-2R

<400> SEQUENCE: 73
gcgggtacct catggctttt ccagctg    27

<210> SEQ ID NO 74
<211> LENGTH: 33
<212> TYPE: DNA
<213> ORGANISM: Artificial Sequence
<220> FEATURE:
<223> OTHER INFORMATION: primer 1F oligonucleotide B29-1F

<400> SEQUENCE: 74
gcggctagcg ccgccaccat ggccacactg gtg    33

<210> SEQ ID NO 75
<211> LENGTH: 30
<212> TYPE: DNA
<213> ORGANISM: Artificial Sequence
<220> FEATURE:
<223> OTHER INFORMATION: primer 1R oligonucleotide B29-1R

<400> SEQUENCE: 75
cacagcctgg ctgatcggct cacctgagaa    30

<210> SEQ ID NO 76
<211> LENGTH: 30
<212> TYPE: DNA
<213> ORGANISM: Artificial Sequence
<220> FEATURE:
<223> OTHER INFORMATION: primer 2F oligonucleotide B29-2F (30mer)

<400> SEQUENCE: 76
ctgaaggctg ccgctattat cttgatccag    30

<210> SEQ ID NO 77
<211> LENGTH: 27
<212> TYPE: DNA
<213> ORGANISM: Artificial Sequence
<220> FEATURE:
<223> OTHER INFORMATION: primer 2R oligonucleotide B29-2R (27mer)

<400> SEQUENCE: 77
gccggtacct cattcctggc ctggatg    27

<210> SEQ ID NO 78
<211> LENGTH: 21
<212> TYPE: DNA
<213> ORGANISM: Artificial Sequence
<220> FEATURE:
<223> OTHER INFORMATION: pUC4K amplification primer

```
<400> SEQUENCE: 78
tctgatgtta cattgcacaa g                                              21

<210> SEQ ID NO 79
<211> LENGTH: 33
<212> TYPE: DNA
<213> ORGANISM: Artificial Sequence
<220> FEATURE:
<223> OTHER INFORMATION: pUC4K amplification primer

<400> SEQUENCE: 79
gcgcactcat gatgctctgc cagtgttaca acc                                 33

<210> SEQ ID NO 80
<211> LENGTH: 30
<212> TYPE: DNA
<213> ORGANISM: Artificial Sequence
<220> FEATURE:
<223> OTHER INFORMATION: CMV DNA amplification primer

<400> SEQUENCE: 80
gcgtctagag taagtaccgc ctatagactc                                     30

<210> SEQ ID NO 81
<211> LENGTH: 30
<212> TYPE: DNA
<213> ORGANISM: Artificial Sequence
<220> FEATURE:
<223> OTHER INFORMATION: CMV DNA amplification primer

<400> SEQUENCE: 81
ccggctagcc tgcagaaaag acccatggaa                                     30

<210> SEQ ID NO 82
<211> LENGTH: 49
<212> TYPE: DNA
<213> ORGANISM: Artificial Sequence
<220> FEATURE:
<223> OTHER INFORMATION: polylinker oligo

<400> SEQUENCE: 82
ggccgcaagg aaaaaatcta gagtcggcca tagactaatg ccggtaccg                49

<210> SEQ ID NO 83
<211> LENGTH: 50
<212> TYPE: DNA
<213> ORGANISM: Artificial Sequence
<220> FEATURE:
<223> OTHER INFORMATION: polylinker oligo

<400> SEQUENCE: 83
ctagcggtac cggcattagt ctatggcccg actctagatt ttttccttgc               50

<210> SEQ ID NO 84
<211> LENGTH: 72
<212> TYPE: DNA
<213> ORGANISM: Artificial Sequence
<220> FEATURE:
<223> OTHER INFORMATION: oligo annealed to produce fragment with
      polylinker, polyadenylation signal and EcoRI and
      XhoI cohesive ends

<400> SEQUENCE: 84
aattcggata tccaagcttg atgaataaaa gatcagagct ctagtgatct gtgtgttggt    60
```

-continued tttttttgtgt gc                                                          72

<210> SEQ ID NO 85
<211> LENGTH: 72
<212> TYPE: DNA
<213> ORGANISM: Artificial Sequence
<220> FEATURE:
<223> OTHER INFORMATION: oligo annealed to produce fragment with
      polylinker, polyadenylation signal and EcoRI and
      XhoI cohesive ends

<400> SEQUENCE: 85
tcgagcacac aaaaaaccaa cacacagatc actagagctc tgatcttttt attcatcaag       60
cttggatatc cg                                                           72

<210> SEQ ID NO 86
<211> LENGTH: 20
<212> TYPE: PRT
<213> ORGANISM: Artificial Sequence
<220> FEATURE:
<223> OTHER INFORMATION: consensus mouse Ig Kappa signal sequence

<400> SEQUENCE: 86

Met Gln Val Gln Ile Gln Ser Leu Phe Leu Leu Leu Leu Trp Val Pro
  1               5                  10                  15

Gly Ser Arg Gly
           20

<210> SEQ ID NO 87
<211> LENGTH: 60
<212> TYPE: DNA
<213> ORGANISM: Artificial Sequence
<220> FEATURE:
<223> OTHER INFORMATION: nucleotides encoding consensus mouse Ig Kappa
      signal sequence

<400> SEQUENCE: 87
atgcaggtgc agatccagag cctgtttctg ctcctcctgt gggtgcccgg gtccagagga      60

<210> SEQ ID NO 88
<211> LENGTH: 11
<212> TYPE: PRT
<213> ORGANISM: Artificial Sequence
<220> FEATURE:
<223> OTHER INFORMATION: HBV pol 149-159 (A11 restricted) (peptide
      1147.16)

<400> SEQUENCE: 88

His Thr Leu Trp Lys Ala Gly Ile Leu Tyr Lys
  1               5                  10

<210> SEQ ID NO 89
<211> LENGTH: 33
<212> TYPE: DNA
<213> ORGANISM: Artificial Sequence
<220> FEATURE:
<223> OTHER INFORMATION: nucleotides encoding HBV pol 149-159 (A11
      restricted)

<400> SEQUENCE: 89
cacaccctgt ggaaggccgg aatcctgtat aag                                   33

<210> SEQ ID NO 90
<211> LENGTH: 39
<212> TYPE: DNA
<213> ORGANISM: Artificial Sequence

```
<220> FEATURE:
<223> OTHER INFORMATION: nucleotides encoding PADRE-universal MHC class
      II epitope

<400> SEQUENCE: 90
gccaagttcg tggctgcctg gaccctgaag gctgccgct                              39

<210> SEQ ID NO 91
<211> LENGTH: 10
<212> TYPE: PRT
<213> ORGANISM: Artificial Sequence
<220> FEATURE:
<223> OTHER INFORMATION: HBV core 18-27 (A2 restricted) (peptide
      924.07)

<400> SEQUENCE: 91

Phe Leu Pro Ser Asp Phe Phe Pro Ser Val
 1               5                  10

<210> SEQ ID NO 92
<211> LENGTH: 30
<212> TYPE: DNA
<213> ORGANISM: Artificial Sequence
<220> FEATURE:
<223> OTHER INFORMATION: nucleotides encoding HBV core 18-27 (A2
      restricted)

<400> SEQUENCE: 92
ttcctgccta gcgatttctt tcctagcgtg                                        30

<210> SEQ ID NO 93
<211> LENGTH: 9
<212> TYPE: PRT
<213> ORGANISM: Artificial Sequence
<220> FEATURE:
<223> OTHER INFORMATION: HIV env 120-128 (A2 restricted) (peptide
      1211.04)

<400> SEQUENCE: 93

Lys Leu Thr Pro Leu Cys Val Thr Leu
 1               5

<210> SEQ ID NO 94
<211> LENGTH: 27
<212> TYPE: DNA
<213> ORGANISM: Artificial Sequence
<220> FEATURE:
<223> OTHER INFORMATION: nucleotides encoding HIV env 120-128 (A2
      restricted)

<400> SEQUENCE: 94
aagctgaccc cactgtgcgt gaccctg                                           27

<210> SEQ ID NO 95
<211> LENGTH: 9
<212> TYPE: PRT
<213> ORGANISM: Artificial Sequence
<220> FEATURE:
<223> OTHER INFORMATION: HBV pol 551-559 (A2 restricted) (peptide
      1090.14)

<400> SEQUENCE: 95

Tyr Met Asp Asp Val Val Leu Gly Ala
 1               5

<210> SEQ ID NO 96
<211> LENGTH: 27
```

```
<212> TYPE: DNA
<213> ORGANISM: Artificial Sequence
<220> FEATURE:
<223> OTHER INFORMATION: nucleotides encoding HBV pol 551-559 (A2
      restricted)

<400> SEQUENCE: 96
tatatggatg acgtggtgct gggagcc                                      27

<210> SEQ ID NO 97
<211> LENGTH: 8
<212> TYPE: PRT
<213> ORGANISM: Artificial Sequence
<220> FEATURE:
<223> OTHER INFORMATION: mouse ovalbumin 257-264 (Kb restricted)

<400> SEQUENCE: 97

Ser Ile Ile Asn Phe Glu Lys Leu
 1               5

<210> SEQ ID NO 98
<211> LENGTH: 24
<212> TYPE: DNA
<213> ORGANISM: Artificial Sequence
<220> FEATURE:
<223> OTHER INFORMATION: nucleotides encoding mouse ovalbumin 257-264
      (Kb restricted)

<400> SEQUENCE: 98
agcatcatca acttcgagaa gctg                                         24

<210> SEQ ID NO 99
<211> LENGTH: 9
<212> TYPE: PRT
<213> ORGANISM: Artificial Sequence
<220> FEATURE:
<223> OTHER INFORMATION: HBV pol 455-463 (A2 restricted) (peptide
      1168.02)

<400> SEQUENCE: 99

Gly Leu Ser Arg Tyr Val Ala Arg Leu
 1               5

<210> SEQ ID NO 100
<211> LENGTH: 27
<212> TYPE: DNA
<213> ORGANISM: Artificial Sequence
<220> FEATURE:
<223> OTHER INFORMATION: nucleotides encoding HBV pol 455-463 (A2
      restricted)

<400> SEQUENCE: 100
ggactgttca gatacgtggc taggctg                                      27

<210> SEQ ID NO 101
<211> LENGTH: 9
<212> TYPE: PRT
<213> ORGANISM: Artificial Sequence
<220> FEATURE:
<223> OTHER INFORMATION: HIV pol 476-484 (A2 restricted) (peptide
      941.031)

<400> SEQUENCE: 101

Ile Leu Lys Glu Pro Val His Gly Val
 1               5

<210> SEQ ID NO 102
```

```
<211> LENGTH: 27
<212> TYPE: DNA
<213> ORGANISM: Artificial Sequence
<220> FEATURE:
<223> OTHER INFORMATION: nucleotides encoding HIV pol 476-484 (A2
      restricted)

<400> SEQUENCE: 102
atcctgaagg agcctgtgca cggcgtg                                        27

<210> SEQ ID NO 103
<211> LENGTH: 11
<212> TYPE: PRT
<213> ORGANISM: Artificial Sequence
<220> FEATURE:
<223> OTHER INFORMATION: HBV core 141-151 (A11 restricted) (peptide
      1083.01)

<400> SEQUENCE: 103

Ser Thr Leu Pro Glu Thr Thr Val Val Arg Arg
 1               5                  10

<210> SEQ ID NO 104
<211> LENGTH: 33
<212> TYPE: DNA
<213> ORGANISM: Artificial Sequence
<220> FEATURE:
<223> OTHER INFORMATION: nucleotides encoding HBV core 141-151 (A11
      restricted)

<400> SEQUENCE: 104
tccaccctgc cagagaccac cgtggtgagg aga                                 33

<210> SEQ ID NO 105
<211> LENGTH: 10
<212> TYPE: PRT
<213> ORGANISM: Artificial Sequence
<220> FEATURE:
<223> OTHER INFORMATION: HIV env 49-58 (A11 restricted) (peptide
      1069.43)

<400> SEQUENCE: 105

Thr Val Tyr Tyr Gly Val Pro Val Trp Lys
 1               5                  10

<210> SEQ ID NO 106
<211> LENGTH: 30
<212> TYPE: DNA
<213> ORGANISM: Artificial Sequence
<220> FEATURE:
<223> OTHER INFORMATION: nucleotides encoding HIV env 49-58 (A11
      restricted)

<400> SEQUENCE: 106
accgtgtact atggagtgcc tgtgtggaag                                     30

<210> SEQ ID NO 107
<211> LENGTH: 9
<212> TYPE: PRT
<213> ORGANISM: Artificial Sequence
<220> FEATURE:
<223> OTHER INFORMATION: HBVadr-ENV (S Ag 335-343) (A2 restricted)
      (peptide 1013.0102)

<400> SEQUENCE: 107

Trp Leu Ser Leu Leu Val Pro Phe Val
 1               5
```

<210> SEQ ID NO 108
<211> LENGTH: 27
<212> TYPE: DNA
<213> ORGANISM: Artificial Sequence
<220> FEATURE:
<223> OTHER INFORMATION: nucleotides encoding HBV env 335-343 (A2 restricted)

<400> SEQUENCE: 108
tggctgagcc tgctggtgcc ctttgtg                                27

<210> SEQ ID NO 109
<211> LENGTH: 12
<212> TYPE: DNA
<213> ORGANISM: Artificial Sequence
<220> FEATURE:
<223> OTHER INFORMATION: consensus Kozak sequence

<400> SEQUENCE: 109
gccgccacca tg                                                12

<210> SEQ ID NO 110
<211> LENGTH: 70
<212> TYPE: DNA
<213> ORGANISM: Artificial Sequence
<220> FEATURE:
<223> OTHER INFORMATION: Min1 oligo

<400> SEQUENCE: 110
gaggagcaga aacaggctct ggatctgcac ctgcattccc atggtggcgg cgctagcaag    60
cttcttgcgc                                                          70

<210> SEQ ID NO 111
<211> LENGTH: 71
<212> TYPE: DNA
<213> ORGANISM: Artificial Sequence
<220> FEATURE:
<223> OTHER INFORMATION: Min2 oligo

<400> SEQUENCE: 111
cctgtttctg ctcctcctgt gggtgcccgg gtccagagga cacaccctgt ggaaggccgg    60
aatcctgtat a                                                        71

<210> SEQ ID NO 112
<211> LENGTH: 70
<212> TYPE: DNA
<213> ORGANISM: Artificial Sequence
<220> FEATURE:
<223> OTHER INFORMATION: Min3 oligo

<400> SEQUENCE: 112
tcgctaggca ggaaagcggc agccttcagg gtccaggcag ccacgaactt ggccttatac    60
aggattccgg                                                          70

<210> SEQ ID NO 113
<211> LENGTH: 71
<212> TYPE: DNA
<213> ORGANISM: Artificial Sequence
<220> FEATURE:
<223> OTHER INFORMATION: Min4 oligo

<400> SEQUENCE: 113
ctttcctgcc tagcgatttc tttcctagcg tgaagctgac cccactgtgc gtgaccctgt    60
atatggatga c 71

<210> SEQ ID NO 114
<211> LENGTH: 70
<212> TYPE: DNA
<213> ORGANISM: Artificial Sequence
<220> FEATURE:
<223> OTHER INFORMATION: Min5 oligo

<400> SEQUENCE: 114
cgtacctgga cagtcccagc ttctcgaagt tgatgatgct ggctcccagc accacgtcat 60
ccatatacag 70

<210> SEQ ID NO 115
<211> LENGTH: 71
<212> TYPE: DNA
<213> ORGANISM: Artificial Sequence
<220> FEATURE:
<223> OTHER INFORMATION: Min6 oligo

<400> SEQUENCE: 115
ggactgtcca gatacgtggc taggctgatc ctgaaggagc ctgtgcacgg cgtgtccacc 60
ctgccagaga c 71

<210> SEQ ID NO 116
<211> LENGTH: 70
<212> TYPE: DNA
<213> ORGANISM: Artificial Sequence
<220> FEATURE:
<223> OTHER INFORMATION: Min7 oligo

<400> SEQUENCE: 116
gctcagccac ttccacacag gcactccata gtacacggtc ctcctcacca cggtggtctc 60
tggcagggtg 70

<210> SEQ ID NO 117
<211> LENGTH: 51
<212> TYPE: DNA
<213> ORGANISM: Artificial Sequence
<220> FEATURE:
<223> OTHER INFORMATION: Min8 oligo

<400> SEQUENCE: 117
gtggaagtgg ctgagcctgc tggtgccctt tgtgggtacc tgatctagag c 51

<210> SEQ ID NO 118
<211> LENGTH: 20
<212> TYPE: DNA
<213> ORGANISM: Artificial Sequence
<220> FEATURE:
<223> OTHER INFORMATION: flanking primer 5'

<400> SEQUENCE: 118
gcgcaagaag cttgctagcg 20

<210> SEQ ID NO 119
<211> LENGTH: 21
<212> TYPE: DNA
<213> ORGANISM: Artificial Sequence
<220> FEATURE:
<223> OTHER INFORMATION: flanking primer 3'

<400> SEQUENCE: 119
gctctagatc aggtacccca c 21

```
<210> SEQ ID NO 120
<211> LENGTH: 30
<212> TYPE: DNA
<213> ORGANISM: Artificial Sequence
<220> FEATURE:
<223> OTHER INFORMATION: primer Min-ovaR

<400> SEQUENCE: 120
tggacagtcc cactcccagc accacgtcat                                     30

<210> SEQ ID NO 121
<211> LENGTH: 30
<212> TYPE: DNA
<213> ORGANISM: Artificial Sequence
<220> FEATURE:
<223> OTHER INFORMATION: primer Min-ovaF

<400> SEQUENCE: 121
gctgggagtg ggactgtcca ggtacgtggc                                     30

<210> SEQ ID NO 122
<211> LENGTH: 29
<212> TYPE: DNA
<213> ORGANISM: Artificial Sequence
<220> FEATURE:
<223> OTHER INFORMATION: primer Min-StopR

<400> SEQUENCE: 122
ggtacctcac acaaagggca ccagcaggc                                      29

<210> SEQ ID NO 123
<211> LENGTH: 8
<212> TYPE: PRT
<213> ORGANISM: Artificial Sequence
<220> FEATURE:
<223> OTHER INFORMATION: HBV Env-HIV Pol 476

<400> SEQUENCE: 123

Leu Leu Val Pro Phe Val Ile Leu
 1               5

<210> SEQ ID NO 124
<211> LENGTH: 14
<212> TYPE: PRT
<213> ORGANISM: Artificial Sequence
<220> FEATURE:
<223> OTHER INFORMATION: HBVcore128

<400> SEQUENCE: 124

Thr Pro Pro Ala Tyr Arg Pro Pro Asn Ala Pro Ile Leu Phe
 1               5                  10

<210> SEQ ID NO 125
<211> LENGTH: 9
<212> TYPE: PRT
<213> ORGANISM: Artificial Sequence
<220> FEATURE:
<223> OTHER INFORMATION: HBV Pol 551-V (peptide 1090.77)

<400> SEQUENCE: 125

Tyr Met Asp Asp Val Val Leu Gly Val
 1               5

<210> SEQ ID NO 126
<211> LENGTH: 30
<212> TYPE: DNA
```

```
<213> ORGANISM: Artificial Sequence
<220> FEATURE:
<223> OTHER INFORMATION: first reaction amplification primer for
      pMin.1-No PADRE

<400> SEQUENCE: 126
atcgctaggc aggaacttat acaggattcc                                    30

<210> SEQ ID NO 127
<211> LENGTH: 27
<212> TYPE: DNA
<213> ORGANISM: Artificial Sequence
<220> FEATURE:
<223> OTHER INFORMATION: first reaction amplification primer for
      pMin.1-Anchor

<400> SEQUENCE: 127
tggacagtcc ggctcccagc accacgt                                       27

<210> SEQ ID NO 128
<211> LENGTH: 18
<212> TYPE: DNA
<213> ORGANISM: Artificial Sequence
<220> FEATURE:
<223> OTHER INFORMATION: 3' amplification primer (No PADRE)

<400> SEQUENCE: 128
ttcctgccta gcgatttc                                                 18

<210> SEQ ID NO 129
<211> LENGTH: 27
<212> TYPE: DNA
<213> ORGANISM: Artificial Sequence
<220> FEATURE:
<223> OTHER INFORMATION: 3' amplification primer (Anchor)

<400> SEQUENCE: 129
gctgggagcc ggactgtcca ggtacgt                                       27

<210> SEQ ID NO 130
<211> LENGTH: 42
<212> TYPE: DNA
<213> ORGANISM: Artificial Sequence
<220> FEATURE:
<223> OTHER INFORMATION: PCR amplification primer for Ig signal sequence
      deletion from pMin.1 for pMin.1-No Sig

<400> SEQUENCE: 130
gctagcgccg ccaccatgca caccctgtgg aaggccggaa tc                      42

<210> SEQ ID NO 131
<211> LENGTH: 39
<212> TYPE: DNA
<213> ORGANISM: Artificial Sequence
<220> FEATURE:
<223> OTHER INFORMATION: pMin.1-Switch 5' fragment amplification primer

<400> SEQUENCE: 131
gggcaccagc aggctcagcc acactcccag caccacgtc                          39

<210> SEQ ID NO 132
<211> LENGTH: 40
<212> TYPE: DNA
<213> ORGANISM: Artificial Sequence
<220> FEATURE:
<223> OTHER INFORMATION: pMin.1-Switch second overlapping fragment
      amplification primer
```

<400> SEQUENCE: 132
agcctgctgg tgccctttgt gatcctgaag gagcctgtgc                                    40

<210> SEQ ID NO 133
<211> LENGTH: 41
<212> TYPE: DNA
<213> ORGANISM: Artificial Sequence
<220> FEATURE:
<223> OTHER INFORMATION: pMin.1-Switch second overlapping fragment
      amplification primer

<400> SEQUENCE: 133
agccacgtac ctggacagtc ccttccacac aggcactcca t                                  41

<210> SEQ ID NO 134
<211> LENGTH: 32
<212> TYPE: DNA
<213> ORGANISM: Artificial Sequence
<220> FEATURE:
<223> OTHER INFORMATION: pMin.1-Switch 3' third fragment amplification
      primer

<400> SEQUENCE: 134
tgtccaggta cgtggctagg ctgtgaggta cc                                            32

<210> SEQ ID NO 135
<211> LENGTH: 42
<212> TYPE: DNA
<213> ORGANISM: Artificial Sequence
<220> FEATURE:
<223> OTHER INFORMATION: PCR amplification primer Min.0-No Sig-5' for
      deletion of signal sequence from pMin.0 for
      pMin.2-GFP

<400> SEQUENCE: 135
gctagcgccg ccaccatgca caccctgtgg aaggccggaa tc                                 42

<210> SEQ ID NO 136
<211> LENGTH: 10
<212> TYPE: PRT
<213> ORGANISM: Artificial Sequence
<220> FEATURE:
<223> OTHER INFORMATION: HBV Env 335-HBV Pol 551

<400> SEQUENCE: 136

Val Leu Gly Val Trp Leu Ser Leu Leu Val
 1               5                  10

<210> SEQ ID NO 137
<211> LENGTH: 15
<212> TYPE: PRT
<213> ORGANISM: Artificial Sequence
<220> FEATURE:
<223> OTHER INFORMATION: HBV POL 661 (peptide 1298.06)

<400> SEQUENCE: 137

Lys Gln Ala Phe Thr Phe Ser Pro Thr Tyr Lys Ala Phe Leu Cys
 1               5                  10                  15

<210> SEQ ID NO 138
<211> LENGTH: 15
<212> TYPE: PRT
<213> ORGANISM: Artificial Sequence
<220> FEATURE:
<223> OTHER INFORMATION: HBV POL 412 (peptide F107.03)

<400> SEQUENCE: 138

Leu Gln Ser Leu Thr Asn Leu Leu Ser Ser Asn Leu Ser Trp Leu
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: HBV ENV 180 (peptide 1280.06)

<400> SEQUENCE: 139

Ala Gly Phe Phe Leu Leu Thr Arg Ile Leu Thr Ile Pro Gln Ser
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: HBV POL 774 (peptide 1280.09)

<400> SEQUENCE: 140

Gly Thr Ser Phe Val Tyr Val Pro Ser Ala Leu Asn Pro Ala Asp
1               5                   10                  15

<210> SEQ ID NO 141
<211> LENGTH: 20
<212> TYPE: PRT
<213> ORGANISM: Artificial Sequence
<220> FEATURE:
<223> OTHER INFORMATION: HBV NUC 120 (peptide CF-08)

<400> SEQUENCE: 141

Val Ser Phe Gly Val Trp Ile Arg Thr Pro Pro Ala Tyr Arg Pro Pro
1               5                   10                  15

Asn Ala Pro Ile
            20

<210> SEQ ID NO 142
<211> LENGTH: 15
<212> TYPE: PRT
<213> ORGANISM: Artificial Sequence
<220> FEATURE:
<223> OTHER INFORMATION: HBV NUC 123 (peptide 27.0280)

<400> SEQUENCE: 142

Gly Val Trp Ile Arg Thr Pro Pro Ala Tyr Arg Pro Pro Asn Ala
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: HBV NUC 121 (peptide 1186.25)

<400> SEQUENCE: 143

Ser Phe Gly Val Trp Ile Arg Thr Pro Pro Ala Tyr Arg Pro Pro
1               5                   10                  15

<210> SEQ ID NO 144
<211> LENGTH: 15
<212> TYPE: PRT
<213> ORGANISM: Artificial Sequence
<220> FEATURE:

<223> OTHER INFORMATION: HBV POL 145 (peptide 27.0281)

<400> SEQUENCE: 144

Arg His Tyr Leu His Thr Leu Trp Lys Ala Gly Ile Leu Tyr Lys
 1               5                  10                  15

<210> SEQ ID NO 145
<211> LENGTH: 15
<212> TYPE: PRT
<213> ORGANISM: Artificial Sequence
<220> FEATURE:
<223> OTHER INFORMATION: HBV POL 523 (peptide F107.04)

<400> SEQUENCE: 145

Pro Phe Leu Leu Ala Gln Phe Thr Ser Ala Ile Cys Ser Val Val
 1               5                  10                  15

<210> SEQ ID NO 146
<211> LENGTH: 15
<212> TYPE: PRT
<213> ORGANISM: Artificial Sequence
<220> FEATURE:
<223> OTHER INFORMATION: HBV ENV 339 (peptide 1186.15)

<400> SEQUENCE: 146

Leu Val Pro Phe Val Gln Trp Phe Val Gly Leu Ser Pro Thr Val
 1               5                  10                  15

<210> SEQ ID NO 147
<211> LENGTH: 15
<212> TYPE: PRT
<213> ORGANISM: Artificial Sequence
<220> FEATURE:
<223> OTHER INFORMATION: HBV POL 501 (peptide 1280.15)

<400> SEQUENCE: 147

Leu His Leu Tyr Ser His Pro Ile Ile Leu Gly Phe Arg Lys Ile
 1               5                  10                  15

<210> SEQ ID NO 148
<211> LENGTH: 15
<212> TYPE: PRT
<213> ORGANISM: Artificial Sequence
<220> FEATURE:
<223> OTHER INFORMATION: HBV POL 615 (peptide 1298.04)

<400> SEQUENCE: 148

Lys Gln Cys Phe Arg Lys Leu Pro Val Asn Arg Pro Ile Asp Trp
 1               5                  10                  15

<210> SEQ ID NO 149
<211> LENGTH: 15
<212> TYPE: PRT
<213> ORGANISM: Artificial Sequence
<220> FEATURE:
<223> OTHER INFORMATION: HBV POL 764 (peptide 1298.07)

<400> SEQUENCE: 149

Ala Ala Asn Trp Ile Leu Arg Gly Thr Ser Phe Val Tyr Val Pro
 1               5                  10                  15

<210> SEQ ID NO 150
<211> LENGTH: 20
<212> TYPE: PRT
<213> ORGANISM: Artificial Sequence
<220> FEATURE:
<223> OTHER INFORMATION: HBV CORE 50 (peptide 857.02)

```
<400> SEQUENCE: 150

Pro His His Thr Ala Leu Arg Gln Ala Ile Leu Cys Trp Gly Glu Leu
  1               5                  10                  15

Met Thr Leu Ala
            20

<210> SEQ ID NO 151
<211> LENGTH: 15
<212> TYPE: PRT
<213> ORGANISM: Artificial Sequence
<220> FEATURE:
<223> OTHER INFORMATION: HBV POL 683 (peptide 35.0100)

<400> SEQUENCE: 151

Leu Cys Gln Val Phe Ala Asp Ala Thr Pro Thr Gly Trp Gly Leu
  1               5                  10                  15

<210> SEQ ID NO 152
<211> LENGTH: 15
<212> TYPE: PRT
<213> ORGANISM: Artificial Sequence
<220> FEATURE:
<223> OTHER INFORMATION: HBV POL 387 (peptide 35.0096)

<400> SEQUENCE: 152

Glu Ser Arg Leu Val Val Asp Phe Ser Gln Phe Ser Arg Gly Asn
  1               5                  10                  15

<210> SEQ ID NO 153
<211> LENGTH: 15
<212> TYPE: PRT
<213> ORGANISM: Artificial Sequence
<220> FEATURE:
<223> OTHER INFORMATION: HBV POL 96 (peptide 35.0093)

<400> SEQUENCE: 153

Val Gly Pro Leu Thr Val Asn Glu Lys Arg Arg Leu Lys Leu Ile
  1               5                  10                  15

<210> SEQ ID NO 154
<211> LENGTH: 15
<212> TYPE: PRT
<213> ORGANISM: Artificial Sequence
<220> FEATURE:
<223> OTHER INFORMATION: HBV POL 422 (peptide 1186.18)

<400> SEQUENCE: 154

Asn Leu Ser Trp Leu Ser Leu Asp Val Ser Ala Ala Phe Tyr His
  1               5                  10                  15

<210> SEQ ID NO 155
<211> LENGTH: 9
<212> TYPE: PRT
<213> ORGANISM: Artificial Sequence
<220> FEATURE:
<223> OTHER INFORMATION: HBV ENV ayw 183 (peptide 777.03)

<400> SEQUENCE: 155

Phe Leu Leu Thr Arg Ile Leu Thr Ile
  1               5

<210> SEQ ID NO 156
<211> LENGTH: 9
<212> TYPE: PRT
<213> ORGANISM: Artificial Sequence
```

```
<220> FEATURE:
<223> OTHER INFORMATION: HBV ayw pol 642 (peptide 927.15)

<400> SEQUENCE: 156

Ala Leu Met Pro Leu Tyr Ala Cys Ile
 1               5

<210> SEQ ID NO 157
<211> LENGTH: 9
<212> TYPE: PRT
<213> ORGANISM: Artificial Sequence
<220> FEATURE:
<223> OTHER INFORMATION: HBV pol 562 (peptide 927.11)

<400> SEQUENCE: 157

Phe Leu Leu Ser Leu Gly Ile His Leu
 1               5

<210> SEQ ID NO 158
<211> LENGTH: 9
<212> TYPE: PRT
<213> ORGANISM: Artificial Sequence
<220> FEATURE:
<223> OTHER INFORMATION: HBV POL 531 (peptide 1090.11)

<400> SEQUENCE: 158

Ser Ala Ile Cys Ser Val Val Arg Arg
 1               5

<210> SEQ ID NO 159
<211> LENGTH: 10
<212> TYPE: PRT
<213> ORGANISM: Artificial Sequence
<220> FEATURE:
<223> OTHER INFORMATION: HBV pol 665 (peptide 1090.10)

<400> SEQUENCE: 159

Gln Ala Phe Thr Phe Ser Pro Thr Tyr Lys
 1               5                  10

<210> SEQ ID NO 160
<211> LENGTH: 9
<212> TYPE: PRT
<213> ORGANISM: Artificial Sequence
<220> FEATURE:
<223> OTHER INFORMATION: HBV pol 47 (peptide 1069.16)

<400> SEQUENCE: 160

Asn Val Ser Ile Pro Trp Thr His Lys
 1               5

<210> SEQ ID NO 161
<211> LENGTH: 10
<212> TYPE: PRT
<213> ORGANISM: Artificial Sequence
<220> FEATURE:
<223> OTHER INFORMATION: HBV pol 388 (peptide 1069.20)

<400> SEQUENCE: 161

Leu Val Val Asp Phe Ser Gln Phe Ser Arg
 1               5                  10

<210> SEQ ID NO 162
<211> LENGTH: 9
<212> TYPE: PRT
<213> ORGANISM: Artificial Sequence
<220> FEATURE:
```

```
<223> OTHER INFORMATION: HBV adr POL 629 (peptide 1142.05) (peptide
      1.0166)

<400> SEQUENCE: 162

Lys Val Gly Asn Phe Thr Gly Leu Tyr
1               5

<210> SEQ ID NO 163
<211> LENGTH: 10
<212> TYPE: PRT
<213> ORGANISM: Artificial Sequence
<220> FEATURE:
<223> OTHER INFORMATION: HBV pol 150 (peptide 1069.15)

<400> SEQUENCE: 163

Thr Leu Trp Lys Ala Gly Ile Leu Tyr Lys
1               5                   10

<210> SEQ ID NO 164
<211> LENGTH: 9
<212> TYPE: PRT
<213> ORGANISM: Artificial Sequence
<220> FEATURE:
<223> OTHER INFORMATION: HBV ENV 313 (peptide 1145.04)

<400> SEQUENCE: 164

Ile Pro Ile Pro Ser Ser Trp Ala Phe
1               5

<210> SEQ ID NO 165
<211> LENGTH: 9
<212> TYPE: PRT
<213> ORGANISM: Artificial Sequence
<220> FEATURE:
<223> OTHER INFORMATION: HBV core 19-27 (peptide 988.05)

<400> SEQUENCE: 165

Leu Pro Ser Asp Phe Phe Pro Ser Val
1               5

<210> SEQ ID NO 166
<211> LENGTH: 10
<212> TYPE: PRT
<213> ORGANISM: Artificial Sequence
<220> FEATURE:
<223> OTHER INFORMATION: HBV POL 354 (peptide 1147.04)

<400> SEQUENCE: 166

Thr Pro Ala Arg Val Thr Gly Gly Val Phe
1               5                   10

<210> SEQ ID NO 167
<211> LENGTH: 10
<212> TYPE: PRT
<213> ORGANISM: Artificial Sequence
<220> FEATURE:
<223> OTHER INFORMATION: HBV env 338-347 (peptide 1069.06)

<400> SEQUENCE: 167

Leu Leu Val Pro Phe Val Gln Trp Phe Val
1               5                   10

<210> SEQ ID NO 168
<211> LENGTH: 10
<212> TYPE: PRT
<213> ORGANISM: Artificial Sequence
<220> FEATURE:
```

<223> OTHER INFORMATION: HBV POL 513 (peptide 1147.13)

<400> SEQUENCE: 168

Phe Leu Leu Ala Gln Phe Thr Ser Ala Ile
1               5                   10

<210> SEQ ID NO 169
<211> LENGTH: 11
<212> TYPE: PRT
<213> ORGANISM: Artificial Sequence
<220> FEATURE:
<223> OTHER INFORMATION: HBV ENV 259 (peptide 1147.14)

<400> SEQUENCE: 169

Val Leu Leu Asp Tyr Gln Gly Met Leu Pro Val
1               5                   10

<210> SEQ ID NO 170
<211> LENGTH: 9
<212> TYPE: PRT
<213> ORGANISM: Artificial Sequence
<220> FEATURE:
<223> OTHER INFORMATION: HBV ENV 339 (peptide 1132.01)

<400> SEQUENCE: 170

Leu Val Pro Phe Val Gln Trp Phe Val
1               5

<210> SEQ ID NO 171
<211> LENGTH: 9
<212> TYPE: PRT
<213> ORGANISM: Artificial Sequence
<220> FEATURE:
<223> OTHER INFORMATION: HBV pol 504-512 (peptide1069.05)

<400> SEQUENCE: 171

Leu Leu Ala Gln Phe Thr Ser Ala Ile
1               5

<210> SEQ ID NO 172
<211> LENGTH: 9
<212> TYPE: PRT
<213> ORGANISM: Artificial Sequence
<220> FEATURE:
<223> OTHER INFORMATION: HBV pol 411 (peptide 927.42)

<400> SEQUENCE: 172

Asn Leu Ser Trp Leu Ser Leu Asp Val
1               5

<210> SEQ ID NO 173
<211> LENGTH: 9
<212> TYPE: PRT
<213> ORGANISM: Artificial Sequence
<220> FEATURE:
<223> OTHER INFORMATION: HBV pol 992 (peptide 927.41)

<400> SEQUENCE: 173

Leu Leu Ser Ser Asn Leu Ser Trp Leu
1               5

<210> SEQ ID NO 174
<211> LENGTH: 9
<212> TYPE: PRT
<213> ORGANISM: Artificial Sequence
<220> FEATURE:
<223> OTHER INFORMATION: HBV pol 489 (peptide 927.46)

```
<400> SEQUENCE: 174

Lys Leu His Leu Tyr Ser His Pro Ile
 1               5

<210> SEQ ID NO 175
<211> LENGTH: 9
<212> TYPE: PRT
<213> ORGANISM: Artificial Sequence
<220> FEATURE:
<223> OTHER INFORMATION: HBV pol 503 (peptide 1069.071)

<400> SEQUENCE: 175

Phe Leu Leu Ala Gln Phe Thr Ser Ala
 1               5

<210> SEQ ID NO 176
<211> LENGTH: 9
<212> TYPE: PRT
<213> ORGANISM: Artificial Sequence
<220> FEATURE:
<223> OTHER INFORMATION: HBV ENV 62 (peptide 1142.07)

<400> SEQUENCE: 176

Gly Leu Leu Gly Trp Ser Pro Gln Ala
 1               5

<210> SEQ ID NO 177
<211> LENGTH: 9
<212> TYPE: PRT
<213> ORGANISM: Artificial Sequence
<220> FEATURE:
<223> OTHER INFORMATION: HBV ayw pol 1076 (peptide 927.47)

<400> SEQUENCE: 177

His Leu Tyr Ser His Pro Ile Ile Leu
 1               5

<210> SEQ ID NO 178
<211> LENGTH: 9
<212> TYPE: PRT
<213> ORGANISM: Artificial Sequence
<220> FEATURE:
<223> OTHER INFORMATION: HBV env 377-385 (peptide 1069.13)

<400> SEQUENCE: 178

Pro Leu Leu Pro Ile Phe Phe Cys Leu
 1               5

<210> SEQ ID NO 179
<211> LENGTH: 9
<212> TYPE: PRT
<213> ORGANISM: Artificial Sequence
<220> FEATURE:
<223> OTHER INFORMATION: HBV adr-ENV 177 (peptide 1013.1402)

<400> SEQUENCE: 179

Val Leu Gln Ala Gly Phe Phe Leu Leu
 1               5

<210> SEQ ID NO 180
<211> LENGTH: 11
<212> TYPE: PRT
<213> ORGANISM: Artificial Sequence
<220> FEATURE:
<223> OTHER INFORMATION: HBV pol 376 (peptide 26.0539)
```

```
<400> SEQUENCE: 180

Arg Leu Val Val Asp Phe Ser Gln Phe Ser Arg
 1               5                  10

<210> SEQ ID NO 181
<211> LENGTH: 11
<212> TYPE: PRT
<213> ORGANISM: Artificial Sequence
<220> FEATURE:
<223> OTHER INFORMATION: HBV X nuc fus 299 (peptide 26.0535)

<400> SEQUENCE: 181

Gly Val Trp Ile Arg Thr Pro Pro Ala Tyr Arg
 1               5                  10

<210> SEQ ID NO 182
<211> LENGTH: 9
<212> TYPE: PRT
<213> ORGANISM: Artificial Sequence
<220> FEATURE:
<223> OTHER INFORMATION: HBV X 64 (peptide 26.0153)

<400> SEQUENCE: 182

Ser Ser Ala Gly Pro Cys Ala Leu Arg
 1               5

<210> SEQ ID NO 183
<211> LENGTH: 9
<212> TYPE: PRT
<213> ORGANISM: Artificial Sequence
<220> FEATURE:
<223> OTHER INFORMATION: HBV adr "X" 1548 (peptide 1.0993)

<400> SEQUENCE: 183

Lys Val Phe Val Leu Gly Gly Cys Arg
 1               5

<210> SEQ ID NO 184
<211> LENGTH: 9
<212> TYPE: PRT
<213> ORGANISM: Artificial Sequence
<220> FEATURE:
<223> OTHER INFORMATION: HBV X 69 (peptide 26.0149)

<400> SEQUENCE: 184

Cys Ala Leu Arg Phe Thr Ser Ala Arg
 1               5

<210> SEQ ID NO 185
<211> LENGTH: 8
<212> TYPE: PRT
<213> ORGANISM: Artificial Sequence
<220> FEATURE:
<223> OTHER INFORMATION: HBV x nuc fus 296 (peptide 26.0023)

<400> SEQUENCE: 185

Val Ser Phe Gly Val Trp Ile Arg
 1               5

<210> SEQ ID NO 186
<211> LENGTH: 11
<212> TYPE: PRT
<213> ORGANISM: Artificial Sequence
<220> FEATURE:
<223> OTHER INFORMATION: HBV x nuc fus 318 (peptide 26.0545)

<400> SEQUENCE: 186
```

```
Thr Leu Pro Glu Thr Thr Val Val Arg Arg Arg
 1               5                  10
```

<210> SEQ ID NO 187
<211> LENGTH: 9
<212> TYPE: PRT
<213> ORGANISM: Artificial Sequence
<220> FEATURE:
<223> OTHER INFORMATION: HBV POL 524 (peptide 20.0131)

<400> SEQUENCE: 187

```
Ser Val Val Arg Arg Ala Phe Pro His
 1               5
```

<210> SEQ ID NO 188
<211> LENGTH: 9
<212> TYPE: PRT
<213> ORGANISM: Artificial Sequence
<220> FEATURE:
<223> OTHER INFORMATION: HBV adr "X" 1550 (peptide 1.0219)

<400> SEQUENCE: 188

```
Phe Val Leu Gly Gly Cys Arg His Lys
 1               5
```

<210> SEQ ID NO 189
<211> LENGTH: 8
<212> TYPE: PRT
<213> ORGANISM: Artificial Sequence
<220> FEATURE:
<223> OTHER INFORMATION: HBV pol 656 (peptide 26.0008)

<400> SEQUENCE: 189

```
Phe Thr Phe Ser Pro Thr Tyr Lys
 1               5
```

<210> SEQ ID NO 190
<211> LENGTH: 9
<212> TYPE: PRT
<213> ORGANISM: Artificial Sequence
<220> FEATURE:
<223> OTHER INFORMATION: HBV POL 655 (peptide 20.0130)

<400> SEQUENCE: 190

```
Ala Phe Thr Glu Ser Pro Thr Tyr Lys
 1               5
```

<210> SEQ ID NO 191
<211> LENGTH: 10
<212> TYPE: PRT
<213> ORGANISM: Artificial Sequence
<220> FEATURE:
<223> OTHER INFORMATION: HBV POL 530 (peptide 1147.05)

<400> SEQUENCE: 191

```
Phe Pro His Cys Leu Ala Phe Ser Tyr Met
 1               5                  10
```

<210> SEQ ID NO 192
<211> LENGTH: 9
<212> TYPE: PRT
<213> ORGANISM: Artificial Sequence
<220> FEATURE:
<223> OTHER INFORMATION: HBV POL 640 (peptide 1147.08)

<400> SEQUENCE: 192

Tyr Pro Ala Leu Met Pro Leu Tyr Ala
1               5

<210> SEQ ID NO 193
<211> LENGTH: 9
<212> TYPE: PRT
<213> ORGANISM: Artificial Sequence
<220> FEATURE:
<223> OTHER INFORMATION: HBV X 58 (peptide 1147.06)

<400> SEQUENCE: 193

Leu Pro Val Cys Ala Phe Ser Ser Ala
1               5

<210> SEQ ID NO 194
<211> LENGTH: 9
<212> TYPE: PRT
<213> ORGANISM: Artificial Sequence
<220> FEATURE:
<223> OTHER INFORMATION: HBV POL 429 (peptide 1147.02)

<400> SEQUENCE: 194

His Pro Ala Ala Met Pro His Leu Leu
1               5

<210> SEQ ID NO 195
<211> LENGTH: 11
<212> TYPE: PRT
<213> ORGANISM: Artificial Sequence
<220> FEATURE:
<223> OTHER INFORMATION: HBV pol 640 (peptide 26.0570)

<400> SEQUENCE: 195

Tyr Pro Ala Leu Met Pro Leu Tyr Ala Cys Ile
1               5                   10

<210> SEQ ID NO 196
<211> LENGTH: 8
<212> TYPE: PRT
<213> ORGANISM: Artificial Sequence
<220> FEATURE:
<223> OTHER INFORMATION: HBV POL 640 (peptide 19.0014)

<400> SEQUENCE: 196

Tyr Pro Ala Leu Met Pro Leu Tyr
1               5

<210> SEQ ID NO 197
<211> LENGTH: 9
<212> TYPE: PRT
<213> ORGANISM: Artificial Sequence
<220> FEATURE:
<223> OTHER INFORMATION: HBV POL 541 (peptide 1145.08)

<400> SEQUENCE: 197

Phe Pro His Cys Leu Ala Phe Ser Tyr
1               5

<210> SEQ ID NO 198
<211> LENGTH: 9
<212> TYPE: PRT
<213> ORGANISM: Artificial Sequence
<220> FEATURE:
<223> OTHER INFORMATION: HBV NUC 131 (peptide 1090.02)

<400> SEQUENCE: 198

Ala Tyr Arg Pro Pro Asn Ala Pro Ile

<210> SEQ ID NO 199
<211> LENGTH: 10
<212> TYPE: PRT
<213> ORGANISM: Artificial Sequence
<220> FEATURE:
<223> OTHER INFORMATION: HBV adr CORE 419 (peptide 1.0519)

<400> SEQUENCE: 199

Asp Leu Leu Asp Thr Ala Ser Ala Leu Tyr
 1               5                  10

<210> SEQ ID NO 200
<211> LENGTH: 10
<212> TYPE: PRT
<213> ORGANISM: Artificial Sequence
<220> FEATURE:
<223> OTHER INFORMATION: HBV NUC 117 (peptide 13.0129)

<400> SEQUENCE: 200

Glu Tyr Leu Val Ser Phe Gly Val Trp Ile
 1               5                  10

<210> SEQ ID NO 201
<211> LENGTH: 10
<212> TYPE: PRT
<213> ORGANISM: Artificial Sequence
<220> FEATURE:
<223> OTHER INFORMATION: HBV POL 631 (peptide 20.0254)

<400> SEQUENCE: 201

Phe Ala Ala Pro Phe Thr Gln Cys Gly Tyr
 1               5                  10

<210> SEQ ID NO 202
<211> LENGTH: 9
<212> TYPE: PRT
<213> ORGANISM: Artificial Sequence
<220> FEATURE:
<223> OTHER INFORMATION: HBV ALL 1224 (peptide 2.0060)

<400> SEQUENCE: 202

Gly Tyr Pro Ala Leu Met Pro Leu Tyr
 1               5

<210> SEQ ID NO 203
<211> LENGTH: 10
<212> TYPE: PRT
<213> ORGANISM: Artificial Sequence
<220> FEATURE:
<223> OTHER INFORMATION: HBV pol 149 (peptide 1069.04)

<400> SEQUENCE: 203

His Thr Leu Trp Lys Ala Gly Ile Leu Tyr
 1               5                  10

<210> SEQ ID NO 204
<211> LENGTH: 10
<212> TYPE: PRT
<213> ORGANISM: Artificial Sequence
<220> FEATURE:
<223> OTHER INFORMATION: HBV env 249-258 (peptide 1069.08)

<400> SEQUENCE: 204

Ile Leu Leu Leu Cys Leu Ile Phe Leu Leu
 1               5                  10

```
<210> SEQ ID NO 205
<211> LENGTH: 9
<212> TYPE: PRT
<213> ORGANISM: Artificial Sequence
<220> FEATURE:
<223> OTHER INFORMATION: HBV POL 745 (peptide 1069.23)

<400> SEQUENCE: 205

Lys Tyr Thr Ser Phe Pro Trp Leu Leu
 1               5

<210> SEQ ID NO 206
<211> LENGTH: 9
<212> TYPE: PRT
<213> ORGANISM: Artificial Sequence
<220> FEATURE:
<223> OTHER INFORMATION: HBV core 59 (peptide 1069.01)

<400> SEQUENCE: 206

Leu Leu Asp Thr Ala Ser Ala Leu Tyr
 1               5

<210> SEQ ID NO 207
<211> LENGTH: 10
<212> TYPE: PRT
<213> ORGANISM: Artificial Sequence
<220> FEATURE:
<223> OTHER INFORMATION: HBV ALL 1000 (peptide 2.0239)

<400> SEQUENCE: 207

Leu Ser Leu Asp Val Ser Ala Ala Phe Tyr
 1               5                  10

<210> SEQ ID NO 208
<211> LENGTH: 10
<212> TYPE: PRT
<213> ORGANISM: Artificial Sequence
<220> FEATURE:
<223> OTHER INFORMATION: HBV POL 492 (peptide 2.0181)

<400> SEQUENCE: 208

Leu Tyr Ser His Pro Ile Ile Leu Gly Phe
 1               5                  10

<210> SEQ ID NO 209
<211> LENGTH: 10
<212> TYPE: PRT
<213> ORGANISM: Artificial Sequence
<220> FEATURE:
<223> OTHER INFORMATION: HBV 360 (peptide 1039.01)

<400> SEQUENCE: 209

Met Met Trp Tyr Trp Gly Pro Ser Leu Tyr
 1               5                  10

<210> SEQ ID NO 210
<211> LENGTH: 9
<212> TYPE: PRT
<213> ORGANISM: Artificial Sequence
<220> FEATURE:
<223> OTHER INFORMATION: HBV adr 1521 (peptide 2.0126)

<400> SEQUENCE: 210

Met Ser Thr Thr Asp Leu Glu Ala Tyr
 1               5
```

<210> SEQ ID NO 211
<211> LENGTH: 10
<212> TYPE: PRT
<213> ORGANISM: Artificial Sequence
<220> FEATURE:
<223> OTHER INFORMATION: HBV pol 124 (peptide 1069.03)

<400> SEQUENCE: 211

Pro Leu Asp Lys Gly Ile Lys Pro Tyr Tyr
1               5                   10

<210> SEQ ID NO 212
<211> LENGTH: 9
<212> TYPE: PRT
<213> ORGANISM: Artificial Sequence
<220> FEATURE:
<223> OTHER INFORMATION: HBV pol 808 (peptide 1090.09)

<400> SEQUENCE: 212

Pro Thr Thr Gly Arg Thr Ser Leu Tyr
1               5

<210> SEQ ID NO 213
<211> LENGTH: 9
<212> TYPE: PRT
<213> ORGANISM: Artificial Sequence
<220> FEATURE:
<223> OTHER INFORMATION: HBV POL 51 (peptide 20.0138)

<400> SEQUENCE: 213

Pro Trp Thr His Lys Val Gly Asn Phe
1               5

<210> SEQ ID NO 214
<211> LENGTH: 9
<212> TYPE: PRT
<213> ORGANISM: Artificial Sequence
<220> FEATURE:
<223> OTHER INFORMATION: HBV ENV 236 (peptide 20.0135)

<400> SEQUENCE: 214

Arg Trp Met Cys Leu Arg Arg Phe Ile
1               5

<210> SEQ ID NO 215
<211> LENGTH: 10
<212> TYPE: PRT
<213> ORGANISM: Artificial Sequence
<220> FEATURE:
<223> OTHER INFORMATION: HBV ENV 236 (peptide 20.0269)

<400> SEQUENCE: 215

Arg Trp Met Cys Leu Arg Arg Phe Ile Ile
1               5                   10

<210> SEQ ID NO 216
<211> LENGTH: 9
<212> TYPE: PRT
<213> ORGANISM: Artificial Sequence
<220> FEATURE:
<223> OTHER INFORMATION: HBV POL 167 (peptide 20.0139)

<400> SEQUENCE: 216

Ser Phe Cys Gly Ser Pro Tyr Ser Trp
1               5

```
<210> SEQ ID NO 217
<211> LENGTH: 9
<212> TYPE: PRT
<213> ORGANISM: Artificial Sequence
<220> FEATURE:
<223> OTHER INFORMATION: HBV pol 427 (peptide 1069.02)

<400> SEQUENCE: 217

Ser Leu Asp Val Ser Ala Ala Phe Tyr
 1               5

<210> SEQ ID NO 218
<211> LENGTH: 9
<212> TYPE: PRT
<213> ORGANISM: Artificial Sequence
<220> FEATURE:
<223> OTHER INFORMATION: HBV ENV 334 (peptide 20.0136)

<400> SEQUENCE: 218

Ser Trp Leu Ser Leu Leu Val Pro Phe
 1               5

<210> SEQ ID NO 219
<211> LENGTH: 10
<212> TYPE: PRT
<213> ORGANISM: Artificial Sequence
<220> FEATURE:
<223> OTHER INFORMATION: HBV POL 392 (peptide 20.0271)

<400> SEQUENCE: 219

Ser Trp Pro Lys Phe Ala Val Pro Asn Leu
 1               5                  10

<210> SEQ ID NO 220
<211> LENGTH: 9
<212> TYPE: PRT
<213> ORGANISM: Artificial Sequence
<220> FEATURE:
<223> OTHER INFORMATION: HBV ENV 197 (peptide 20.0137)

<400> SEQUENCE: 220

Ser Trp Trp Thr Ser Leu Asn Phe Leu
 1               5

<210> SEQ ID NO 221
<211> LENGTH: 10
<212> TYPE: PRT
<213> ORGANISM: Artificial Sequence
<220> FEATURE:
<223> OTHER INFORMATION: HBV POL 4 (peptide 2.0173)

<400> SEQUENCE: 221

Ser Tyr Gln His Phe Arg Lys Leu Leu Leu
 1               5                  10

<210> SEQ ID NO 222
<211> LENGTH: 9
<212> TYPE: PRT
<213> ORGANISM: Artificial Sequence
<220> FEATURE:
<223> OTHER INFORMATION: HBV NUC 102 (peptide 13.0073)

<400> SEQUENCE: 222

Trp Phe His Ile Ser Cys Leu Thr Phe
 1               5

<210> SEQ ID NO 223
```

```
<211> LENGTH: 10
<212> TYPE: PRT
<213> ORGANISM: Artificial Sequence
<220> FEATURE:
<223> OTHER INFORMATION: HBV adr CORE 416 (peptide 1.0774)

<400> SEQUENCE: 223

Trp Leu Trp Gly Met Asp Ile Asp Pro Tyr
 1               5                  10

<210> SEQ ID NO 224
<211> LENGTH: 11
<212> TYPE: PRT
<213> ORGANISM: Artificial Sequence
<220> FEATURE:
<223> OTHER INFORMATION: HBV env 359 (peptide 1039.06)

<400> SEQUENCE: 224

Trp Met Met Trp Tyr Trp Gly Pro Ser Leu Tyr
 1               5                  10

<210> SEQ ID NO 225
<211> LENGTH: 10
<212> TYPE: PRT
<213> ORGANISM: Artificial Sequence
<220> FEATURE:
<223> OTHER INFORMATION: HBv 18-27 I10 var. (peptide 924.14)

<400> SEQUENCE: 225

Phe Leu Pro Ser Asp Phe Phe Pro Ser Ile
 1               5                  10

<210> SEQ ID NO 226
<211> LENGTH: 10
<212> TYPE: PRT
<213> ORGANISM: Artificial Sequence
<220> FEATURE:
<223> OTHER INFORMATION: HBc 18-27 analog (peptide 941.01)

<400> SEQUENCE: 226

Phe Leu Pro Ser Asp Tyr Phe Pro Ser Val
 1               5                  10

<210> SEQ ID NO 227
<211> LENGTH: 11
<212> TYPE: PRT
<213> ORGANISM: Artificial Sequence
<220> FEATURE:
<223> OTHER INFORMATION: HBV core 141-151 analog (peptide 1083.02)

<400> SEQUENCE: 227

Ser Thr Leu Pro Glu Thr Tyr Val Val Arg Arg
 1               5                  10

<210> SEQ ID NO 228
<211> LENGTH: 9
<212> TYPE: PRT
<213> ORGANISM: Artificial Sequence
<220> FEATURE:
<223> OTHER INFORMATION: HBV ENV 313 analog (peptide 1145.05)

<400> SEQUENCE: 228

Phe Pro Ile Pro Ser Ser Trp Ala Phe
 1               5

<210> SEQ ID NO 229
<211> LENGTH: 9
```

-continued

<212> TYPE: PRT
<213> ORGANISM: Artificial Sequence
<220> FEATURE:
<223> OTHER INFORMATION: HBV POL 541 analog (peptide 1145.11)

<400> SEQUENCE: 229

Phe Pro His Cys Leu Ala Phe Ser Leu
1 5

<210> SEQ ID NO 230
<211> LENGTH: 9
<212> TYPE: PRT
<213> ORGANISM: Artificial Sequence
<220> FEATURE:
<223> OTHER INFORMATION: HBV POL 541 analog (peptide 1145.24)

<400> SEQUENCE: 230

Phe Pro His Cys Leu Ala Phe Ala Leu
1 5

<210> SEQ ID NO 231
<211> LENGTH: 9
<212> TYPE: PRT
<213> ORGANISM: Artificial Sequence
<220> FEATURE:
<223> OTHER INFORMATION: HBV ENV 313 analog (peptide 1145.06)

<400> SEQUENCE: 231

Ile Pro Ile Thr Ser Ser Trp Ala Phe
1 5

<210> SEQ ID NO 232
<211> LENGTH: 9
<212> TYPE: PRT
<213> ORGANISM: Artificial Sequence
<220> FEATURE:
<223> OTHER INFORMATION: HBV ENV 313 analog (peptide 1145.23)

<400> SEQUENCE: 232

Ile Pro Ile Pro Met Ser Trp Ala Phe
1 5

<210> SEQ ID NO 233
<211> LENGTH: 9
<212> TYPE: PRT
<213> ORGANISM: Artificial Sequence
<220> FEATURE:
<223> OTHER INFORMATION: HBV ENV 313 analog (peptide 1145.07)

<400> SEQUENCE: 233

Ile Pro Ile Leu Ser Ser Trp Ala Phe
1 5

<210> SEQ ID NO 234
<211> LENGTH: 9
<212> TYPE: PRT
<213> ORGANISM: Artificial Sequence
<220> FEATURE:
<223> OTHER INFORMATION: HBV POL 541 analog (peptide 1145.09)

<400> SEQUENCE: 234

Phe Pro Val Cys Leu Ala Phe Ser Tyr
1 5

<210> SEQ ID NO 235
<211> LENGTH: 9
<212> TYPE: PRT

```
<213> ORGANISM: Artificial Sequence
<220> FEATURE:
<223> OTHER INFORMATION: HBV POL 541 analog (peptide 1145.10)

<400> SEQUENCE: 235

Phe Pro His Cys Leu Ala Phe Ala Tyr
 1               5

<210> SEQ ID NO 236
<211> LENGTH: 26
<212> TYPE: PRT
<213> ORGANISM: Artificial Sequence
<220> FEATURE:
<223> OTHER INFORMATION: HCV NS3 1242-1267

<400> SEQUENCE: 236

Ala Ala Tyr Ala Ala Gln Gly Tyr Lys Val Leu Val Leu Asn Pro Ser
 1               5                  10                  15

Val Ala Ala Thr Leu Gly Phe Gly Ala Tyr
            20                  25

<210> SEQ ID NO 237
<211> LENGTH: 20
<212> TYPE: PRT
<213> ORGANISM: Artificial Sequence
<220> FEATURE:
<223> OTHER INFORMATION: HCV NS3 1242 (peptide P98.03)

<400> SEQUENCE: 237

Ala Ala Tyr Ala Ala Gln Gly Tyr Lys Val Leu Val Leu Asn Pro Ser
 1               5                  10                  15

Val Ala Ala Thr
            20

<210> SEQ ID NO 238
<211> LENGTH: 20
<212> TYPE: PRT
<213> ORGANISM: Artificial Sequence
<220> FEATURE:
<223> OTHER INFORMATION: HCV NS3 1248 (peptide P98.04)

<400> SEQUENCE: 238

Gly Tyr Lys Val Leu Val Leu Asn Pro Ser Val Ala Ala Thr Leu Gly
 1               5                  10                  15

Phe Gly Ala Tyr
            20

<210> SEQ ID NO 239
<211> LENGTH: 14
<212> TYPE: PRT
<213> ORGANISM: Artificial Sequence
<220> FEATURE:
<223> OTHER INFORMATION: HCV NS3 1248 (peptide P98.05)

<400> SEQUENCE: 239

Gly Tyr Lys Val Leu Val Leu Asn Pro Ser Val Ala Ala Thr
 1               5                  10

<210> SEQ ID NO 240
<211> LENGTH: 15
<212> TYPE: PRT
<213> ORGANISM: Artificial Sequence
<220> FEATURE:
<223> OTHER INFORMATION: HCV NS3 1253 (peptide 1283.21)

<400> SEQUENCE: 240
```

Gly Tyr Lys Val Leu Val Leu Asn Pro Ser Val Ala Ala Thr Leu
1               5                   10                  15

<210> SEQ ID NO 241
<211> LENGTH: 15
<212> TYPE: PRT
<213> ORGANISM: Artificial Sequence
<220> FEATURE:
<223> OTHER INFORMATION: HCV NS3 1251 (peptide 1283.20)

<400> SEQUENCE: 241

Ala Gln Gly Tyr Lys Val Leu Val Leu Asn Pro Ser Val Ala Ala
1               5                   10                  15

<210> SEQ ID NO 242
<211> LENGTH: 22
<212> TYPE: PRT
<213> ORGANISM: Artificial Sequence
<220> FEATURE:
<223> OTHER INFORMATION: HCV NS4 1914-1935

<400> SEQUENCE: 242

Gly Glu Gly Ala Val Gln Trp Met Asn Arg Leu Ile Ala Phe Ala Ser
1               5                   10                  15

Arg Gly Asn His Val Ser
            20

<210> SEQ ID NO 243
<211> LENGTH: 21
<212> TYPE: PRT
<213> ORGANISM: Artificial Sequence
<220> FEATURE:
<223> OTHER INFORMATION: HCV NS4 1914 (peptide F134.08)

<400> SEQUENCE: 243

Gly Glu Gly Ala Val Gln Trp Met Asn Arg Leu Ile Ala Phe Ala Ser
1               5                   10                  15

Arg Gly Asn His Val
            20

<210> SEQ ID NO 244
<211> LENGTH: 15
<212> TYPE: PRT
<213> ORGANISM: Artificial Sequence
<220> FEATURE:
<223> OTHER INFORMATION: HCV NS4 1921 (peptide 1283.44)

<400> SEQUENCE: 244

Met Asn Arg Leu Ile Ala Phe Ala Ser Arg Gly Asn His Val Ser
1               5                   10                  15

<210> SEQ ID NO 245
<211> LENGTH: 15
<212> TYPE: PRT
<213> ORGANISM: Artificial Sequence
<220> FEATURE:
<223> OTHER INFORMATION: HCV NS3 1025 (peptide 1283.16)

<400> SEQUENCE: 245

Ser Lys Gly Trp Arg Leu Leu Ala Pro Ile Thr Ala Tyr Ala Gln
1               5                   10                  15

<210> SEQ ID NO 246
<211> LENGTH: 15
<212> TYPE: PRT

```
<213> ORGANISM: Artificial Sequence
<220> FEATURE:
<223> OTHER INFORMATION: HCV NS5 2641 (peptide 1283.55)

<400> SEQUENCE: 246

Gly Ser Ser Tyr Gly Phe Gln Tyr Ser Pro Gly Gln Arg Val Glu
 1               5                  10                  15

<210> SEQ ID NO 247
<211> LENGTH: 20
<212> TYPE: PRT
<213> ORGANISM: Artificial Sequence
<220> FEATURE:
<223> OTHER INFORMATION: HCV NS4 1772 (peptide F134.05)

<400> SEQUENCE: 247

Asn Phe Ile Ser Gly Ile Gln Tyr Leu Ala Gly Leu Ser Thr Leu Pro
 1               5                  10                  15

Gly Asn Pro Ala
            20

<210> SEQ ID NO 248
<211> LENGTH: 15
<212> TYPE: PRT
<213> ORGANISM: Artificial Sequence
<220> FEATURE:
<223> OTHER INFORMATION: HCV NS5 2939 (peptide 1283.61)

<400> SEQUENCE: 248

Ala Ser Cys Leu Arg Lys Leu Gly Val Pro Pro Leu Arg Val Trp
 1               5                  10                  15

<210> SEQ ID NO 249
<211> LENGTH: 15
<212> TYPE: PRT
<213> ORGANISM: Artificial Sequence
<220> FEATURE:
<223> OTHER INFORMATION: HCV NS3 1393 (peptide 1283.25)

<400> SEQUENCE: 249

Gly Arg His Leu Ile Phe Cys His Ser Lys Lys Lys Cys Asp Glu
 1               5                  10                  15

<210> SEQ ID NO 250
<211> LENGTH: 15
<212> TYPE: PRT
<213> ORGANISM: Artificial Sequence
<220> FEATURE:
<223> OTHER INFORMATION: HCV 1466 (peptide 35.0107)

<400> SEQUENCE: 250

Thr Val Asp Phe Ser Leu Asp Pro Thr Phe Thr Ile Glu Thr Thr
 1               5                  10                  15

<210> SEQ ID NO 251
<211> LENGTH: 15
<212> TYPE: PRT
<213> ORGANISM: Artificial Sequence
<220> FEATURE:
<223> OTHER INFORMATION: HCV 1437 (peptide 35.0106)

<400> SEQUENCE: 251

Val Val Val Val Ala Thr Asp Ala Leu Met Thr Gly Tyr Thr Gly
 1               5                  10                  15

<210> SEQ ID NO 252
```

```
<211> LENGTH: 9
<212> TYPE: PRT
<213> ORGANISM: Artificial Sequence
<220> FEATURE:
<223> OTHER INFORMATION: HCV NS1/E2 728 (peptide 1090.18)

<400> SEQUENCE: 252

Phe Leu Leu Leu Ala Asp Ala Arg Val
 1               5

<210> SEQ ID NO 253
<211> LENGTH: 10
<212> TYPE: PRT
<213> ORGANISM: Artificial Sequence
<220> FEATURE:
<223> OTHER INFORMATION: HCV NS4 1812 (peptide 1073.05)

<400> SEQUENCE: 253

Leu Leu Phe Asn Ile Leu Gly Gly Trp Val
 1               5                  10

<210> SEQ ID NO 254
<211> LENGTH: 9
<212> TYPE: PRT
<213> ORGANISM: Artificial Sequence
<220> FEATURE:
<223> OTHER INFORMATION: HCV NS3 1590 (peptide 1013.02)

<400> SEQUENCE: 254

Tyr Leu Val Ala Tyr Gln Ala Thr Val
 1               5

<210> SEQ ID NO 255
<211> LENGTH: 9
<212> TYPE: PRT
<213> ORGANISM: Artificial Sequence
<220> FEATURE:
<223> OTHER INFORMATION: HCV Core 132 (peptide 1013.1002)

<400> SEQUENCE: 255

Asp Leu Met Gly Tyr Ile Pro Leu Val
 1               5

<210> SEQ ID NO 256
<211> LENGTH: 10
<212> TYPE: PRT
<213> ORGANISM: Artificial Sequence
<220> FEATURE:
<223> OTHER INFORMATION: HCV NS5 2611 (peptide 1090.22)

<400> SEQUENCE: 256

Arg Leu Ile Val Phe Pro Asp Leu Gly Val
 1               5                  10

<210> SEQ ID NO 257
<211> LENGTH: 9
<212> TYPE: PRT
<213> ORGANISM: Artificial Sequence
<220> FEATURE:
<223> OTHER INFORMATION: HCV NS4 1666 (peptide 24.0075)

<400> SEQUENCE: 257

Val Leu Val Gly Gly Val Leu Ala Ala
 1               5

<210> SEQ ID NO 258
<211> LENGTH: 9
```

<212> TYPE: PRT
<213> ORGANISM: Artificial Sequence
<220> FEATURE:
<223> OTHER INFORMATION: HCV NS4 1920 (peptide 24.0073)

<400> SEQUENCE: 258

Trp Met Asn Arg Leu Ile Ala Phe Ala
1               5

<210> SEQ ID NO 259
<211> LENGTH: 9
<212> TYPE: PRT
<213> ORGANISM: Artificial Sequence
<220> FEATURE:
<223> OTHER INFORMATION: HCV NS4 1769 (peptide 1174.08)

<400> SEQUENCE: 259

His Met Trp Asn Phe Ile Ser Gly Ile
1               5

<210> SEQ ID NO 260
<211> LENGTH: 9
<212> TYPE: PRT
<213> ORGANISM: Artificial Sequence
<220> FEATURE:
<223> OTHER INFORMATION: HCV NS4 1851 (peptide 1073.06)

<400> SEQUENCE: 260

Ile Leu Ala Gly Tyr Gly Ala Gly Val
1               5

<210> SEQ ID NO 261
<211> LENGTH: 9
<212> TYPE: PRT
<213> ORGANISM: Artificial Sequence
<220> FEATURE:
<223> OTHER INFORMATION: HCV NS1/E2 726 (peptide 24.0071)

<400> SEQUENCE: 261

Leu Leu Phe Leu Leu Leu Ala Asp Ala
1               5

<210> SEQ ID NO 262
<211> LENGTH: 10
<212> TYPE: PRT
<213> ORGANISM: Artificial Sequence
<220> FEATURE:
<223> OTHER INFORMATION: HCV Core 35 (peptide 1073.07)

<400> SEQUENCE: 262

Tyr Leu Leu Pro Arg Arg Gly Pro Arg Leu
1               5                   10

<210> SEQ ID NO 263
<211> LENGTH: 9
<212> TYPE: PRT
<213> ORGANISM: Artificial Sequence
<220> FEATURE:
<223> OTHER INFORMATION: HCV NS3 1136 (peptide 1.0119)

<400> SEQUENCE: 263

Tyr Leu Val Thr Arg His Ala Asp Val
1               5

<210> SEQ ID NO 264
<211> LENGTH: 9
<212> TYPE: PRT

```
<213> ORGANISM: Artificial Sequence
<220> FEATURE:
<223> OTHER INFORMATION: HCV Core 51 (peptide 1.0952)

<400> SEQUENCE: 264

Lys Thr Ser Glu Arg Ser Gln Pro Arg
 1               5

<210> SEQ ID NO 265
<211> LENGTH: 10
<212> TYPE: PRT
<213> ORGANISM: Artificial Sequence
<220> FEATURE:
<223> OTHER INFORMATION: HCV NS4 1863 (peptide 1073.10)

<400> SEQUENCE: 265

Gly Val Ala Gly Ala Leu Val Ala Phe Lys
 1               5                  10

<210> SEQ ID NO 266
<211> LENGTH: 9
<212> TYPE: PRT
<213> ORGANISM: Artificial Sequence
<220> FEATURE:
<223> OTHER INFORMATION: HCV NS3 1391 (peptide 1.0123)

<400> SEQUENCE: 266

Leu Ile Phe Cys His Ser Lys Lys Lys
 1               5

<210> SEQ ID NO 267
<211> LENGTH: 9
<212> TYPE: PRT
<213> ORGANISM: Artificial Sequence
<220> FEATURE:
<223> OTHER INFORMATION: HCV E1 290 (peptide 1.0955)

<400> SEQUENCE: 267

Gln Leu Phe Thr Phe Ser Pro Arg Arg
 1               5

<210> SEQ ID NO 268
<211> LENGTH: 9
<212> TYPE: PRT
<213> ORGANISM: Artificial Sequence
<220> FEATURE:
<223> OTHER INFORMATION: HCV Core 43 (peptide 1073.11)

<400> SEQUENCE: 268

Arg Leu Gly Val Arg Ala Thr Arg Lys
 1               5

<210> SEQ ID NO 269
<211> LENGTH: 10
<212> TYPE: PRT
<213> ORGANISM: Artificial Sequence
<220> FEATURE:
<223> OTHER INFORMATION: HCV NS1/E2 635 (peptide 1073.13)

<400> SEQUENCE: 269

Arg Met Tyr Val Gly Gly Val Glu His Arg
 1               5                  10

<210> SEQ ID NO 270
<211> LENGTH: 9
<212> TYPE: PRT
<213> ORGANISM: Artificial Sequence
```

```
<220> FEATURE:
<223> OTHER INFORMATION: HCV NS4 1864 (peptide 24.0090)

<400> SEQUENCE: 270

Val Ala Gly Ala Leu Val Ala Phe Lys
1               5

<210> SEQ ID NO 271
<211> LENGTH: 9
<212> TYPE: PRT
<213> ORGANISM: Artificial Sequence
<220> FEATURE:
<223> OTHER INFORMATION: HCV NS5 3036 (peptide F104.01)

<400> SEQUENCE: 271

Val Gly Ile Tyr Leu Leu Pro Asn Arg
1               5

<210> SEQ ID NO 272
<211> LENGTH: 9
<212> TYPE: PRT
<213> ORGANISM: Artificial Sequence
<220> FEATURE:
<223> OTHER INFORMATION: HCV Core 168 (peptide 1145.12)

<400> SEQUENCE: 272

Leu Pro Gly Cys Ser Phe Ser Ile Phe
1               5

<210> SEQ ID NO 273
<211> LENGTH: 8
<212> TYPE: PRT
<213> ORGANISM: Artificial Sequence
<220> FEATURE:
<223> OTHER INFORMATION: HCV 1378 (peptide 29.0035)

<400> SEQUENCE: 273

Ile Pro Phe Tyr Gly Lys Ala Ile
1               5

<210> SEQ ID NO 274
<211> LENGTH: 9
<212> TYPE: PRT
<213> ORGANISM: Artificial Sequence
<220> FEATURE:
<223> OTHER INFORMATION: HCV NS3 1128 (peptide 1069.62)

<400> SEQUENCE: 274

Cys Thr Cys Gly Ser Ser Asp Leu Tyr
1               5

<210> SEQ ID NO 275
<211> LENGTH: 9
<212> TYPE: PRT
<213> ORGANISM: Artificial Sequence
<220> FEATURE:
<223> OTHER INFORMATION: HCV NS4 1765 (peptide 24.0092)

<400> SEQUENCE: 275

Phe Trp Ala Lys His Met Trp Asn Phe
1               5

<210> SEQ ID NO 276
<211> LENGTH: 9
<212> TYPE: PRT
<213> ORGANISM: Artificial Sequence
<220> FEATURE:
```

<223> OTHER INFORMATION: HCV NS5 2922 (peptide 13.0019)

<400> SEQUENCE: 276

Leu Ser Ala Phe Ser Leu His Ser Tyr
 1               5

<210> SEQ ID NO 277
<211> LENGTH: 9
<212> TYPE: PRT
<213> ORGANISM: Artificial Sequence
<220> FEATURE:
<223> OTHER INFORMATION: HCV NS3 1267 (peptide 24.0086)

<400> SEQUENCE: 277

Leu Gly Phe Gly Ala Tyr Met Ser Lys
 1               5

<210> SEQ ID NO 278
<211> LENGTH: 9
<212> TYPE: PRT
<213> ORGANISM: Artificial Sequence
<220> FEATURE:
<223> OTHER INFORMATION: HCV NS5 2621 (peptide 1174.21)

<400> SEQUENCE: 278

Arg Val Cys Glu Lys Met Ala Leu Tyr
 1               5

<210> SEQ ID NO 279
<211> LENGTH: 9
<212> TYPE: PRT
<213> ORGANISM: Artificial Sequence
<220> FEATURE:
<223> OTHER INFORMATION: HCV NS1/E2 557 (peptide 1174.16)

<400> SEQUENCE: 279

Trp Met Asn Ser Thr Gly Phe Thr Lys
 1               5

<210> SEQ ID NO 280
<211> LENGTH: 10
<212> TYPE: PRT
<213> ORGANISM: Artificial Sequence
<220> FEATURE:
<223> OTHER INFORMATION: HCV NS3 1622 (peptide 1073.04)

<400> SEQUENCE: 280

Thr Leu His Gly Pro Thr Pro Leu Leu Tyr
 1               5                   10

<210> SEQ ID NO 281
<211> LENGTH: 9
<212> TYPE: PRT
<213> ORGANISM: Artificial Sequence
<220> FEATURE:
<223> OTHER INFORMATION: HCV NS3 1588 (peptide 16.0012)

<400> SEQUENCE: 281

Phe Pro Tyr Leu Val Ala Tyr Gln Ala
 1               5

<210> SEQ ID NO 282
<211> LENGTH: 9
<212> TYPE: PRT
<213> ORGANISM: Artificial Sequence
<220> FEATURE:
<223> OTHER INFORMATION: HCV NS1/E2 623 (peptide 15.0047)

```
<400> SEQUENCE: 282

Tyr Pro Cys Thr Val Asn Phe Thr Ile
 1               5

<210> SEQ ID NO 283
<211> LENGTH: 10
<212> TYPE: PRT
<213> ORGANISM: Artificial Sequence
<220> FEATURE:
<223> OTHER INFORMATION: HCV NS5 2129 (peptide 24.0093)

<400> SEQUENCE: 283

Glu Val Asp Gly Val Arg Leu His Arg Tyr
 1               5                  10

<210> SEQ ID NO 284
<211> LENGTH: 11
<212> TYPE: PRT
<213> ORGANISM: Artificial Sequence
<220> FEATURE:
<223> OTHER INFORMATION: HCV 126 (peptide 3.0417)

<400> SEQUENCE: 284

Leu Thr Cys Gly Phe Ala Asp Leu Met Gly Tyr
 1               5                  10

<210> SEQ ID NO 285
<211> LENGTH: 9
<212> TYPE: PRT
<213> ORGANISM: Artificial Sequence
<220> FEATURE:
<223> OTHER INFORMATION: HCV E1 700 (peptide 1073.01)

<400> SEQUENCE: 285

Asn Ile Val Asp Val Gln Tyr Leu Tyr
 1               5

<210> SEQ ID NO 286
<211> LENGTH: 10
<212> TYPE: PRT
<213> ORGANISM: Artificial Sequence
<220> FEATURE:
<223> OTHER INFORMATION: HCV NS5 2921 (peptide 1.0509)

<400> SEQUENCE: 286

Gly Leu Ser Ala Phe Ser Leu His Ser Tyr
 1               5                  10

<210> SEQ ID NO 287
<211> LENGTH: 11
<212> TYPE: PRT
<213> ORGANISM: Artificial Sequence
<220> FEATURE:
<223> OTHER INFORMATION: HCV E1 275 (peptide 1073.17)

<400> SEQUENCE: 287

Met Tyr Val Gly Asp Leu Cys Gly Ser Val Phe
 1               5                  10

<210> SEQ ID NO 288
<211> LENGTH: 10
<212> TYPE: PRT
<213> ORGANISM: Artificial Sequence
<220> FEATURE:
<223> OTHER INFORMATION: HCV NS1/E2 633 (peptide 1073.18)
```

-continued

```
<400> SEQUENCE: 288

Met Tyr Val Gly Gly Val Glu His Arg Leu
 1               5                  10

<210> SEQ ID NO 289
<211> LENGTH: 9
<212> TYPE: PRT
<213> ORGANISM: Artificial Sequence
<220> FEATURE:
<223> OTHER INFORMATION: HCV NS4 1778 (peptide 13.075)

<400> SEQUENCE: 289

Gln Tyr Leu Ala Gly Leu Ser Thr Leu
 1               5

<210> SEQ ID NO 290
<211> LENGTH: 9
<212> TYPE: PRT
<213> ORGANISM: Artificial Sequence
<220> FEATURE:
<223> OTHER INFORMATION: HCV Core 168 (peptide 1145.13)

<400> SEQUENCE: 290

Phe Pro Gly Cys Ser Phe Ser Ile Phe
 1               5

<210> SEQ ID NO 291
<211> LENGTH: 9
<212> TYPE: PRT
<213> ORGANISM: Artificial Sequence
<220> FEATURE:
<223> OTHER INFORMATION: HCV Core 168 (peptide 1145.25)

<400> SEQUENCE: 291

Leu Pro Gly Cys Met Phe Ser Ile Phe
 1               5

<210> SEQ ID NO 292
<211> LENGTH: 9
<212> TYPE: PRT
<213> ORGANISM: Artificial Sequence
<220> FEATURE:
<223> OTHER INFORMATION: HCV Core 169 (peptide 1292.24)

<400> SEQUENCE: 292

Leu Pro Gly Cys Ser Phe Ser Ile Ile
 1               5

<210> SEQ ID NO 293
<211> LENGTH: 9
<212> TYPE: PRT
<213> ORGANISM: Artificial Sequence
<220> FEATURE:
<223> OTHER INFORMATION: HCV Core 168 (peptide 1145.14)

<400> SEQUENCE: 293

Leu Pro Val Cys Ser Phe Ser Ile Phe
 1               5

<210> SEQ ID NO 294
<211> LENGTH: 9
<212> TYPE: PRT
<213> ORGANISM: Artificial Sequence
<220> FEATURE:
<223> OTHER INFORMATION: HCV Core 168 (peptide 1145.15)

<400> SEQUENCE: 294
```

-continued

```
Leu Pro Gly Cys Ser Phe Ser Tyr Phe
 1               5
```

<210> SEQ ID NO 295
<211> LENGTH: 26
<212> TYPE: PRT
<213> ORGANISM: Artificial Sequence
<220> FEATURE:
<223> OTHER INFORMATION: HIV1 GAG 294-319

<400> SEQUENCE: 295

```
Gly Glu Ile Tyr Lys Arg Trp Ile Ile Leu Gly Leu Asn Lys Ile Val
 1               5                  10                  15

Arg Met Tyr Ser Pro Thr Ser Ile Leu Asp
            20                  25
```

<210> SEQ ID NO 296
<211> LENGTH: 22
<212> TYPE: PRT
<213> ORGANISM: Artificial Sequence
<220> FEATURE:
<223> OTHER INFORMATION: HIV gag 298-319

<400> SEQUENCE: 296

```
Lys Arg Trp Ile Ile Leu Gly Leu Asn Lys Ile Val Arg Met Tyr Ser
 1               5                  10                  15

Pro Thr Ser Ile Leu Asp
            20
```

<210> SEQ ID NO 297
<211> LENGTH: 15
<212> TYPE: PRT
<213> ORGANISM: Artificial Sequence
<220> FEATURE:
<223> OTHER INFORMATION: HIV1 GAG 298 (peptide 27.0313)

<400> SEQUENCE: 297

```
Lys Arg Trp Ile Ile Leu Gly Leu Asn Lys Ile Val Arg Met Tyr
 1               5                  10                  15
```

<210> SEQ ID NO 298
<211> LENGTH: 15
<212> TYPE: PRT
<213> ORGANISM: Artificial Sequence
<220> FEATURE:
<223> OTHER INFORMATION: HIV1 GAG 294 (peptide 27.0311)

<400> SEQUENCE: 298

```
Gly Glu Ile Tyr Lys Arg Trp Ile Ile Leu Gly Leu Asn Lys Ile
 1               5                  10                  15
```

<210> SEQ ID NO 299
<211> LENGTH: 15
<212> TYPE: PRT
<213> ORGANISM: Artificial Sequence
<220> FEATURE:
<223> OTHER INFORMATION: HIV1 POL 596 (peptide 27.0354)

<400> SEQUENCE: 299

```
Trp Glu Phe Val Asn Thr Pro Pro Leu Val Lys Leu Trp Tyr Gln
 1               5                  10                  15
```

<210> SEQ ID NO 300
<211> LENGTH: 15
<212> TYPE: PRT

```
<213> ORGANISM: Artificial Sequence
<220> FEATURE:
<223> OTHER INFORMATION: HIV1 POL 956 (peptide 27.0377)

<400> SEQUENCE: 300

Gln Lys Gln Ile Thr Lys Ile Gln Asn Phe Arg Val Tyr Tyr Arg
 1               5                  10                  15

<210> SEQ ID NO 301
<211> LENGTH: 16
<212> TYPE: PRT
<213> ORGANISM: Artificial Sequence
<220> FEATURE:
<223> OTHER INFORMATION: HIV1 POL 711-726

<400> SEQUENCE: 301

Glu Lys Val Tyr Leu Ala Trp Val Pro Ala His Lys Gly Ile Gly Gly
 1               5                  10                  15

<210> SEQ ID NO 302
<211> LENGTH: 15
<212> TYPE: PRT
<213> ORGANISM: Artificial Sequence
<220> FEATURE:
<223> OTHER INFORMATION: HIV POL 712 (peptide 1280.03)

<400> SEQUENCE: 302

Lys Val Tyr Leu Ala Trp Val Pro Ala His Lys Gly Ile Gly Gly
 1               5                  10                  15

<210> SEQ ID NO 303
<211> LENGTH: 15
<212> TYPE: PRT
<213> ORGANISM: Artificial Sequence
<220> FEATURE:
<223> OTHER INFORMATION: HIV1 POL 711 (peptide 27.0361)

<400> SEQUENCE: 303

Glu Lys Val Tyr Leu Ala Trp Val Pro Ala His Lys Gly Ile Gly
 1               5                  10                  15

<210> SEQ ID NO 304
<211> LENGTH: 22
<212> TYPE: PRT
<213> ORGANISM: Artificial Sequence
<220> FEATURE:
<223> OTHER INFORMATION: HIV1 gag 165-186

<400> SEQUENCE: 304

Pro Ile Val Gln Asn Ile Gln Gly Gln Met Val His Gln Ala Ile Ser
 1               5                  10                  15

Pro Arg Thr Leu Asn Ala
             20

<210> SEQ ID NO 305
<211> LENGTH: 15
<212> TYPE: PRT
<213> ORGANISM: Artificial Sequence
<220> FEATURE:
<223> OTHER INFORMATION: HIV1 GAG 171 (peptide 27.0304)

<400> SEQUENCE: 305

Gln Gly Gln Met Val His Gln Ala Ile Ser Pro Arg Thr Leu Asn
 1               5                  10                  15

<210> SEQ ID NO 306
```

```
<211> LENGTH: 15
<212> TYPE: PRT
<213> ORGANISM: Artificial Sequence
<220> FEATURE:
<223> OTHER INFORMATION: HIV1 ENV 729 (peptide 27.0297)

<400> SEQUENCE: 306

Gln His Leu Leu Gln Leu Thr Val Trp Gly Ile Lys Gln Leu Gln
 1               5                  10                  15

<210> SEQ ID NO 307
<211> LENGTH: 15
<212> TYPE: PRT
<213> ORGANISM: Artificial Sequence
<220> FEATURE:
<223> OTHER INFORMATION: HIV1 POL 335 (peptide 27.0344)

<400> SEQUENCE: 307

Ser Pro Ala Ile Phe Gln Ser Ser Met Thr Lys Ile Leu Glu Pro
 1               5                  10                  15

<210> SEQ ID NO 308
<211> LENGTH: 16
<212> TYPE: PRT
<213> ORGANISM: Artificial Sequence
<220> FEATURE:
<223> OTHER INFORMATION: HIV1 ENV 566 (peptide F091.15)

<400> SEQUENCE: 308

Ile Lys Gln Phe Ile Asn Met Trp Gln Glu Val Gly Lys Ala Met Tyr
 1               5                  10                  15

<210> SEQ ID NO 309
<211> LENGTH: 15
<212> TYPE: PRT
<213> ORGANISM: Artificial Sequence
<220> FEATURE:
<223> OTHER INFORMATION: HIV1 POL 303 (peptide 27.0341)

<400> SEQUENCE: 309

Phe Arg Lys Tyr Thr Ala Phe Thr Ile Pro Ser Ile Asn Asn Glu
 1               5                  10                  15

<210> SEQ ID NO 310
<211> LENGTH: 15
<212> TYPE: PRT
<213> ORGANISM: Artificial Sequence
<220> FEATURE:
<223> OTHER INFORMATION: HIV1 POL 758 (peptide 27.0364)

<400> SEQUENCE: 310

His Ser Asn Trp Arg Ala Met Ala Ser Asp Phe Asn Leu Pro Pro
 1               5                  10                  15

<210> SEQ ID NO 311
<211> LENGTH: 15
<212> TYPE: PRT
<213> ORGANISM: Artificial Sequence
<220> FEATURE:
<223> OTHER INFORMATION: HIV1 POL 915 (peptide 27.0373)

<400> SEQUENCE: 311

Lys Thr Ala Val Gln Met Ala Val Phe Ile His Asn Phe Lys Arg
 1               5                  10                  15

<210> SEQ ID NO 312
<211> LENGTH: 22
```

```
<212> TYPE: PRT
<213> ORGANISM: Artificial Sequence
<220> FEATURE:
<223> OTHER INFORMATION: HIV GAG 245

<400> SEQUENCE: 312

Asp Arg Val His Pro Val His Ala Gly Pro Ile Ala Pro Gly Gln Met
 1               5                  10                  15

Arg Glu Pro Arg Gly Ser
            20

<210> SEQ ID NO 313
<211> LENGTH: 26
<212> TYPE: PRT
<213> ORGANISM: Artificial Sequence
<220> FEATURE:
<223> OTHER INFORMATION: HIV gag 195-220

<400> SEQUENCE: 313

Ala Phe Ser Pro Glu Val Ile Pro Met Phe Ser Ala Leu Ser Glu Gly
 1               5                  10                  15

Ala Thr Pro Gln Asp Leu Asn Thr Met Leu
            20                  25

<210> SEQ ID NO 314
<211> LENGTH: 22
<212> TYPE: PRT
<213> ORGANISM: Artificial Sequence
<220> FEATURE:
<223> OTHER INFORMATION: HIV gag 195-216

<400> SEQUENCE: 314

Ala Phe Ser Pro Glu Val Ile Pro Met Phe Ser Ala Leu Ser Glu Gly
 1               5                  10                  15

Ala Thr Pro Gln Asp Leu
            20

<210> SEQ ID NO 315
<211> LENGTH: 16
<212> TYPE: PRT
<213> ORGANISM: Artificial Sequence
<220> FEATURE:
<223> OTHER INFORMATION: HIV gag 205 (peptide 200.06)

<400> SEQUENCE: 315

Ser Ala Leu Ser Glu Gly Ala Thr Pro Gln Asp Leu Asn Thr Met Leu
 1               5                  10                  15

<210> SEQ ID NO 316
<211> LENGTH: 15
<212> TYPE: PRT
<213> ORGANISM: Artificial Sequence
<220> FEATURE:
<223> OTHER INFORMATION: HIV gag 197 (peptide 27.0307)

<400> SEQUENCE: 316

Ser Pro Glu Val Ile Pro Met Phe Ser Ala Leu Ser Glu Gly Ala
 1               5                  10                  15

<210> SEQ ID NO 317
<211> LENGTH: 22
<212> TYPE: PRT
<213> ORGANISM: Artificial Sequence
<220> FEATURE:
<223> OTHER INFORMATION: HIV gag 275
```

-continued

```
<400> SEQUENCE: 317

Leu Gln Glu Gln Ile Gly Trp Met Thr Asn Asn Pro Pro Ile Pro Val
 1               5                  10                  15

Gly Glu Ile Tyr Lys Arg
            20

<210> SEQ ID NO 318
<211> LENGTH: 15
<212> TYPE: PRT
<213> ORGANISM: Artificial Sequence
<220> FEATURE:
<223> OTHER INFORMATION: HIV gag 276 (peptide 27.0310)

<400> SEQUENCE: 318

Gln Glu Gln Ile Gly Trp Met Thr Asn Asn Pro Pro Ile Pro Val
 1               5                  10                  15

<210> SEQ ID NO 319
<211> LENGTH: 15
<212> TYPE: PRT
<213> ORGANISM: Artificial Sequence
<220> FEATURE:
<223> OTHER INFORMATION: HIV VPU 31 (peptide 35.0135)

<400> SEQUENCE: 319

Tyr Arg Lys Ile Leu Arg Gln Arg Lys Ile Asp Arg Leu Ile Asp
 1               5                  10                  15

<210> SEQ ID NO 320
<211> LENGTH: 15
<212> TYPE: PRT
<213> ORGANISM: Artificial Sequence
<220> FEATURE:
<223> OTHER INFORMATION: HIV POL 874 (peptide 35.0131)

<400> SEQUENCE: 320

Trp Ala Gly Ile Lys Gln Glu Phe Gly Ile Pro Tyr Asn Pro Gln
 1               5                  10                  15

<210> SEQ ID NO 321
<211> LENGTH: 15
<212> TYPE: PRT
<213> ORGANISM: Artificial Sequence
<220> FEATURE:
<223> OTHER INFORMATION: HIV POL 674 (peptide 35.0127)

<400> SEQUENCE: 321

Glu Val Asn Ile Val Thr Asp Ser Gln Tyr Ala Leu Gly Ile Ile
 1               5                  10                  15

<210> SEQ ID NO 322
<211> LENGTH: 15
<212> TYPE: PRT
<213> ORGANISM: Artificial Sequence
<220> FEATURE:
<223> OTHER INFORMATION: HIV POL 619 (peptide 35.0125)

<400> SEQUENCE: 322

Ala Glu Thr Phe Tyr Val Asp Gly Ala Ala Asn Arg Glu Thr Lys
 1               5                  10                  15

<210> SEQ ID NO 323
<211> LENGTH: 15
<212> TYPE: PRT
<213> ORGANISM: Artificial Sequence
<220> FEATURE:
```

<223> OTHER INFORMATION: HIV POL 989 (peptide 35.0133)

<400> SEQUENCE: 323

Gly Ala Val Val Ile Gln Asp Asn Ser Asp Ile Lys Val Val Pro
1               5                   10                  15

<210> SEQ ID NO 324
<211> LENGTH: 10
<212> TYPE: PRT
<213> ORGANISM: Artificial Sequence
<220> FEATURE:
<223> OTHER INFORMATION: HIV1 POL 70 (peptide 25.0148)

<400> SEQUENCE: 324

Met Ala Ser Asp Phe Asn Leu Pro Pro Val
1               5                   10

<210> SEQ ID NO 325
<211> LENGTH: 9
<212> TYPE: PRT
<213> ORGANISM: Artificial Sequence
<220> FEATURE:
<223> OTHER INFORMATION: HIV gag 397 (peptide 1069.32)

<400> SEQUENCE: 325

Val Leu Ala Glu Ala Met Ser Gln Val
1               5

<210> SEQ ID NO 326
<211> LENGTH: 9
<212> TYPE: PRT
<213> ORGANISM: Artificial Sequence
<220> FEATURE:
<223> OTHER INFORMATION: HIV1 POL 87 (peptide 25.0062)

<400> SEQUENCE: 326

Lys Leu Val Gly Lys Leu Asn Trp Ala
1               5

<210> SEQ ID NO 327
<211> LENGTH: 9
<212> TYPE: PRT
<213> ORGANISM: Artificial Sequence
<220> FEATURE:
<223> OTHER INFORMATION: HIV1 NEF 62 (peptide 25.0039)

<400> SEQUENCE: 327

Leu Thr Phe Gly Trp Cys Phe Lys Leu
1               5

<210> SEQ ID NO 328
<211> LENGTH: 9
<212> TYPE: PRT
<213> ORGANISM: Artificial Sequence
<220> FEATURE:
<223> OTHER INFORMATION: HIV1 GAG 34 (peptide 25. 0035)

<400> SEQUENCE: 328

Met Thr Asn Asn Pro Pro Ile Pro Val
1               5

<210> SEQ ID NO 329
<211> LENGTH: 9
<212> TYPE: PRT
<213> ORGANISM: Artificial Sequence
<220> FEATURE:
<223> OTHER INFORMATION: HIV1 VPR 72 (peptide 25.0057)

```
<400> SEQUENCE: 329

Arg Ile Leu Gln Gln Leu Leu Phe Ile
 1               5

<210> SEQ ID NO 330
<211> LENGTH: 9
<212> TYPE: PRT
<213> ORGANISM: Artificial Sequence
<220> FEATURE:
<223> OTHER INFORMATION: HIV POL 1434 (peptide 1.0944)

<400> SEQUENCE: 330

Ala Val Phe Ile His Asn Phe Lys Arg
 1               5

<210> SEQ ID NO 331
<211> LENGTH: 10
<212> TYPE: PRT
<213> ORGANISM: Artificial Sequence
<220> FEATURE:
<223> OTHER INFORMATION: HIV POL 1474 (peptide 1.1056)

<400> SEQUENCE: 331

Lys Ile Gln Asn Phe Arg Val Tyr Tyr Arg
 1               5                   10

<210> SEQ ID NO 332
<211> LENGTH: 10
<212> TYPE: PRT
<213> ORGANISM: Artificial Sequence
<220> FEATURE:
<223> OTHER INFORMATION: HIV pol 1432 (peptide 1069.49)

<400> SEQUENCE: 332

Gln Met Ala Val Phe Ile His Asn Phe Lys
 1               5                   10

<210> SEQ ID NO 333
<211> LENGTH: 9
<212> TYPE: PRT
<213> ORGANISM: Artificial Sequence
<220> FEATURE:
<223> OTHER INFORMATION: HIV pol 337 (peptide 966.0102)

<400> SEQUENCE: 333

Ala Ile Phe Gln Ser Ser Met Thr Lys
 1               5

<210> SEQ ID NO 334
<211> LENGTH: 9
<212> TYPE: PRT
<213> ORGANISM: Artificial Sequence
<220> FEATURE:
<223> OTHER INFORMATION: HIV pol 909 (peptide 1150.14)

<400> SEQUENCE: 334

Met Ala Val Phe Ile His Asn Phe Lys
 1               5

<210> SEQ ID NO 335
<211> LENGTH: 10
<212> TYPE: PRT
<213> ORGANISM: Artificial Sequence
<220> FEATURE:
<223> OTHER INFORMATION: HIV nef 73-82 (peptide 940.03)
```

-continued

```
<400> SEQUENCE: 335

Gln Val Pro Leu Arg Pro Met Thr Tyr Lys
 1               5                  10

<210> SEQ ID NO 336
<211> LENGTH: 10
<212> TYPE: PRT
<213> ORGANISM: Artificial Sequence
<220> FEATURE:
<223> OTHER INFORMATION: HIV1 ENV 81 (peptide 25.0175)

<400> SEQUENCE: 336

Thr Thr Leu Phe Cys Ala Ser Asp Ala Lys
 1               5                  10

<210> SEQ ID NO 337
<211> LENGTH: 10
<212> TYPE: PRT
<213> ORGANISM: Artificial Sequence
<220> FEATURE:
<223> OTHER INFORMATION: HIV POL 65 (peptide 25.0209)

<400> SEQUENCE: 337

Val Thr Ile Lys Ile Gly Gly Gln Leu Lys
 1               5                  10

<210> SEQ ID NO 338
<211> LENGTH: 9
<212> TYPE: PRT
<213> ORGANISM: Artificial Sequence
<220> FEATURE:
<223> OTHER INFORMATION: HIV nef 84-92 (peptide 1146.01)

<400> SEQUENCE: 338

Phe Pro Val Arg Pro Gln Val Pro Leu
 1               5

<210> SEQ ID NO 339
<211> LENGTH: 9
<212> TYPE: PRT
<213> ORGANISM: Artificial Sequence
<220> FEATURE:
<223> OTHER INFORMATION: HIV env 293 (peptide 29.0060)

<400> SEQUENCE: 339

Ile Pro Ile His Tyr Cys Ala Pro Ala
 1               5

<210> SEQ ID NO 340
<211> LENGTH: 9
<212> TYPE: PRT
<213> ORGANISM: Artificial Sequence
<220> FEATURE:
<223> OTHER INFORMATION: HIV POL 171 (peptide 15.0073)

<400> SEQUENCE: 340

Phe Pro Ile Ser Pro Ile Glu Thr Val
 1               5

<210> SEQ ID NO 341
<211> LENGTH: 9
<212> TYPE: PRT
<213> ORGANISM: Artificial Sequence
<220> FEATURE:
<223> OTHER INFORMATION: HIV env 285 (peptide 29.0056)

<400> SEQUENCE: 341
```

```
Cys Pro Lys Val Ser Phe Glu Pro Ile
  1               5
```

<210> SEQ ID NO 342
<211> LENGTH: 11
<212> TYPE: PRT
<213> ORGANISM: Artificial Sequence
<220> FEATURE:
<223> OTHER INFORMATION: HIV pol 883 (peptide 29.0107)

<400> SEQUENCE: 342

```
Ile Pro Tyr Asn Pro Gln Ser Gln Gly Val Val
  1               5                  10
```

<210> SEQ ID NO 343
<211> LENGTH: 10
<212> TYPE: PRT
<213> ORGANISM: Artificial Sequence
<220> FEATURE:
<223> OTHER INFORMATION: HIV1 POL 96 (peptide 25.0151)

<400> SEQUENCE: 343

```
Cys Thr Leu Asn Phe Pro Ile Ser Pro Ile
  1               5                  10
```

<210> SEQ ID NO 344
<211> LENGTH: 10
<212> TYPE: PRT
<213> ORGANISM: Artificial Sequence
<220> FEATURE:
<223> OTHER INFORMATION: HIV1 NEF 62 (peptide 25.0143)

<400> SEQUENCE: 344

```
Leu Thr Pro Gly Trp Cys Phe Lys Leu Val
  1               5                  10
```

<210> SEQ ID NO 345
<211> LENGTH: 9
<212> TYPE: PRT
<213> ORGANISM: Artificial Sequence
<220> FEATURE:
<223> OTHER INFORMATION: HIV1 POL 83 (peptide 25.0043)

<400> SEQUENCE: 345

```
Tyr Thr Ala Phe Thr Ile Pro Ser Ile
  1               5
```

<210> SEQ ID NO 346
<211> LENGTH: 9
<212> TYPE: PRT
<213> ORGANISM: Artificial Sequence
<220> FEATURE:
<223> OTHER INFORMATION: HIV1 VPR 76 (peptide 25.0055)

<400> SEQUENCE: 346

```
Ala Ile Ile Arg Ile Leu Gln Gln Leu
  1               5
```

<210> SEQ ID NO 347
<211> LENGTH: 9
<212> TYPE: PRT
<213> ORGANISM: Artificial Sequence
<220> FEATURE:
<223> OTHER INFORMATION: HIV1 POL 52 (peptide 25.0049)

<400> SEQUENCE: 347

```
Ala Leu Val Glu Ile Cys Thr Glu Met
  1               5

<210> SEQ ID NO 348
<211> LENGTH: 9
<212> TYPE: PRT
<213> ORGANISM: Artificial Sequence
<220> FEATURE:
<223> OTHER INFORMATION: HIV1 ENV 61 (peptide 25.0032)

<400> SEQUENCE: 348

Leu Leu Gln Leu Thr Val Trp Gly Ile
  1               5

<210> SEQ ID NO 349
<211> LENGTH: 9
<212> TYPE: PRT
<213> ORGANISM: Artificial Sequence
<220> FEATURE:
<223> OTHER INFORMATION: HIV1 POL 100 (peptide 25.0050)

<400> SEQUENCE: 349

Leu Val Gly Pro Thr Pro Val Asn Ile
  1               5

<210> SEQ ID NO 350
<211> LENGTH: 9
<212> TYPE: PRT
<213> ORGANISM: Artificial Sequence
<220> FEATURE:
<223> OTHER INFORMATION: HIV1 POL 65 (peptide 25.0047)

<400> SEQUENCE: 350

Lys Ala Ala Cys Trp Trp Ala Gly Ile
  1               5

<210> SEQ ID NO 351
<211> LENGTH: 10
<212> TYPE: PRT
<213> ORGANISM: Artificial Sequence
<220> FEATURE:
<223> OTHER INFORMATION: HIV1 POL 96 (peptide 25.0162)

<400> SEQUENCE: 351

Lys Met Ile Gly Gly Ile Gly Gly Phe Ile
  1               5                  10

<210> SEQ ID NO 352
<211> LENGTH: 9
<212> TYPE: PRT
<213> ORGANISM: Artificial Sequence
<220> FEATURE:
<223> OTHER INFORMATION: HIV1 POL 78 (peptide 25.0052)

<400> SEQUENCE: 352

Arg Ala Met Ala Ser Asp Phe Asn Leu
  1               5

<210> SEQ ID NO 353
<211> LENGTH: 10
<212> TYPE: PRT
<213> ORGANISM: Artificial Sequence
<220> FEATURE:
<223> OTHER INFORMATION: HIV ENV 814 (peptide 1211.09)

<400> SEQUENCE: 353

Ser Leu Leu Asn Ala Thr Asp Ile Ala Val
```

-continued

```
1               5               10

<210> SEQ ID NO 354
<211> LENGTH: 9
<212> TYPE: PRT
<213> ORGANISM: Artificial Sequence
<220> FEATURE:
<223> OTHER INFORMATION: HIV1 POL 96 (peptide 25.0041)

<400> SEQUENCE: 354

Thr Leu Asn Phe Pro Ile Ser Pro Ile
 1               5

<210> SEQ ID NO 355
<211> LENGTH: 9
<212> TYPE: PRT
<213> ORGANISM: Artificial Sequence
<220> FEATURE:
<223> OTHER INFORMATION: HIV POL 1075 (peptide 1.0046)

<400> SEQUENCE: 355

Ile Val Ile Trp Gly Lys Thr Pro Lys
 1               5

<210> SEQ ID NO 356
<211> LENGTH: 9
<212> TYPE: PRT
<213> ORGANISM: Artificial Sequence
<220> FEATURE:
<223> OTHER INFORMATION: HIV1 GAG 45 (peptide 25.0064)

<400> SEQUENCE: 356

Met Val His Gln Ala Ile Ser Pro Arg
 1               5

<210> SEQ ID NO 357
<211> LENGTH: 9
<212> TYPE: PRT
<213> ORGANISM: Artificial Sequence
<220> FEATURE:
<223> OTHER INFORMATION: HIV POL 1227 (peptide 1.0062)

<400> SEQUENCE: 357

Tyr Leu Ala Trp Val Pro Ala His Lys
 1               5

<210> SEQ ID NO 358
<211> LENGTH: 9
<212> TYPE: PRT
<213> ORGANISM: Artificial Sequence
<220> FEATURE:
<223> OTHER INFORMATION: HIV POL 859 (peptide 1.0942)

<400> SEQUENCE: 358

Met Thr Lys Ile Leu Glu Pro Phe Arg
 1               5

<210> SEQ ID NO 359
<211> LENGTH: 10
<212> TYPE: PRT
<213> ORGANISM: Artificial Sequence
<220> FEATURE:
<223> OTHER INFORMATION: HIV1 GAG 45 (peptide 25.0184)

<400> SEQUENCE: 359

Gln Met Val His Gln Ala Ile Ser Pro Arg
 1               5               10
```

<210> SEQ ID NO 360
<211> LENGTH: 10
<212> TYPE: PRT
<213> ORGANISM: Artificial Sequence
<220> FEATURE:
<223> OTHER INFORMATION: HIV pol 1434 (peptide 1069.48)

<400> SEQUENCE: 360

Ala Val Phe Ile His Asn Phe Lys Arg Lys
 1               5                  10

<210> SEQ ID NO 361
<211> LENGTH: 9
<212> TYPE: PRT
<213> ORGANISM: Artificial Sequence
<220> FEATURE:
<223> OTHER INFORMATION: HIV pol 1358 (peptide 1069.44)

<400> SEQUENCE: 361

Lys Leu Ala Gly Arg Trp Pro Val Lys
 1               5

<210> SEQ ID NO 362
<211> LENGTH: 11
<212> TYPE: PRT
<213> ORGANISM: Artificial Sequence
<220> FEATURE:
<223> OTHER INFORMATION: HIV pol 1225 (peptide 1069.42)

<400> SEQUENCE: 362

Lys Val Tyr Leu Ala Trp Val Pro Ala His Lys
 1               5                  10

<210> SEQ ID NO 363
<211> LENGTH: 9
<212> TYPE: PRT
<213> ORGANISM: Artificial Sequence
<220> FEATURE:
<223> OTHER INFORMATION: HIV pol 752 (peptide 1.0024)

<400> SEQUENCE: 363

Asn Thr Pro Val Phe Ala Ile Lys Lys
 1               5

<210> SEQ ID NO 364
<211> LENGTH: 9
<212> TYPE: PRT
<213> ORGANISM: Artificial Sequence
<220> FEATURE:
<223> OTHER INFORMATION: HIV1 ENV 53 (peptide 25.0062)

<400> SEQUENCE: 364

Arg Ile Val Glu Leu Leu Gly Arg Arg
 1               5

<210> SEQ ID NO 365
<211> LENGTH: 9
<212> TYPE: PRT
<213> ORGANISM: Artificial Sequence
<220> FEATURE:
<223> OTHER INFORMATION: HIV1 POL 65 (peptide 25.0095)

<400> SEQUENCE: 365

Thr Ile Lys Ile Gly Gly Gln Leu Lys
 1               5

```
<210> SEQ ID NO 366
<211> LENGTH: 9
<212> TYPE: PRT
<213> ORGANISM: Artificial Sequence
<220> FEATURE:
<223> OTHER INFORMATION: HIV1 ENV 82 (peptide 25.0078)

<400> SEQUENCE: 366

Thr Leu Phe Cys Ala Ser Asp Ala Lys
 1               5

<210> SEQ ID NO 367
<211> LENGTH: 9
<212> TYPE: PRT
<213> ORGANISM: Artificial Sequence
<220> FEATURE:
<223> OTHER INFORMATION: HIV1 VIF 83 (peptide 25.0104)

<400> SEQUENCE: 367

Val Met Ile Val Trp Gln Val Asp Arg
 1               5

<210> SEQ ID NO 368
<211> LENGTH: 11
<212> TYPE: PRT
<213> ORGANISM: Artificial Sequence
<220> FEATURE:
<223> OTHER INFORMATION: HIV env 48 (peptide 1069.47)

<400> SEQUENCE: 368

Val Thr Val Tyr Tyr Gly Val Pro Val Trp Lys
 1               5                  10

<210> SEQ ID NO 369
<211> LENGTH: 10
<212> TYPE: PRT
<213> ORGANISM: Artificial Sequence
<220> FEATURE:
<223> OTHER INFORMATION: HIV GAG 507 (peptide 15.0268)

<400> SEQUENCE: 369

Tyr Pro Leu Ala Ser Leu Arg Ser Leu Phe
 1               5                  10

<210> SEQ ID NO 370
<211> LENGTH: 9
<212> TYPE: PRT
<213> ORGANISM: Artificial Sequence
<220> FEATURE:
<223> OTHER INFORMATION: HIV GAG 248 (peptide 1292.13)

<400> SEQUENCE: 370

His Pro Val His Ala Gly Pro Ile Ala
 1               5

<210> SEQ ID NO 371
<211> LENGTH: 8
<212> TYPE: PRT
<213> ORGANISM: Artificial Sequence
<220> FEATURE:
<223> OTHER INFORMATION: HIV con. REV 71 (peptide 19.0044)

<400> SEQUENCE: 371

Val Pro Leu Gln Leu Pro Pro Leu
 1               5
```

```
<210> SEQ ID NO 372
<211> LENGTH: 10
<212> TYPE: PRT
<213> ORGANISM: Artificial Sequence
<220> FEATURE:
<223> OTHER INFORMATION: HIV POL 1187 (peptide 1.0431)

<400> SEQUENCE: 372

Glu Val Asn Ile Val Thr Asp Ser Gln Tyr
 1               5                  10

<210> SEQ ID NO 373
<211> LENGTH: 9
<212> TYPE: PRT
<213> ORGANISM: Artificial Sequence
<220> FEATURE:
<223> OTHER INFORMATION: HIV GAG 298 (peptide 1.0014)

<400> SEQUENCE: 373

Phe Arg Asp Tyr Val Asp Arg Phe Tyr
 1               5

<210> SEQ ID NO 374
<211> LENGTH: 9
<212> TYPE: PRT
<213> ORGANISM: Artificial Sequence
<220> FEATURE:
<223> OTHER INFORMATION: HIV1 ENV 69 (peptide 25.0113)

<400> SEQUENCE: 374

Ile Trp Gly Cys Ser Gly Lys Leu Ile
 1               5

<210> SEQ ID NO 375
<211> LENGTH: 9
<212> TYPE: PRT
<213> ORGANISM: Artificial Sequence
<220> FEATURE:
<223> OTHER INFORMATION: HIV1 VPR 92 (peptide 25.0127)

<400> SEQUENCE: 375

Ile Tyr Glu Thr Tyr Gly Asp Thr Trp
 1               5

<210> SEQ ID NO 376
<211> LENGTH: 9
<212> TYPE: PRT
<213> ORGANISM: Artificial Sequence
<220> FEATURE:
<223> OTHER INFORMATION: HIV pol 1036 (peptide 1069.60)

<400> SEQUENCE: 376

Ile Tyr Gln Glu Pro Phe Lys Asn Leu
 1               5

<210> SEQ ID NO 377
<211> LENGTH: 9
<212> TYPE: PRT
<213> ORGANISM: Artificial Sequence
<220> FEATURE:
<223> OTHER INFORMATION: HIV pol 359 (peptide 2.0129)

<400> SEQUENCE: 377

Ile Tyr Gln Tyr Met Asp Asp Leu Tyr
 1               5

<210> SEQ ID NO 378
```

<211> LENGTH: 9
<212> TYPE: PRT
<213> ORGANISM: Artificial Sequence
<220> FEATURE:
<223> OTHER INFORMATION: HIV1 VPR 56 (peptide 25.0128)

<400> SEQUENCE: 378

Pro Tyr Asn Glu Trp Thr Leu Glu Leu
1               5

<210> SEQ ID NO 379
<211> LENGTH: 9
<212> TYPE: PRT
<213> ORGANISM: Artificial Sequence
<220> FEATURE:
<223> OTHER INFORMATION: HIV1 POL 74 (peptide 25.0123)

<400> SEQUENCE: 379

Pro Tyr Asn Thr Pro Val Phe Ala Ile
1               5

<210> SEQ ID NO 380
<211> LENGTH: 9
<212> TYPE: PRT
<213> ORGANISM: Artificial Sequence
<220> FEATURE:
<223> OTHER INFORMATION: HIV env 2778 (peptide 1069.57)

<400> SEQUENCE: 380

Arg Tyr Leu Lys Asp Gln Gln Leu Leu
1               5

<210> SEQ ID NO 381
<211> LENGTH: 9
<212> TYPE: PRT
<213> ORGANISM: Artificial Sequence
<220> FEATURE:
<223> OTHER INFORMATION: HIV env 2778 (peptide 1069.58)

<400> SEQUENCE: 381

Arg Tyr Leu Arg Asp Gln Gln Leu Leu
1               5

<210> SEQ ID NO 382
<211> LENGTH: 9
<212> TYPE: PRT
<213> ORGANISM: Artificial Sequence
<220> FEATURE:
<223> OTHER INFORMATION: HIV pol 1033 (peptide 1069.59)

<400> SEQUENCE: 382

Thr Tyr Gln Ile Tyr Gln Glu Pro Phe
1               5

<210> SEQ ID NO 383
<211> LENGTH: 10
<212> TYPE: PRT
<213> ORGANISM: Artificial Sequence
<220> FEATURE:
<223> OTHER INFORMATION: HIV pol 358 (peptide 1069.27)

<400> SEQUENCE: 383

Val Ile Tyr Gln Tyr Met Asp Asp Leu Tyr
1               5                   10

<210> SEQ ID NO 384
<211> LENGTH: 10

```
<212> TYPE: PRT
<213> ORGANISM: Artificial Sequence
<220> FEATURE:
<223> OTHER INFORMATION: HIV POL 265 (peptide 1069.26)

<400> SEQUENCE: 384

Val Thr Val Leu Asp Val Gly Asp Ala Tyr
1               5                   10

<210> SEQ ID NO 385
<211> LENGTH: 9
<212> TYPE: PRT
<213> ORGANISM: Artificial Sequence
<220> FEATURE:
<223> OTHER INFORMATION: HIV1 ENV 47 (peptide 25.0115)

<400> SEQUENCE: 385

Val Trp Lys Glu Ala Thr Thr Thr Leu
1               5

<210> SEQ ID NO 386
<211> LENGTH: 10
<212> TYPE: PRT
<213> ORGANISM: Artificial Sequence
<220> FEATURE:
<223> OTHER INFORMATION: HIV1 ENV 47 (peptide 25.0218)

<400> SEQUENCE: 386

Val Trp Lys Glu Ala Thr Thr Thr Leu Phe
1               5                   10

<210> SEQ ID NO 387
<211> LENGTH: 10
<212> TYPE: PRT
<213> ORGANISM: Artificial Sequence
<220> FEATURE:
<223> OTHER INFORMATION: HIV1 POL 96 (peptide 25.0219)

<400> SEQUENCE: 387

Tyr Met Gln Ala Thr Trp Ile Pro Glu Trp
1               5                   10

<210> SEQ ID NO 388
<211> LENGTH: 10
<212> TYPE: PRT
<213> ORGANISM: Artificial Sequence
<220> FEATURE:
<223> OTHER INFORMATION: HIV MN GP160 814(a) (peptide 1211.4)

<400> SEQUENCE: 388

Ser Leu Leu Asn Ala Thr Ala Ile Ala Val
1               5                   10

<210> SEQ ID NO 389
<211> LENGTH: 9
<212> TYPE: PRT
<213> ORGANISM: Artificial Sequence
<220> FEATURE:
<223> OTHER INFORMATION: HIV pol 337(a) (peptide F105.21)

<400> SEQUENCE: 389

Ala Ile Phe Gln Arg Ser Met Thr Arg
1               5

<210> SEQ ID NO 390
<211> LENGTH: 9
<212> TYPE: PRT
```

```
<213> ORGANISM: Artificial Sequence
<220> FEATURE:
<223> OTHER INFORMATION: HIV pol 337(a) (peptide F105.17)

<400> SEQUENCE: 390

Ala Ile Phe Gln Ser Ser Met Thr Arg
 1               5

<210> SEQ ID NO 391
<211> LENGTH: 9
<212> TYPE: PRT
<213> ORGANISM: Artificial Sequence
<220> FEATURE:
<223> OTHER INFORMATION: HIV pol 337(a) (peptide F105.02)

<400> SEQUENCE: 391

Gly Ile Phe Gln Ser Ser Met Thr Lys
 1               5

<210> SEQ ID NO 392
<211> LENGTH: 9
<212> TYPE: PRT
<213> ORGANISM: Artificial Sequence
<220> FEATURE:
<223> OTHER INFORMATION: HIV pol 337(a) (peptide F105.03)

<400> SEQUENCE: 392

Ala Ala Phe Gln Ser Ser Met Thr Lys
 1               5

<210> SEQ ID NO 393
<211> LENGTH: 9
<212> TYPE: PRT
<213> ORGANISM: Artificial Sequence
<220> FEATURE:
<223> OTHER INFORMATION: HIV pol 337(a) (peptide F105.04)

<400> SEQUENCE: 393

Ala Ile Ala Gln Ser Ser Met Thr Lys
 1               5

<210> SEQ ID NO 394
<211> LENGTH: 9
<212> TYPE: PRT
<213> ORGANISM: Artificial Sequence
<220> FEATURE:
<223> OTHER INFORMATION: HIV pol 337(a) (peptide F105.05)

<400> SEQUENCE: 394

Ala Ile Phe Ala Ser Ser Met Thr Lys
 1               5

<210> SEQ ID NO 395
<211> LENGTH: 9
<212> TYPE: PRT
<213> ORGANISM: Artificial Sequence
<220> FEATURE:
<223> OTHER INFORMATION: HIV pol 337(a) (peptide F105.06)

<400> SEQUENCE: 395

Ala Ile Phe Gln Ala Ser Met Thr Lys
 1               5

<210> SEQ ID NO 396
<211> LENGTH: 9
<212> TYPE: PRT
<213> ORGANISM: Artificial Sequence
```

```
<220> FEATURE:
<223> OTHER INFORMATION: HIV pol 337(a) (peptide F105.07)

<400> SEQUENCE: 396

Ala Ile Phe Gln Ser Ala Met Thr Lys
 1               5

<210> SEQ ID NO 397
<211> LENGTH: 9
<212> TYPE: PRT
<213> ORGANISM: Artificial Sequence
<220> FEATURE:
<223> OTHER INFORMATION: HIV pol 337(a) (peptide F105.08)

<400> SEQUENCE: 397

Ala Ile Phe Gln Ser Ser Ala Thr Lys
 1               5

<210> SEQ ID NO 398
<211> LENGTH: 9
<212> TYPE: PRT
<213> ORGANISM: Artificial Sequence
<220> FEATURE:
<223> OTHER INFORMATION: HIV pol 337(a) (peptide F105.09)

<400> SEQUENCE: 398

Ala Ile Phe Gln Ser Ser Met Ala Lys
 1               5

<210> SEQ ID NO 399
<211> LENGTH: 9
<212> TYPE: PRT
<213> ORGANISM: Artificial Sequence
<220> FEATURE:
<223> OTHER INFORMATION: HIV pol 337(a) (peptide F105.11)

<400> SEQUENCE: 399

Phe Ile Phe Gln Ser Ser Met Thr Lys
 1               5

<210> SEQ ID NO 400
<211> LENGTH: 9
<212> TYPE: PRT
<213> ORGANISM: Artificial Sequence
<220> FEATURE:
<223> OTHER INFORMATION: HIV pol 337(a) (peptide F105.12)

<400> SEQUENCE: 400

Ser Ile Phe Gln Ser Ser Met Thr Lys
 1               5

<210> SEQ ID NO 401
<211> LENGTH: 9
<212> TYPE: PRT
<213> ORGANISM: Artificial Sequence
<220> FEATURE:
<223> OTHER INFORMATION: HIV pol 337(a) (peptide F105.16)

<400> SEQUENCE: 401

Ala Ile Phe Gln Cys Ser Met Thr Lys
 1               5

<210> SEQ ID NO 402
<211> LENGTH: 9
<212> TYPE: PRT
<213> ORGANISM: Artificial Sequence
<220> FEATURE:
```

<223> OTHER INFORMATION: HIV nef 84-92 analog (peptide 1145.03)

<400> SEQUENCE: 402

Phe Pro Val Arg Pro Gln Phe Pro Leu
 1               5

<210> SEQ ID NO 403
<211> LENGTH: 9
<212> TYPE: PRT
<213> ORGANISM: Artificial Sequence
<220> FEATURE:
<223> OTHER INFORMATION: HIV nef 84-92(a) (peptide 1181.03)

<400> SEQUENCE: 403

Phe Pro Val Arg Pro Gln Val Pro Ile
 1               5

<210> SEQ ID NO 404
<211> LENGTH: 9
<212> TYPE: PRT
<213> ORGANISM: Artificial Sequence
<220> FEATURE:
<223> OTHER INFORMATION: HIV GAG 248 (peptide 1292.14)

<400> SEQUENCE: 404

His Pro Val His Ala Gly Pro Ile Ile
 1               5

<210> SEQ ID NO 405
<211> LENGTH: 9
<212> TYPE: PRT
<213> ORGANISM: Artificial Sequence
<220> FEATURE:
<223> OTHER INFORMATION: HIV POL 179 (peptide 1292.09)

<400> SEQUENCE: 405

Phe Pro Ile Ser Pro Ile Glu Thr Ile
 1               5

<210> SEQ ID NO 406
<211> LENGTH: 9
<212> TYPE: PRT
<213> ORGANISM: Artificial Sequence
<220> FEATURE:
<223> OTHER INFORMATION: HIV nef 84-92 analog (peptide 1145.02)

<400> SEQUENCE: 406

Phe Pro Val Thr Pro Gln Val Pro Leu
 1               5

<210> SEQ ID NO 407
<211> LENGTH: 9
<212> TYPE: PRT
<213> ORGANISM: Artificial Sequence
<220> FEATURE:
<223> OTHER INFORMATION: HIV nef 84-92 analog (peptide 1145.22)

<400> SEQUENCE: 407

Phe Pro Val Arg Met Gln Val Pro Leu
 1               5

<210> SEQ ID NO 408
<211> LENGTH: 9
<212> TYPE: PRT
<213> ORGANISM: Artificial Sequence
<220> FEATURE:
<223> OTHER INFORMATION: HIV nef 84-92(a) (peptide 1181.04)

```
<400> SEQUENCE: 408

Phe Pro Val Arg Pro Gln Val Pro Met
 1               5

<210> SEQ ID NO 409
<211> LENGTH: 9
<212> TYPE: PRT
<213> ORGANISM: Artificial Sequence
<220> FEATURE:
<223> OTHER INFORMATION: HIV nef 84-92(a) (peptide 1181.01)

<400> SEQUENCE: 409

Phe Pro Val Arg Pro Gln Val Pro Ala
 1               5

<210> SEQ ID NO 410
<211> LENGTH: 9
<212> TYPE: PRT
<213> ORGANISM: Artificial Sequence
<220> FEATURE:
<223> OTHER INFORMATION: HIV nef 84-92(a) (peptide 1181.02)

<400> SEQUENCE: 410

Phe Pro Val Arg Pro Gln Val Pro Val
 1               5

<210> SEQ ID NO 411
<211> LENGTH: 9
<212> TYPE: PRT
<213> ORGANISM: Artificial Sequence
<220> FEATURE:
<223> OTHER INFORMATION: HIV nef 84-92(a) (peptide 1181.05)

<400> SEQUENCE: 411

Phe Pro Val Arg Pro Gln Val Pro Phe
 1               5

<210> SEQ ID NO 412
<211> LENGTH: 9
<212> TYPE: PRT
<213> ORGANISM: Artificial Sequence
<220> FEATURE:
<223> OTHER INFORMATION: HIV nef 84-92(a) (peptide 1181.06)

<400> SEQUENCE: 412

Phe Pro Val Arg Pro Gln Val Pro Trp
 1               5

<210> SEQ ID NO 413
<211> LENGTH: 16
<212> TYPE: PRT
<213> ORGANISM: Artificial Sequence
<220> FEATURE:
<223> OTHER INFORMATION: Pf SSP2 61 (peptide F125.04)

<400> SEQUENCE: 413

Arg His Asn Trp Val Asn His Ala Val Pro Leu Ala Met Lys Leu Ile
 1               5                  10                  15

<210> SEQ ID NO 414
<211> LENGTH: 15
<212> TYPE: PRT
<213> ORGANISM: Artificial Sequence
<220> FEATURE:
<223> OTHER INFORMATION: Pf SSP2 62 (peptide 1188.34)
```

<400> SEQUENCE: 414

His Asn Trp Val Asn His Ala Val Pro Leu Ala Met Lys Leu Ile
1               5                   10                  15

<210> SEQ ID NO 415
<211> LENGTH: 15
<212> TYPE: PRT
<213> ORGANISM: Artificial Sequence
<220> FEATURE:
<223> OTHER INFORMATION: Pf EXP1 71 (peptide1188.16)

<400> SEQUENCE: 415

Lys Ser Lys Tyr Lys Leu Ala Thr Ser Val Leu Ala Gly Leu Leu
1               5                   10                  15

<210> SEQ ID NO 416
<211> LENGTH: 18
<212> TYPE: PRT
<213> ORGANISM: Artificial Sequence
<220> FEATURE:
<223> OTHER INFORMATION: Pf LSA1 13

<400> SEQUENCE: 416

Leu Val Asn Leu Leu Ile Phe His Ile Asn Gly Lys Ile Ile Lys Asn
1               5                   10                  15

Ser Glu

<210> SEQ ID NO 417
<211> LENGTH: 17
<212> TYPE: PRT
<213> ORGANISM: Artificial Sequence
<220> FEATURE:
<223> OTHER INFORMATION: Pf LSA 13 (peptide F125.02)

<400> SEQUENCE: 417

Leu Val Asn Leu Leu Ile Phe His Ile Asn Gly Lys Ile Ile Lys Asn
1               5                   10                  15

Ser

<210> SEQ ID NO 418
<211> LENGTH: 15
<212> TYPE: PRT
<213> ORGANISM: Artificial Sequence
<220> FEATURE:
<223> OTHER INFORMATION: Pf LSA1 16 (peptide 27.0402)

<400> SEQUENCE: 418

Leu Leu Ile Phe His Ile Asn Gly Lys Ile Ile Lys Asn Ser Glu
1               5                   10                  15

<210> SEQ ID NO 419
<211> LENGTH: 15
<212> TYPE: PRT
<213> ORGANISM: Artificial Sequence
<220> FEATURE:
<223> OTHER INFORMATION: Pf SSP2 512 (peptide 1188.32)

<400> SEQUENCE: 419

Gly Leu Ala Tyr Lys Phe Val Val Pro Gly Ala Ala Thr Pro Tyr
1               5                   10                  15

<210> SEQ ID NO 420
<211> LENGTH: 15
<212> TYPE: PRT
<213> ORGANISM: Artificial Sequence

```
<220> FEATURE:
<223> OTHER INFORMATION: Pf CSP 410 (peptide 27.0392)

<400> SEQUENCE: 420

Ser Ser Val Phe Asn Val Val Asn Ser Ser Ile Gly Leu Ile Met
 1               5                  10                  15

<210> SEQ ID NO 421
<211> LENGTH: 15
<212> TYPE: PRT
<213> ORGANISM: Artificial Sequence
<220> FEATURE:
<223> OTHER INFORMATION: Pf SSP2 223 (peptide 27.0417)

<400> SEQUENCE: 421

Val Lys Asn Val Ile Gly Pro Phe Met Lys Ala Val Cys Val Glu
 1               5                  10                  15

<210> SEQ ID NO 422
<211> LENGTH: 15
<212> TYPE: PRT
<213> ORGANISM: Artificial Sequence
<220> FEATURE:
<223> OTHER INFORMATION: Pf CSP 2 (peptide 27.0388)

<400> SEQUENCE: 422

Met Arg Lys Leu Ala Ile Leu Ser Val Ser Ser Phe Leu Phe Val
 1               5                  10                  15

<210> SEQ ID NO 423
<211> LENGTH: 15
<212> TYPE: PRT
<213> ORGANISM: Artificial Sequence
<220> FEATURE:
<223> OTHER INFORMATION: Pf CSP 53 (peptide 27.0387)

<400> SEQUENCE: 423

Met Asn Tyr Tyr Gly Lys Gln Glu Asn Trp Tyr Ser Leu Lys Lys
 1               5                  10                  15

<210> SEQ ID NO 424
<211> LENGTH: 15
<212> TYPE: PRT
<213> ORGANISM: Artificial Sequence
<220> FEATURE:
<223> OTHER INFORMATION: Pf SSP2 494 (peptide 1188.38)

<400> SEQUENCE: 424

Lys Tyr Lys Ile Ala Gly Gly Ile Ala Gly Gly Leu Ala Leu Leu
 1               5                  10                  15

<210> SEQ ID NO 425
<211> LENGTH: 15
<212> TYPE: PRT
<213> ORGANISM: Artificial Sequence
<220> FEATURE:
<223> OTHER INFORMATION: Pf EXP1 82 (peptide 1188.13)

<400> SEQUENCE: 425

Ala Gly Leu Leu Gly Asn Val Ser Thr Val Leu Leu Gly Gly Val
 1               5                  10                  15

<210> SEQ ID NO 426
<211> LENGTH: 15
<212> TYPE: PRT
<213> ORGANISM: Artificial Sequence
<220> FEATURE:
```

-continued

```
<223> OTHER INFORMATION: Pf LSA1 94 (peptide 27.0408)

<400> SEQUENCE: 426

Gln Thr Asn Phe Lys Ser Leu Leu Arg Asn Leu Gly Val Ser Glu
 1               5                  10                  15

<210> SEQ ID NO 427
<211> LENGTH: 15
<212> TYPE: PRT
<213> ORGANISM: Artificial Sequence
<220> FEATURE:
<223> OTHER INFORMATION: Pf SSP2 165 (peptide 35.0171)

<400> SEQUENCE: 427

Pro Asp Ser Ile Gln Asp Ser Leu Lys Glu Ser Arg Lys Leu Asn
 1               5                  10                  15

<210> SEQ ID NO 428
<211> LENGTH: 15
<212> TYPE: PRT
<213> ORGANISM: Artificial Sequence
<220> FEATURE:
<223> OTHER INFORMATION: Pf SSP2 211 (peptide 35.0172)

<400> SEQUENCE: 428

Lys Cys Asn Leu Tyr Ala Asp Ser Ala Trp Glu Asn Val Lys Asn
 1               5                  10                  15

<210> SEQ ID NO 429
<211> LENGTH: 10
<212> TYPE: PRT
<213> ORGANISM: Artificial Sequence
<220> FEATURE:
<223> OTHER INFORMATION: Pf SSP2 14 (peptide 1167.21)

<400> SEQUENCE: 429

Phe Leu Ile Phe Phe Asp Leu Phe Leu Val
 1               5                  10

<210> SEQ ID NO 430
<211> LENGTH: 9
<212> TYPE: PRT
<213> ORGANISM: Artificial Sequence
<220> FEATURE:
<223> OTHER INFORMATION: Pf CSP 425 (peptide 1167.08)

<400> SEQUENCE: 430

Gly Leu Ile Met Val Leu Ser Phe Leu
 1               5

<210> SEQ ID NO 431
<211> LENGTH: 9
<212> TYPE: PRT
<213> ORGANISM: Artificial Sequence
<220> FEATURE:
<223> OTHER INFORMATION: Pf EXP1 80 (peptide 1167.12)

<400> SEQUENCE: 431

Val Leu Ala Gly Leu Leu Gly Asn Val
 1               5

<210> SEQ ID NO 432
<211> LENGTH: 9
<212> TYPE: PRT
<213> ORGANISM: Artificial Sequence
<220> FEATURE:
<223> OTHER INFORMATION: Pf EXP1 2 (peptide 1167.13)
```

-continued

```
<400> SEQUENCE: 432

Lys Ile Leu Ser Val Phe Phe Leu Ala
 1               5

<210> SEQ ID NO 433
<211> LENGTH: 9
<212> TYPE: PRT
<213> ORGANISM: Artificial Sequence
<220> FEATURE:
<223> OTHER INFORMATION: Pf EXP1 83 (peptide 1167.10)

<400> SEQUENCE: 433

Gly Leu Leu Gly Asn Val Ser Thr Val
 1               5

<210> SEQ ID NO 434
<211> LENGTH: 10
<212> TYPE: PRT
<213> ORGANISM: Artificial Sequence
<220> FEATURE:
<223> OTHER INFORMATION: Pf CSP 7 (peptide 1167.18)

<400> SEQUENCE: 434

Ile Leu Ser Val Ser Ser Phe Leu Phe Val
 1               5                  10

<210> SEQ ID NO 435
<211> LENGTH: 10
<212> TYPE: PRT
<213> ORGANISM: Artificial Sequence
<220> FEATURE:
<223> OTHER INFORMATION: Pf EXP1 91 (peptide 1167.19)

<400> SEQUENCE: 435

Val Leu Leu Gly Gly Val Gly Leu Val Leu
 1               5                  10

<210> SEQ ID NO 436
<211> LENGTH: 9
<212> TYPE: PRT
<213> ORGANISM: Artificial Sequence
<220> FEATURE:
<223> OTHER INFORMATION: Pf SSP2 511 (peptide 1167.36)

<400> SEQUENCE: 436

Leu Ala Cys Ala Gly Leu Ala Tyr Lys
 1               5

<210> SEQ ID NO 437
<211> LENGTH: 9
<212> TYPE: PRT
<213> ORGANISM: Artificial Sequence
<220> FEATURE:
<223> OTHER INFORMATION: Pf LSA1 94 (peptide 1167.32)

<400> SEQUENCE: 437

Gln Thr Asn Phe Lys Ser Leu Leu Arg
 1               5

<210> SEQ ID NO 438
<211> LENGTH: 10
<212> TYPE: PRT
<213> ORGANISM: Artificial Sequence
<220> FEATURE:
<223> OTHER INFORMATION: Pf CSP 375 (peptide 1167.43)
```

```
<400> SEQUENCE: 438

Val Thr Cys Gly Asn Gly Ile Gln Val Arg
 1               5                  10

<210> SEQ ID NO 439
<211> LENGTH: 9
<212> TYPE: PRT
<213> ORGANISM: Artificial Sequence
<220> FEATURE:
<223> OTHER INFORMATION: Pf EXP1 10 (peptide 1167.24)

<400> SEQUENCE: 439

Ala Leu Phe Phe Ile Ile Phe Asn Lys
 1               5

<210> SEQ ID NO 440
<211> LENGTH: 9
<212> TYPE: PRT
<213> ORGANISM: Artificial Sequence
<220> FEATURE:
<223> OTHER INFORMATION: Pf LSA 1 105 (peptide 1167.28)

<400> SEQUENCE: 440

Gly Val Ser Glu Asn Ile Phe Leu Lys
 1               5

<210> SEQ ID NO 441
<211> LENGTH: 10
<212> TYPE: PRT
<213> ORGANISM: Artificial Sequence
<220> FEATURE:
<223> OTHER INFORMATION: Pf LSA1 59 (peptide 1167.47)

<400> SEQUENCE: 441

His Val Leu Ser His Asn Ser Tyr Glu Lys
 1               5                  10

<210> SEQ ID NO 442
<211> LENGTH: 10
<212> TYPE: PRT
<213> ORGANISM: Artificial Sequence
<220> FEATURE:
<223> OTHER INFORMATION: Pf SSP2 510 (peptide 1167.51)

<400> SEQUENCE: 442

Leu Leu Ala Cys Ala Gly Leu Ala Tyr Lys
 1               5                  10

<210> SEQ ID NO 443
<211> LENGTH: 10
<212> TYPE: PRT
<213> ORGANISM: Artificial Sequence
<220> FEATURE:
<223> OTHER INFORMATION: Pf LSA1 11 (peptide 1167.46)

<400> SEQUENCE: 443

Phe Ile Leu Val Asn Leu Leu Ile Phe His
 1               5                  10

<210> SEQ ID NO 444
<211> LENGTH: 9
<212> TYPE: PRT
<213> ORGANISM: Artificial Sequence
<220> FEATURE:
<223> OTHER INFORMATION: Pf SHEBA 77 (peptide 1101.03)

<400> SEQUENCE: 444
```

```
Met Pro Leu Glu Thr Gln Leu Ala Ile
1               5
```

<210> SEQ ID NO 445
<211> LENGTH: 10
<212> TYPE: PRT
<213> ORGANISM: Artificial Sequence
<220> FEATURE:
<223> OTHER INFORMATION: Pf SSP2 539 (peptide 1167.61)

<400> SEQUENCE: 445

```
Thr Pro Tyr Ala Gly Glu Pro Ala Pro Phe
1               5                   10
```

<210> SEQ ID NO 446
<211> LENGTH: 9
<212> TYPE: PRT
<213> ORGANISM: Artificial Sequence
<220> FEATURE:
<223> OTHER INFORMATION: Pf SSP2 14 (peptide 1167.14)

<400> SEQUENCE: 446

```
Phe Leu Ile Phe Phe Asp Leu Phe Leu
1               5
```

<210> SEQ ID NO 447
<211> LENGTH: 9
<212> TYPE: PRT
<213> ORGANISM: Artificial Sequence
<220> FEATURE:
<223> OTHER INFORMATION: Pf SSP2 230 (peptide 1167.16)

<400> SEQUENCE: 447

```
Phe Met Lys Ala Val Cys Val Glu Val
1               5
```

<210> SEQ ID NO 448
<211> LENGTH: 9
<212> TYPE: PRT
<213> ORGANISM: Artificial Sequence
<220> FEATURE:
<223> OTHER INFORMATION: Pf SSP2 15 (peptide 1167.15)

<400> SEQUENCE: 448

```
Leu Ile Phe Phe Asp Leu Phe Leu Val
1               5
```

<210> SEQ ID NO 449
<211> LENGTH: 9
<212> TYPE: PRT
<213> ORGANISM: Artificial Sequence
<220> FEATURE:
<223> OTHER INFORMATION: Pf SSP2 51 (peptide 1167.17)

<400> SEQUENCE: 449

```
Leu Leu Met Asp Cys Ser Gly Ser Ile
1               5
```

<210> SEQ ID NO 450
<211> LENGTH: 9
<212> TYPE: PRT
<213> ORGANISM: Artificial Sequence
<220> FEATURE:
<223> OTHER INFORMATION: Pf EXP1 91 (peptide 1167.09)

<400> SEQUENCE: 450

Val Leu Leu Gly Gly Val Gly Leu Val
1               5

<210> SEQ ID NO 451
<211> LENGTH: 8
<212> TYPE: PRT
<213> ORGANISM: Artificial Sequence
<220> FEATURE:
<223> OTHER INFORMATION: Pf SSP2 126 (peptide 19.0051)

<400> SEQUENCE: 451

Leu Pro Tyr Gly Arg Thr Asn Leu
1               5

<210> SEQ ID NO 452
<211> LENGTH: 10
<212> TYPE: PRT
<213> ORGANISM: Artificial Sequence
<220> FEATURE:
<223> OTHER INFORMATION: Pf LSA1 1794 (peptide 16.0245)

<400> SEQUENCE: 452

Phe Gln Asp Glu Glu Asn Ile Gly Ile Tyr
1               5                   10

<210> SEQ ID NO 453
<211> LENGTH: 9
<212> TYPE: PRT
<213> ORGANISM: Artificial Sequence
<220> FEATURE:
<223> OTHER INFORMATION: Pf CSP 15 (peptide 16.0040)

<400> SEQUENCE: 453

Phe Val Glu Ala Leu Phe Gln Glu Tyr
1               5

<210> SEQ ID NO 454
<211> LENGTH: 9
<212> TYPE: PRT
<213> ORGANISM: Artificial Sequence
<220> FEATURE:
<223> OTHER INFORMATION: Pf LSA1 9 (peptide 1167.54)

<400> SEQUENCE: 454

Phe Tyr Phe Ile Leu Val Asn Leu Leu
1               5

<210> SEQ ID NO 455
<211> LENGTH: 9
<212> TYPE: PRT
<213> ORGANISM: Artificial Sequence
<220> FEATURE:
<223> OTHER INFORMATION: Pf EXP1 73 (peptide 1167.53)

<400> SEQUENCE: 455

Lys Tyr Lys Leu Ala Thr Ser Val Leu
1               5

<210> SEQ ID NO 456
<211> LENGTH: 9
<212> TYPE: PRT
<213> ORGANISM: Artificial Sequence
<220> FEATURE:
<223> OTHER INFORMATION: Pf SSP2 8 (peptide 1167.56)

<400> SEQUENCE: 456

Lys Tyr Leu Val Ile Val Phe Leu Ile

```
1               5
```

<210> SEQ ID NO 457
<211> LENGTH: 9
<212> TYPE: PRT
<213> ORGANISM: Artificial Sequence
<220> FEATURE:
<223> OTHER INFORMATION: Pf LSA1 1663 (peptide 15.0184)

<400> SEQUENCE: 457

```
Leu Pro Ser Glu Asn Glu Arg Gly Tyr
 1               5
```

<210> SEQ ID NO 458
<211> LENGTH: 9
<212> TYPE: PRT
<213> ORGANISM: Artificial Sequence
<220> FEATURE:
<223> OTHER INFORMATION: Pf SSP2 207 (peptide 16.0130)

<400> SEQUENCE: 458

```
Pro Ser Asp Gly Lys Cys Asn Leu Tyr
 1               5
```

<210> SEQ ID NO 459
<211> LENGTH: 9
<212> TYPE: PRT
<213> ORGANISM: Artificial Sequence
<220> FEATURE:
<223> OTHER INFORMATION: Pf LSA1 1664 (peptide 16.0077)

<400> SEQUENCE: 459

```
Pro Ser Glu Asn Glu Arg Gly Tyr Tyr
 1               5
```

<210> SEQ ID NO 460
<211> LENGTH: 9
<212> TYPE: PRT
<213> ORGANISM: Artificial Sequence
<220> FEATURE:
<223> OTHER INFORMATION: Pf SSP2 528 (peptide 1167.57)

<400> SEQUENCE: 460

```
Pro Tyr Ala Gly Glu Pro Ala Pro Phe
 1               5
```

<210> SEQ ID NO 461
<211> LENGTH: 9
<212> TYPE: PRT
<213> ORGANISM: Artificial Sequence
<220> FEATURE:
<223> OTHER INFORMATION: Pf LSA1 1671 (peptide 1167.55)

<400> SEQUENCE: 461

```
Tyr Tyr Ile Pro His Gln Ser Ser Leu
 1               5
```

<210> SEQ ID NO 462
<211> LENGTH: 9
<212> TYPE: PRT
<213> ORGANISM: Artificial sequence
<220> FEATURE:
<223> OTHER INFORMATION: HBV pol 538-546 sub (peptide 1090.77)

<400> SEQUENCE: 462

```
Tyr Met Asp Asp Val Val Leu Gly Val
 1               5
```

```
<210> SEQ ID NO 463
<211> LENGTH: 9
<212> TYPE: PRT
<213> ORGANISM: Artificial sequence
<220> FEATURE:
<223> OTHER INFORMATION: HIV 1 pol 87(peptide 25.0062)

<400> SEQUENCE:

Lys Leu Val Gly Lys Leu Asn Trp Ala
1               5
```

What is claimed is:

1. An expression system which comprises a promoter operably linked to a nucleotide sequence which encodes a peptide comprising a first amino acid sequence which is a major histocompatibility (MHC) targeting sequence fused to a second amino acid sequence encoding one Class I MHC restricted CTL peptide epitope and one universal HTL peptide epitope, wherein the CTL peptide epitope is selected from the group consisting of the HIV peptides set forth as SEQ ID NOs: 101, 105, 324–412, and 463.

2. An expression system which comprises a promoter operably linked to a nucleotide sequence which encodes a peptide comprising a first amino acid sequence which is an MHC targeting sequence fused to a second amino acid sequence encoding one Class I MHC restricted CTL peptide epitope and one universal HTL peptide epitope, wherein the CTL peptide epitope is selected from the group consisting of an analog of an HIV peptide set forth as SEQ ID NOs: 101, 105, 324–412, and 463.

3. A method to induce an immune response in a subject which comprises administering to a mammalian subject an expression system, wherein the expression system comprises a promoter operably linked to a nucleotide sequence which encodes a peptide comprising a first amino acid sequence which is a major histocompatibility (MHC) targeting sequence fused to a second amino acid sequence encoding one Class I MHC restricted CTL peptide epitope and one universal HTL peptide epitope, and wherein the CTL peptide epitope is selected from the group consisting of the HIV peptides set forth as SEQ ID NOs: 101, 105, 324–412, and 463.

4. A method to induce an immune response in a subject which comprises administering to a mammalian subject an expression system, wherein the expression system comprises a promoter operably linked to a nucleotide sequence which encodes a peptide comprising a first amino acid sequence which is a major histocompatibility (MHC) targeting sequence fused to a second amino acid sequence encoding one Class I MHC restricted CTL peptide epitope and one universal HTL peptide epitope, and wherein the CTL peptide epitope is selected from the group consisting of an analog of the HIV peptides set forth as SEQ ID NOs: 101, 105, 324–412, and 463.

* * * * *

UNITED STATES PATENT AND TRADEMARK OFFICE
CERTIFICATE OF CORRECTION

PATENT NO. : 6,534,482 B1  Page 1 of 1
DATED : March 18, 2003
INVENTOR(S) : John Fikes et al.

It is certified that error appears in the above-identified patent and that said Letters Patent is hereby corrected as shown below:

<u>Column 46,</u>
Table 2, replace peptide 927.42 Sequence "NLSWLSLD-V" with -- NLSWLSLDV --.

<u>Column 49,</u>
Table 4, replace peptide 1073.10 Sequence "GVAGALVAFR" with
-- GVAGALVAFK --.

<u>Column 50,</u>
Table 4-continued, replace peptide 24.0092 Sequence "FWAKHMVNF" with
-- FWAKHMWNF--.
Table 5, replace peptide 200.06 Sequence "SALSEGATPQDLNIMLT" with
-- SALSEGATPQDLNTML --.
Table 5, replace peptide 27.0310 Sequence "QEQIGWMTNNPPIPV SEQ ID NO. "3218" with -- SEQ ID "318" --.

Signed and Sealed this

Twelfth Day of August, 2003

JAMES E. ROGAN
*Director of the United States Patent and Trademark Office*